(12) United States Patent
Beers et al.

(10) Patent No.: US 9,911,928 B2
(45) Date of Patent: Mar. 6, 2018

(54) ORGANIC ELECTROLUMINESCENT MATERIALS AND DEVICES

(71) Applicant: Universal Display Corporation, Ewing, NJ (US)

(72) Inventors: Scott Beers, Ewing, NJ (US); Geza Szigethy, Ewing, NJ (US); Jason Brooks, Ewing, NJ (US)

(73) Assignee: Universal Display Corporation, Ewing, NJ (US)

( * ) Notice: Subject to any disclaimer, the term of this patent is extended or adjusted under 35 U.S.C. 154(b) by 130 days.

(21) Appl. No.: 15/074,654

(22) Filed: Mar. 18, 2016

(65) Prior Publication Data

US 2016/0276603 A1    Sep. 22, 2016

Related U.S. Application Data

(60) Provisional application No. 62/135,238, filed on Mar. 19, 2015.

(51) Int. Cl.

| | | |
|---|---|---|
| *H01L 51/00* | (2006.01) | |
| *C09K 11/06* | (2006.01) | |
| *C09K 11/02* | (2006.01) | |
| *C07F 15/00* | (2006.01) | |
| *H01L 51/50* | (2006.01) | |

(52) U.S. Cl.
CPC ...... *H01L 51/0085* (2013.01); *C07F 15/0033* (2013.01); *C07F 15/0066* (2013.01); *C09K 11/025* (2013.01); *C09K 11/06* (2013.01); C09K 2211/1007 (2013.01); C09K 2211/1044 (2013.01); C09K 2211/185 (2013.01); *H01L 51/5016* (2013.01); *H01L 2251/5384* (2013.01)

(58) Field of Classification Search
None
See application file for complete search history.

(56) References Cited

U.S. PATENT DOCUMENTS

| | | | |
|---|---|---|---|
| 4,769,292 A | 9/1988 | Tang et al. | |
| 5,061,569 A | 10/1991 | VanSlyke et al. | |
| 5,247,190 A | 9/1993 | Friend at al. | |
| 5,703,436 A | 12/1997 | Forrest et al. | |
| 5,707,745 A | 1/1998 | Forrest et al. | |
| 5,834,893 A | 11/1998 | Bulovic et al. | |
| 5,844,363 A | 12/1998 | Gu et al. | |
| 6,013,982 A | 1/2000 | Thompson et al. | |
| 6,087,196 A | 7/2000 | Sturm et al. | |

(Continued)

FOREIGN PATENT DOCUMENTS

| | | |
|---|---|---|
| EP | 650955 | 5/1995 |
| EP | 1238981 | 9/2002 |

(Continued)

OTHER PUBLICATIONS

Baldo et al., "Highly Efficient Phosphorescent Emission from Organic Electroluminescent Devices," Nature, vol. 395, 151-154, (1998).

(Continued)

*Primary Examiner* — Robert S Loewe
(74) *Attorney, Agent, or Firm* — Riverside Law LLP

(57) ABSTRACT

A new class of blue emissive complexes are described. The compounds comprise pyridyl benzimidazole ligands with twisted aryl groups for improved color.

20 Claims, 4 Drawing Sheets

(56) References Cited

U.S. PATENT DOCUMENTS

| | | | |
|---|---|---|---|
| 6,091,195 A | 7/2000 | Forrest et al. | |
| 6,097,147 A | 8/2000 | Baldo et al. | |
| 6,294,398 B1 | 9/2001 | Kim et al. | |
| 6,303,238 B1 | 10/2001 | Thompson et al. | |
| 6,337,102 B1 | 1/2002 | Forrest et al. | |
| 6,468,819 B1 | 10/2002 | Kim et al. | |
| 6,528,187 B1 | 3/2003 | Okada | |
| 6,687,266 B1* | 2/2004 | Ma | C09K 11/06 257/141 |
| 6,835,469 B2 | 12/2004 | Kwong et al. | |
| 6,921,915 B2 | 7/2005 | Takiguchi et al. | |
| 7,087,321 B2 | 8/2006 | Kwong et al. | |
| 7,090,928 B2 | 8/2006 | Thompson et al. | |
| 7,154,114 B2 | 12/2006 | Brooks et al. | |
| 7,250,226 B2 | 7/2007 | Tokito et al. | |
| 7,279,704 B2 | 10/2007 | Walters et al. | |
| 7,332,232 B2 | 2/2008 | Ma et al. | |
| 7,338,722 B2 | 3/2008 | Thompson et al. | |
| 7,393,599 B2 | 7/2008 | Thompson et al. | |
| 7,396,598 B2 | 7/2008 | Takeuchi et al. | |
| 7,431,968 B1 | 10/2008 | Shtein et al. | |
| 7,445,855 B2 | 11/2008 | Mackenzie et al. | |
| 7,534,505 B2 | 5/2009 | Lin et al. | |
| 7,968,146 B2 | 6/2011 | Wanger et al. | |
| 8,692,241 B1* | 4/2014 | Zeng | C09K 11/06 257/40 |
| 2002/0034656 A1 | 3/2002 | Thompson et al. | |
| 2002/0134984 A1 | 9/2002 | Igarashi | |
| 2002/0158242 A1 | 10/2002 | Son et al. | |
| 2003/0138657 A1 | 7/2003 | Li et al. | |
| 2003/0152802 A1 | 8/2003 | Tsuboyama et al. | |
| 2003/0162053 A1 | 8/2003 | Marks et al. | |
| 2003/0175553 A1 | 9/2003 | Thompson et al. | |
| 2003/0230980 A1 | 12/2003 | Forrest et al. | |
| 2004/0036077 A1 | 2/2004 | Ise | |
| 2004/0137267 A1 | 7/2004 | Igarashi et al. | |
| 2004/0137268 A1 | 7/2004 | Igarashi et al. | |
| 2004/0174116 A1 | 9/2004 | Lu et al. | |
| 2005/0025993 A1 | 2/2005 | Thompson et al. | |
| 2005/0112407 A1 | 5/2005 | Ogasawara et al. | |
| 2005/0238919 A1 | 10/2005 | Ogasawara | |
| 2005/0244673 A1 | 11/2005 | Satoh et al. | |
| 2005/0260441 A1 | 11/2005 | Thompson et al. | |
| 2005/0260449 A1 | 11/2005 | Walters et al. | |
| 2006/0008670 A1 | 1/2006 | Lin et al. | |
| 2006/0202194 A1 | 9/2006 | Jeong et al. | |
| 2006/0240279 A1 | 10/2006 | Adamovich et al. | |
| 2006/0251923 A1 | 11/2006 | Lin et al. | |
| 2006/0263635 A1 | 11/2006 | Ise | |
| 2006/0280965 A1 | 12/2006 | Kwong et al. | |
| 2007/0190359 A1 | 8/2007 | Knowles et al. | |
| 2007/0278938 A1 | 12/2007 | Yabunouchi et al. | |
| 2008/0015355 A1 | 1/2008 | Schafer et al. | |
| 2008/0018221 A1 | 1/2008 | Egen et al. | |
| 2008/0106190 A1 | 5/2008 | Yabunouchi et al. | |
| 2008/0124572 A1 | 5/2008 | Mizuki et al. | |
| 2008/0220265 A1 | 9/2008 | Xia et al. | |
| 2008/0297033 A1 | 12/2008 | Knowles et al. | |
| 2009/0008605 A1 | 1/2009 | Kawamura et al. | |
| 2009/0009065 A1 | 1/2009 | Nishimura et al. | |
| 2009/0017330 A1 | 1/2009 | Iwakuma et al. | |
| 2009/0030202 A1 | 1/2009 | Iwakuma et al. | |
| 2009/0039776 A1 | 2/2009 | Yamada et al. | |
| 2009/0045730 A1 | 2/2009 | Nishimura et al. | |
| 2009/0045731 A1 | 2/2009 | Nishimura et al. | |
| 2009/0101870 A1 | 4/2009 | Prakash et al. | |
| 2009/0108737 A1 | 4/2009 | Kwong et al. | |
| 2009/0115316 A1 | 5/2009 | Zheng et al. | |
| 2009/0165846 A1 | 7/2009 | Johannes et al. | |
| 2009/0167162 A1 | 7/2009 | Lin et al. | |
| 2009/0179554 A1 | 7/2009 | Kuma et al. | |
| 2013/0026452 A1 | 1/2013 | Kottas et al. | |
| 2013/0119354 A1 | 5/2013 | Ma et al. | |
| 2013/0328019 A1* | 12/2013 | Xia | C09K 11/06 257/40 |

FOREIGN PATENT DOCUMENTS

| | | |
|---|---|---|
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 10/2009 |
| JP | 2010/135467 | 6/2010 |
| WO | 2001039234 | 5/2001 |
| WO | 2002002714 | 1/2002 |
| WO | 215645 | 2/2002 |
| WO | 2003040257 | 5/2003 |
| WO | 2003060956 | 7/2003 |
| WO | 2004093207 | 10/2004 |
| WO | 2004/111066 | 12/2004 |
| WO | 2004107822 | 12/2004 |
| WO | 2005014551 | 2/2005 |
| WO | 5019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 6056418 | 6/2006 |
| WO | 2006/072002 | 7/2006 |
| WO | 2006082742 | 8/2006 |
| WO | 6100298 | 9/2006 |
| WO | 2006098120 | 9/2006 |
| WO | 2006103874 | 10/2006 |
| WO | 2006114966 | 11/2006 |
| WO | 2006132173 | 12/2006 |
| WO | 2007/002683 | 1/2007 |
| WO | 2007004380 | 1/2007 |
| WO | 2007063754 | 6/2007 |
| WO | 2007063796 | 6/2007 |
| WO | 2008/044723 | 4/2008 |
| WO | 2008057394 | 5/2008 |
| WO | 8101842 | 8/2008 |
| WO | 8132085 | 11/2008 |
| WO | 9000673 | 12/2008 |
| WO | 2009/003898 | 1/2009 |
| WO | 2009/008311 | 1/2009 |
| WO | 2009/018009 | 2/2009 |
| WO | 9050290 | 4/2009 |
| WO | 2008/056746 | 5/2009 |
| WO | 2009/021126 | 5/2009 |
| WO | 2009/062578 | 5/2009 |
| WO | 2009/063833 | 5/2009 |
| WO | 2009/066778 | 5/2009 |
| WO | 2009/066779 | 5/2009 |
| WO | 2009/086028 | 7/2009 |
| WO | 9100991 | 8/2009 |
| WO | 2010011390 | 1/2010 |
| WO | 2010/111175 | 9/2010 |
| WO | WO2014023377 A2 | 2/2014 |

OTHER PUBLICATIONS

Baldo et al., "Very high-efficiency green organic light-emitting devices based on electrophosphorescence," Appl. Phys. Lett., vol. 75, No. 1, 4-6 (1999).

U.S. Appl. No. 13/193,221, filed Jul. 28, 2011.

U.S. Appl. No. 13/296,806, filed Nov. 15, 2011.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," *Adv. Mater.*, 6(9):677-679 (1994).

Paulose, Betty Marie Jennifer S. et al., "First Examples of Alkenyl Pyridines as Organic Ligands for Phosphorescent Iridium Complexes," *Adv. Mater.*, 16(22):2003-2007 (2004).

Tung, Yung-Liang et al., "Organic Light-Emitting Diodes Based on Charge-Neutral $Ru^{II}$ PHosphorescent Emitters," *Adv. Mater.*, 17(8):1059-1064 (2005).

(56) References Cited

OTHER PUBLICATIONS

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," *Adv. Mater.*, 19:739-743 (2007).

Wong, Wai-Yeung, "Multifunctional Iridium Complexes Based on Carbazole Modules as Highly Efficient Electrophosphors," *Angew. Chem. Int. Ed.*, 45:7800-7803 (2006).

Tang, C.W. and VanSlyke, S.A., "Organic Electroluminescent Diodes," *Appl. Phys. Lett.*, 51(12):913-915 (1987).

Adachi, Chihaya et al., "Organic Electroluminescent Device Having a Hole Conductor as an Emitting Layer," *Appl. Phys. Lett.*, 55(15):1489-1491 (1989).

Ma, Yuguang et al., "Triplet Luminescent Dinuclear-Gold(I) Complex-Based Light-Emitting Diodes with Low Turn-On voltage," *Appl. Phys. Lett.*, 74(10):1361-1363 (1999).

Gao, Zhiqiang et al., "Bright-Blue Electroluminescence From a Silyl-Substituted ter-(phenylene-vinylene) derivative," *Appl. Phys. Lett.*, 74(6):865-867 (1999).

Lee, Chang-Lyoul et al., "Polymer Phosphorescent Light-Emitting Devices Doped with Tris(2-phenylpyridine) Iridium as a Triplet Emitter," *Appl. Phys. Lett.*, 77(15):2280-2282 (2000).

Hung, L.S. et al., "Anode Modification in Organic Light-Emitting Diodes by Low-Frequency Plasma Polymerization of $CHF_3$," *Appl. Phys. Lett.*, 78(5):673-675 (2001).

Ikai, Masamichi and Tokito, Shizuo, "Highly Efficient Phosphorescence From Organic Light-Emitting Devices with an Exciton-Block Layer," *Appl. Phys. Lett.*, 79(2):156-158 (2001).

Wang, Y. et al., "Highly Efficient Electroluminescent Materials Based on Fluorinated Organometallic Iridium Compounds," *Appl. Phys. Lett.*, 79(4):449-451 (2001).

Kwong, Raymond C. et al., "High Operational Stability of Electrophosphorescent Devices," *Appl. Phys. Lett.*, 81(1):162-164 (2002).

Holmes, R.J. et al., "Blue Organic Electrophosphorescence Using Exothermic Host-Guest Energy Transfer," *Appl. Phys. Lett.*, 82(15):2422-2424 (2003).

Sotoyama, Wataru et al., "Efficient Organic Light-Emitting Diodes with Phosphorescent Platinum Complexes Containing $N^\wedge C^\wedge$ N-Coordinating Tridentate Ligand," *Appl. Phys. Lett.*, 86:153505-1-153505-3 (2005).

Okumoto, Kenji et al., "Green Fluorescent Organic Light-Emitting Device with External Quantum Efficiency of Nearly 10%," *Appl. Phys. Lett.*, 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," *Appl. Phys. Lett.*, 90:123509-1-123509-3 (2007).

Aonuma, Masaki et al., "Material Design of Hole Transport Materials Capable of Thick-Film Formation in Organic Light Emitting Diodes," *Appl. Phys. Lett.*, 90:183503-1-183503-3 (2007).

Sun, Yiru and Forrest, Stephen R., "High-Efficiency White Organic Light Emitting Devices with Three Separate Phosphorescent Emission Layers," *Appl. Phys. Lett.*, 91:263503-1-263503-3 (2007).

Adachi, Chihaya et al., "High-Efficiency Red Electrophosphorescence Devices," *Appl. Phys. Lett.*, 78(11):1622-1624 (2001).

Wong, Keith Man-Chung et al., A Novel Class of Phosphorescent Gold(III) Alkynyl-Based Organic Light-Emitting Devices with Tunable Colour, *Chem. Commun.*, 2906-2908 (2005).

Hamada, Yuji et al., "High Luminance in Organic Electroluminescent Devices with Bis(10-hydroxybenzo[h]quinolinato)beryllium as an Emitter," *Chem. Lett.*, 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," *Chem. Lett.*, 34(4):592-593 (2005).

Mi, Bao-Xiu et al., "Thermally Stable Hole-Transporting Material for Organic Light-Emitting Diode: an Isoindole Derivative," *Chem. Mater.*, 15(16):3148-3151 (2003).

Huang, Wei-Sheng et al., "Highly Phosphorescent Bis-Cyclometaiated Iridium Complexes Containing Benzoimidazole-Based Ligands," *Chem. Mater.*, 16(12):2480-2488 (2004).

Niu, Yu-Hua et al., "Highly Efficient Electrophosphorescent Devices with Saturated Red Emission from a Neutral Osmium Complex," *Chem. Mater.*, 17(13):3532-3536 (2005).

Lo, Shih-Chun et al., "Blue Phosphorescence from Indium(III) Complexes at Room Temperature," *Chem. Mater.*, 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," *Inorg. Chem.*, 46(10):4308-4319 (2007).

Lamansky, Sergey et al., "Synthesis and Characterization of Phosphorescent Cyclometalated Iridium Complexes," *Inorg. Chem.*, 40(7):1704-1711 (2001).

Ranjan, Sudhir et al., "Realizing Green Phosphorescent Light-Emitting Materials from Rhenium(I) Pyrazolato Diimine Complexes," *Inorg. Chem.*, 42(4):1248-1255 (2003).

Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," *J. Am. Chem. Soc.*, 120 (37):9714-9715 (1998).

Sakamoto, Youichi et al., "Synthesis, Characterization, and Electron-Transport Property of Perfluorinated Phenylene Dendrimers," *J. Am. Chem. Soc.*, 122(8):1832-1833 (2000).

Adachi, Chihaya et al., "Nearly 100% Internal Phosphorescence Efficiency in an Organic Light Emitting Device," *J. Appl. Phys.*, 90(10):5048-5051 (2001).

Shirota, Yasuhiko et al., "Starburst Molecules Based on p-Electron Systems as Materials for Organic Electroluminescent Devices," *Journal of Luminescence*, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescerit Devices avith Improved Stability," *Appl. Phys. Lett.*, 69(15):2160-2162 (1996).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based on Silole Derivatives and Their Exciplexes," *Organic Electronics*, 4:113-121 (2003).

Ikeda, Hisao et al., "P-185: Low-Drive-Voltage OLEDs with a Buffer Layer Having Molybdenum Oxide" *SID Symposium Digest*, 37:923-926 (2006).

T. Östergård et al., "Langmuir-Blodgett Light-Emitting Diodes of Poly(3-Hexylthiophene): Electro-Optical Characteristics Related to Structure," *Synthetic Metals*, 87:171-177 (1997).

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

\* cited by examiner

ORGANIC ELECTROLUMINESCENT MATERIALS AND DEVICES

CROSS-REFERENCE TO RELATED APPLICATIONS

This application claims priority from U.S. Provisional Patent Application Ser. No. 62/135,238, filed Mar. 19, 2015, the entire contents of which is incorporated herein by reference.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters, and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

One example of a green emissive molecule is tris(2-phenylpyridine)iridium, denoted Ir(ppy)$_3$, which has the following structure:

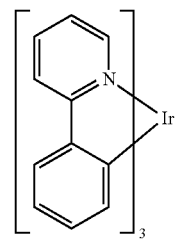

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

Complexes based on the five-member ring imidazole heterocycle are known to be less stable in devices whether they are blue or green emitting complexes compared to phenyl-benzimidazole complexes. It is also known that replacing an N-alkyl on a benzimidazole with N-aryl results in an improvement in device stability due to the higher bond strength of the N-aryl bond. Thus there is a need in the art for new blue phosphorescent emitters based on pyridyl benzimidazole ligands. This invention fulfills this need.

SUMMARY

According to an embodiment, a compound is provided comprising a ligand $L_A$ of Formula I:

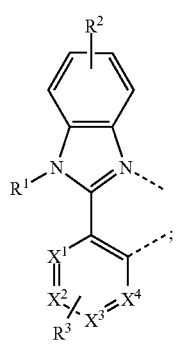

Formula I wherein $R^1$ is a substituted aryl or substituted heteroaryl with at least one substitution on at least one ortho position;
wherein $R^2$ represents mono, di, tri, or tetra substitution, or no substitution;
wherein $R^3$ represents from mono to the maximum number of substitutions it may represent, or no substitution;
wherein $X^1$, $X^2$, $X^3$, and $X^4$ are each independently selected from the group consisting of carbon and nitrogen;
wherein when any of $X^1$, $X^2$, $X^3$, and $X^4$ is nitrogen, there is no substitution on that nitrogen;
wherein at least one of $X^1$, $X^2$, $X^3$, and $X^4$ is nitrogen;
wherein $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein any adjacent $R^2$ and $R^3$ are optionally joined or fused into a ring;
wherein the ligand $L_A$ is coordinated to a metal M; and
wherein the ligand $L_A$ is optionally linked with other ligands to form a tridentate, tetradentate, pentadentate or hexadentate ligand.

According to another embodiment, an organic light emitting diode/device (OLED) is also provided. The OLED can include an anode, a cathode, and an organic layer, disposed between the anode and the cathode. The organic layer can include a compound comprising a ligand $L_A$ of Formula I. According to yet another embodiment, the organic light emitting device is incorporated into a device selected from a consumer product, an electronic component module, and/or a lighting panel.

According to another embodiment, the invention provides a formulation comprising a compound comprising a ligand $L_A$ of Formula I.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
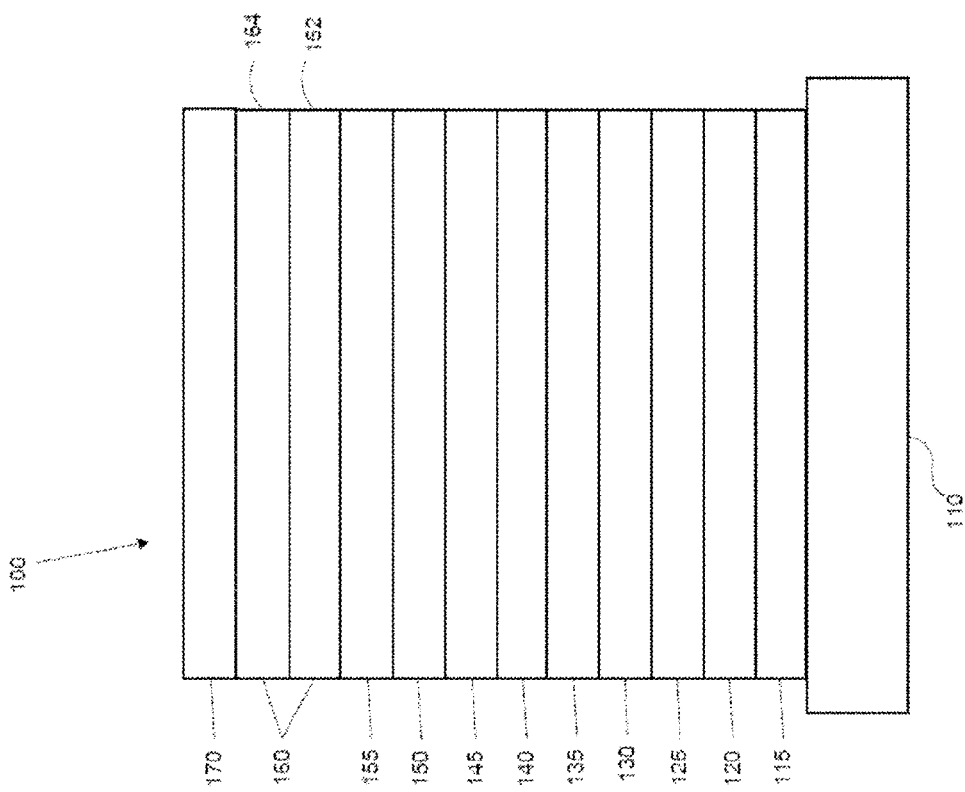
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
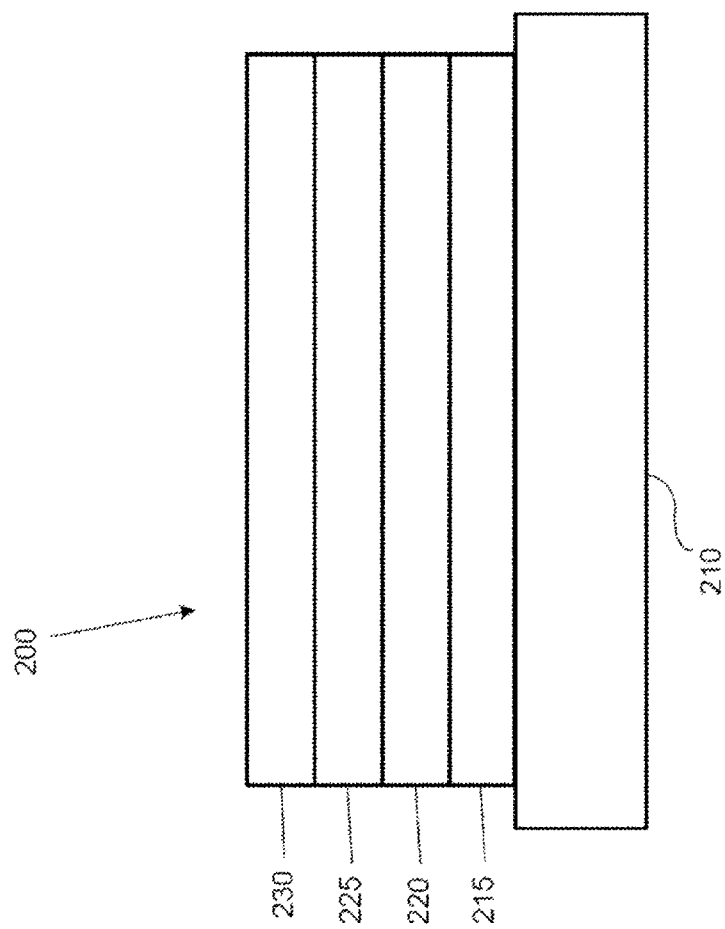
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable device, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" as used herein contemplates cyclic alkyl radicals. Preferred cycloalkyl groups are those containing 3 to 10 ring carbon atoms and includes cyclopropyl, cyclopentyl, cyclohexyl, adamantyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Heteroaromatic cyclic radicals also means heteroaryl. Preferred hetero-non-aromatic cyclic groups are those containing 3 or 7 ring atoms which includes at least one hetero atom, and includes cyclic amines such as morpholino, piperidino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" as used herein contemplates single-ring hetero-aromatic groups that may include from one to five heteroatoms. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, and aza-analogs thereof. Additionally, the heteroaryl group may be optionally substituted.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The invention describes a new class of blue phosphorescent emitters based on a pyridyl benzimidazole ligand with a twisted aryl. It was found that phenyl benzimidazole tris compounds are stable green emitters in OLED devices, with device lifetimes comparable to state of the art phenylpyridine based complexes. Complexes based on the five-member ring imidazole heterocycle, however, are known to be much less stable in devices whether they are blue or green emitting complexes compared to phenyl-benzimidazole complexes. It is also known that replacing an N-alkyl on a benzimidazole with N-aryl results in an improvement in device stability due to the higher bond strength of the N-aryl bond.

The invention shows that a phenyl-benzimidazole complex can be significantly blue-shifted by replacing the phenyl ring with a pyridine, where the nitrogen is located para to the iridium metal. This is a similar blue-shift to what has been described for Iridium tris-pyridyl-pyridine complexes. Furthermore it is found that replacing a phenyl ring on the benzimidazole with a twisted aryl ring, that rotates the pendant N-aryl ring 90 degrees out of the plane of conjugation, results in a significant improvement of the blue emission color at room temperature.

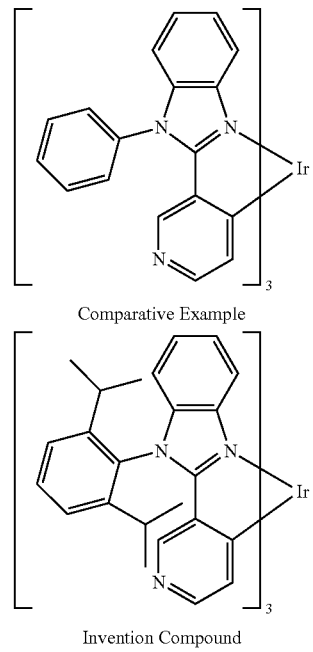

Comparative Example

Invention Compound

Figure 3:
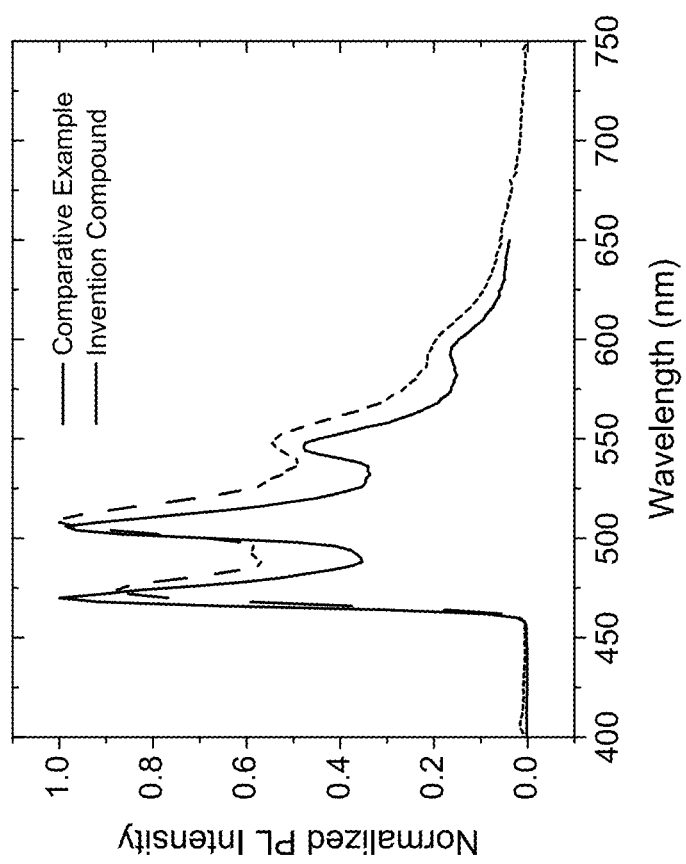
FIG. 3 shows the spectral comparison of the invention compound and Comparative Example in 2-methyl THF at 77 K.

To further explain the significance of the invention, the 77 K emission spectrum for the Comparative Example and Invention Compound are shown in FIG. 3. Both complexes have very similar high energy peak emission around 470 nm, with well-defined vibronic structure. In addition, density functional theory calculations (DFT) were performed at the B3LYP/cep-31g functional and basis set with THF solvent phase using the Gaussian software package. The Comparative Example was calculated to have a triplet energy of 468 nm and the Invention Compound 469 nm, both very close to peak emission observed at 77 K. Therefore the Comparative Example and Invention compound have very similar intrinsic triplet energy.

Figure 4:
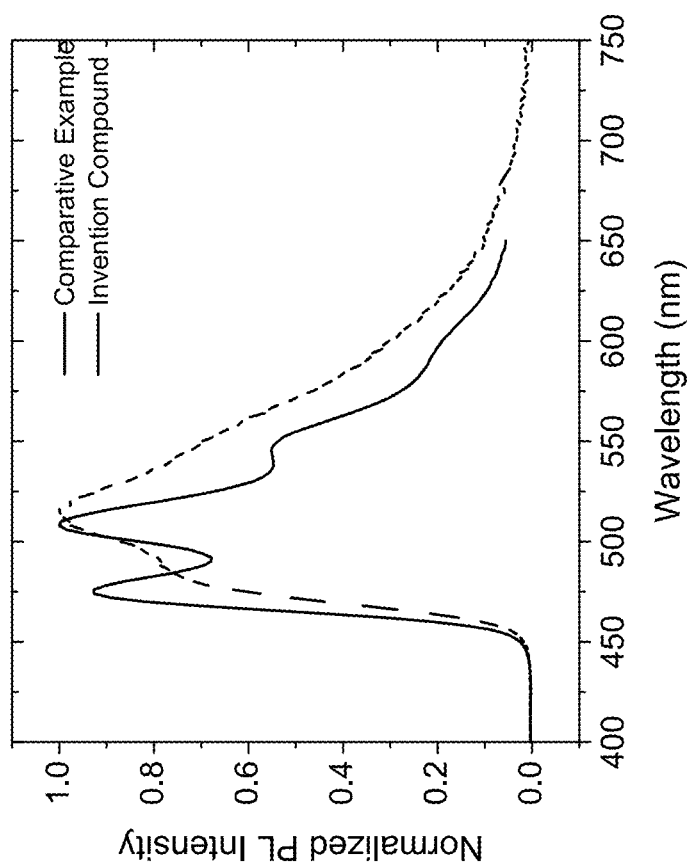
FIG. 4 shows the spectral comparison of the invention compound and Comparative Example in 2-methyl THF at room temperature.

However, while the 77 K emission and calculated triplet energies for the Comparative Example and Invention Compound are very similar, significant differences in emission energy and color are observed in room temperature solution, as shown in FIG. 4. The highest energy peak for the Invention Compound is red-shifted slightly to 475 nm. On the other hand, the highest energy peak for the Comparative Example is poorly defined as a shoulder of the highest intensity peak at 515 nm. Therefore the Invention Compound, with twisted aryl substitution, has superior properties as a more saturated blue emitter which is a significant improvement relative to the Comparative Example. Pyridylbenzimidazoles with twisted aryl substitution are believed to be the best mode with respect to stability and color for this family of blue phosphorescent emitters.

Compounds of the Invention

The compounds of the present invention may be synthesized using techniques well-known in the art of organic synthesis. The starting materials and intermediates required for the synthesis may be obtained from commercial sources or synthesized according to methods known to those skilled in the art.

In one aspect, the invention relates to a compound comprising a ligand $L_A$ of Formula I:

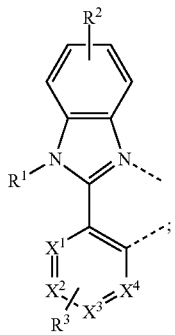

Formula I wherein $R^1$ is a substituted aryl or substituted heteroaryl with at least one substitution on at least one ortho position;

wherein $R^2$ represents mono, di, tri, or tetra substitution, or no substitution;

wherein $R^3$ represents from mono to the maximum number of substitutions it may represent, or no substitution;

wherein $X^1$, $X^2$, $X^3$, and $X^4$ are each independently selected from the group consisting of carbon and nitrogen;

wherein when any of $X^1$, $X^2$, $X^3$, and $X^4$ is nitrogen, there is no substitution on that nitrogen;

wherein at least one of $X^1$, $X^2$, $X^3$, and $X^4$ is nitrogen;

wherein $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any adjacent $R^2$ and $R^3$ are optionally joined or fused into a ring;

wherein the ligand $L_A$ is coordinated to a metal M; and wherein the ligand $L_A$ is optionally linked with other ligands to form a tridentate, tetradentate, pentadentate or hexadentate ligand.

In one embodiment, $R^1$ has substitutions on both ortho positions. In another embodiment, $R^1$ is a substituted aryl. In another embodiment, only one of $X^1$, $X^2$, $X^3$, and $X^4$ is nitrogen. In one embodiment, M is selected from the group consisting of Ir, Rh, Re, Ru, Os, Pt, Au, and Cu. In another embodiment, M is Ir.

In one embodiment, the ligand $L_A$ has the formula:

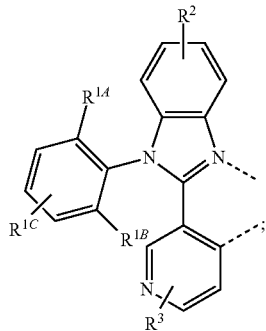

wherein $R^{1C}$ represents mono, di, or tri substitution, or no substitution;

wherein $R^{1A}$, $R^{1B}$ and $R^{1C}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;

wherein any adjacent $R^{1A}$, $R^{1B}$ and $R^{1C}$ are optionally joined or fused into a ring;

wherein at least one of $R^{1A}$, and $R^{1B}$ is not hydrogen or deuterium.

In one embodiment, $R^{1A}$, and $R^{1B}$ are each independently selected from the group consisting of alkyl, cycloalkyl, silyl, aryl, heteroaryl, partially or fully deuterated variants thereof, and combinations thereof. In another embodiment, $R^{1A}$, and $R^{1B}$ are each independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, and combinations thereof.

In another aspect, the invention relates to a compound comprising a ligand $L_A$, wherein the ligand $L_A$ is selected from the group consisting of:

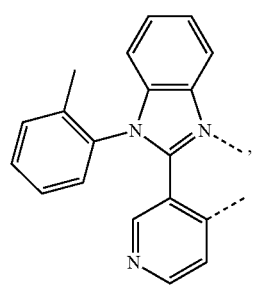

$L_A1$

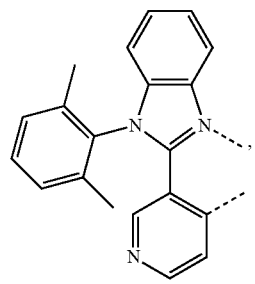

$L_A2$

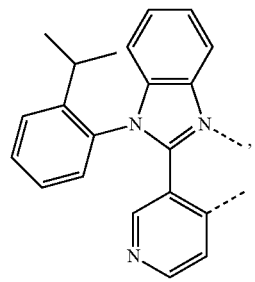

$L_A3$

-continued
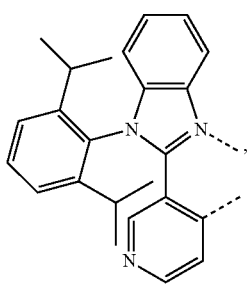 L$_A$4
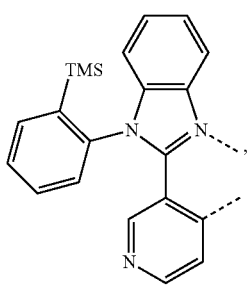 L$_A$5
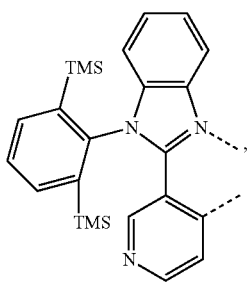 L$_A$6
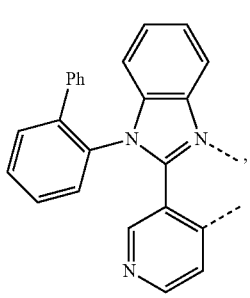 L$_A$7
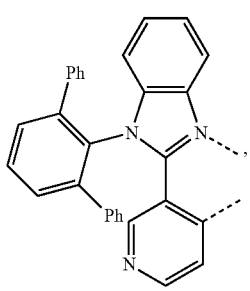 L$_A$8
-continued
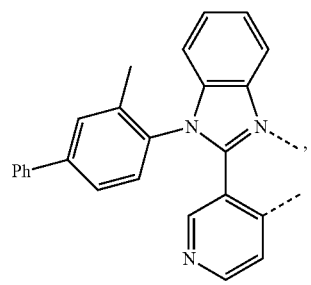 L$_A$9
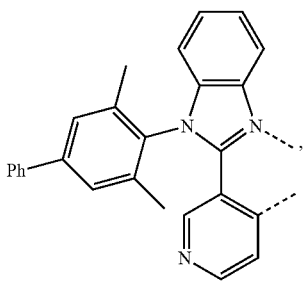 L$_A$10
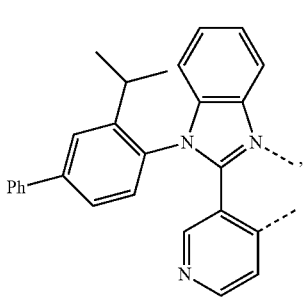 L$_A$11
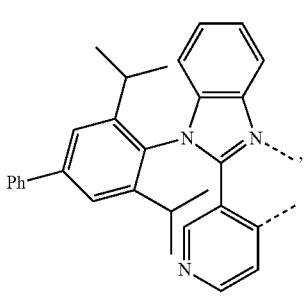 L$_A$12
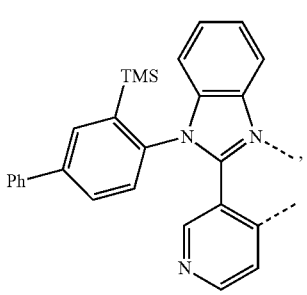 L$_A$13

L<sub>A</sub>14
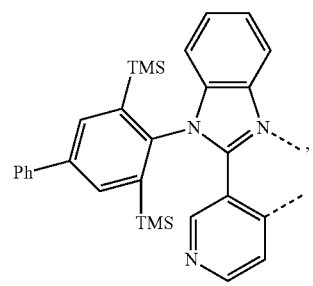
L<sub>A</sub>15
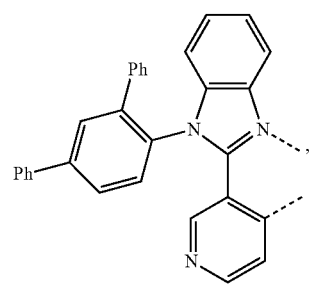
L<sub>A</sub>16
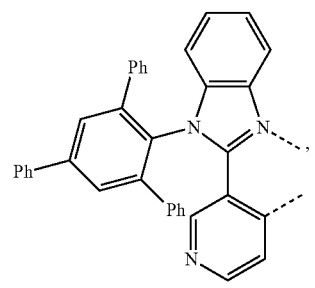
L<sub>A</sub>17
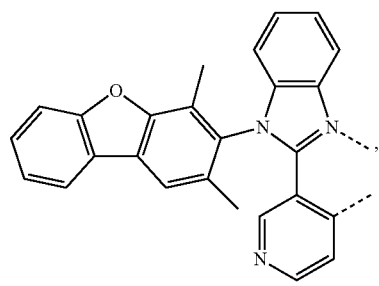
L<sub>A</sub>18
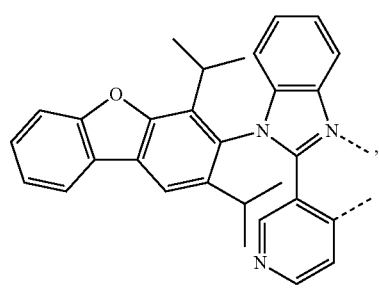
L<sub>A</sub>19
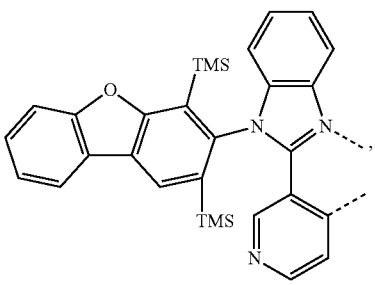
L<sub>A</sub>20
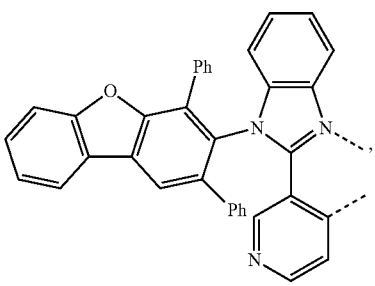
L<sub>A</sub>21
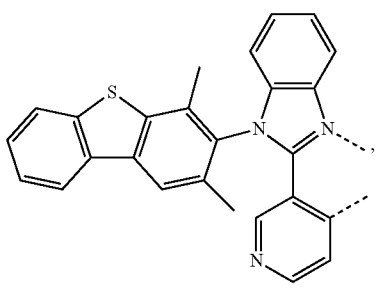
L<sub>A</sub>22
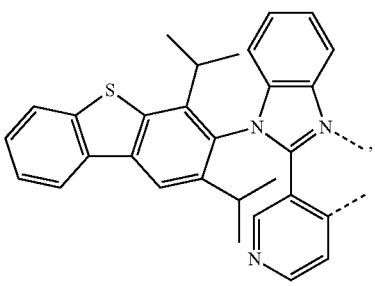
L<sub>A</sub>23
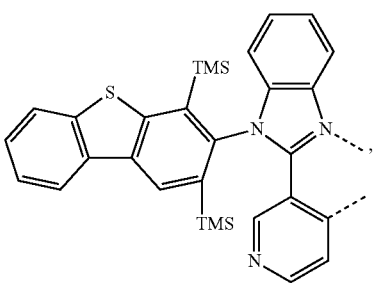

-continued
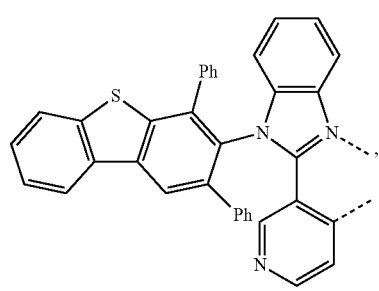 L$_A$24
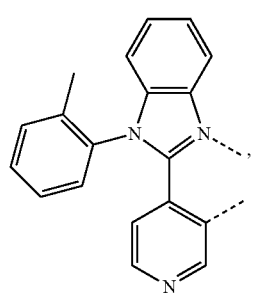 L$_A$25
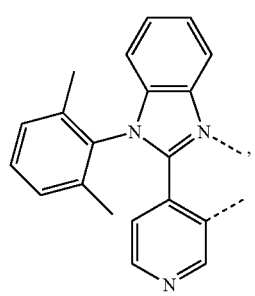 L$_A$26
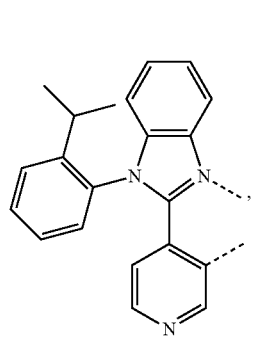 L$_A$27
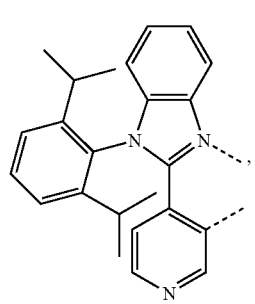 L$_A$28
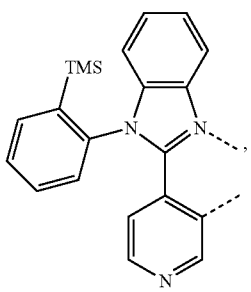 L$_A$29
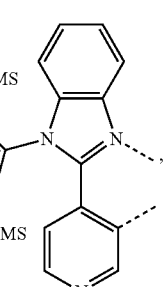 L$_A$30
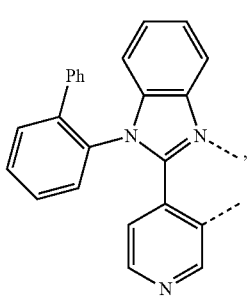 L$_A$31
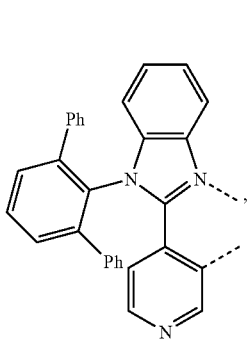 L$_A$32
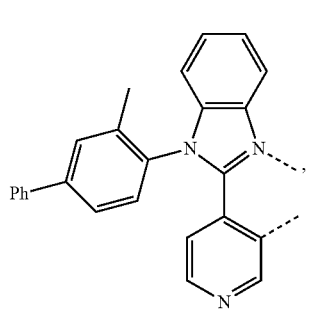 L$_A$33

-continued
L$_A$34
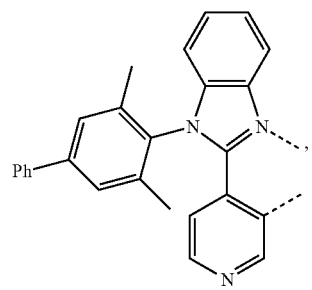
L$_A$35
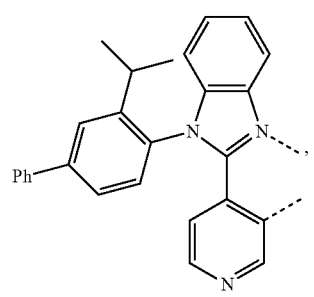
L$_A$36
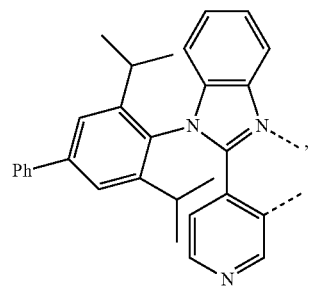
L$_A$37
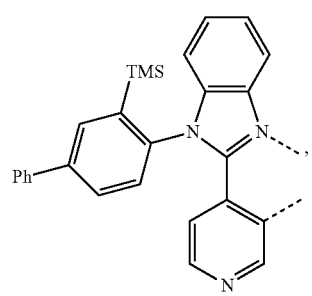
L$_A$38
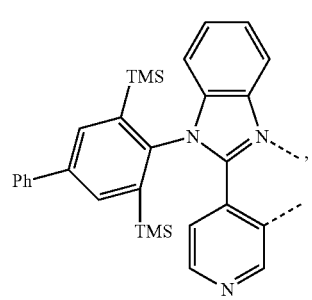
-continued
L$_A$39
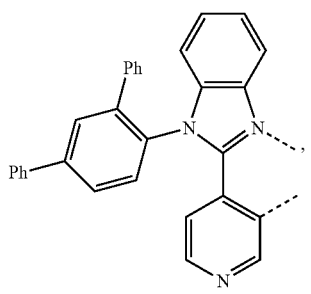
L$_A$40
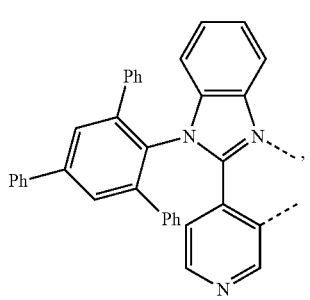
L$_A$41
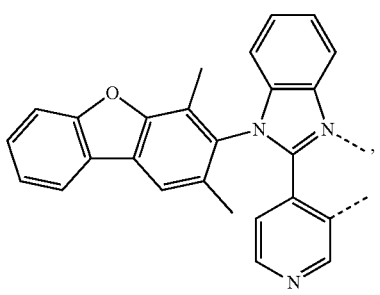
L$_A$42
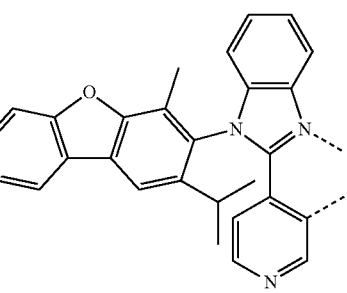
L$_A$43
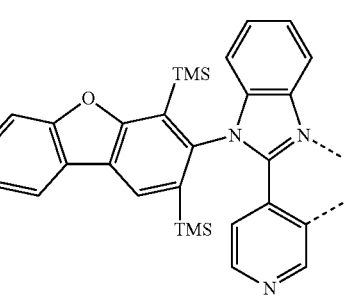

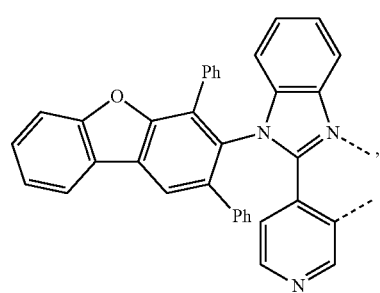 L$_A$44
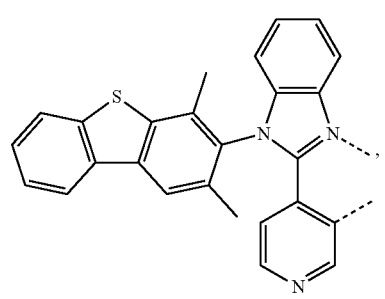 L$_A$45
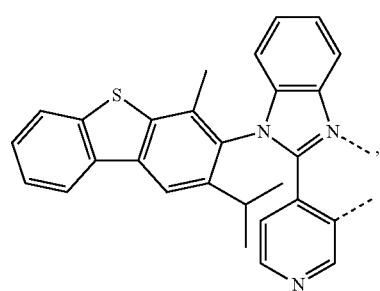 L$_A$46
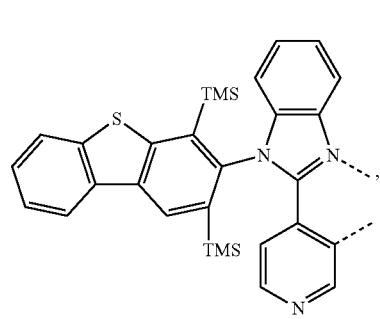 L$_A$47
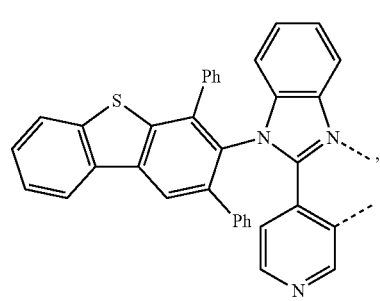 L$_A$48
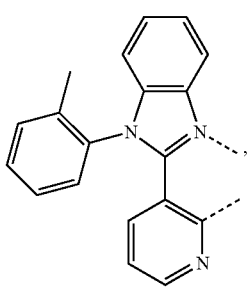 L$_A$49
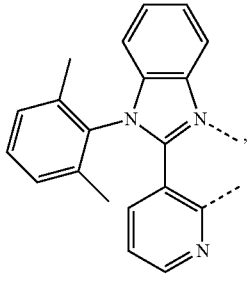 L$_A$50
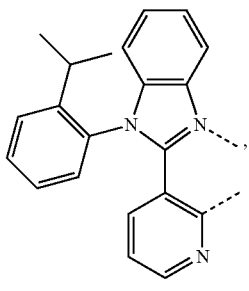 L$_A$51
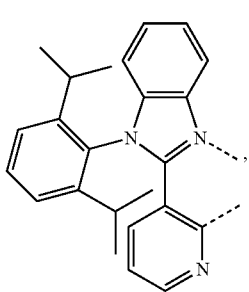 L$_A$52
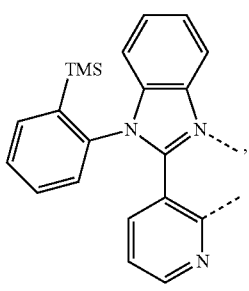 L$_A$53

L<sub>A</sub>54 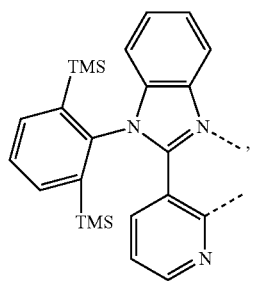
L<sub>A</sub>55 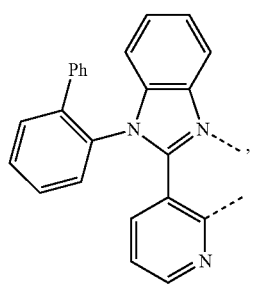
L<sub>A</sub>56 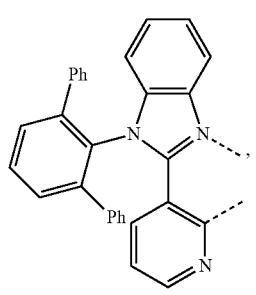
L<sub>A</sub>57 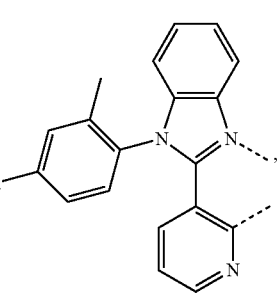
L<sub>A</sub>58 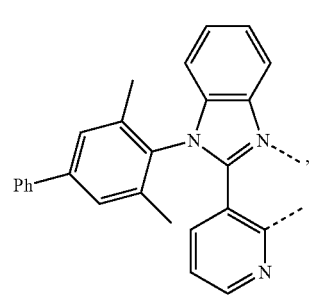
L<sub>A</sub>59 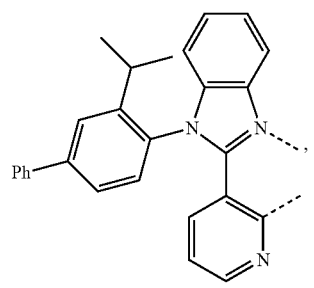
L<sub>A</sub>60 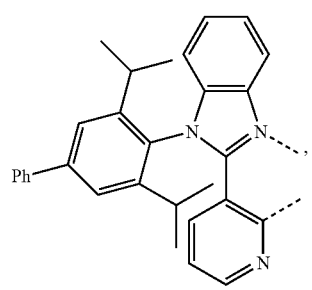
L<sub>A</sub>61 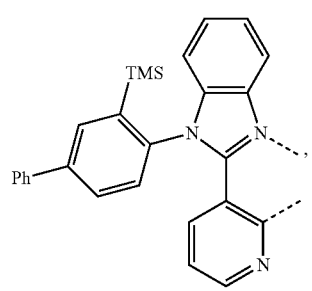
L<sub>A</sub>62 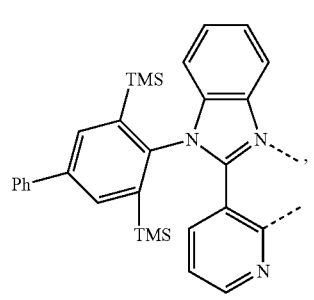
L<sub>A</sub>63 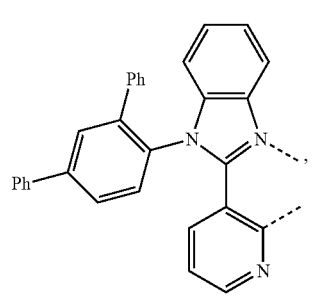

L_A64
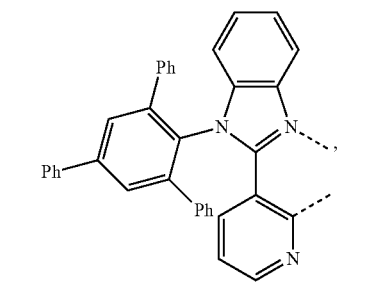
L_A65
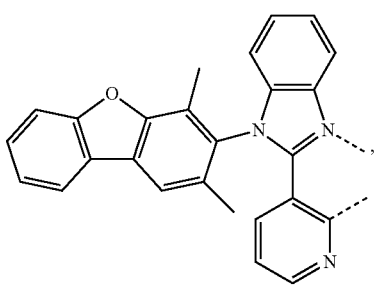
L_A66
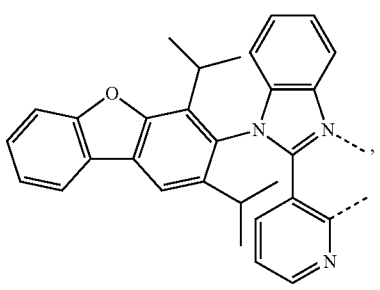
L_A67
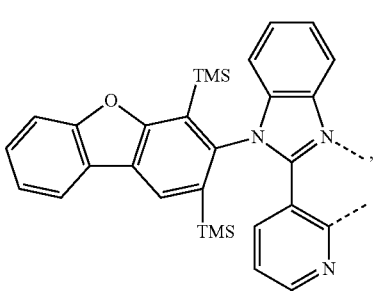
L_A68
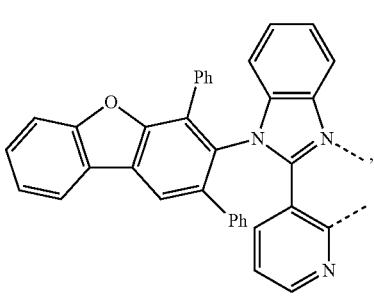
L_A69
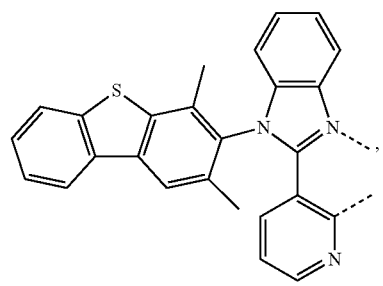
L_A70
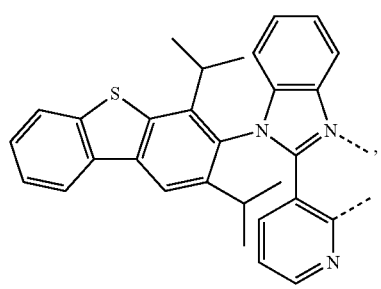
L_A71
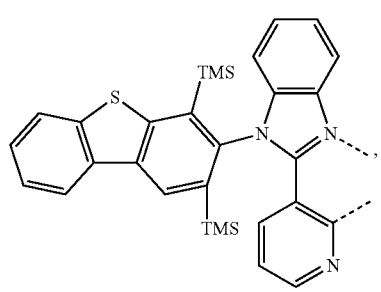
L_A72
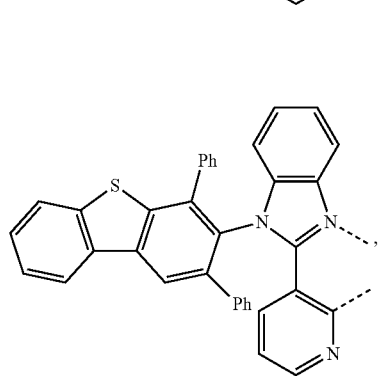
L_A73
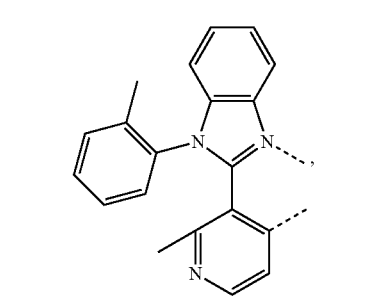

L_A74 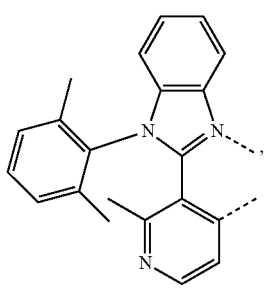
L_A75 
L_A76 
L_A77 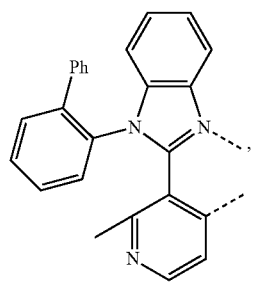
L_A78 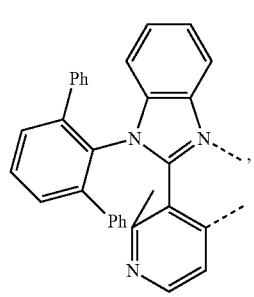
L_A79 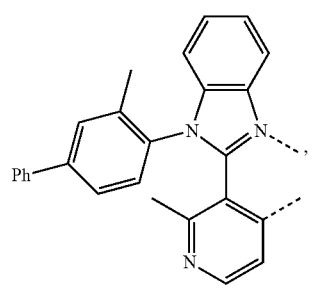
L_A80 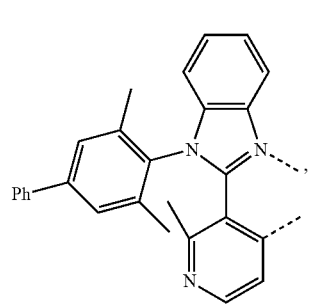
L_A81 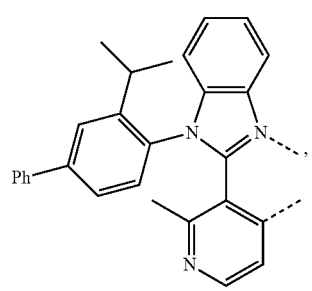
L_A82 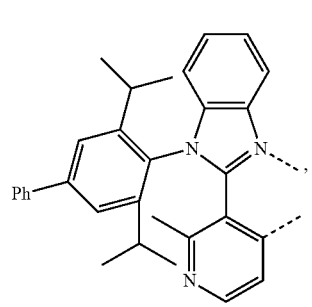
L_A83 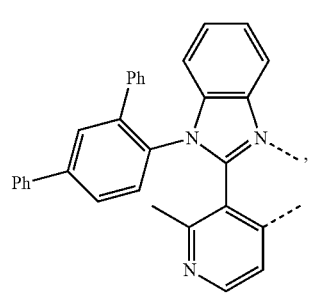

L$_A$84 
L$_A$85 
L$_A$86 
L$_A$87 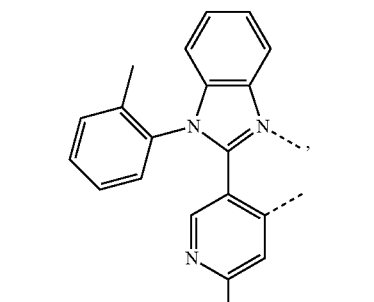
L$_A$88 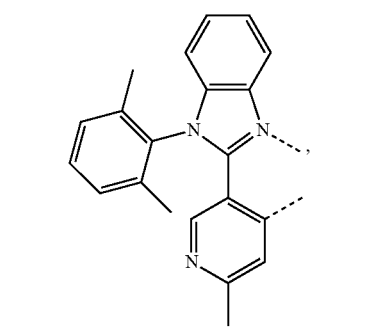
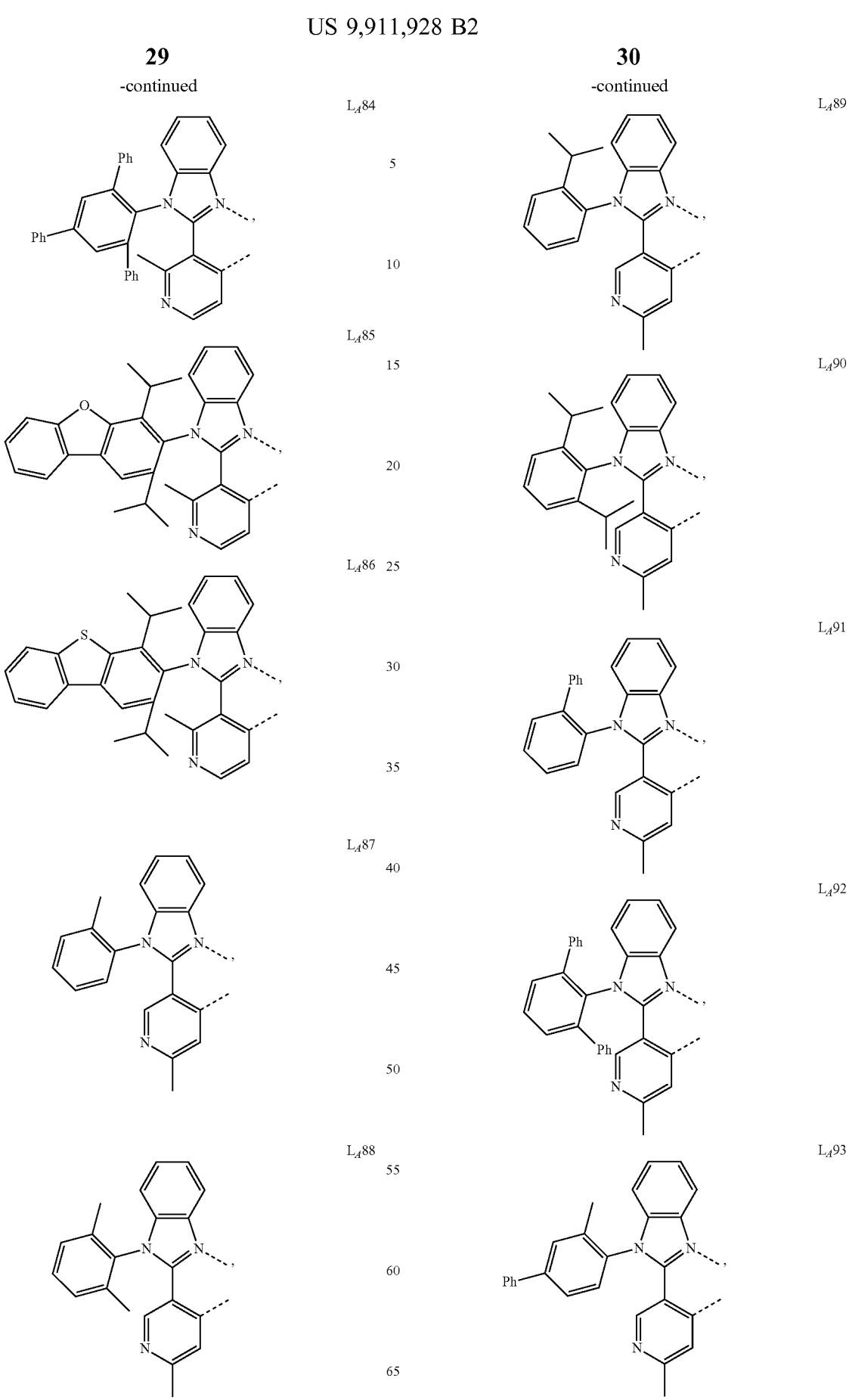

L_A94
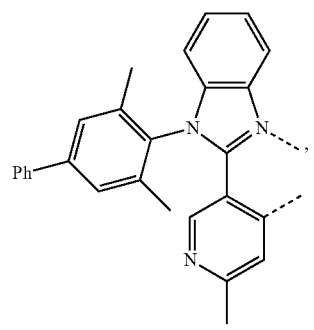
L_A95
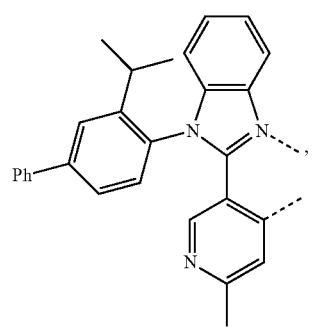
L_A96
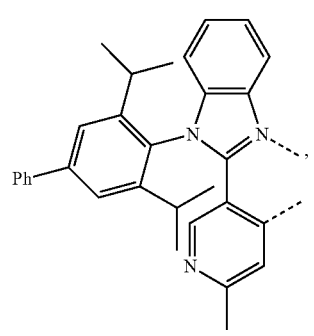
L_A97
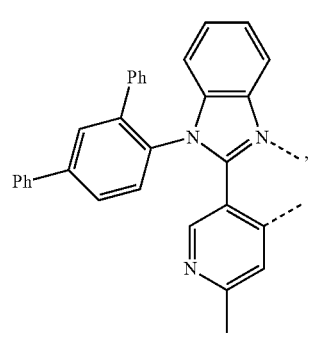
L_A98
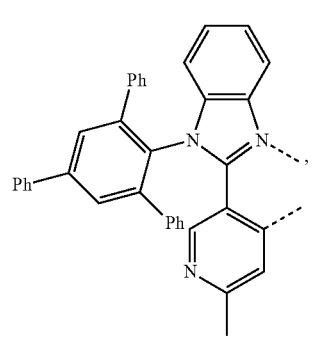
L_A99
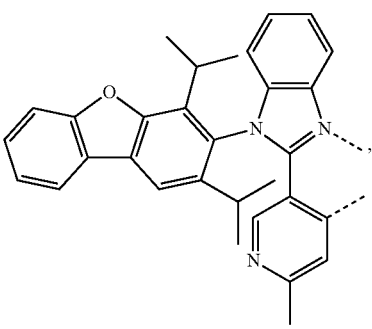
L_A100
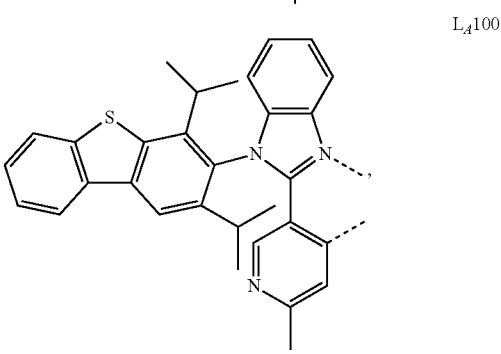
L_A101
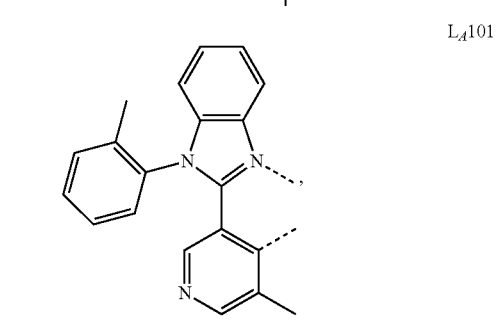
L_A102
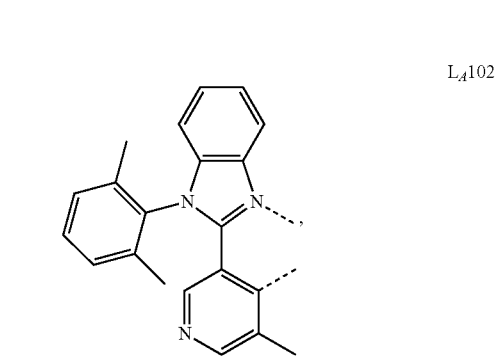
L_A103
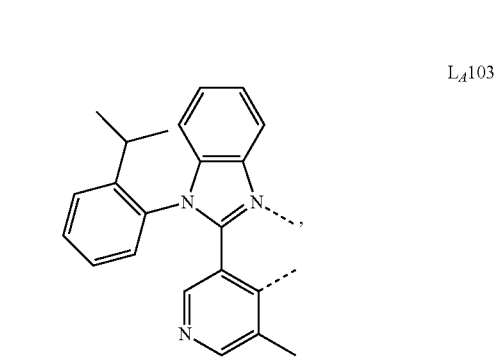

L<sub>A</sub>104 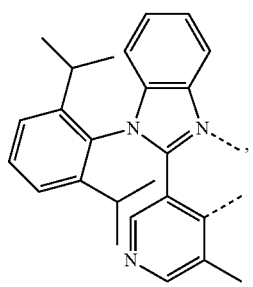
L<sub>A</sub>105 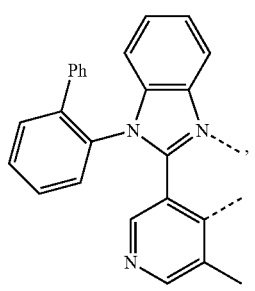
L<sub>A</sub>106 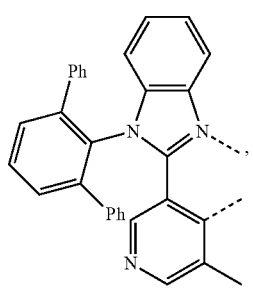
L<sub>A</sub>107 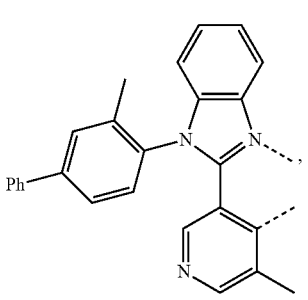
L<sub>A</sub>108 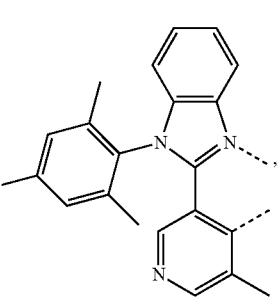
L<sub>A</sub>109 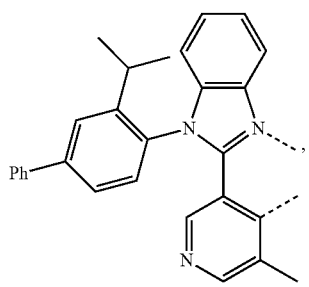
L<sub>A</sub>110 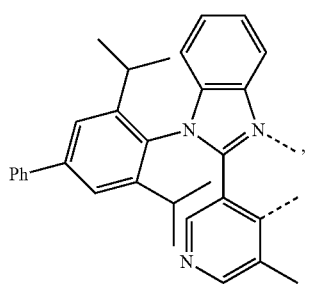
L<sub>A</sub>111 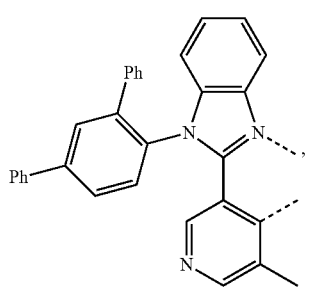
L<sub>A</sub>112 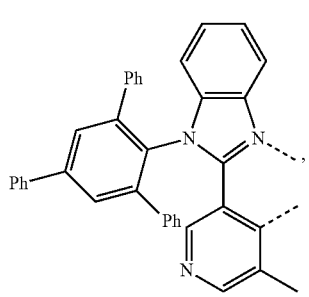
L<sub>A</sub>113 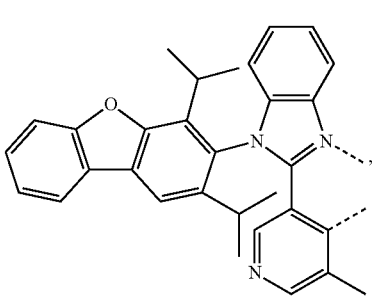

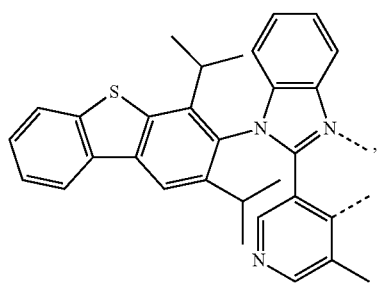 L<sub>A</sub>114
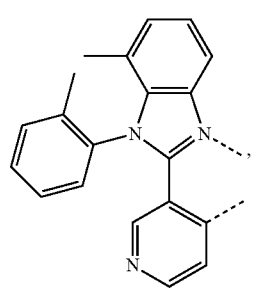 L<sub>A</sub>115
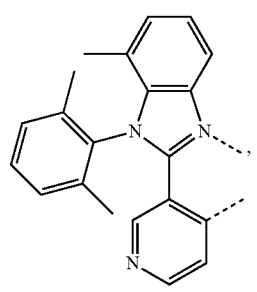 L<sub>A</sub>116
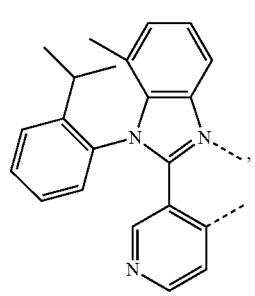 L<sub>A</sub>117
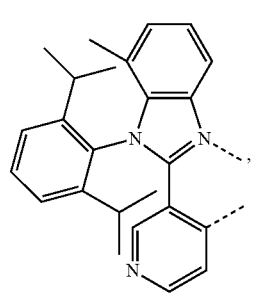 L<sub>A</sub>118
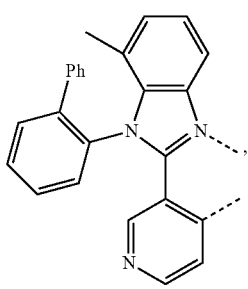 L<sub>A</sub>119
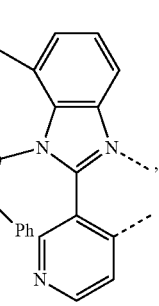 L<sub>A</sub>120
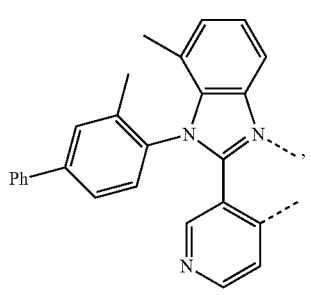 L<sub>A</sub>121
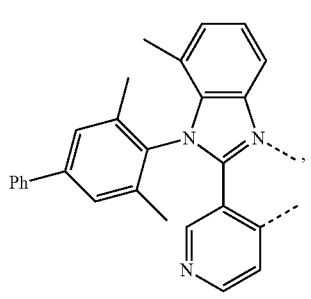 L<sub>A</sub>122
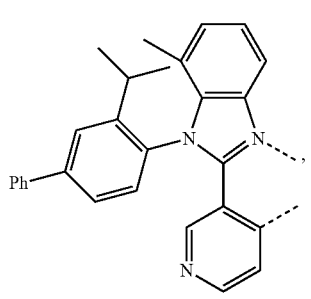 L<sub>A</sub>123

-continued
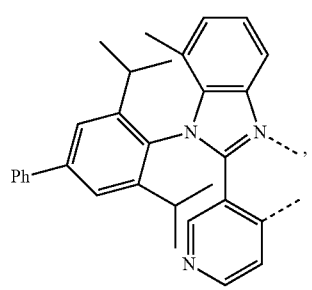 L$_A$124
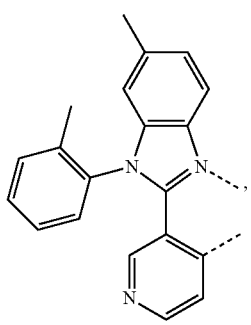 L$_A$129
L$_A$125
L$_A$130
L$_A$126
L$_A$131
L$_A$127
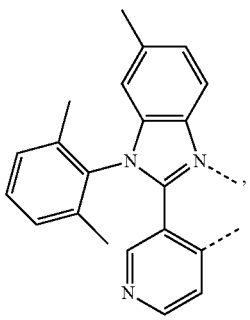
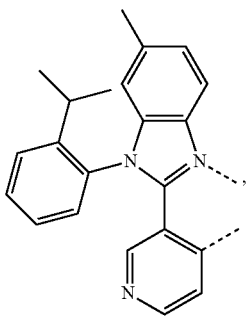
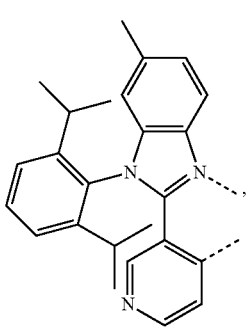 L$_A$132
L$_A$128
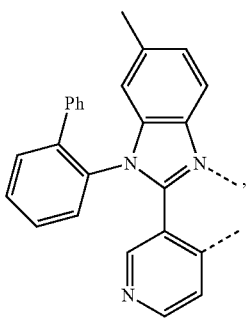 L$_A$133

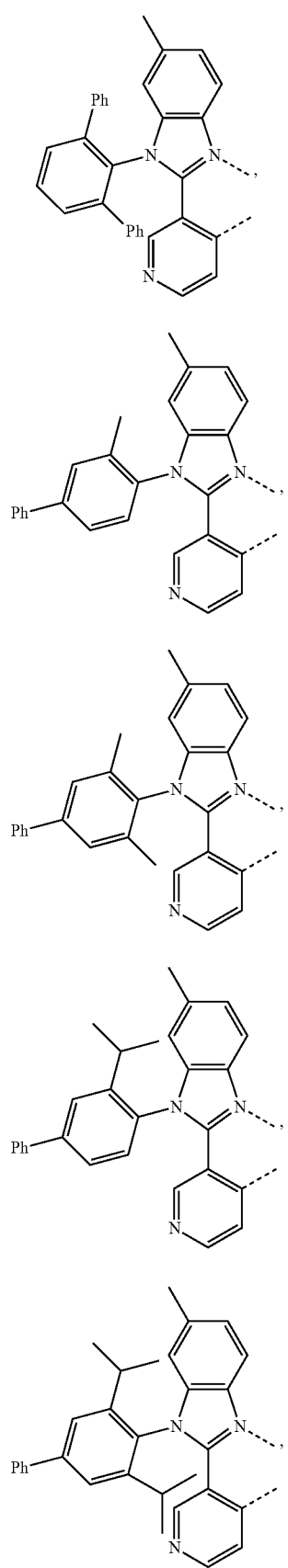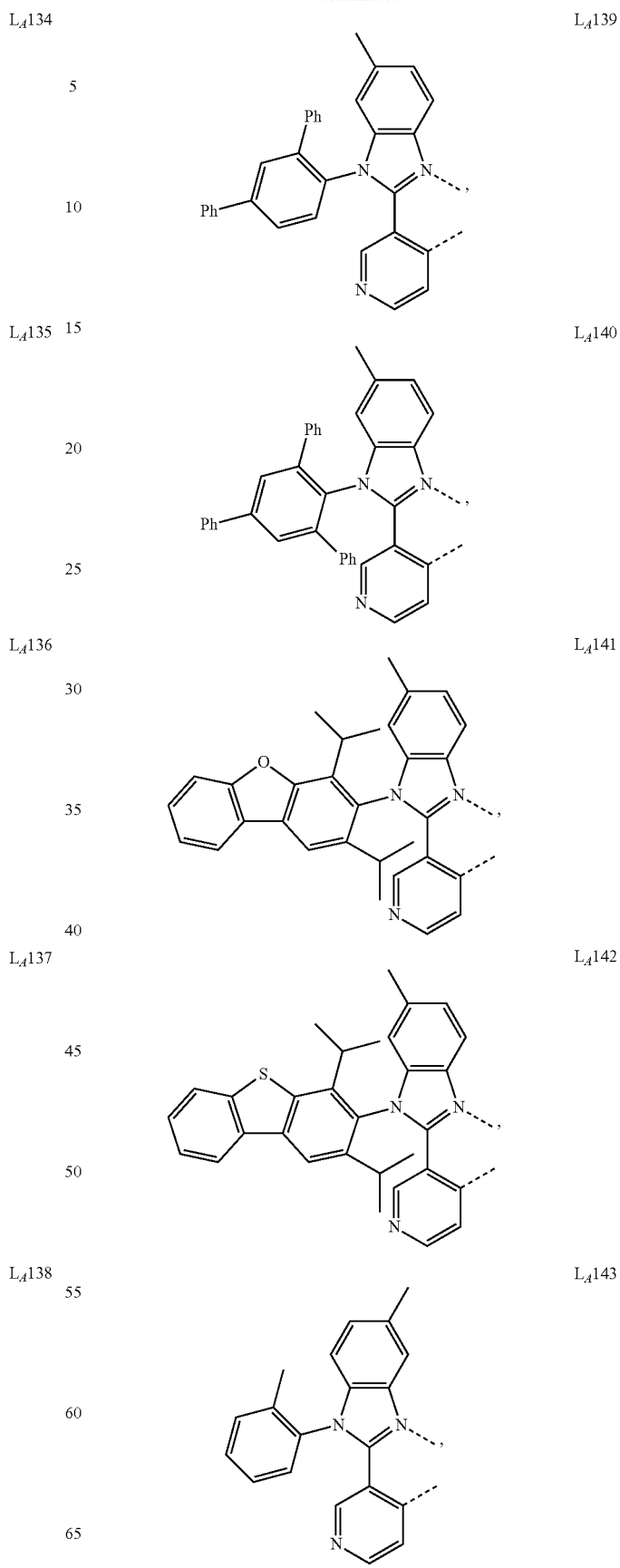

L_A144
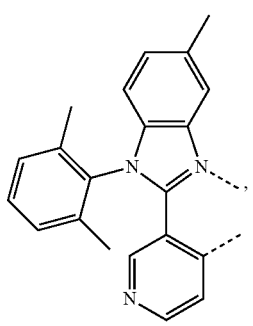
L_A145
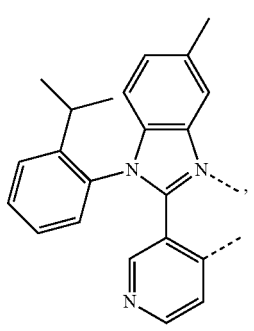
L_A146
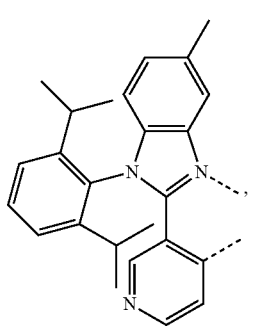
L_A147
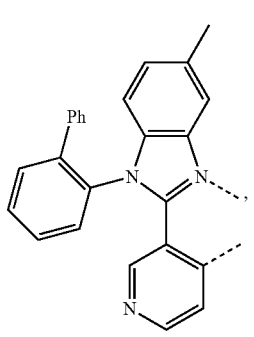
L_A148
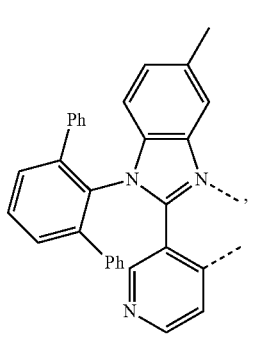
L_A149
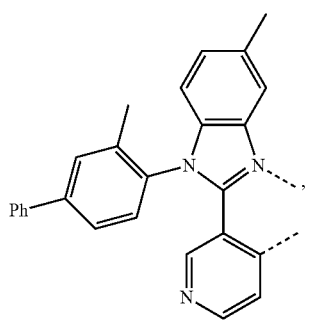
L_A150
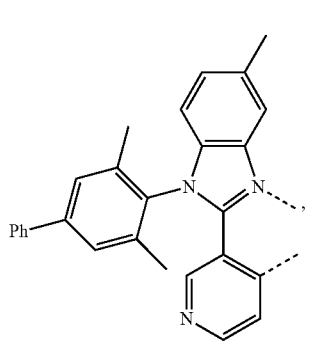
L_A151
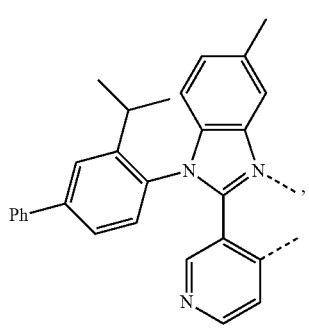
L_A152
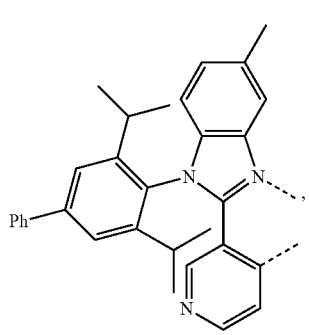
L_A153
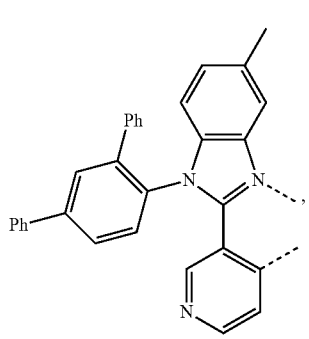

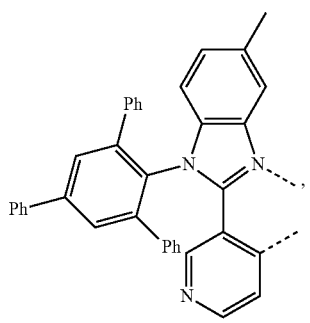 L$_A$154
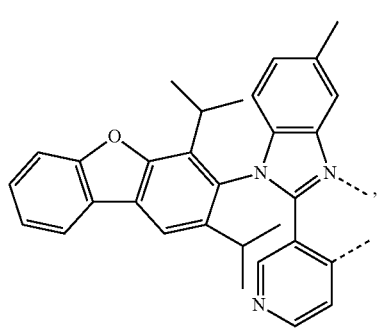 L$_A$155
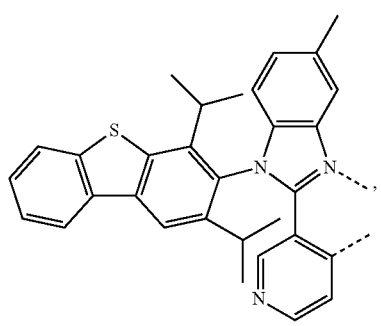 L$_A$156
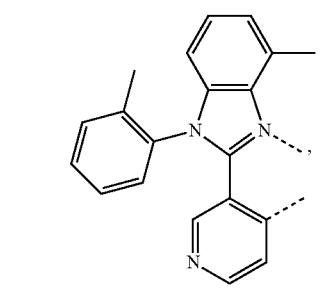 L$_A$157
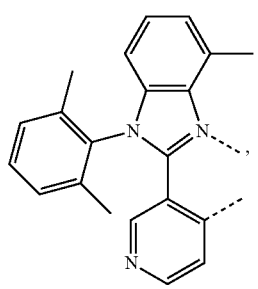 L$_A$158
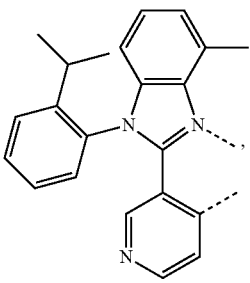 L$_A$159
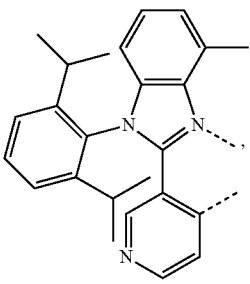 L$_A$160
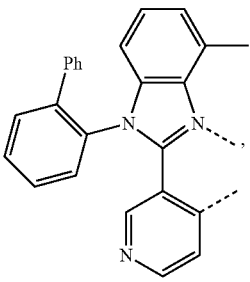 L$_A$161
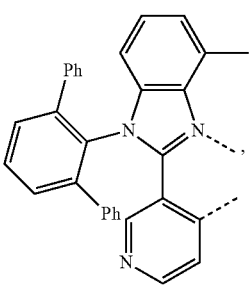 L$_A$162
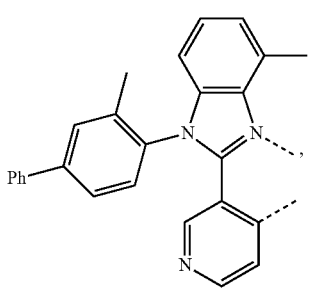 L$_A$163

-continued
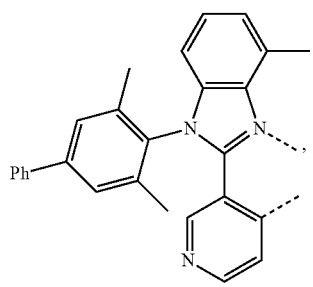
L$_A$164
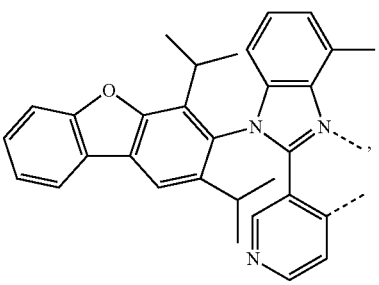
L$_A$169
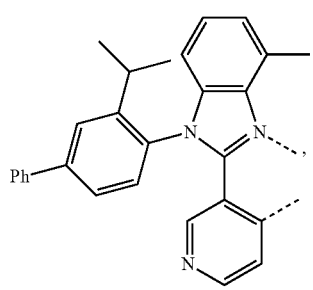
L$_A$165
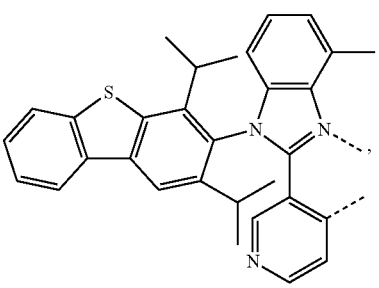
L$_A$170
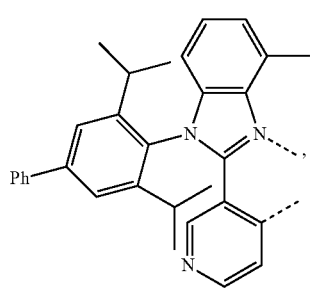
L$_A$166
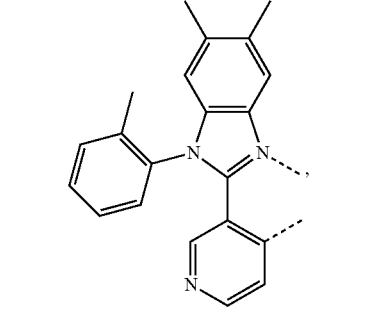
L$_A$171
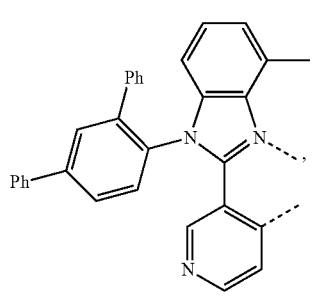
L$_A$167
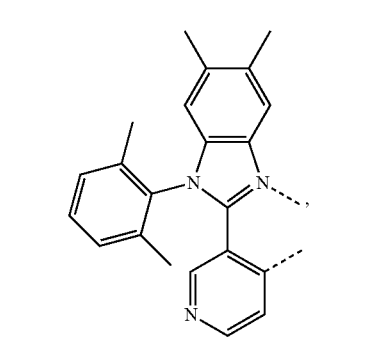
L$_A$172
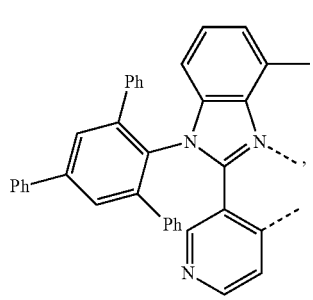
L$_A$168
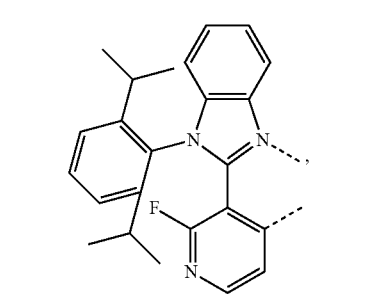
L$_A$173

L_A174
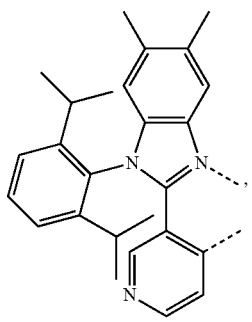
P_A175
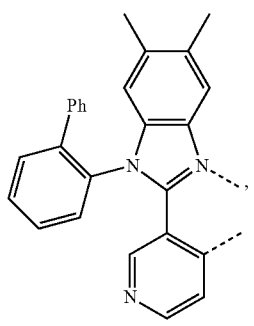
P_A176
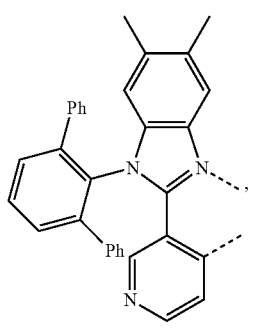
P_A177
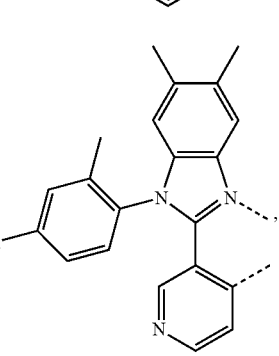
P_A178
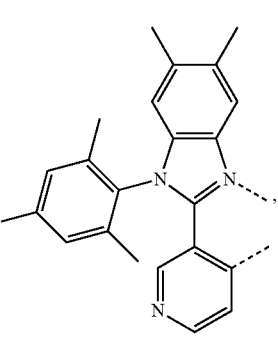
P_A179
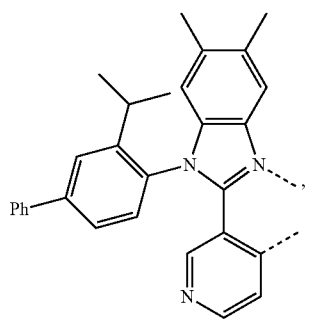
L_A180
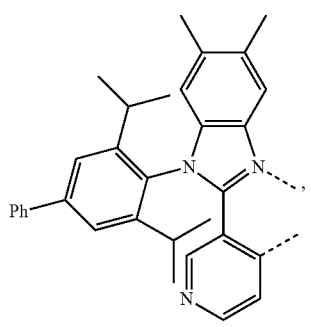
L_A181
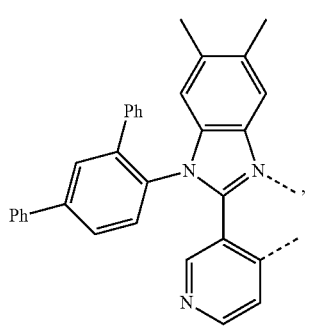
L_A182
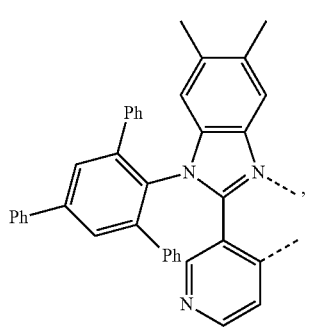
L_A183
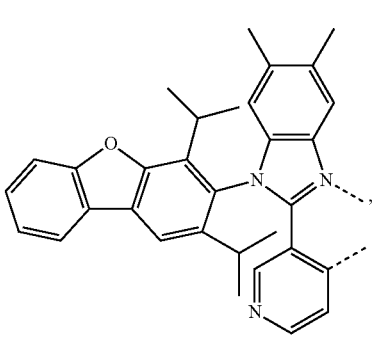

-continued
L$_A$184
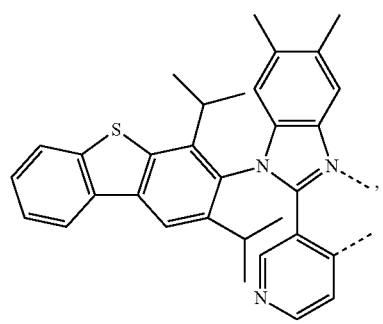
L$_A$185
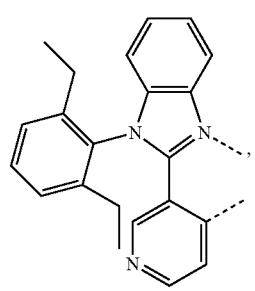
L$_A$186
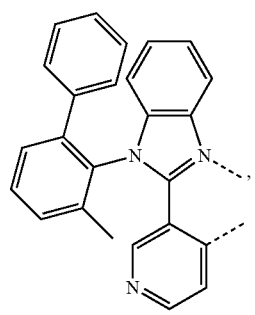
L$_A$187
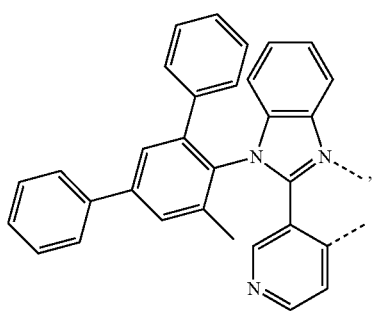
L$_A$188
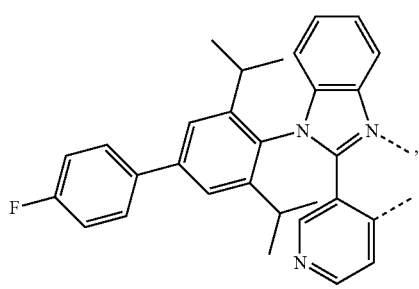
-continued
L$_A$189
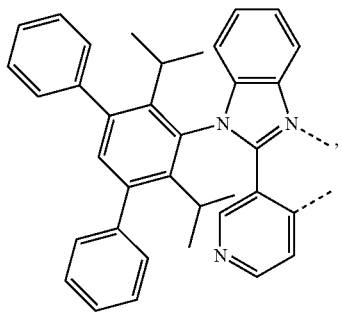
L$_A$190
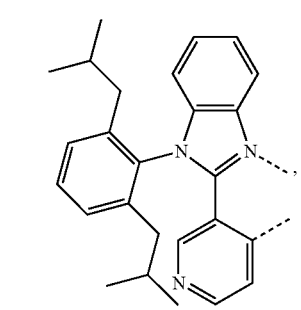
L$_A$191
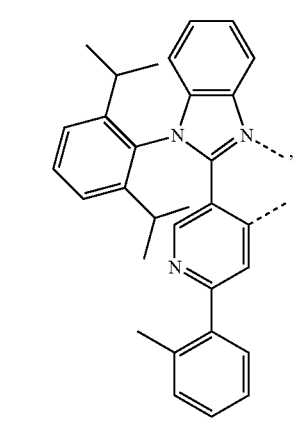
L$_A$192
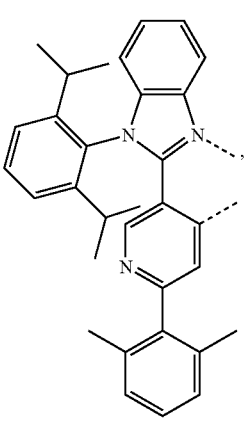

L_A193

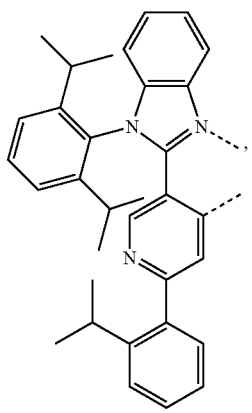

L_A194

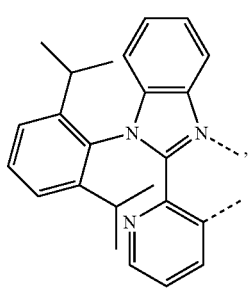

L_A195

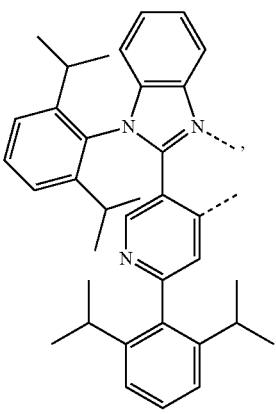

L_A196

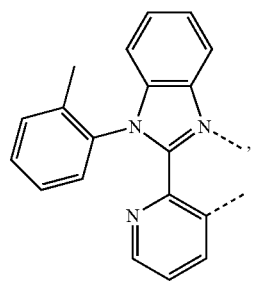

L_A197

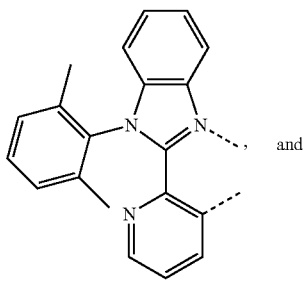

, and

L_A198

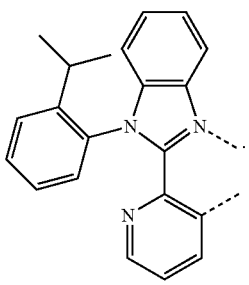

In one aspect, the invention relates to a compound comprising a ligand $L_A$, wherein the compound has a formula of $M(L_A)_n(L_b)_{m-n}$; wherein M is Ir or Pt; $L_B$ is a bidentate ligand; and wherein when M is Ir, m is 3, and n is 1, 2, or 3; when M is Pt, m is 2, and n is 1, or 2. In one embodiment, the compound has a formula of $Ir(L_A)_3$. In another embodiment, the compound has a formula of $Ir(L_A)(L_B)_2$; and wherein $L_B$ is different from $L_A$. In another embodiment, the compound has a formula of $Ir(L_A)_2(L_B)$; and wherein $L_B$ is different from $L_A$. In another embodiment, the compound has a formula of $Pt(L_A)(L_B)$; and wherein $L_A$ and $L_B$ can be same or different. In another embodiment, $L_A$ and $L_B$ are connected to form a tetradentate ligand. In another embodiment, $L_A$ and $L_B$ are connected at two places to form a macrocyclic tetradentate ligand.

In one aspect, the invention relates to a compound comprising a ligand $L_A$, wherein the compound has a formula of $M(L_A)_n(L_B)_{m-n}$, wherein $L_B$ is selected from the group consisting of:

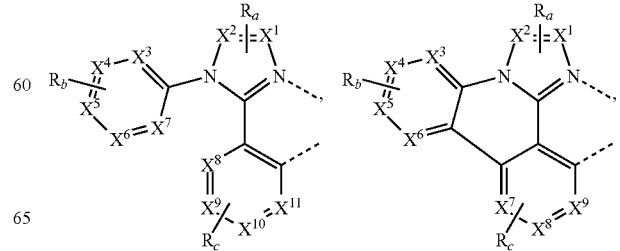

-continued

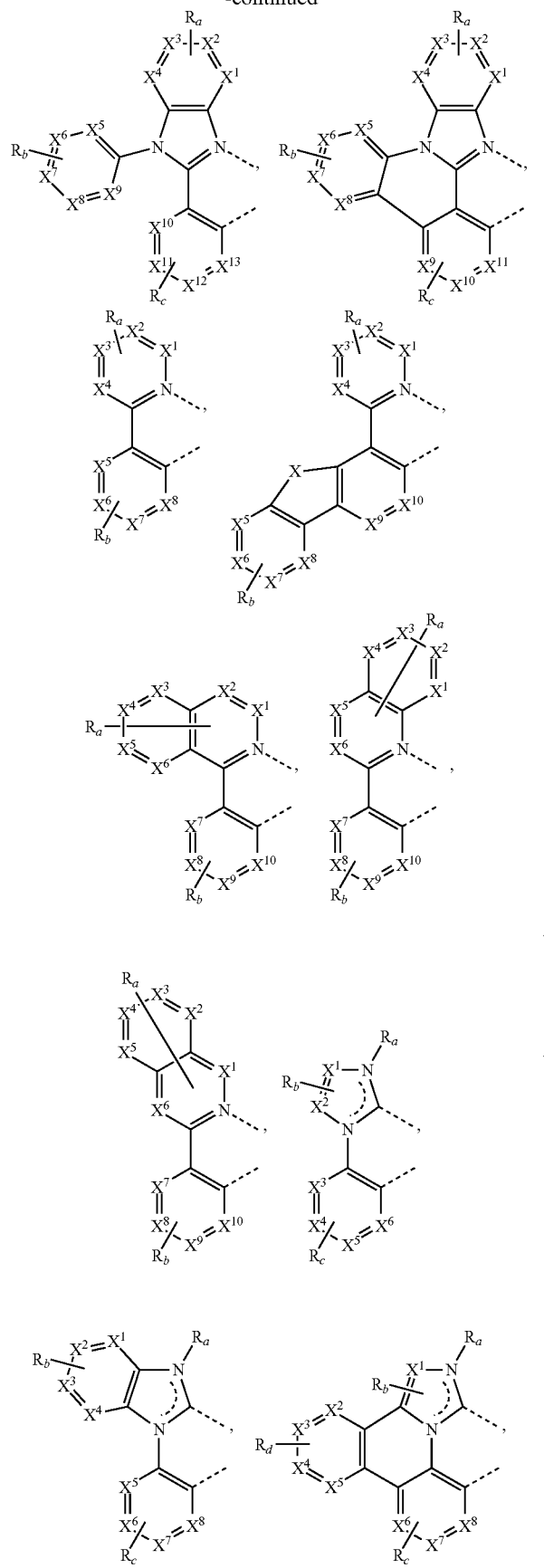

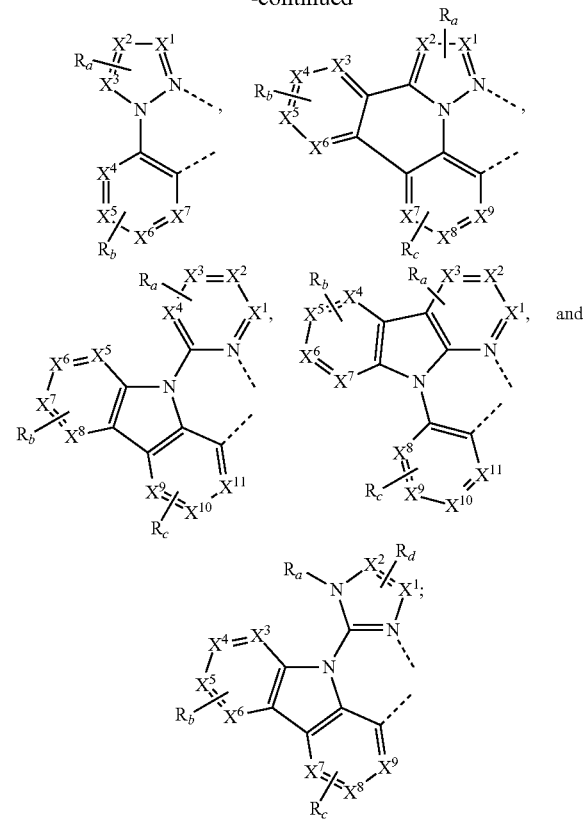

wherein each $X^1$ to $X^{13}$ are independently selected from the group consisting of carbon and nitrogen;

wherein X is selected from the group consisting of BR', NR', PR', O, S, Se, C=O, S=O, SO$_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substituents of $R_a$, $R_b$, $R_c$, and $R_d$ are optionally fused or joined to form a ring or form a multidentate ligand.

In one embodiment, $L_B$ is selected from the group consisting of:

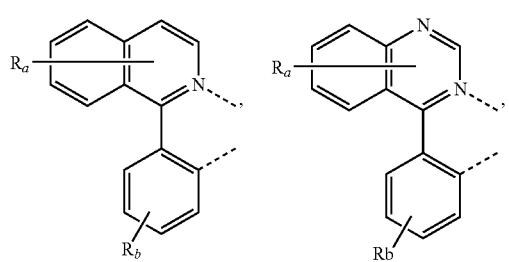

-continued
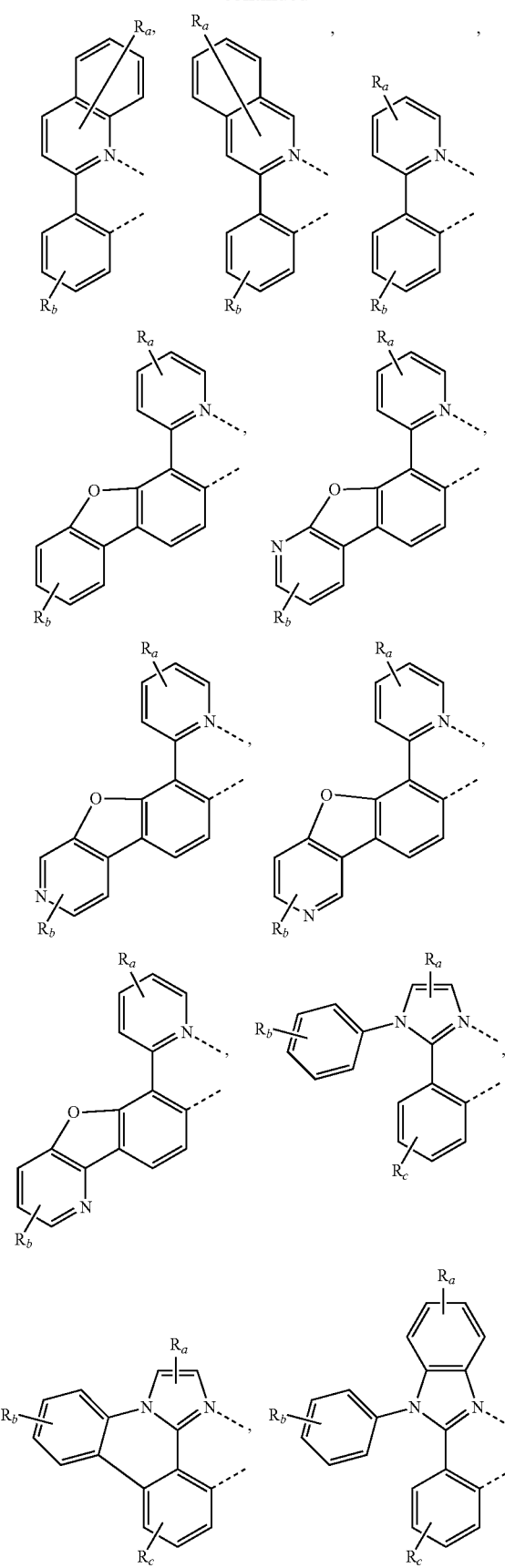
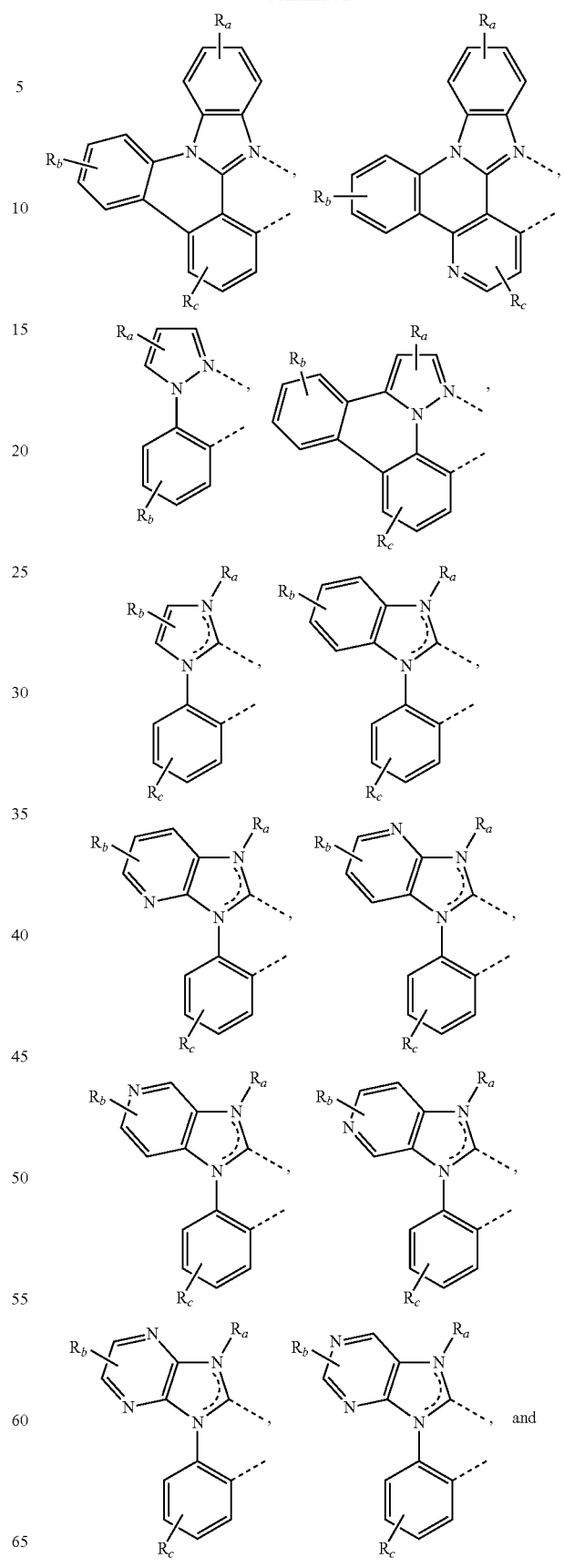

-continued
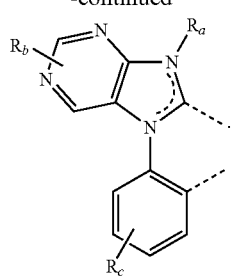
In another embodiment, $L_B$ is selected from the group consisting of:
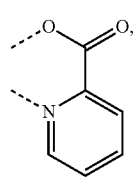 $L_1$
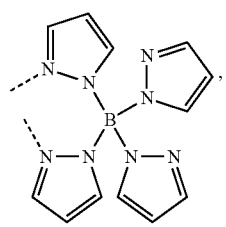 $L_2$
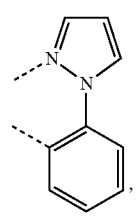 $L_3$
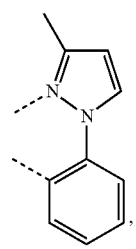 $L_4$
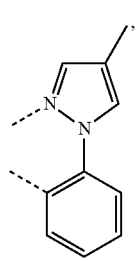 $L_5$
-continued
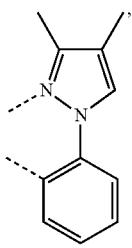 $L_6$
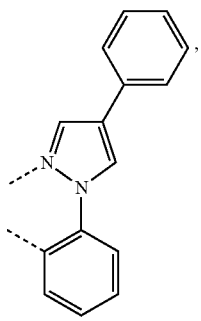 $L_7$
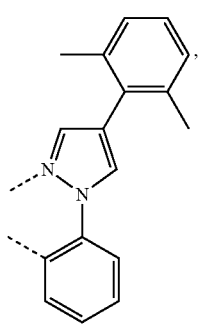 $L_8$
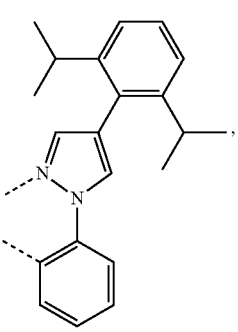 $L_9$
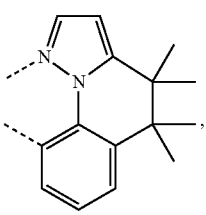 $L_{10}$ -continued
L₁₁
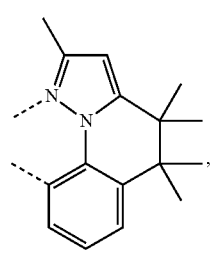
L₁₂
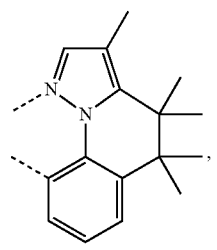
L₁₃
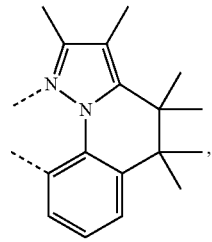
L₁₄
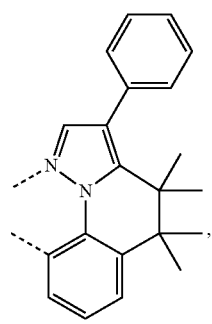
L₁₅
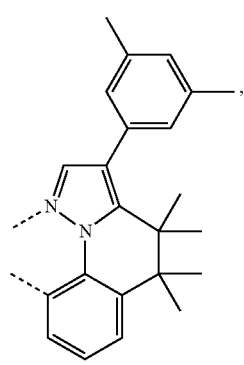
L₁₆
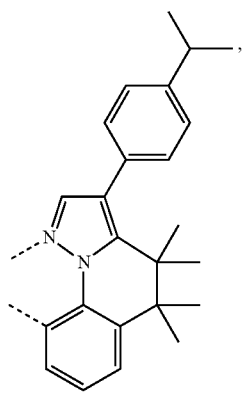
L₁₇
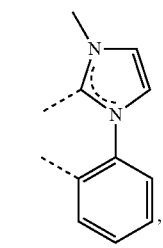
L₁₈
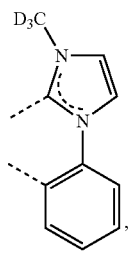
L₁₉
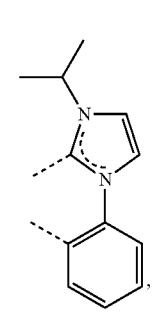
L₂₀
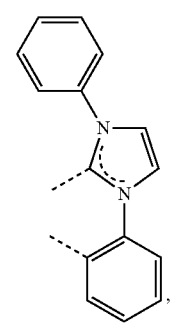

-continued
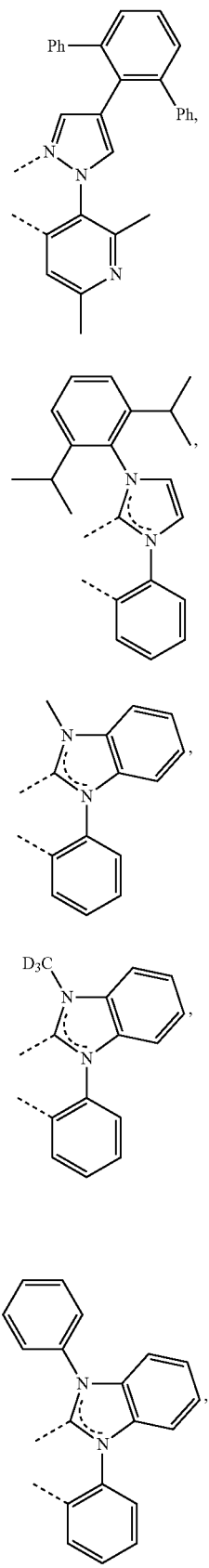
L21
L22
L23
L24
L25
-continued
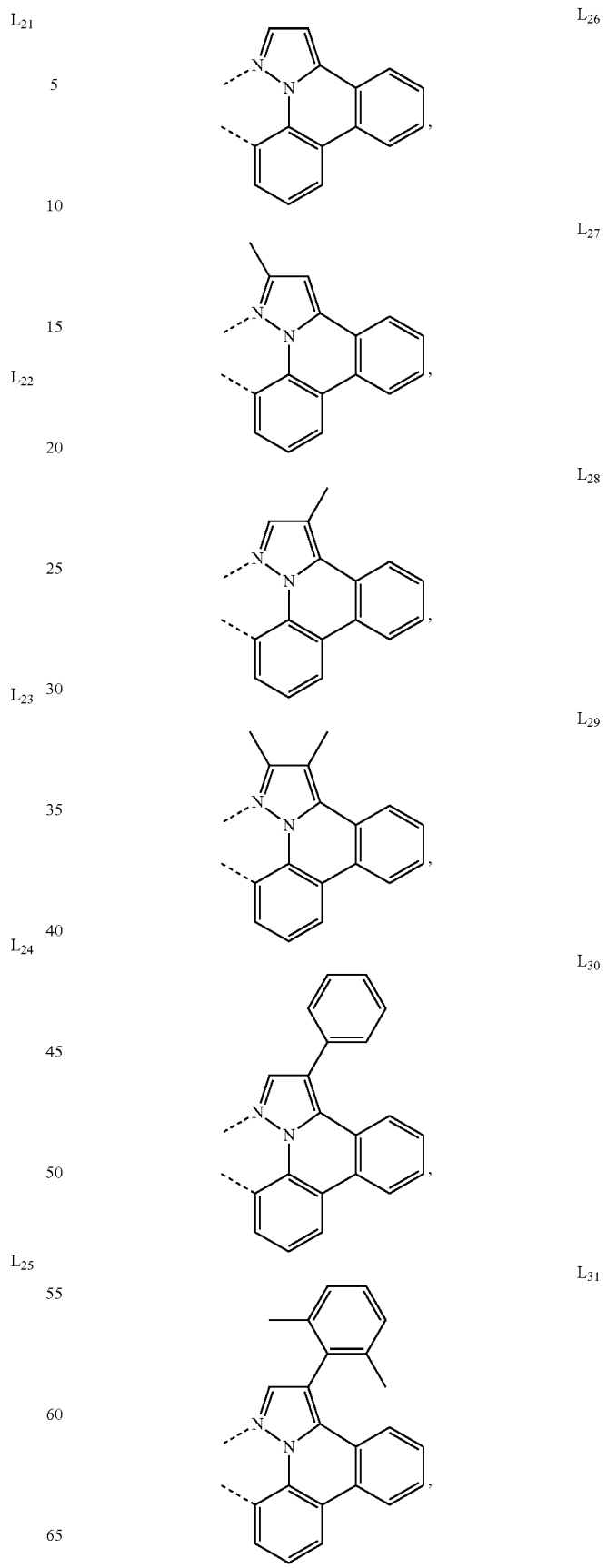
L26
L27
L28
L29
L30
L31

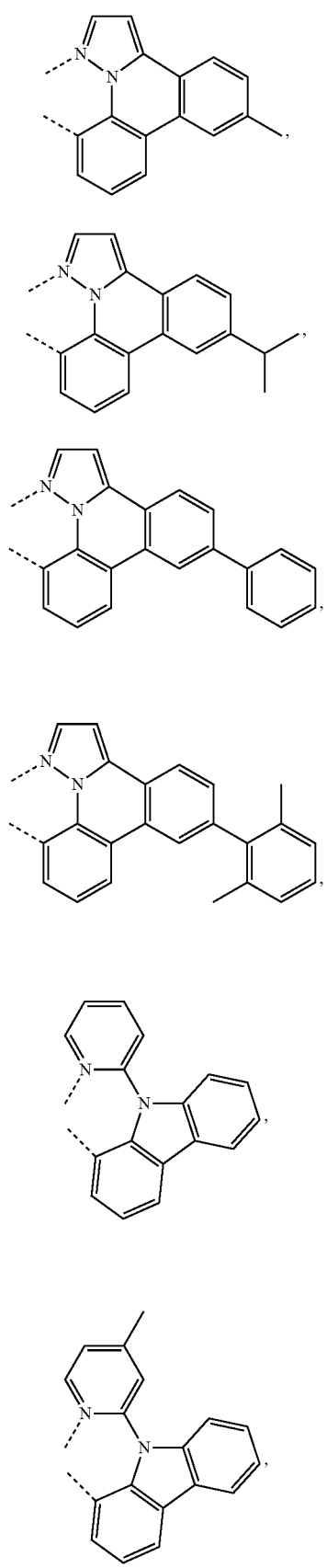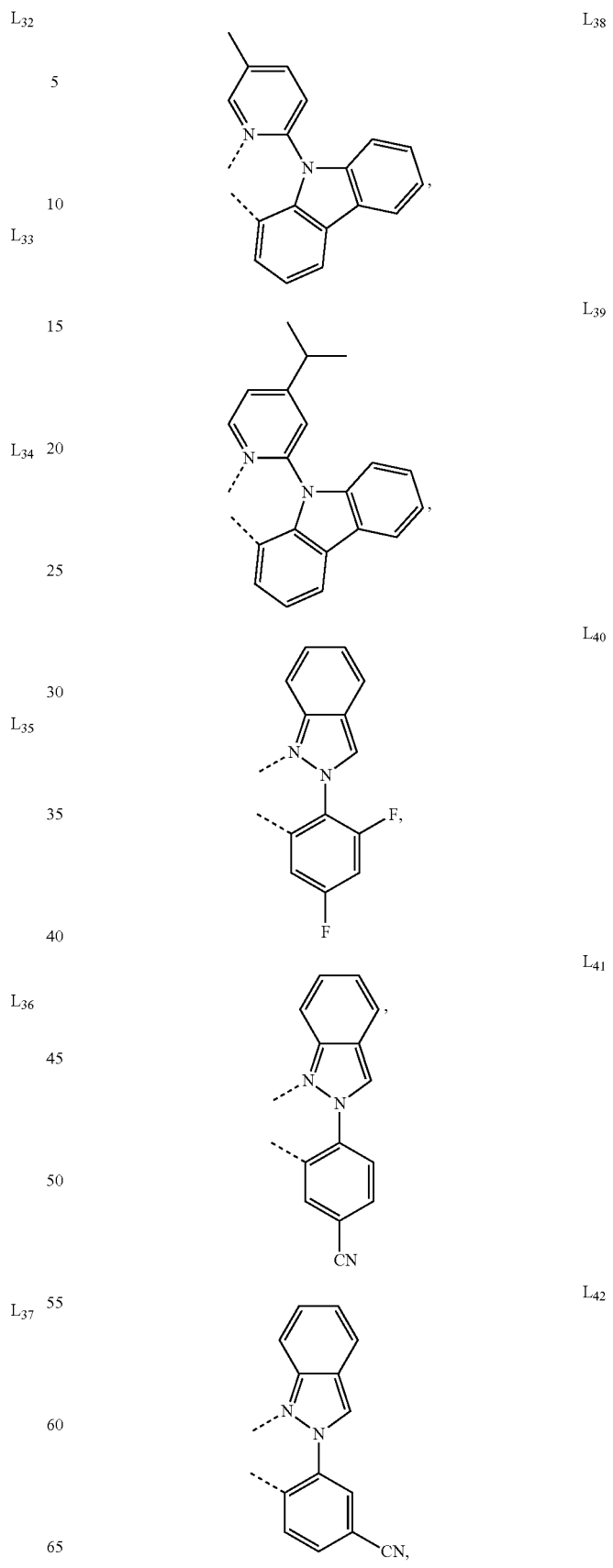

-continued
L43 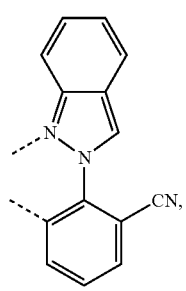
L44 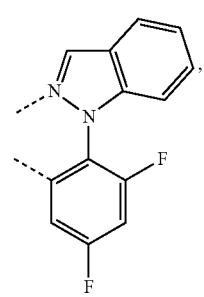
L45 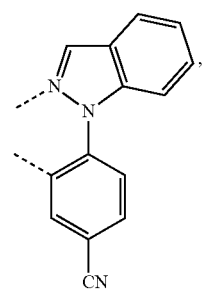
L46 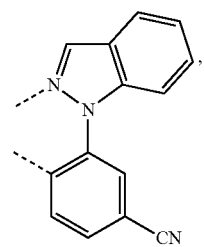
L47 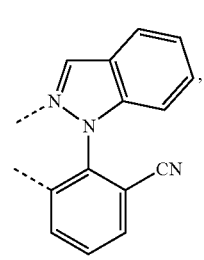
L48 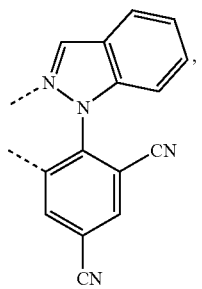
L49 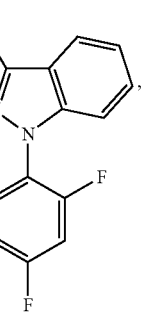
L50 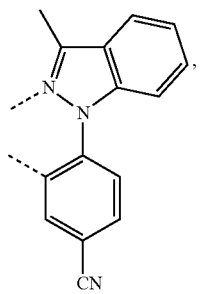
L51 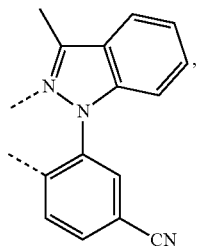
L52 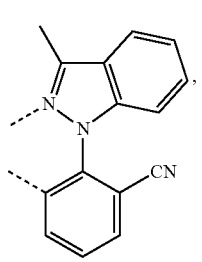

L53 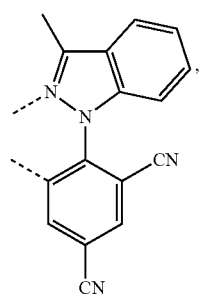
L54 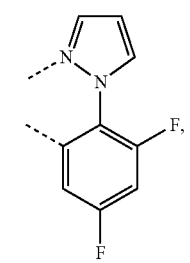
L55 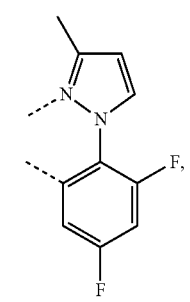
L56 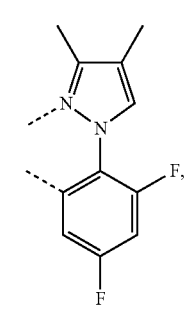
L57 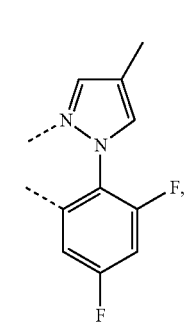
L58 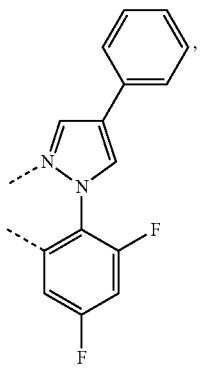
L59 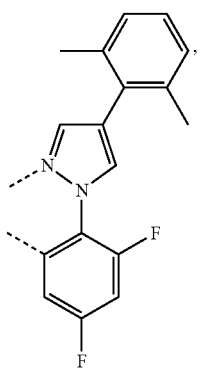
L60 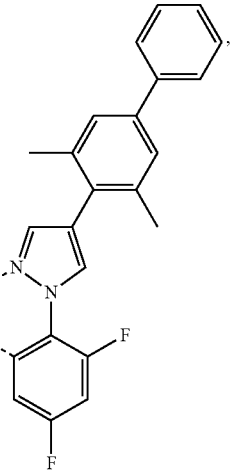
L61 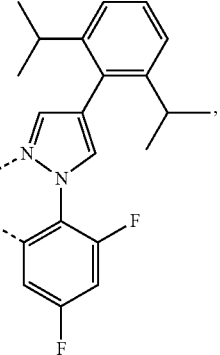

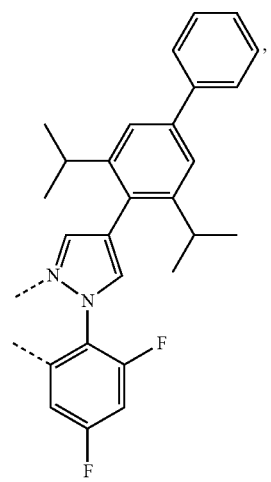 L₆₂
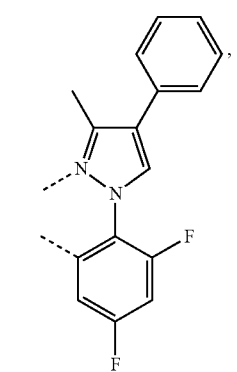 L₆₃
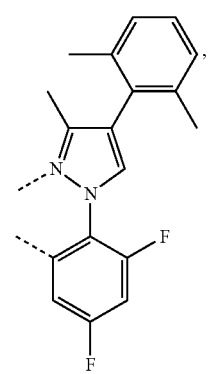 L₆₄
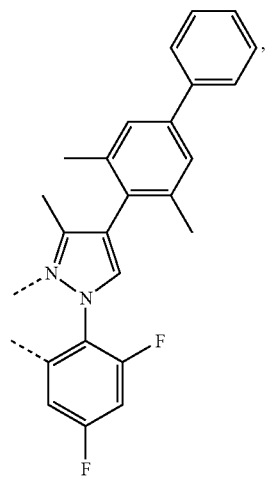 L₆₅
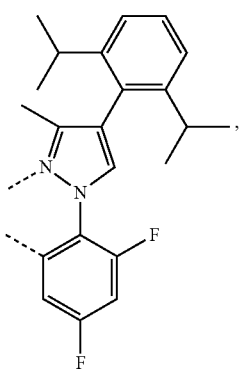 L₆₆
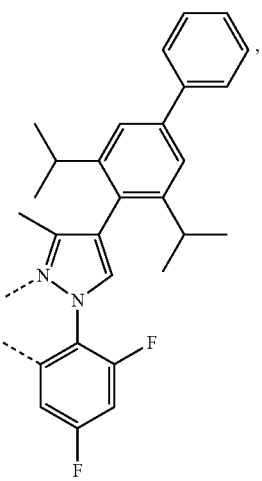 L₆₇
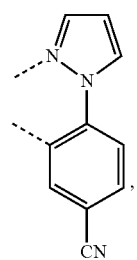 L₆₈

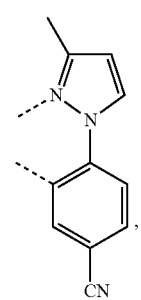 L69
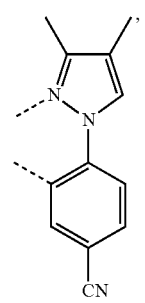 L70
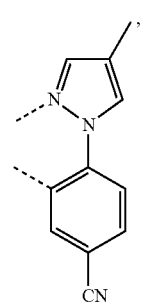 L71
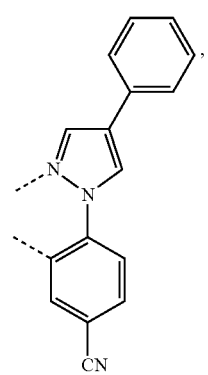 L72
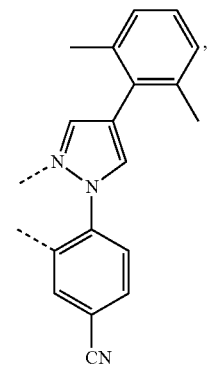 L73
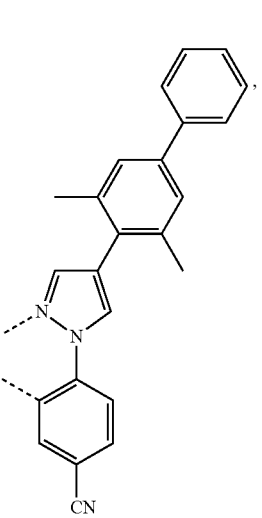 L74
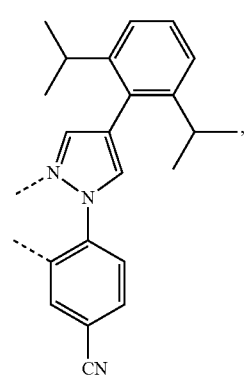 L75

-continued
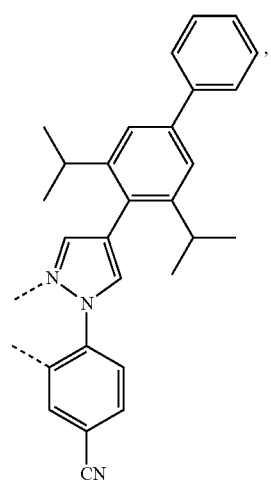
L76
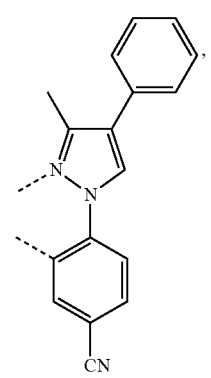
L77
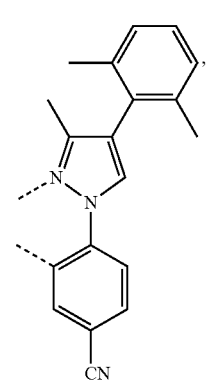
L78
-continued
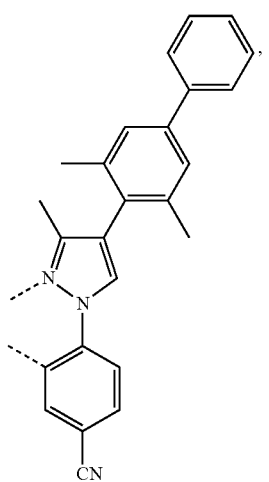
L79
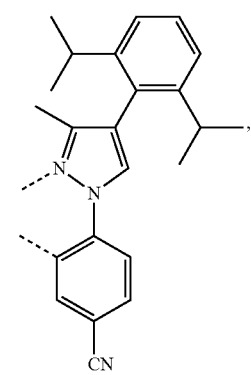
L80
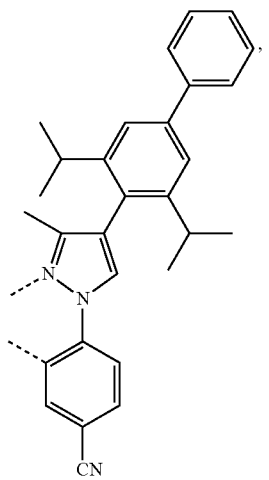
L81
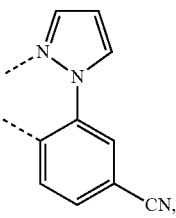
L82

L83 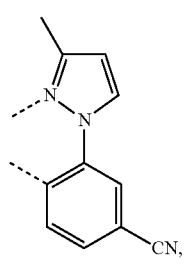
L84 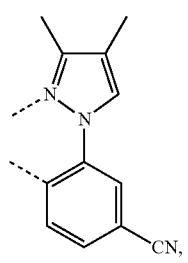
L85 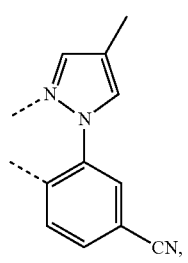
L86 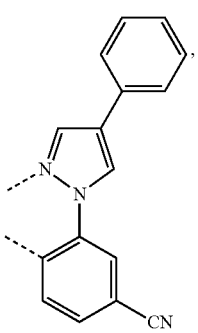
L87 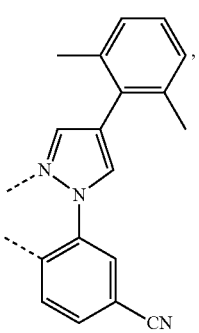
L88 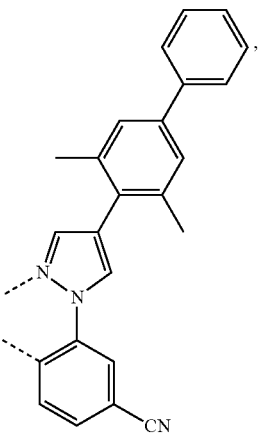
L89 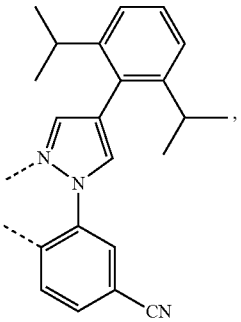
L90 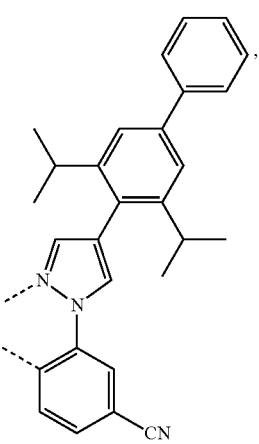
L91 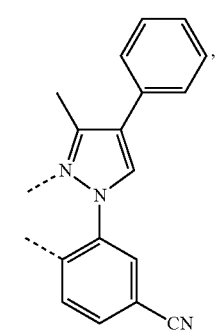

-continued
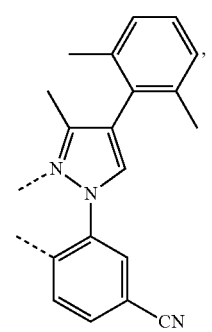 L₉₂
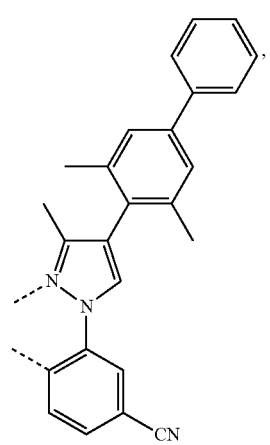
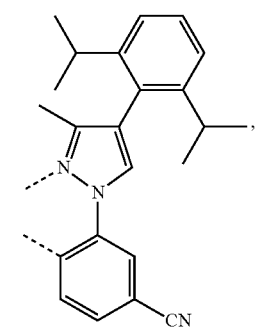 L₉₄
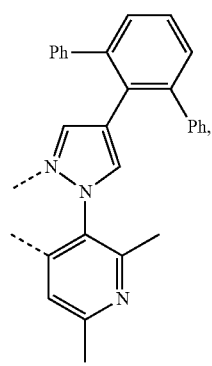 L₉₅
-continued
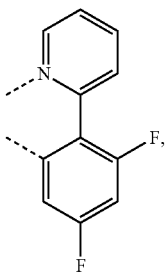 L₉₆
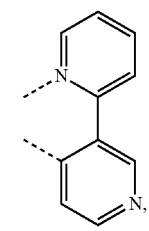 L₉₇
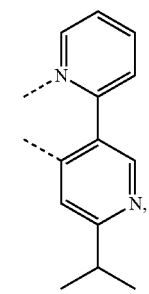 L₉₈
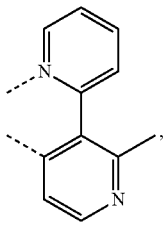 L₉₉
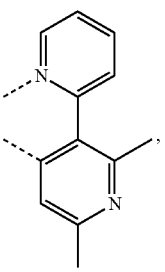 L₁₀₀
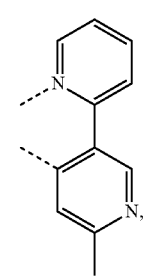 L₁₀₁

-continued
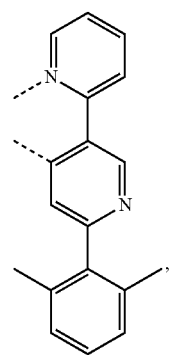 L102
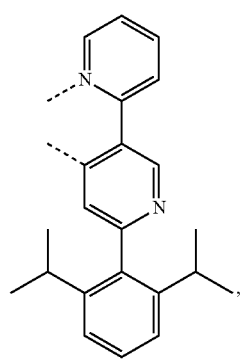 L103
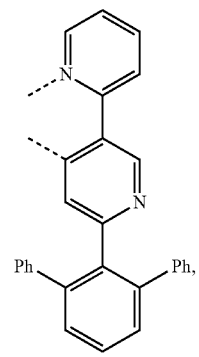 L104
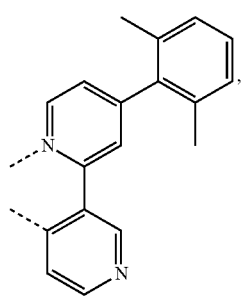 L105
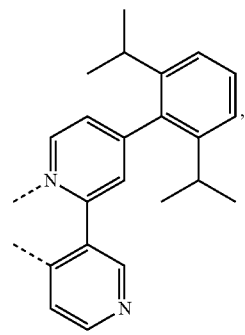 L106
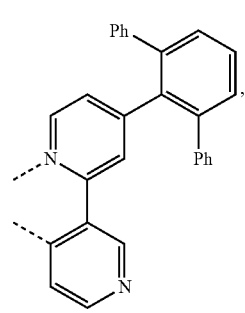 L107
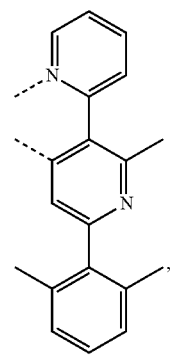 L108
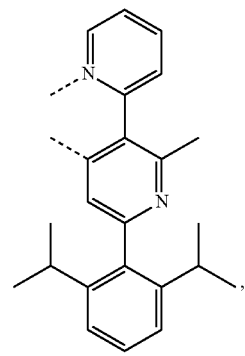 L109

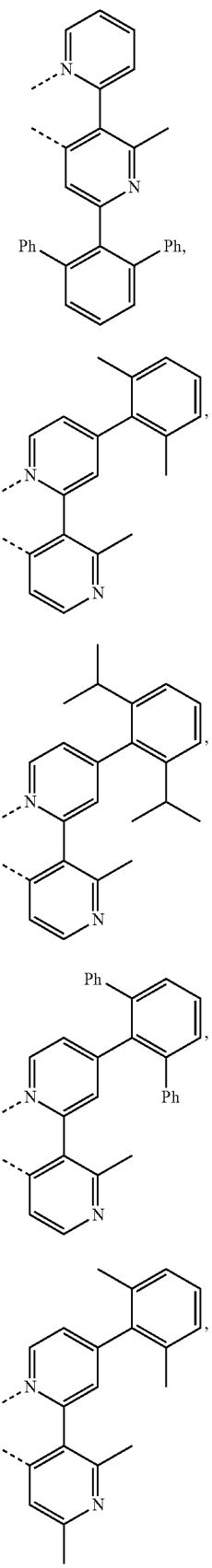
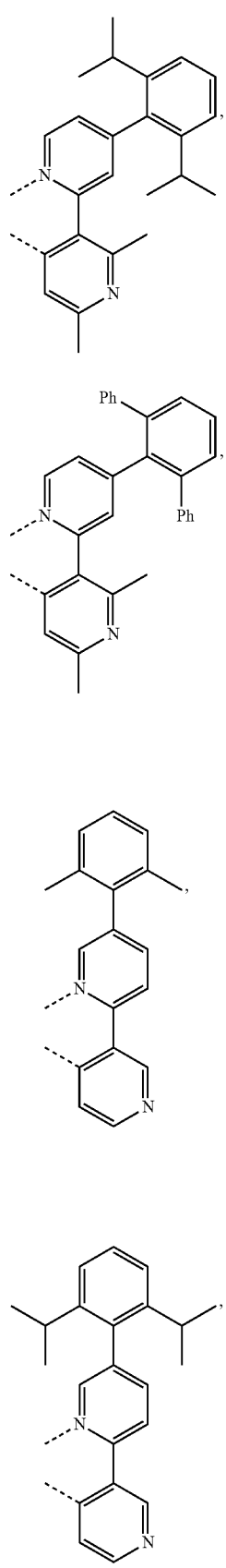

L119 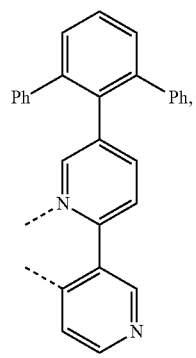
L120 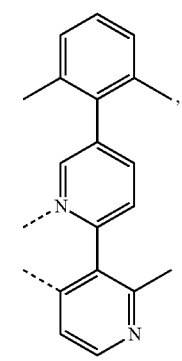
L121 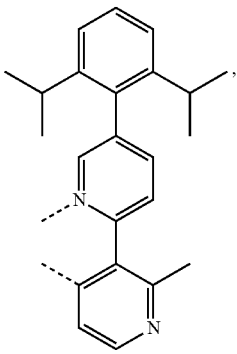
L122 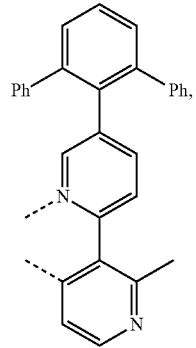
L123 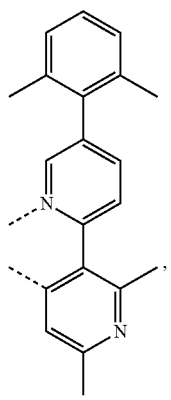
L124 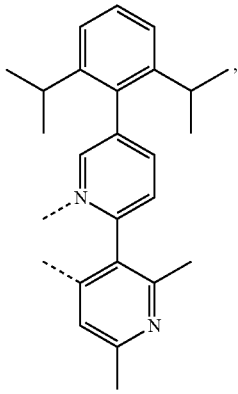
L125 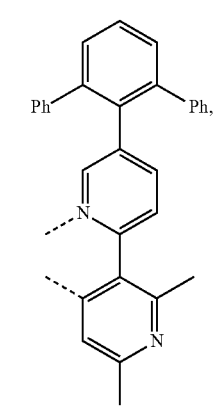
L126 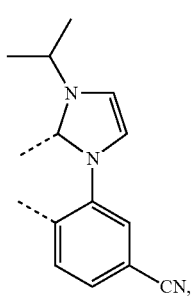

-continued
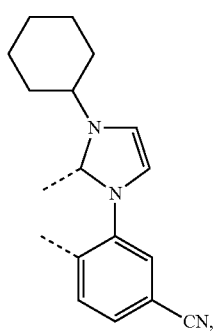 L127
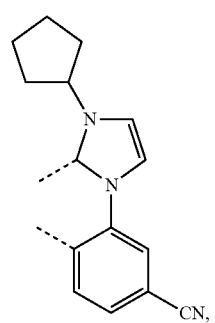 L128
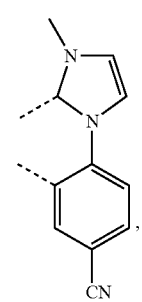 L129
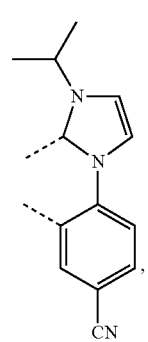 L130
-continued
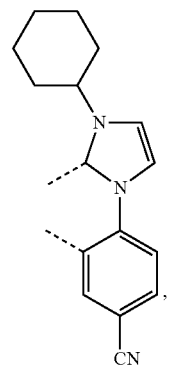 L131
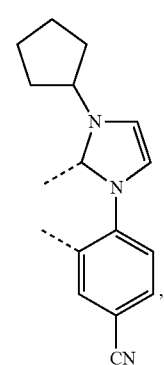 L132
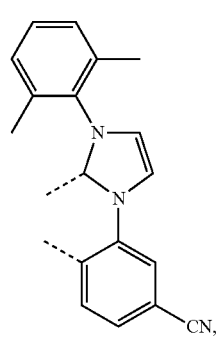 L133
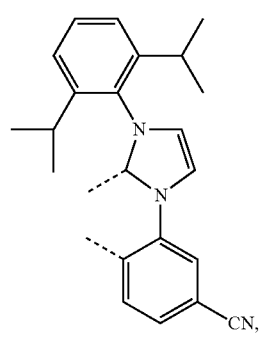 L134

| | |
|---|---|
| 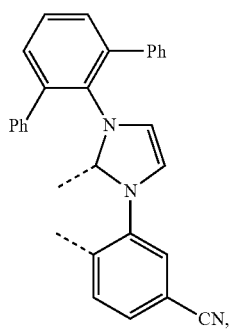 L135 | 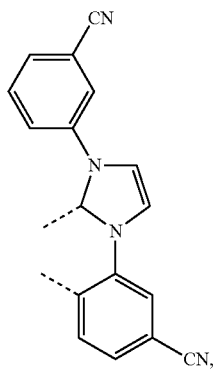 L139 |
| 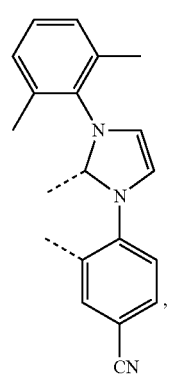 L136 | 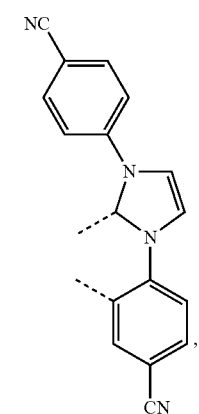 L140 |
| 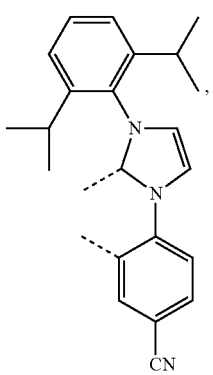 L137 | 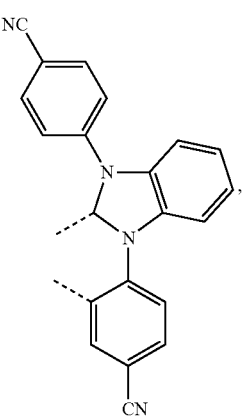 L141 |
| 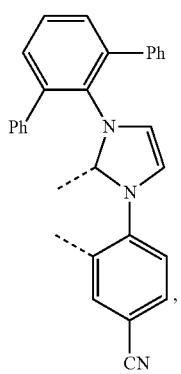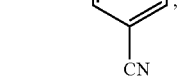 L138 | 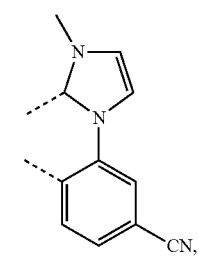 L142 |

-continued
L143
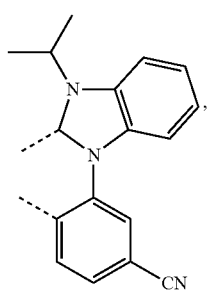
L144
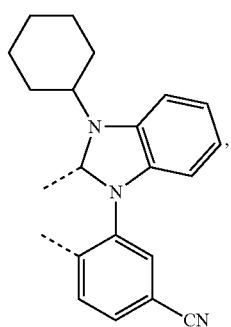
L145
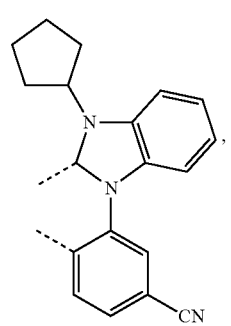
L146
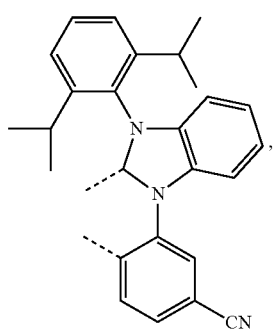
L147
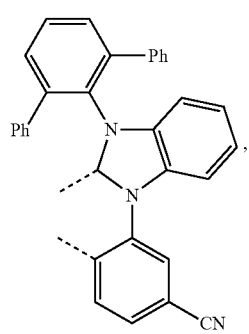
-continued
L148
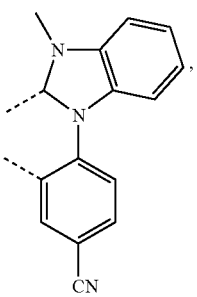
L149
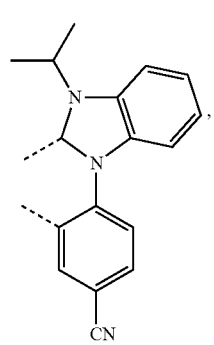
L150
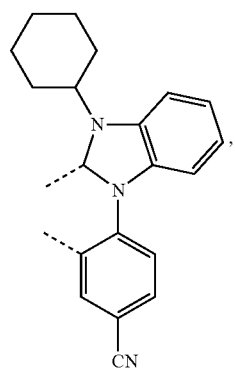
L151
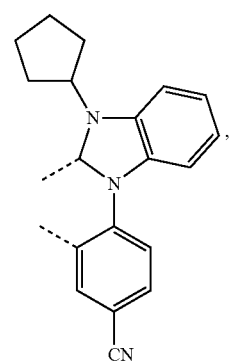

-continued
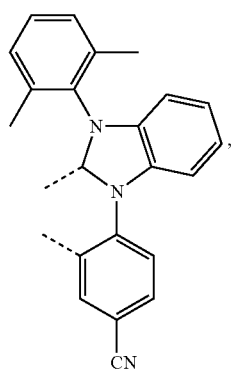
L152
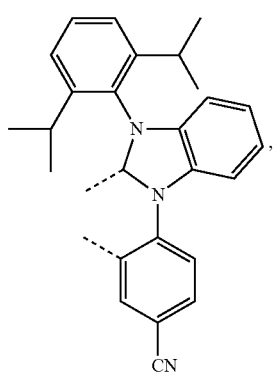
L153
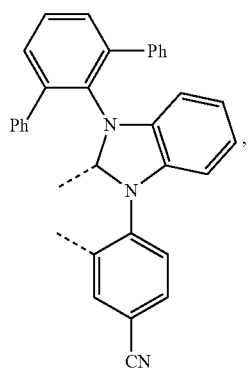
L154
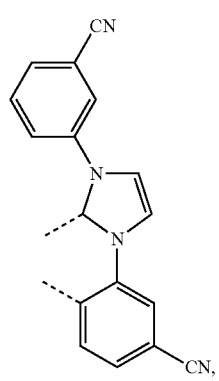
L155
-continued
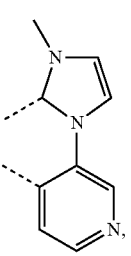
L156
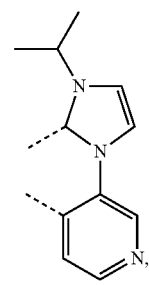
L157
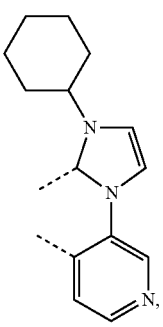
L158
L159
L160

-continued
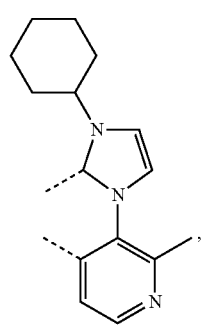
L161
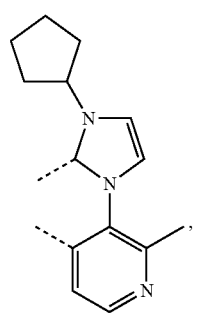
L162
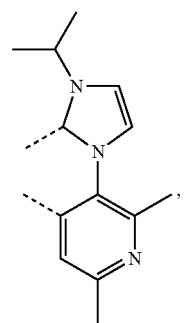
L163
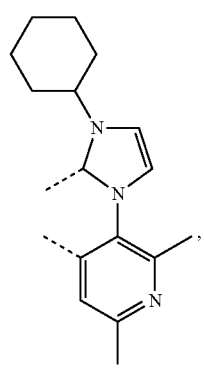
L164
-continued
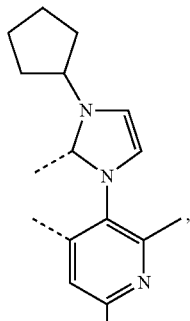
L165
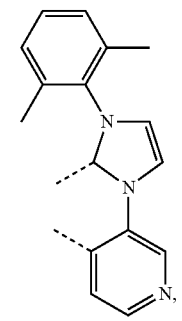
L166
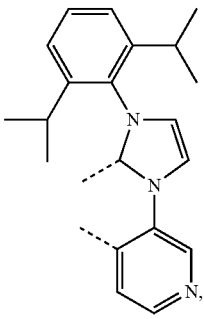
L167
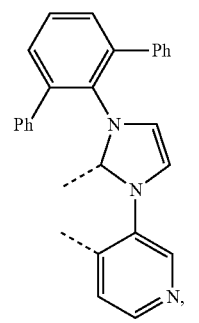
L168
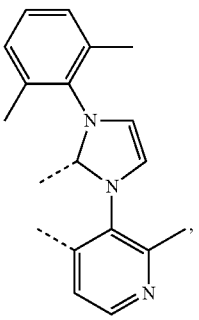
L169

-continued
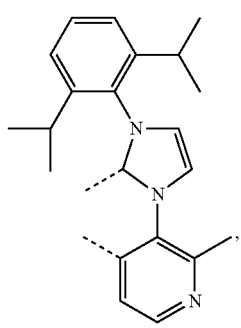 L170
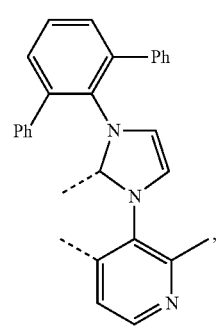 L171
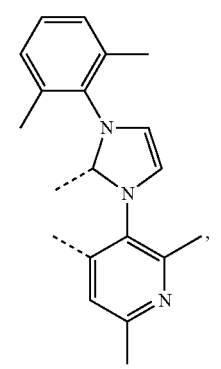 L172
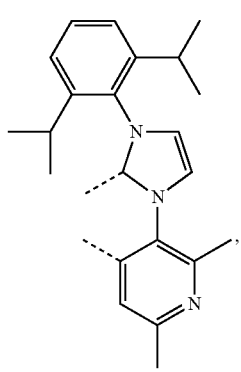 L173
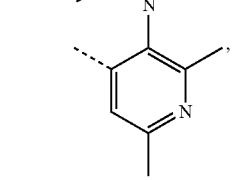
-continued
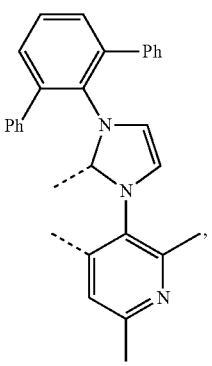 L174
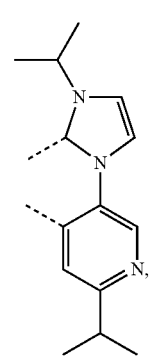 L175
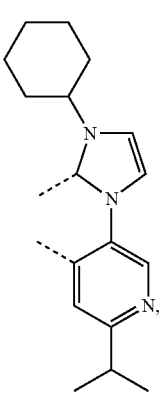 L176
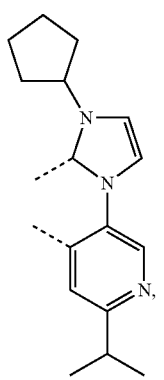 L177

97
-continued
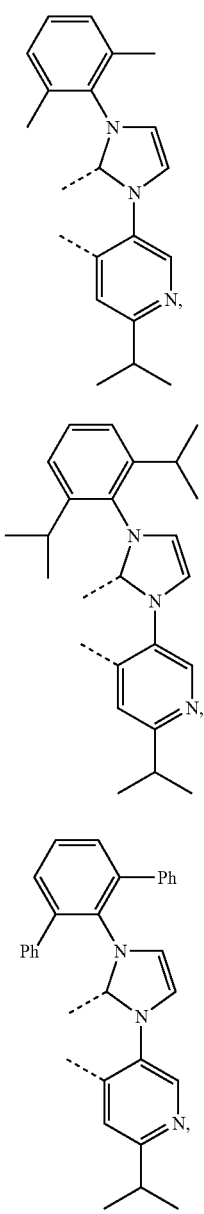
L₁₇₈
L₁₇₉
L₁₈₀
L₁₈₁
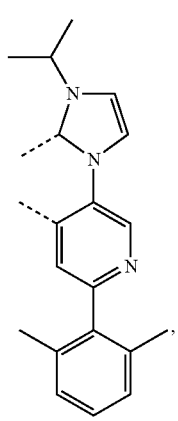
98
-continued
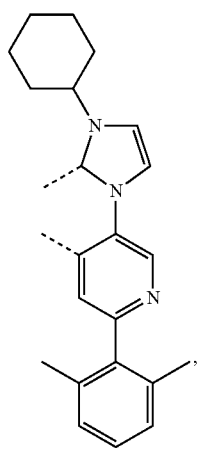
L₁₈₂
L₁₈₃
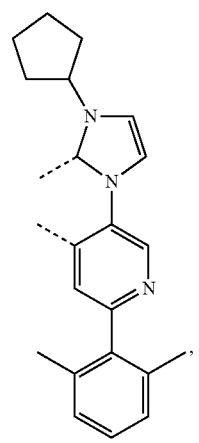
L₁₈₄
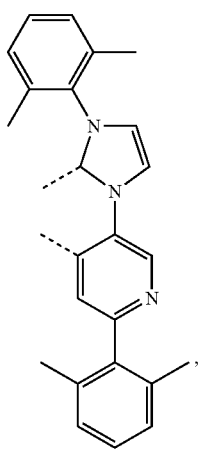

-continued
L185 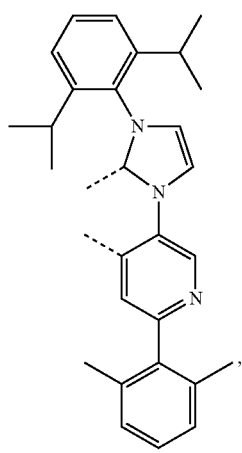
L186 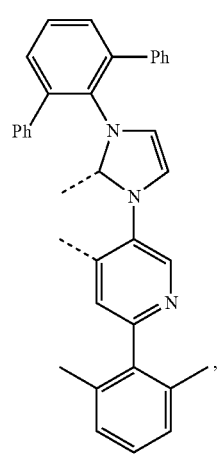
L187 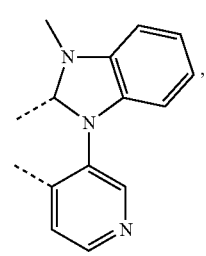
L188 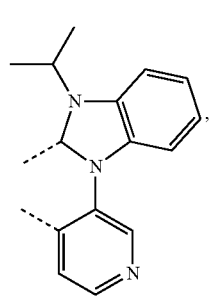
-continued
L189 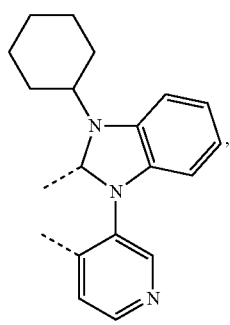
L190 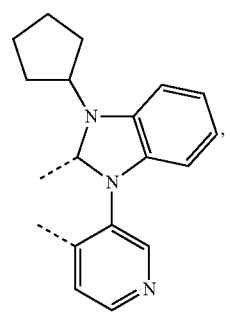
L191 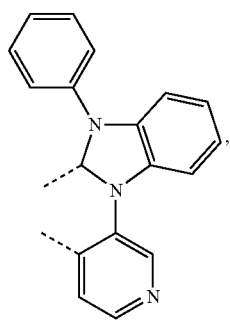
L192 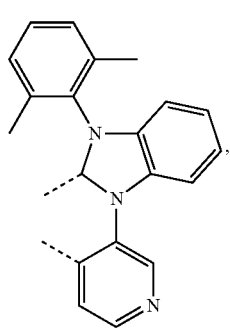
L193 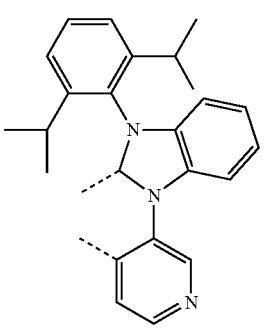

-continued
L194 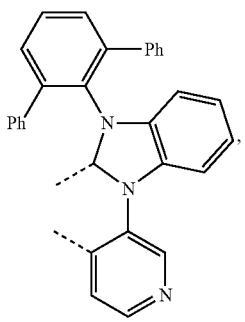
L195 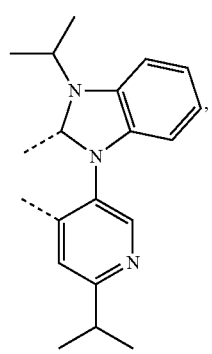
L196 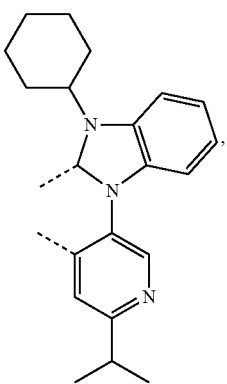
L197 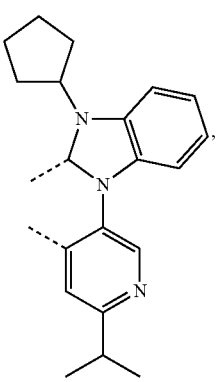
-continued
L198 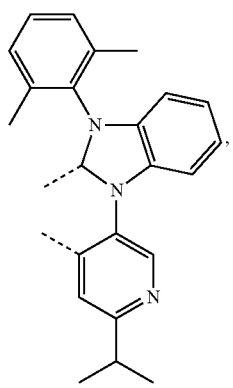
L199 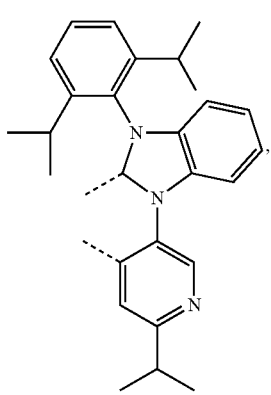
L200 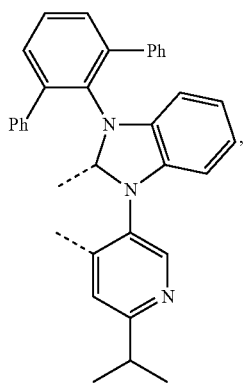
L201 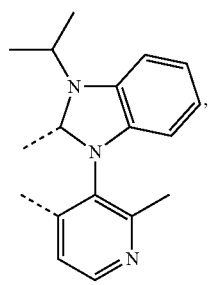

-continued
L$_{202}$
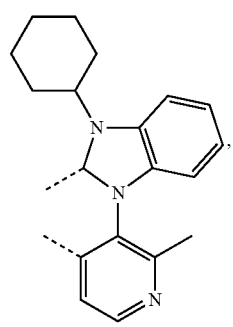
L$_{203}$
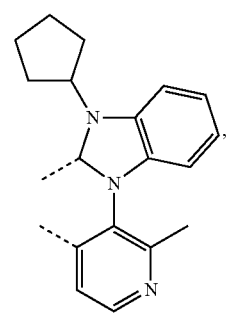
L$_{204}$
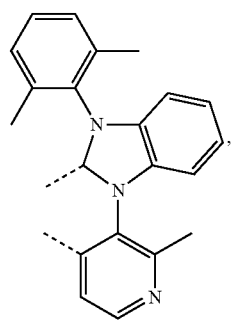
L$_{205}$
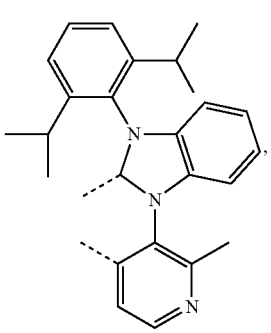
L$_{206}$
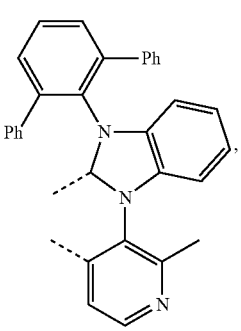
-continued
L$_{207}$
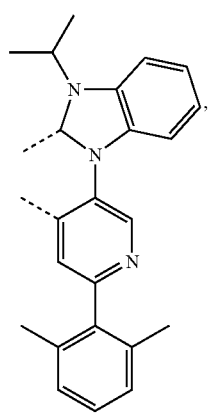
L$_{208}$
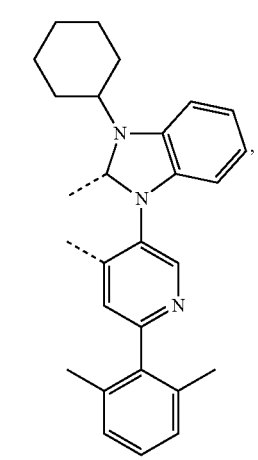
L$_{209}$
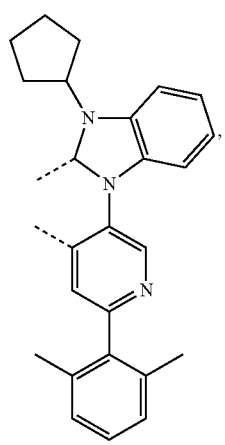

-continued
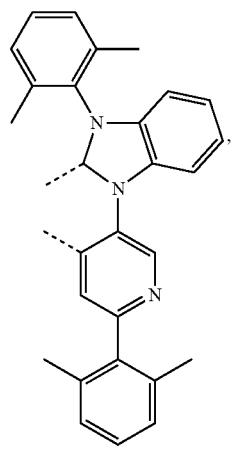
L210
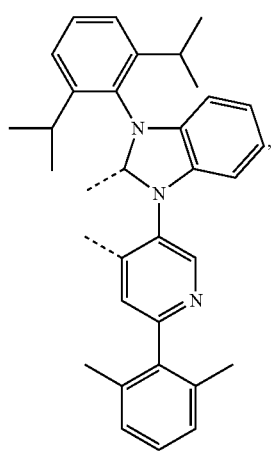
L211
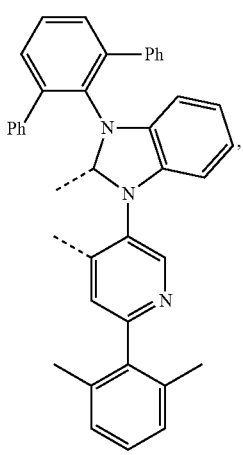
L212
-continued
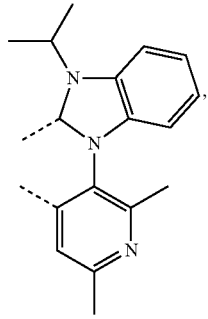
L213
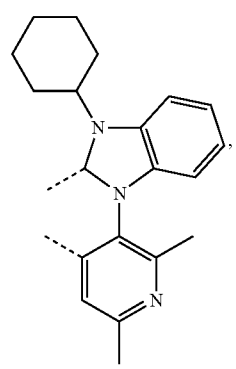
L214
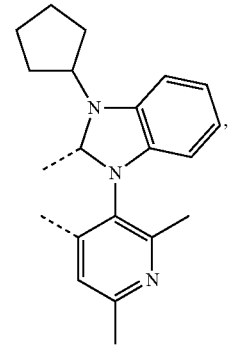
L215
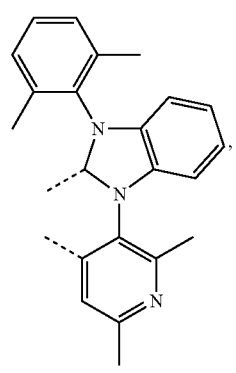
L216

L217 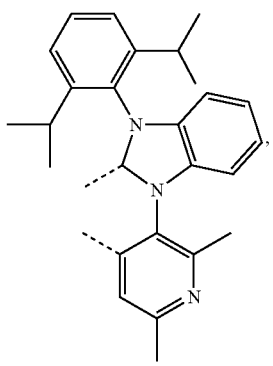
L218 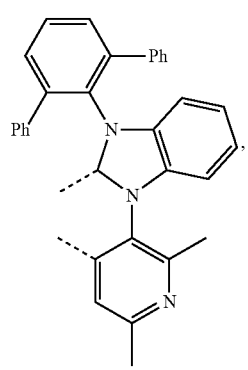
L219 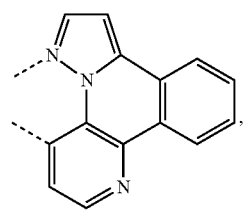
L220 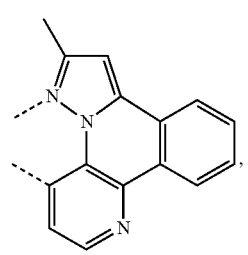
L221 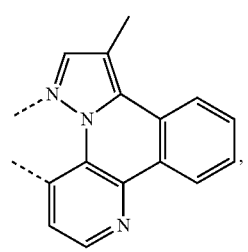
L222 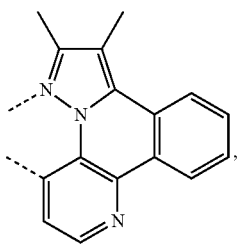
L223 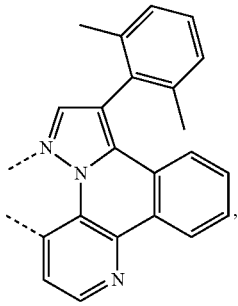
L224 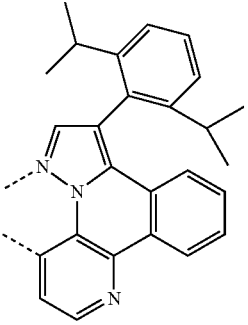
L225 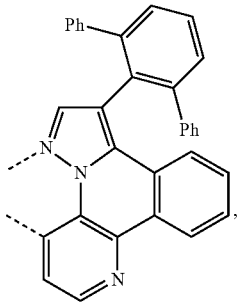
L226 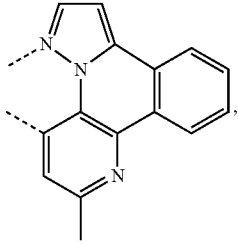

L227 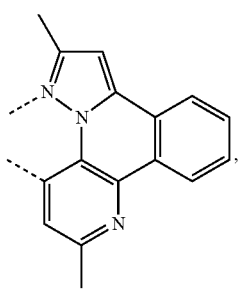
L228 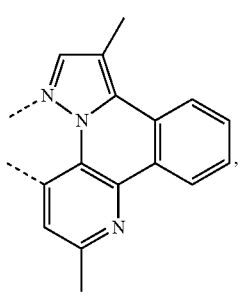
L229 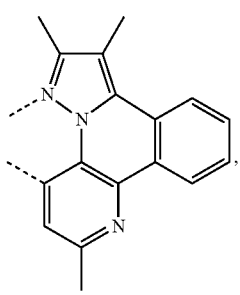
L230 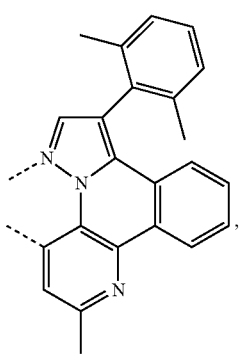
L231 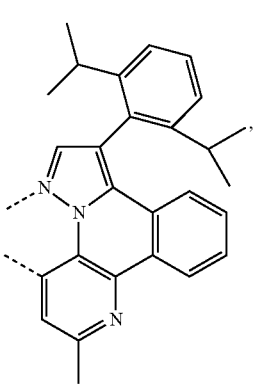
L232 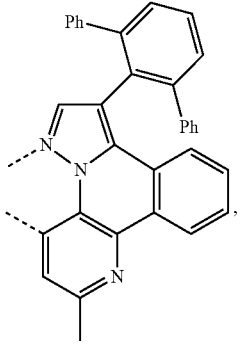
L233 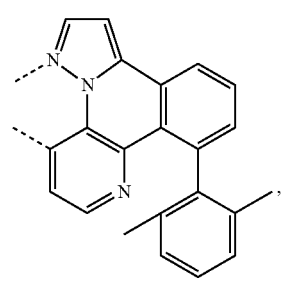
L234 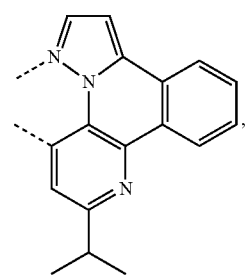
L235 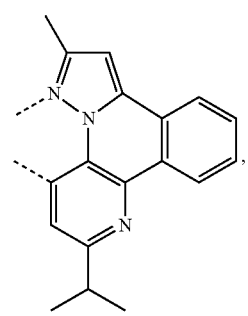
L236 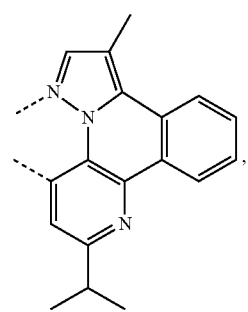

| | |
|---|---|
| 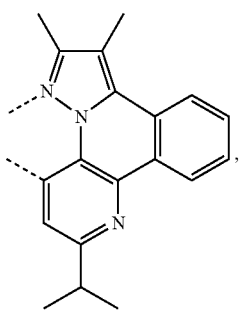 | L237 |
| 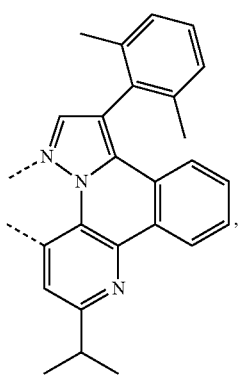 | L238 |
| 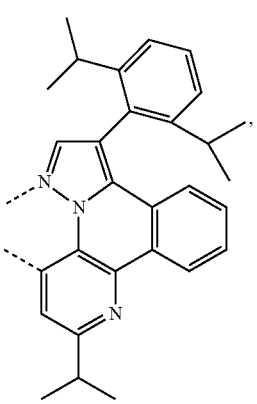 | L239 |
| 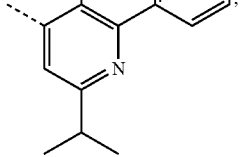 | L240 |
| | |
|---|---|
| 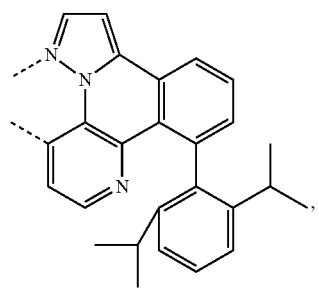 | L241 |
| 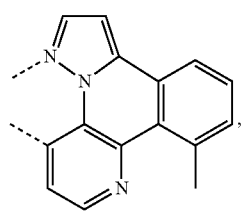 | L242 |
| 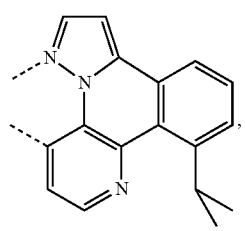 | L243 |
| 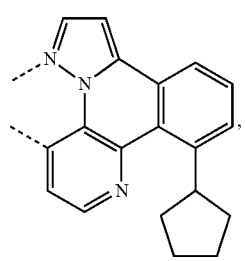 | L244 |
| 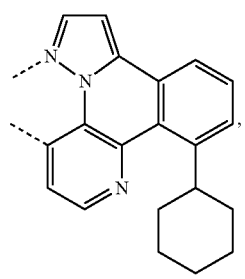 | L245 |
| 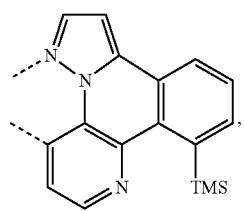 | L246 |

-continued
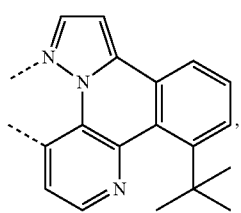
L247
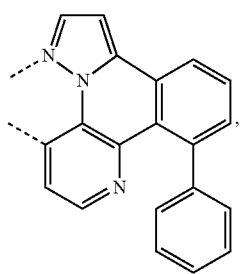
L248
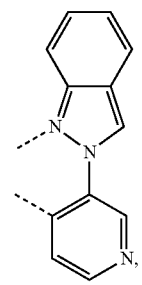
L249
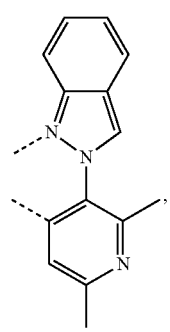
L250
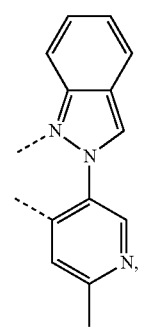
L251
-continued
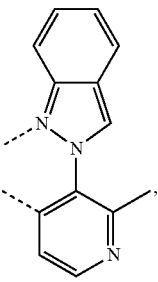
L252
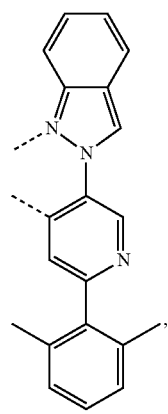
L253
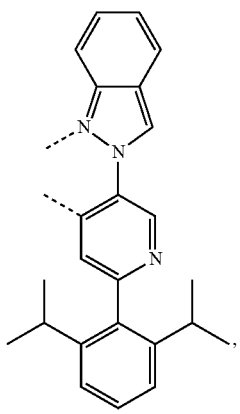
L254
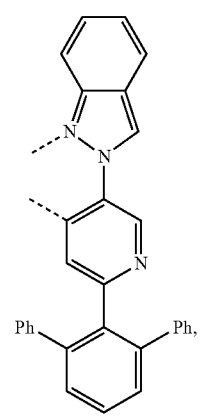
L255

115
-continued
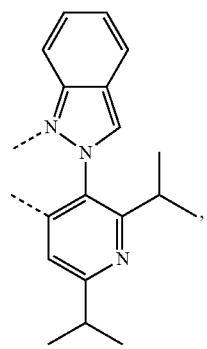
L256
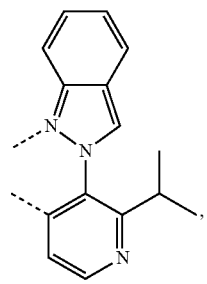
L257
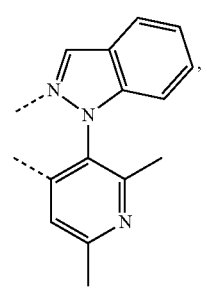
L258
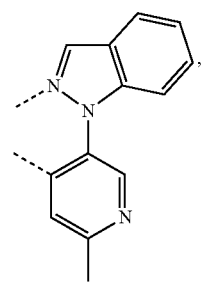
L259
L260
116
-continued
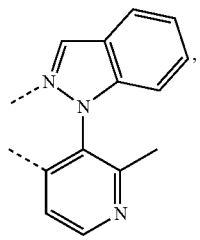
L261
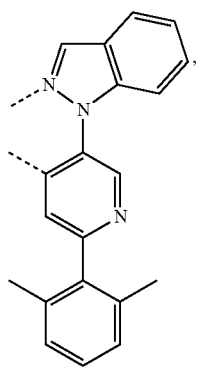
L262
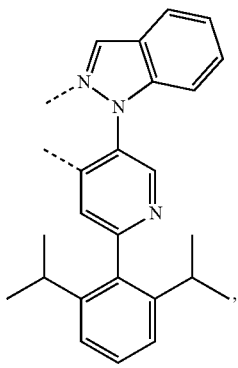
L263
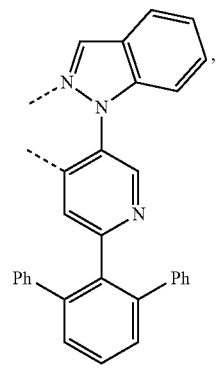
L264

L<sub>265</sub> 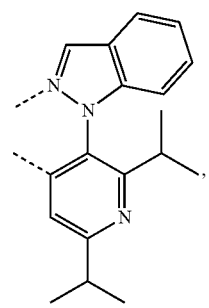
L<sub>266</sub> 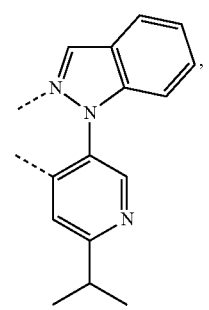
L<sub>267</sub> 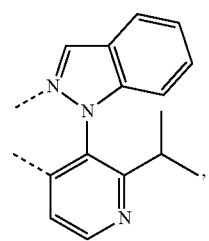
L<sub>268</sub> 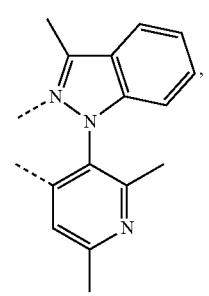
L<sub>269</sub> 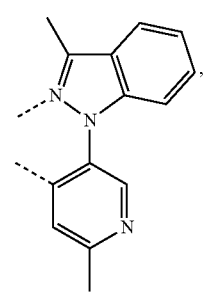
L<sub>270</sub> 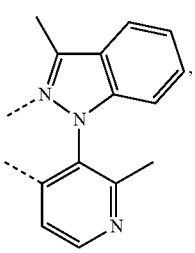
L<sub>271</sub> 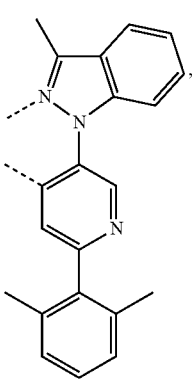
L<sub>272</sub> 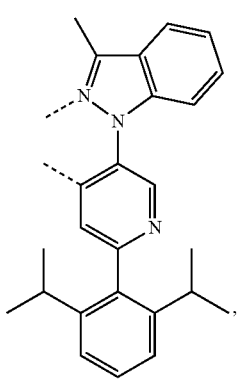
L<sub>273</sub> 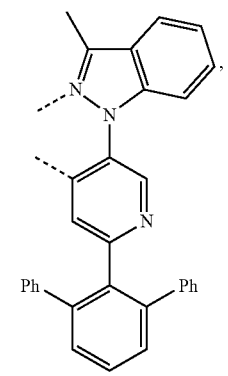

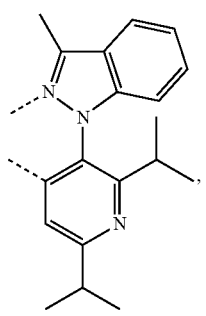
L274

L275
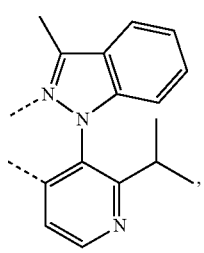
L276
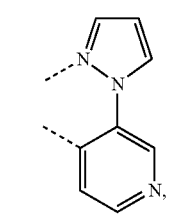
L277
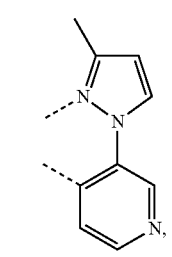
L278
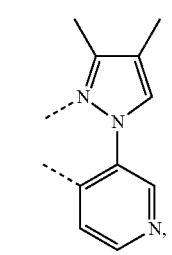
L279
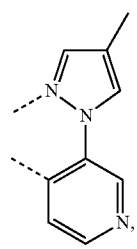
L280
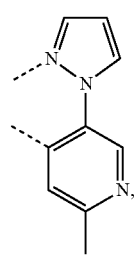
L281
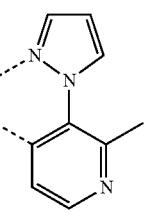
L282
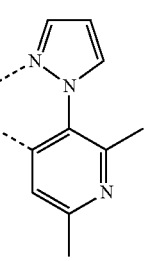
L283
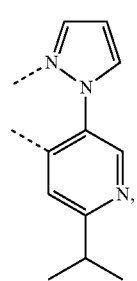
L284
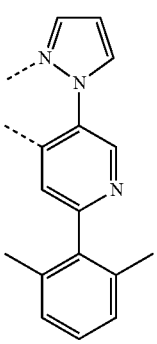
L285

-continued
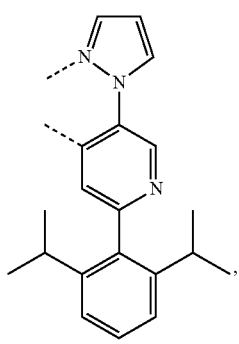  L<sub>286</sub>
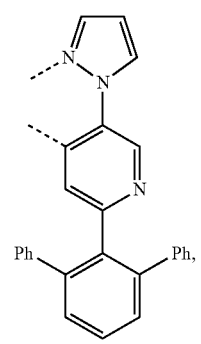  L<sub>287</sub>
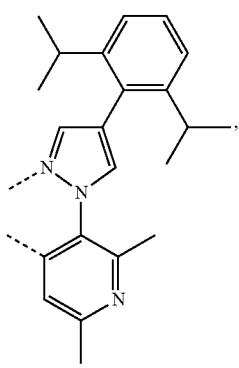  L<sub>288</sub>
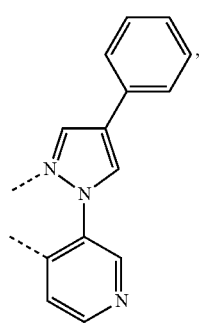  L<sub>289</sub>
-continued
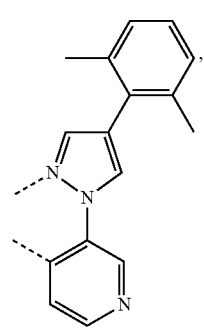  L<sub>290</sub>
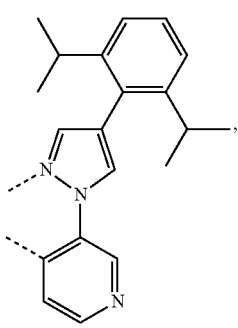  L<sub>291</sub>
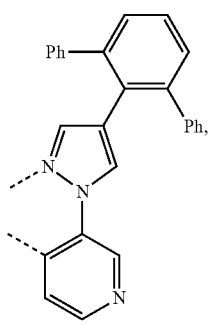  L<sub>292</sub>
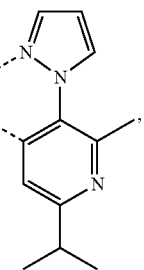  L<sub>293</sub>
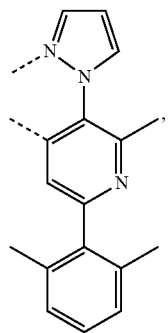  L<sub>294</sub>

L295 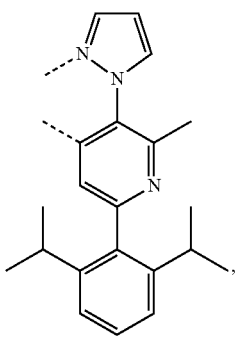

L296 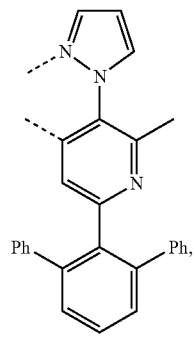

L297 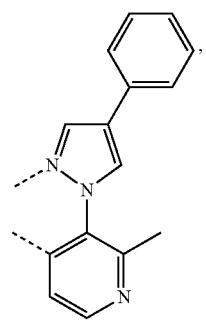

L298 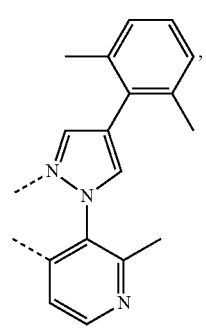

L299 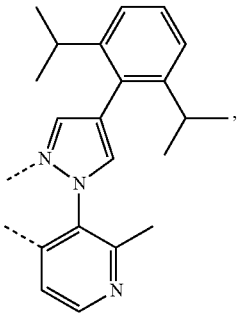

L300 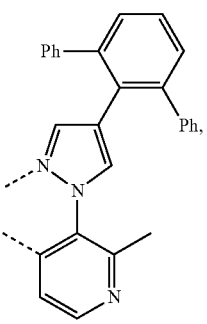

L301 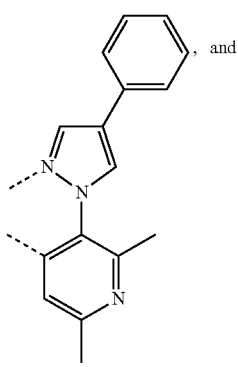, and

L302 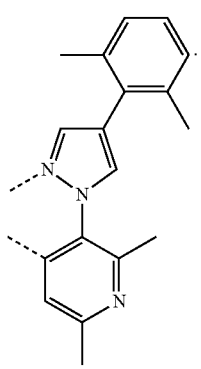

In one aspect, the invention relates to a compound comprising a ligand $L_A$ of Formula I, wherein the compound is Compound Ax having the formula $Ir(L_Ai)_3$, or Compound By having the formula $Ir(L_Ai)(L_j)_2$ or Compound Cz having the formula $Ir(L_Ai)_2(L_j)$;

wherein x=i; i is an integer from 1 to 198;

wherein y=302i+j−302; i is an integer from 1 to 198, and j is an integer from 1 to 302;

wherein z=302i+j−302; i is an integer from 1 to 198, and j is an integer from 1 to 302; and wherein $L_1$ to $L_{302}$ have the following structure:

L1 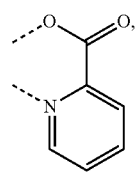

-continued
| | |
|---|---|
| 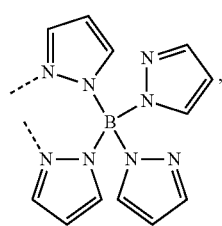 | L₂ |
| 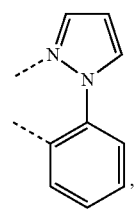 | L₃ |
| 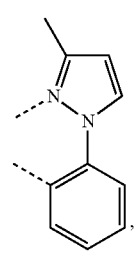 | L₄ |
| 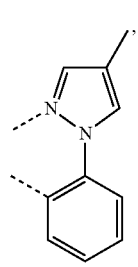 | L₅ |
| 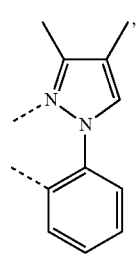 | L₆ |
| 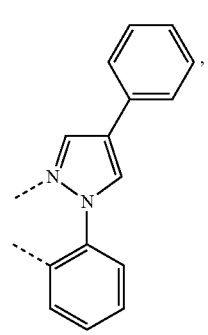 | L₇ |
-continued
| | |
|---|---|
| 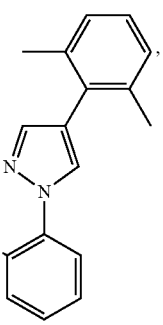 | L₈ |
| 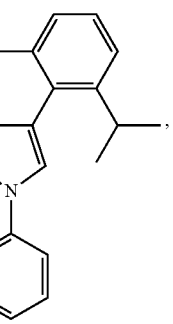 | L₉ |
| 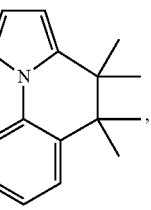 | L₁₀ |
| 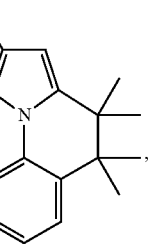 | L₁₁ |
| 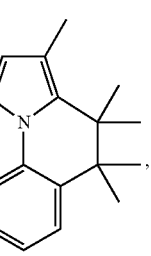 | L₁₂ |
| 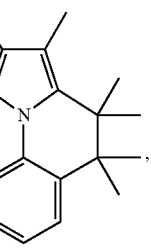 | L₁₃ |

127
-continued
L14
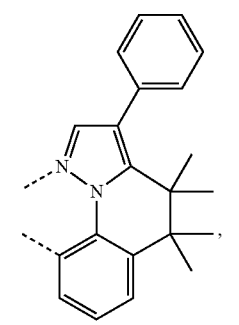
L15
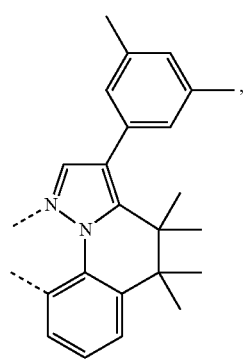
L16
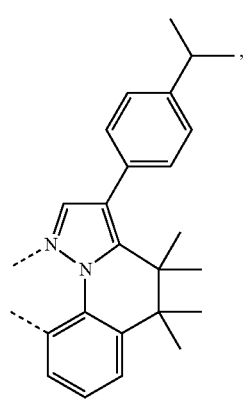
L17
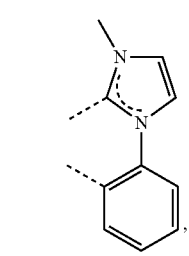
L18
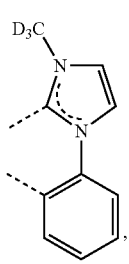
128
-continued
L19
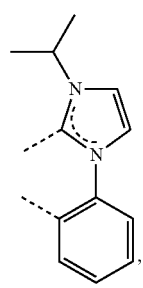
L20
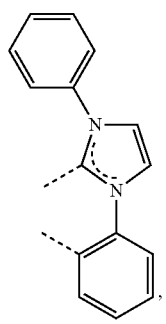
L21
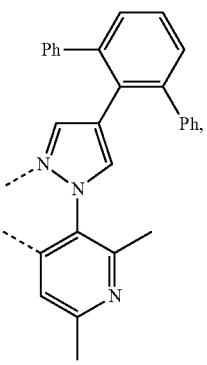
L22
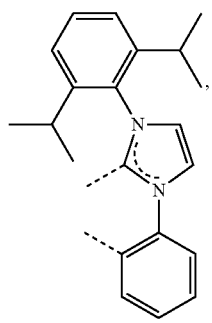
L23
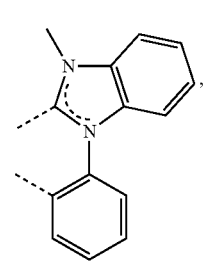

-continued
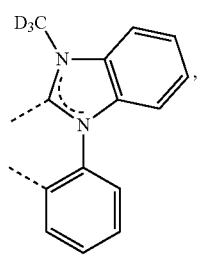,
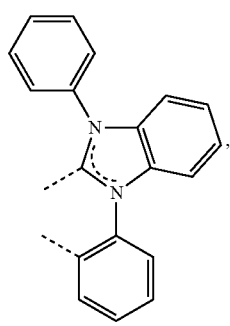,
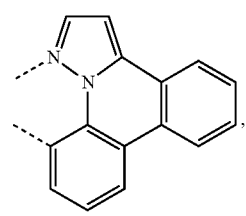,
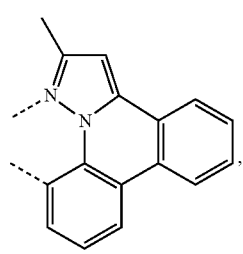,
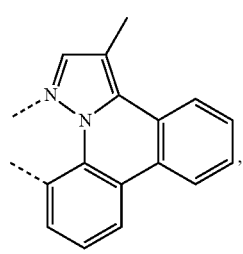,
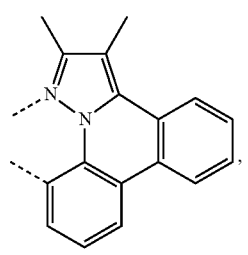,
-continued
L$_{24}$
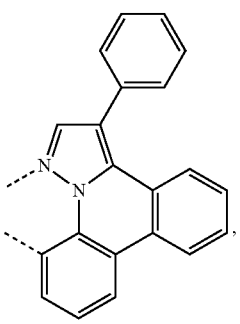,
L$_{25}$
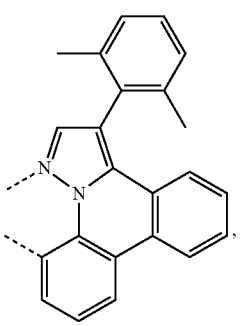,
L$_{26}$
,
L$_{27}$
,
L$_{28}$
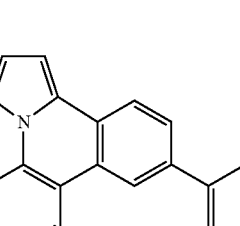,
L$_{29}$
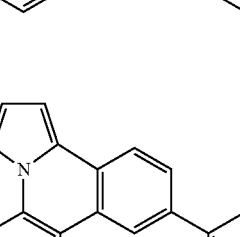,
L$_{30}$
L$_{31}$
L$_{32}$
L$_{33}$
L$_{34}$
L$_{35}$ -continued
| | |
|---|---|
| 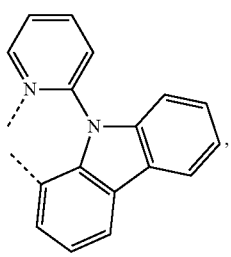 | L36 |
| 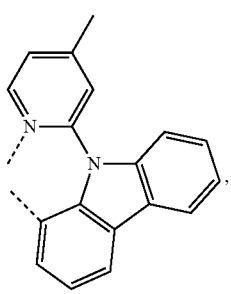 | L37 |
| 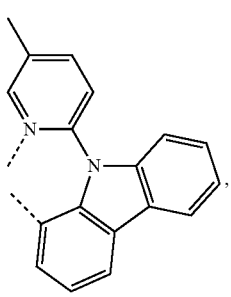 | L38 |
| 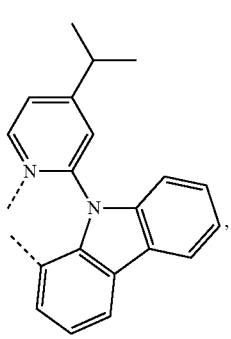 | L39 |
| 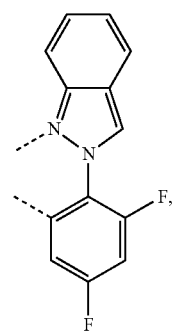 | L40 |
-continued
| | |
|---|---|
| 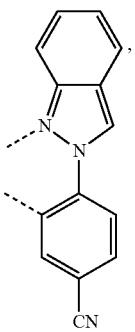 | L41 |
| 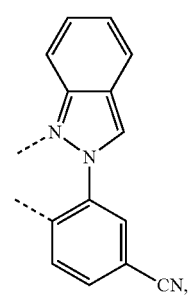 | L42 |
| 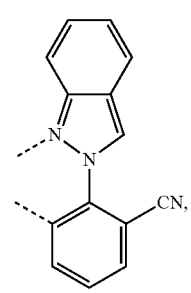 | L43 |
| 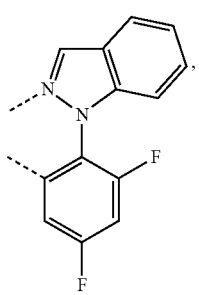 | L44 |
|  | L45 |

-continued
L46 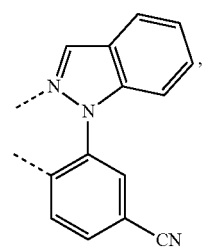
L47 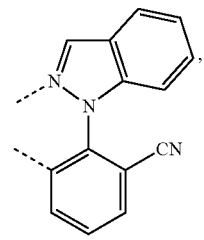
L48 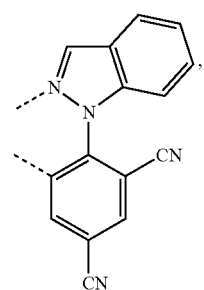
L49 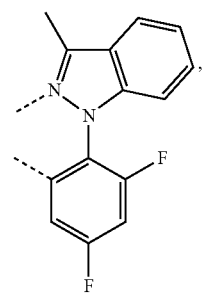
L50 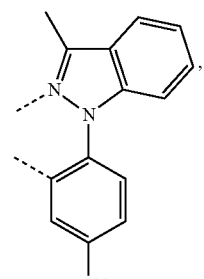
L51 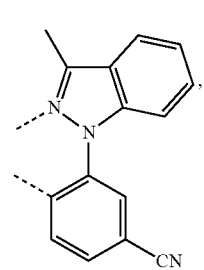
-continued
L52 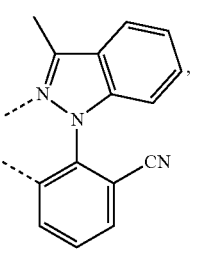
L53 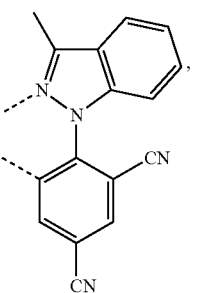
L54 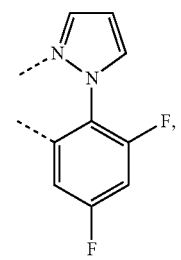
L55 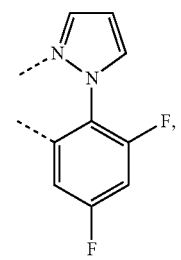
L56 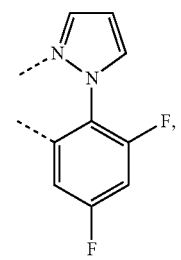

-continued
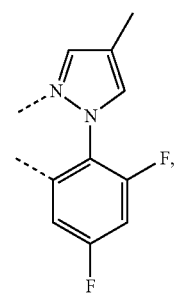 L57
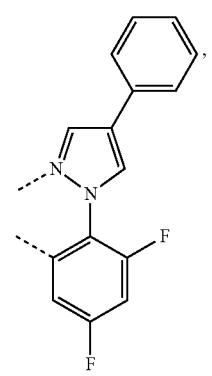 L58
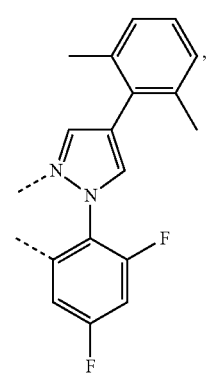 L59
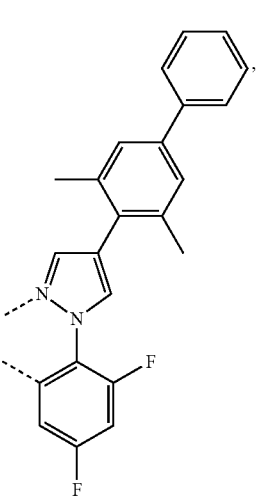 L60
-continued
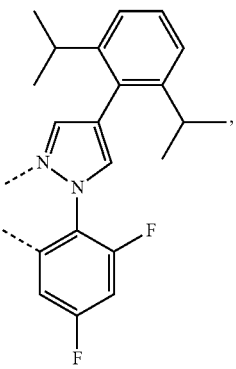 L61
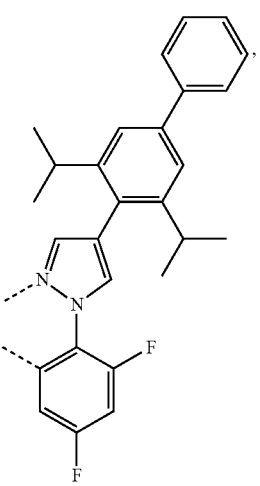 L62
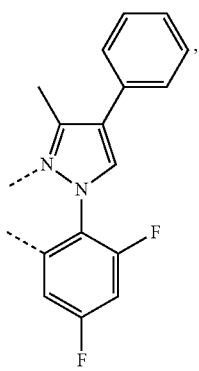 L63
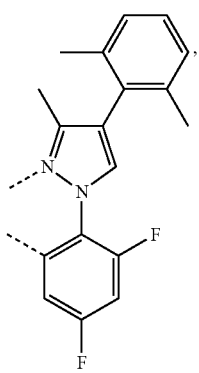 L64

| | |
|---|---|
| 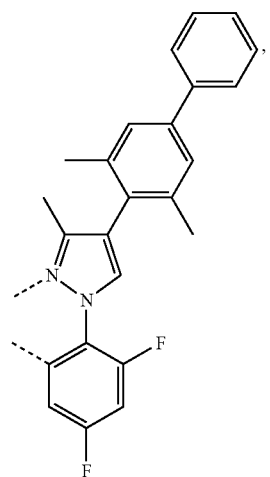 | L65 |
| 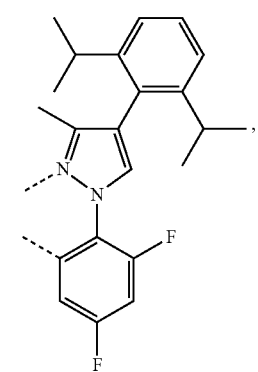 | L66 |
| 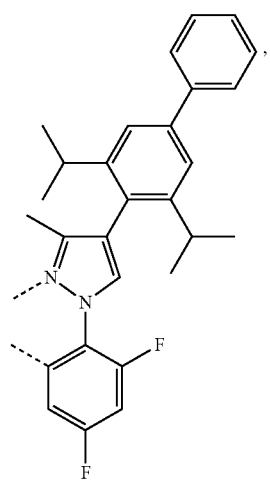 | L67 |
| 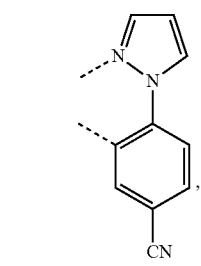 | L68 |
| 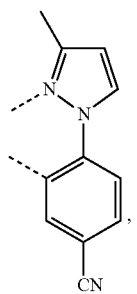 | L69 |
| 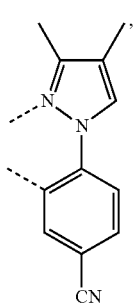 | L70 |
| 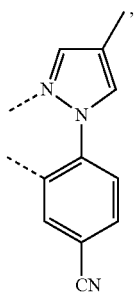 | L71 |
| 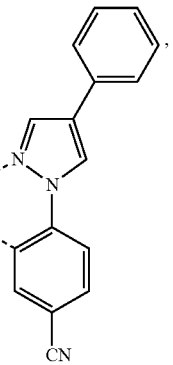 | L72 |

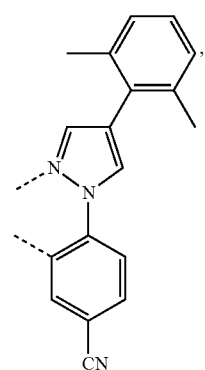
L73 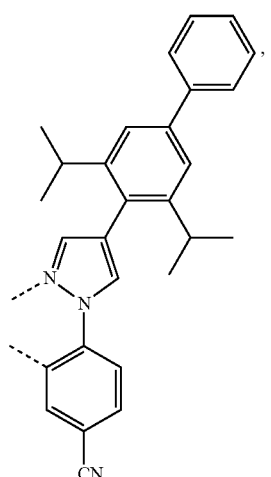
L74 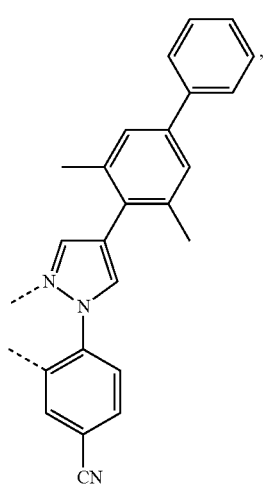
L75 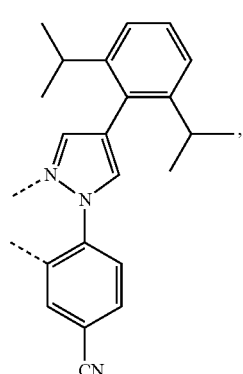
L76
L77 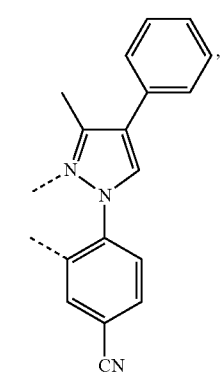
L78 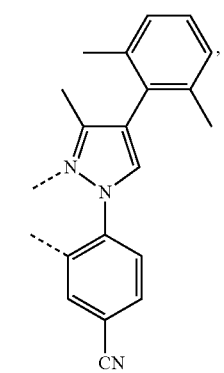

-continued
L₇₉ 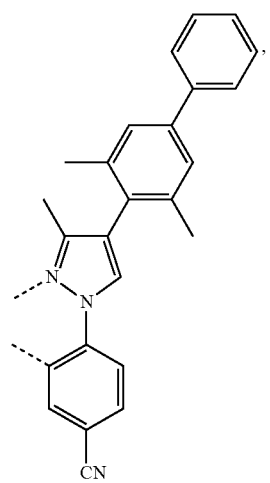
L₈₀ 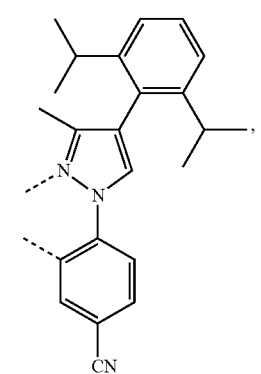
L₈₁ 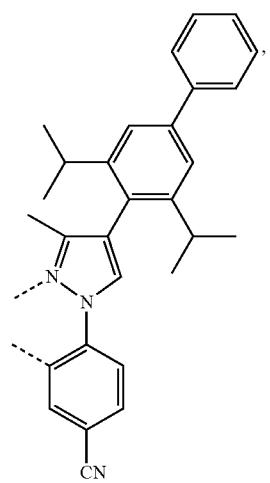
L₈₂ 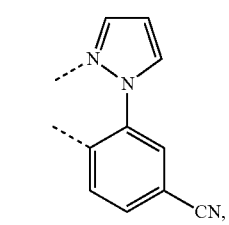
-continued
L₈₃ 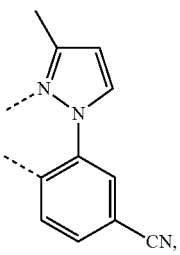
L₈₄ 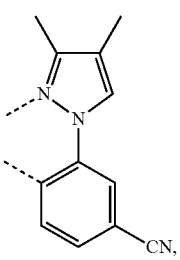
L₈₅ 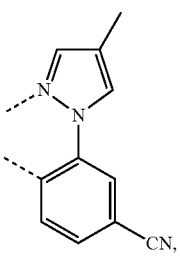
L₈₆ 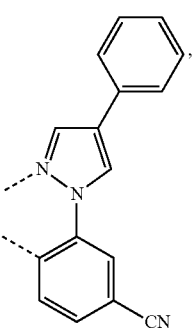
L₈₇ 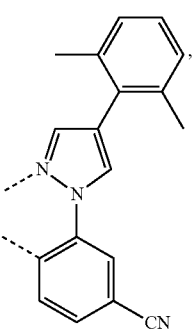

-continued
L-88 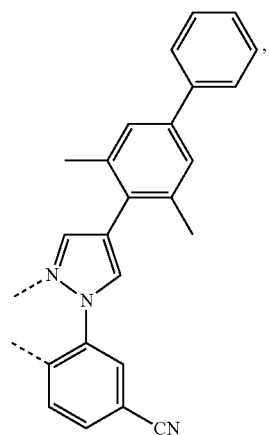
L-89 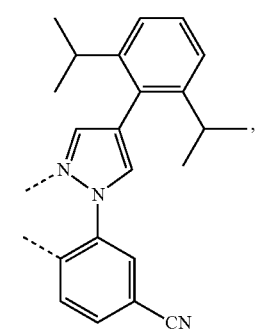
L-90 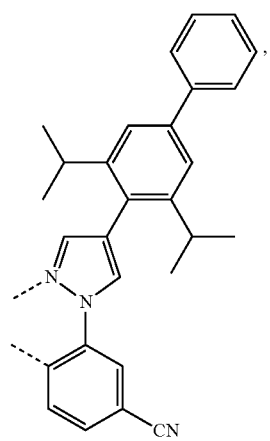
L-91 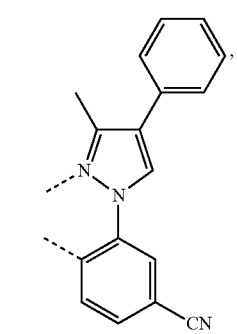
-continued
L-92 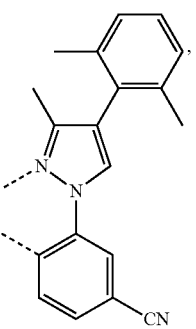
L-93 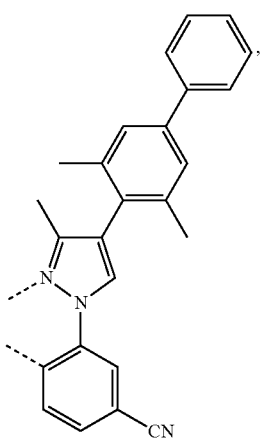
L-94 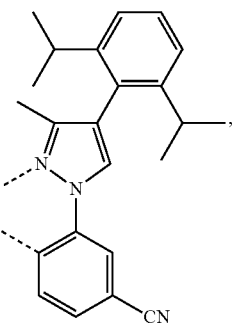
L-95 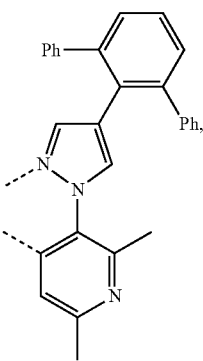

L96 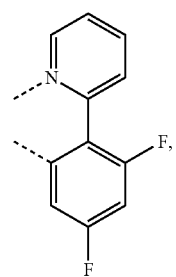
L97 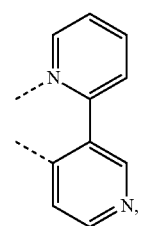
L98 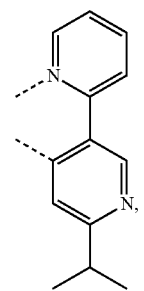
L99 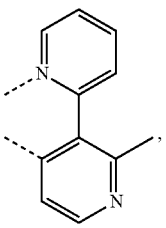
L100 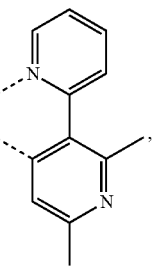
L101 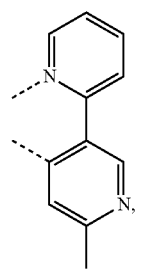
L102 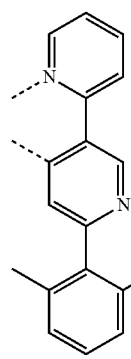
L103 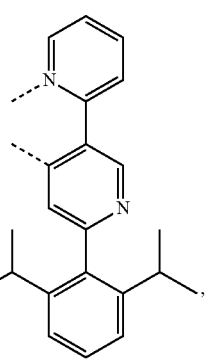
L104 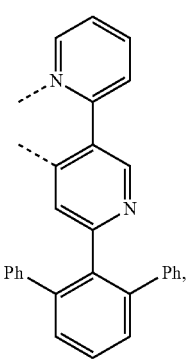
L105 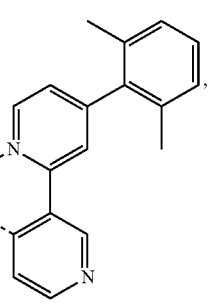

| | |
|---|---|
| 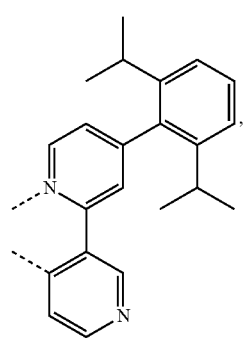 L106 | 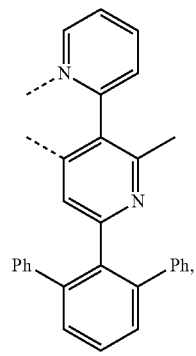 L110 |
| 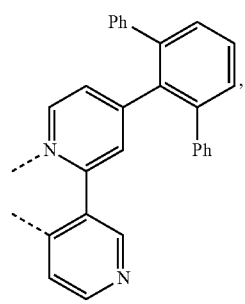 L107 | 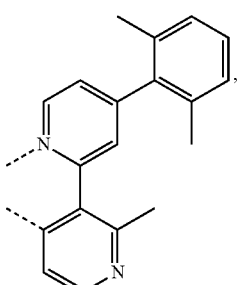 L111 |
| 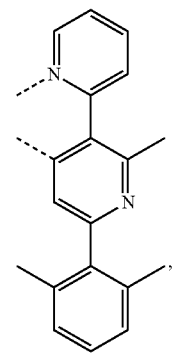 L108 | 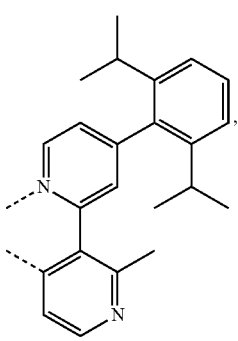 L112 |
| 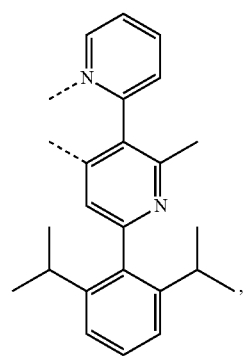 L109 | 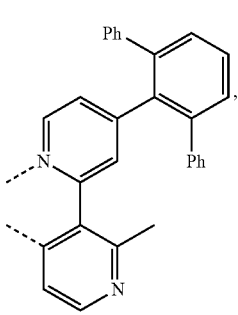 L113 |
| | 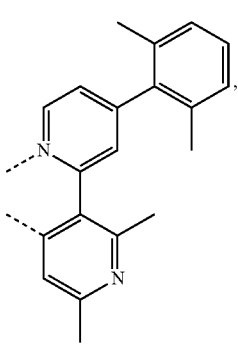 L114 |

L115 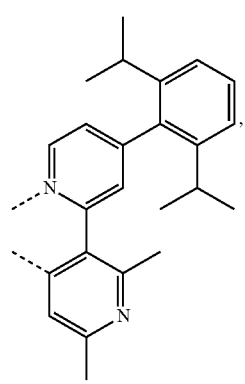
L116 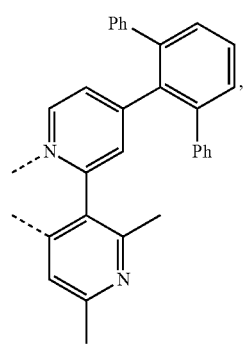
L117 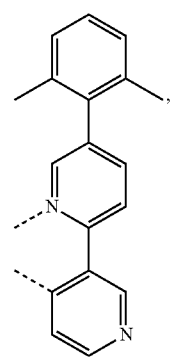
L118 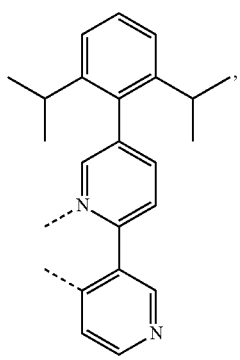
L119 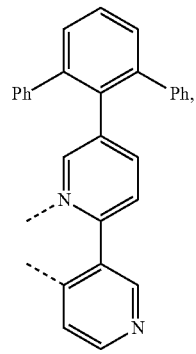
L120 
L121 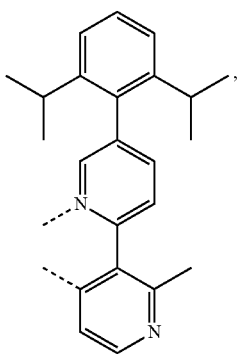
L122 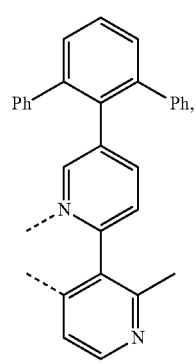

-continued
L123 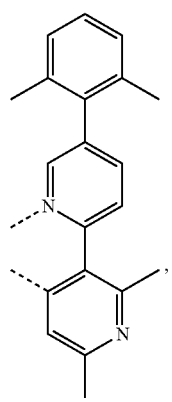
L124 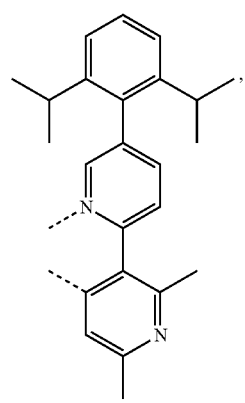
L125 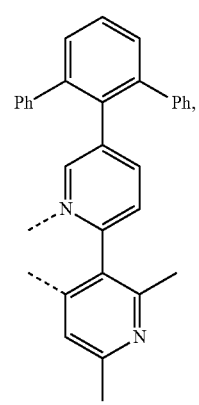
L126 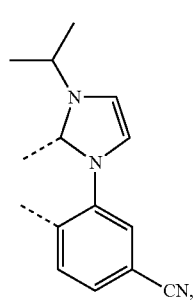
-continued
L127 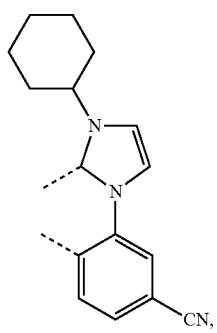
L128 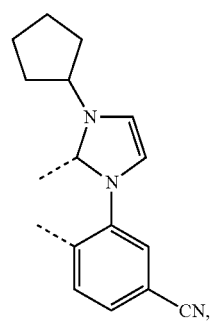
L129 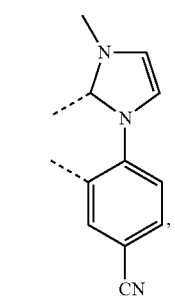
L130 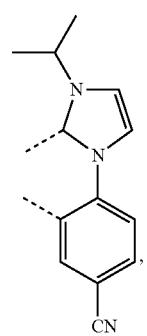

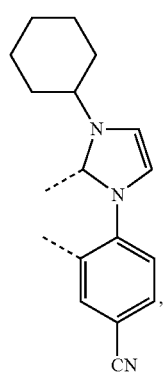 L131
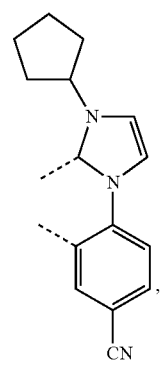 L132
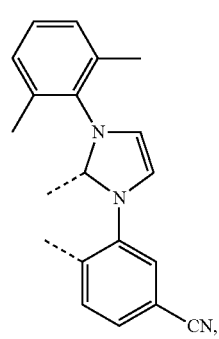 L133
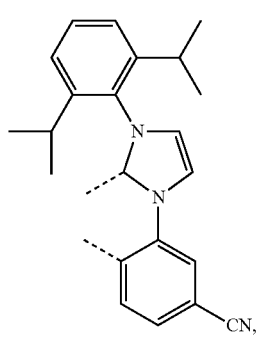 L134
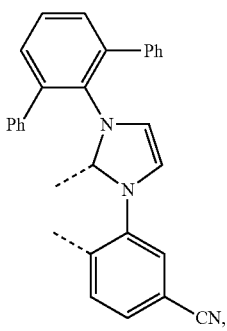 L135
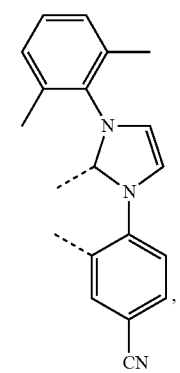 L136
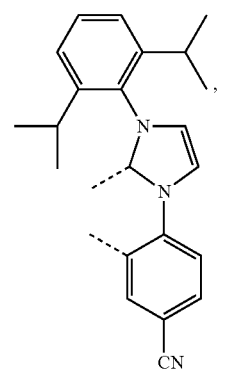 L137
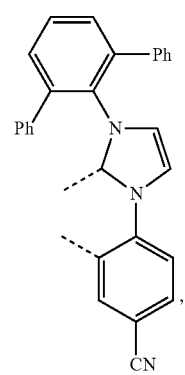 L138

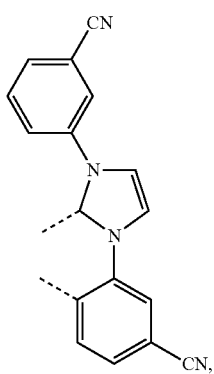
L139
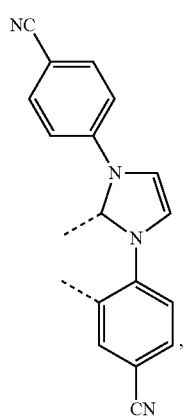
L140
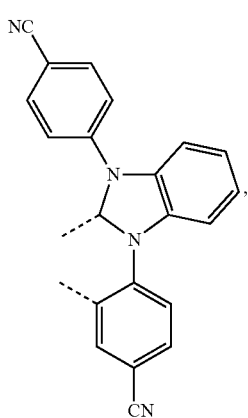
L141
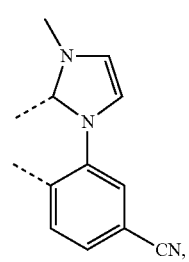
L142
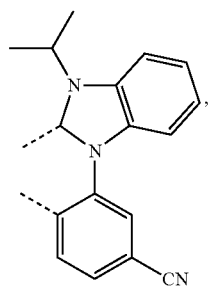
L143
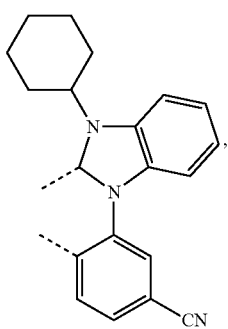
L144
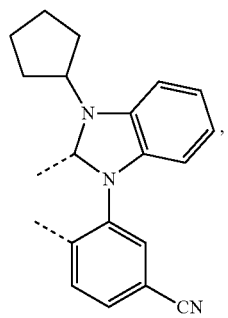
L145
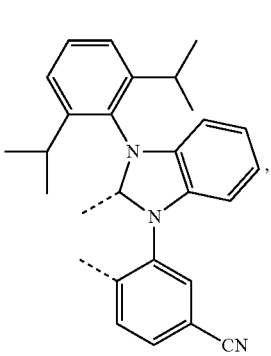
L146
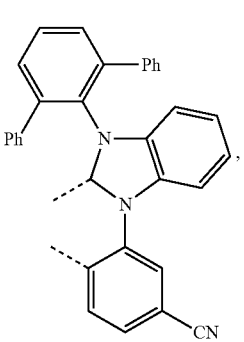
L147

L148 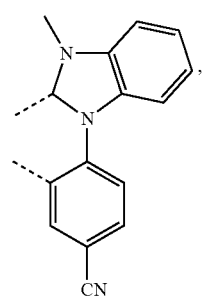
L149 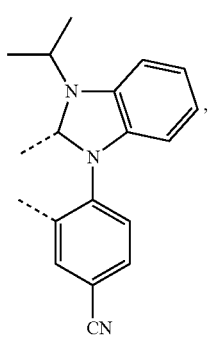
L150 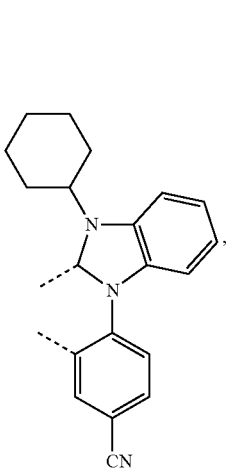
L151 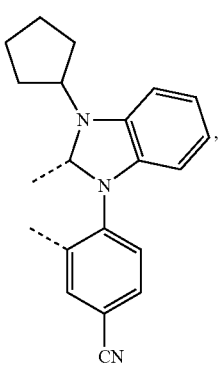
L152 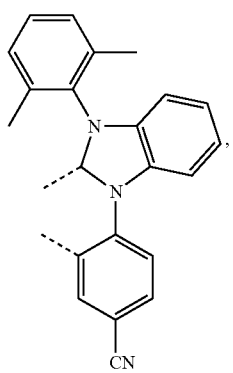
L153 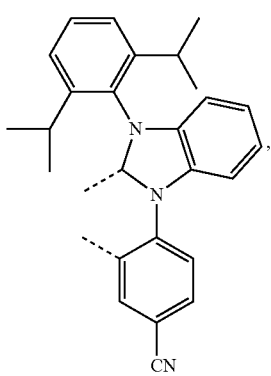
L154 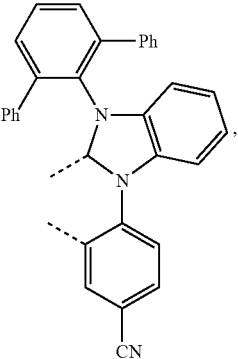
L155 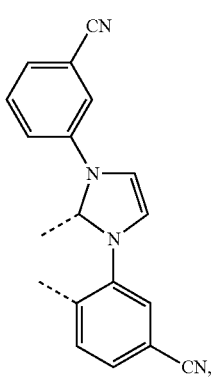

L156 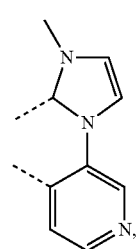
L157 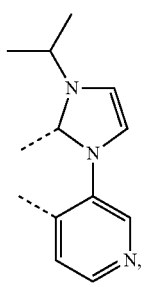
L158 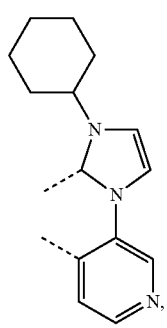
L159 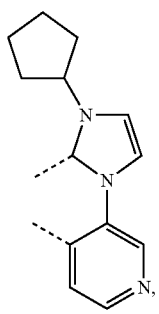
L160 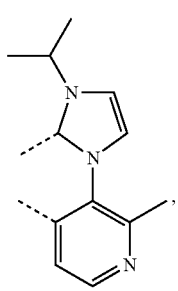
L161 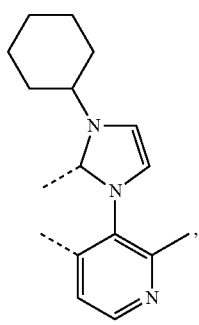
L162 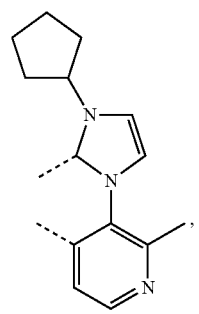
L163 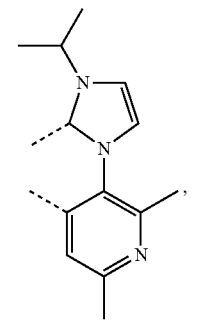
L164 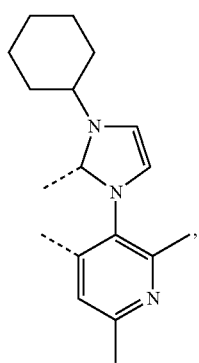

-continued
L165 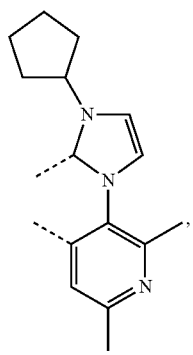
L166 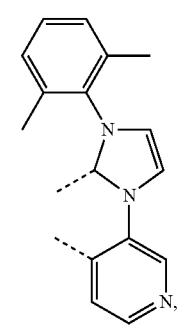
L167 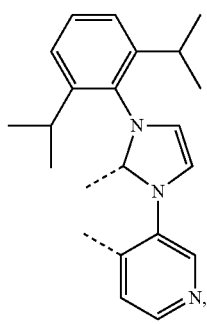
L168 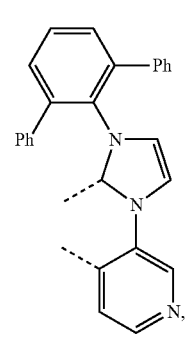
L169 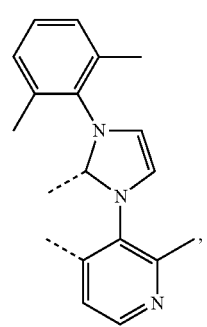
-continued
L170 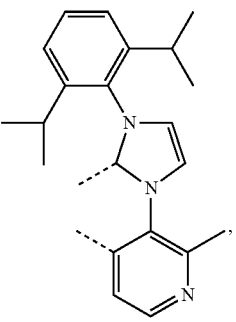
L171 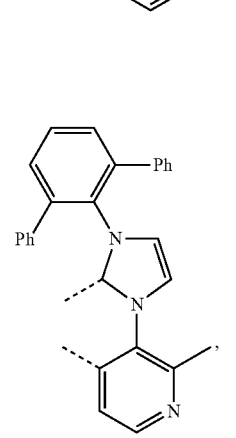
L172 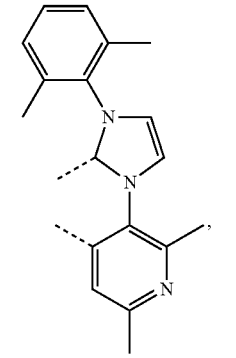
L173 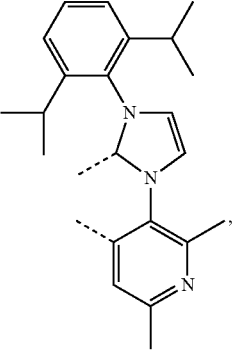

-continued
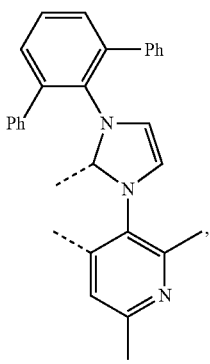 L174
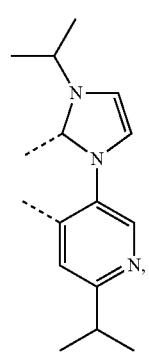 L175
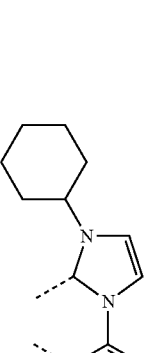 L176
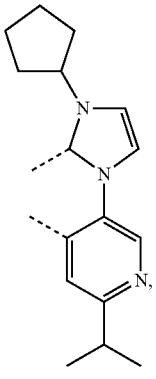 L177
-continued
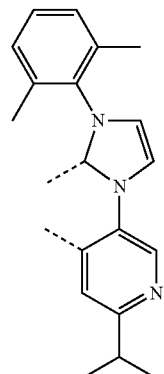 L178
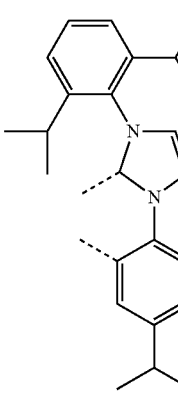 L179
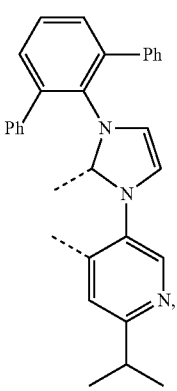 L180
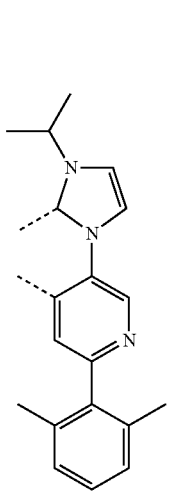 L181

-continued
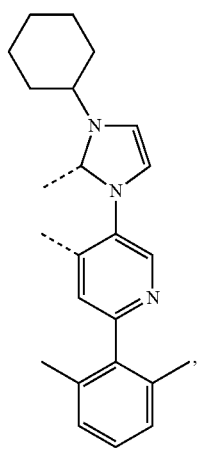
L_{182}
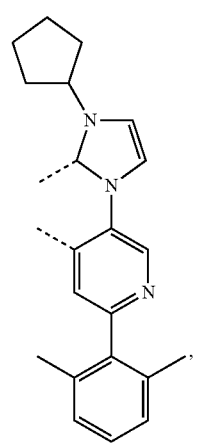
L_{183}
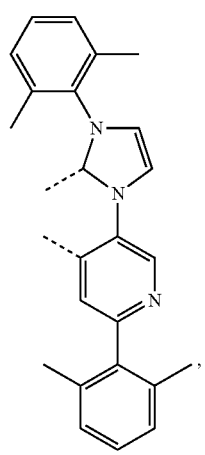
L_{184}
-continued
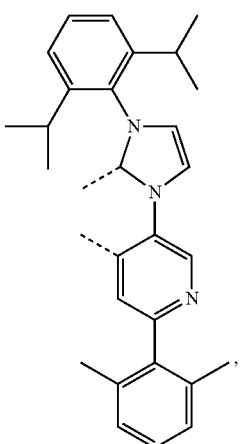
L_{185}
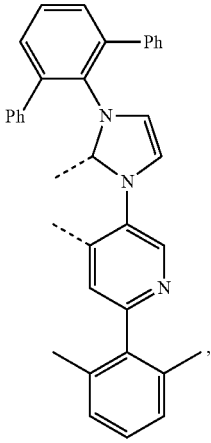
L_{186}
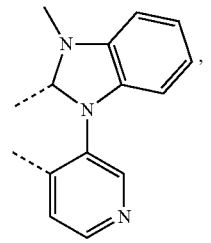
L_{187}
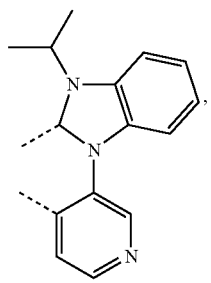
L_{188}

167
-continued
L189 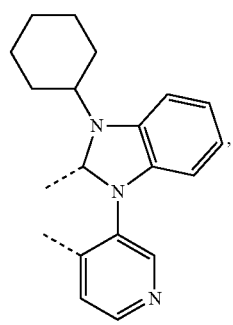
L190 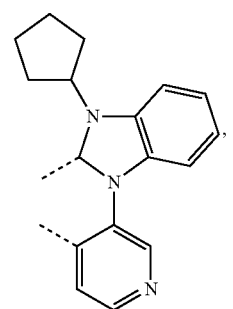
L191 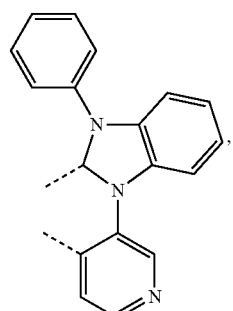
L192 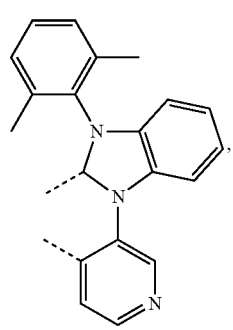
L193 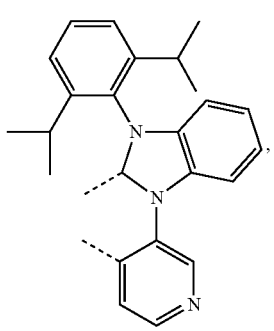
168
-continued
L194 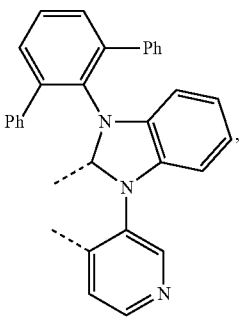
L195 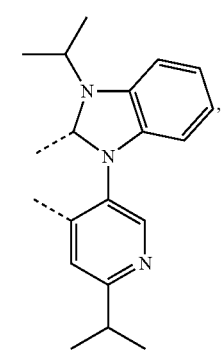
L196 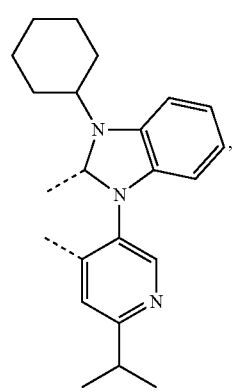
L197 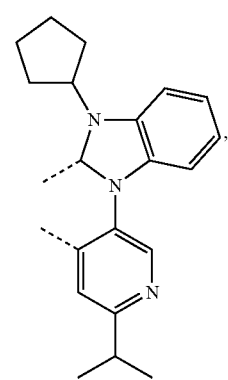

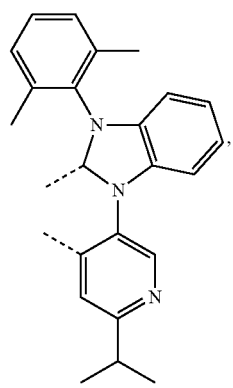
L198
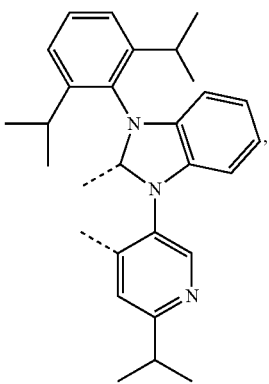
L199
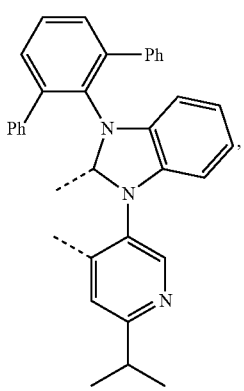
L200
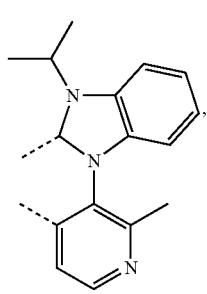
L201
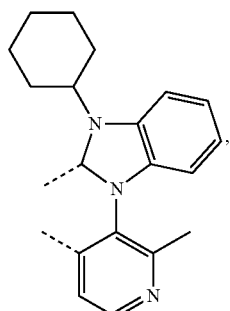
L202
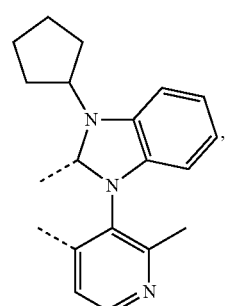
L203
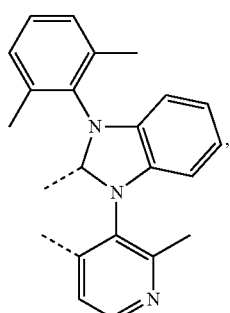
L204
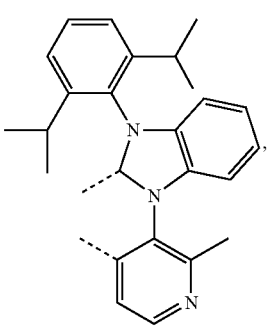
L205
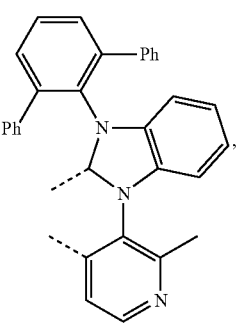
L206

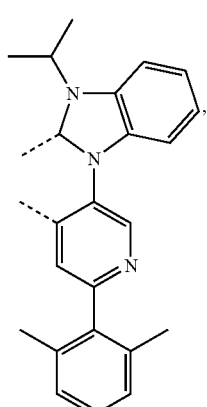 L207
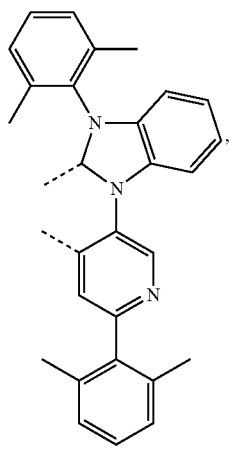 L210
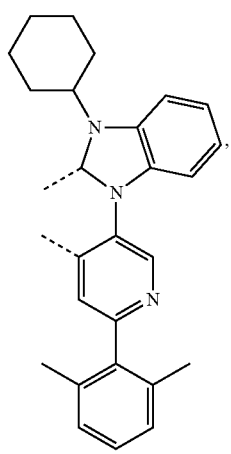 L208
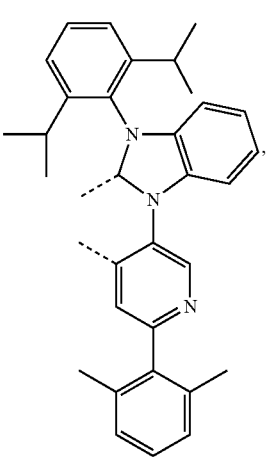 L211
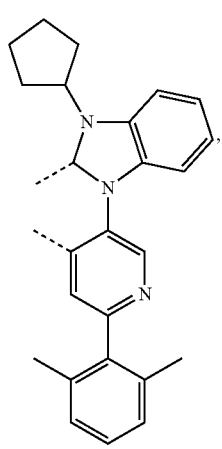 L209
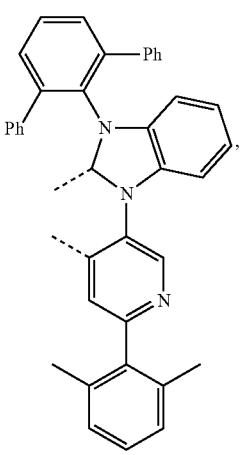 L212

L213 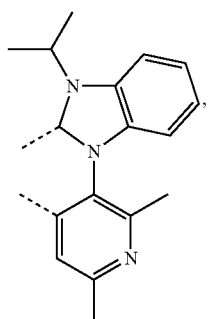
L214 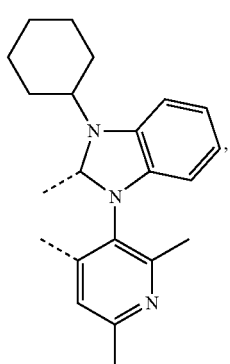
L215 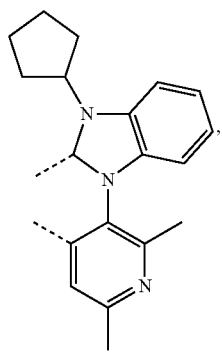
L216 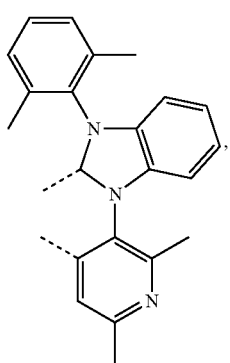
L217 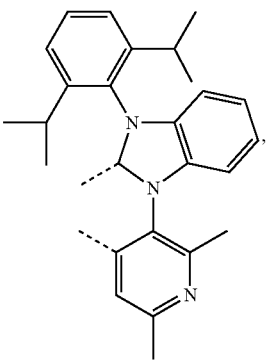
L218 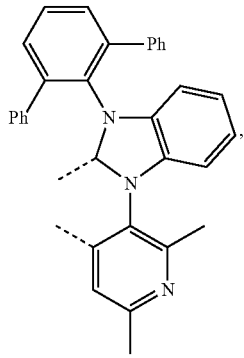
L219 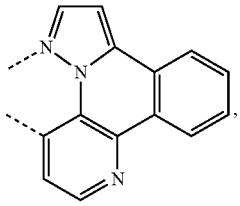
L220 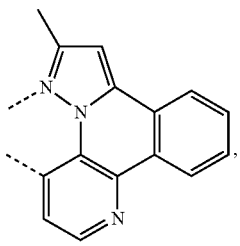
L221 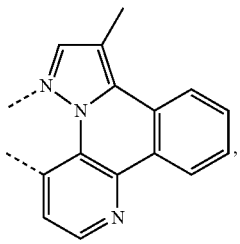

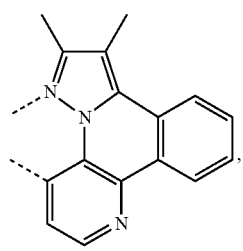 L222,
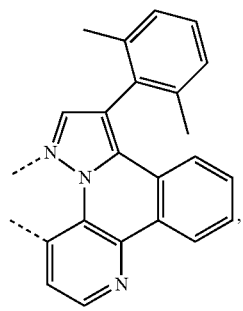 L223,
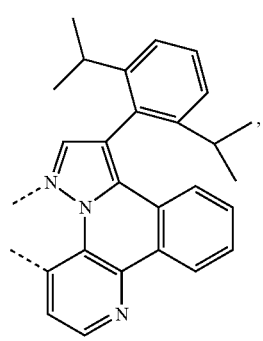 L224,
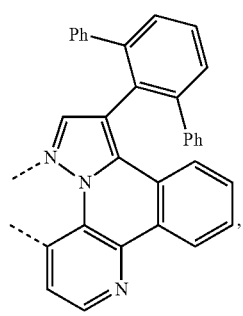 L225,
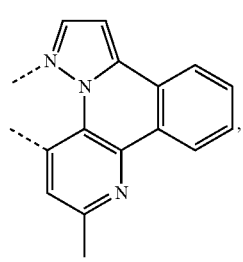 L226,
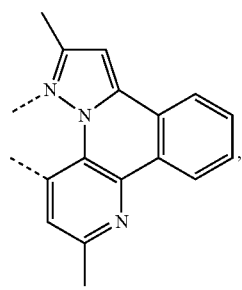 L227,
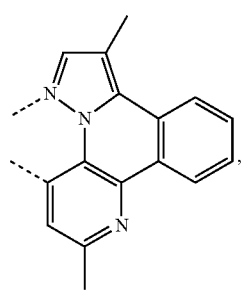 L228,
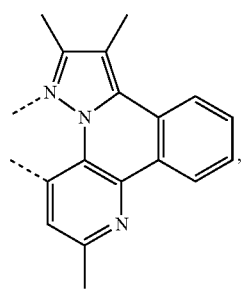 L229,
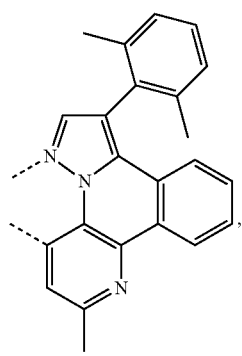 L230,
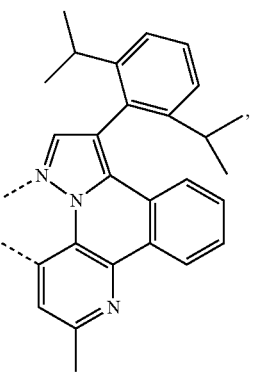 L231, L232 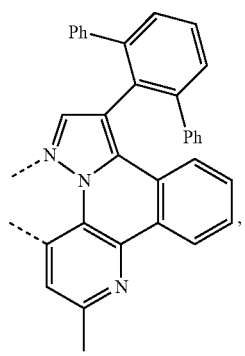
L233 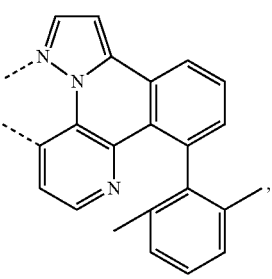
L234 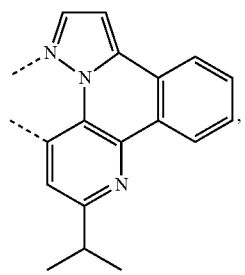
L235 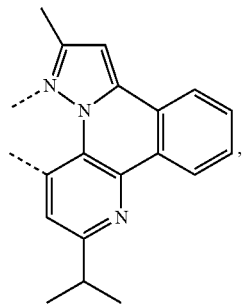
L236 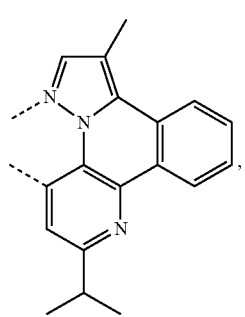
L237 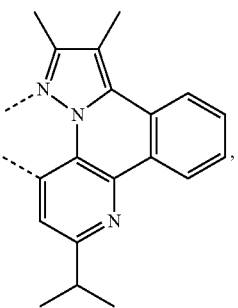
L238 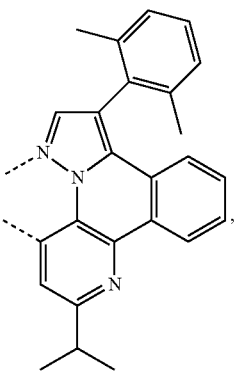
L239 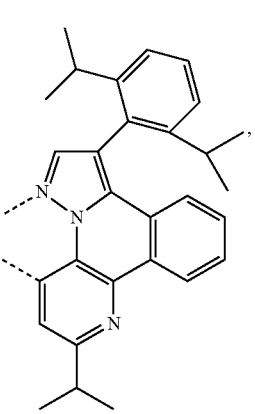
L240 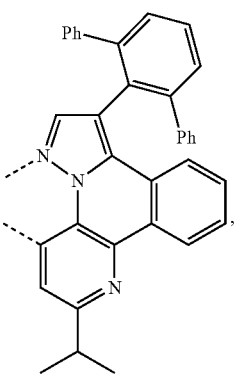

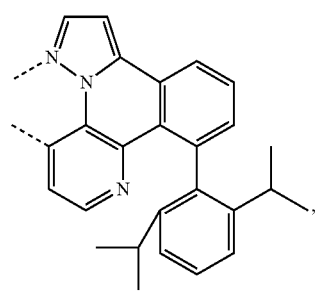 L241
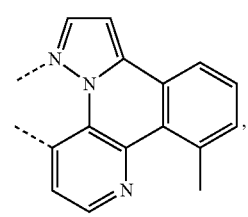 L242
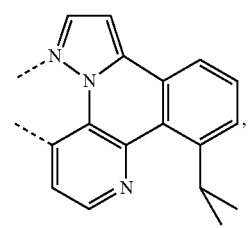 L243
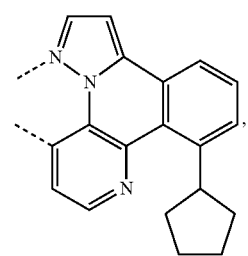 L244
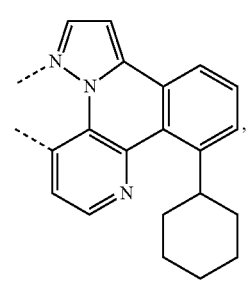 L245
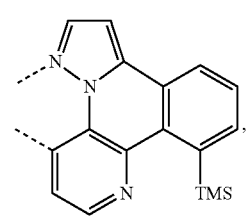 L246
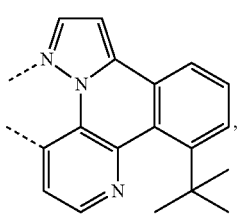 L247
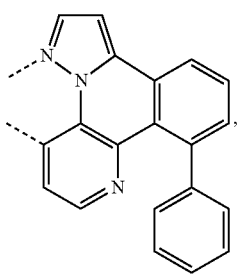 L248
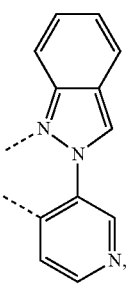 L249
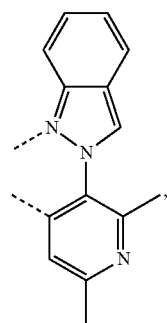 L250
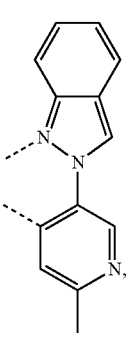 L251

L252 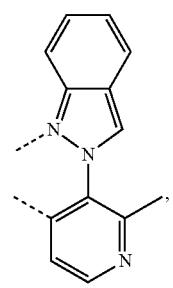
L253 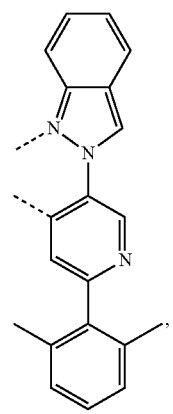
L254 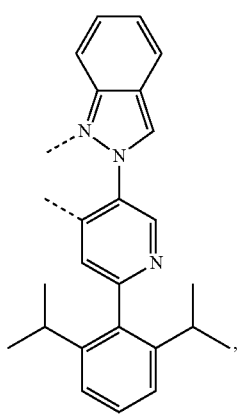
L255 
L256 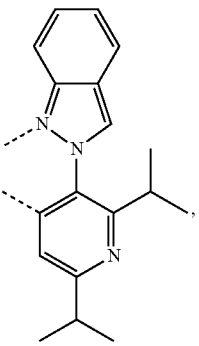
L257 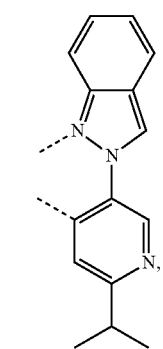
L258 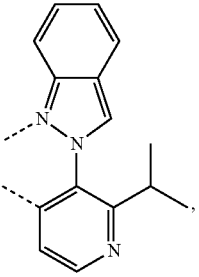
L259 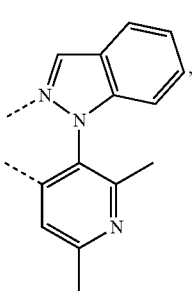
L260 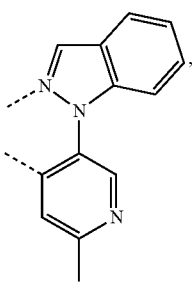

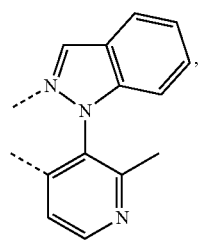
L261
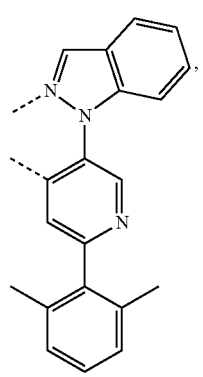
L262
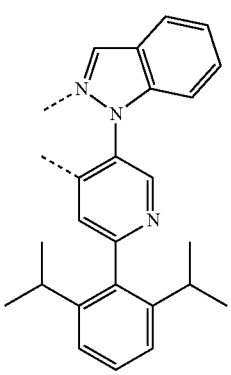
L263
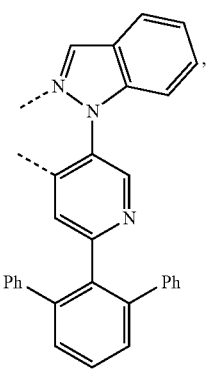
L264
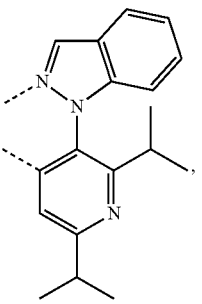
L265
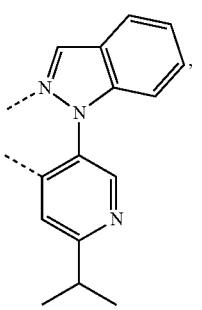
L266
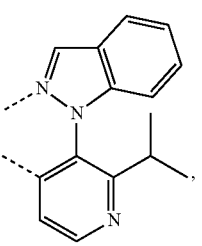
L267
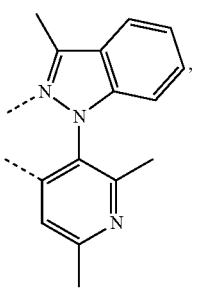
L268
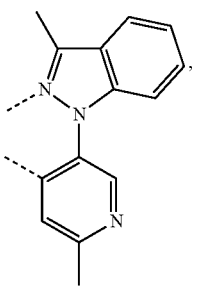
L269

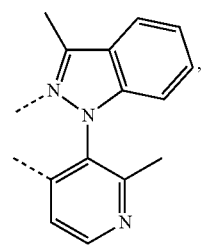 L270
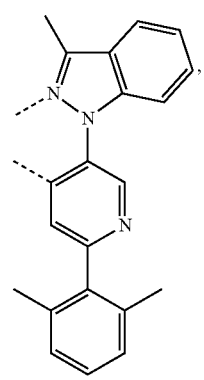 L271
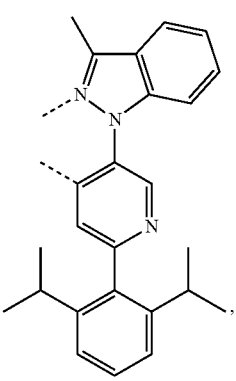 L272
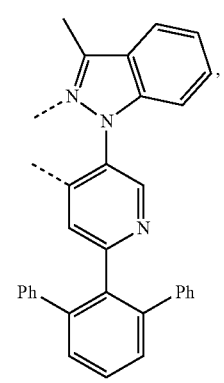 L273
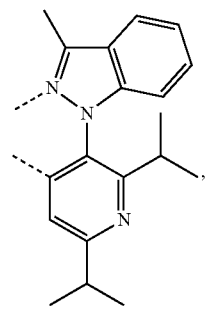 L274
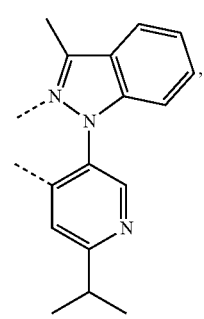 L275
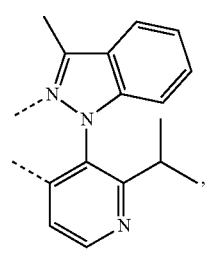 L276
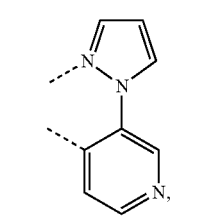 L277
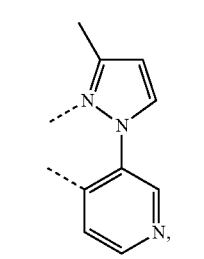 L278
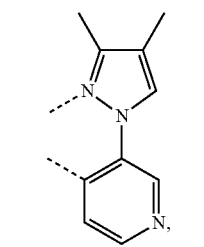 L279

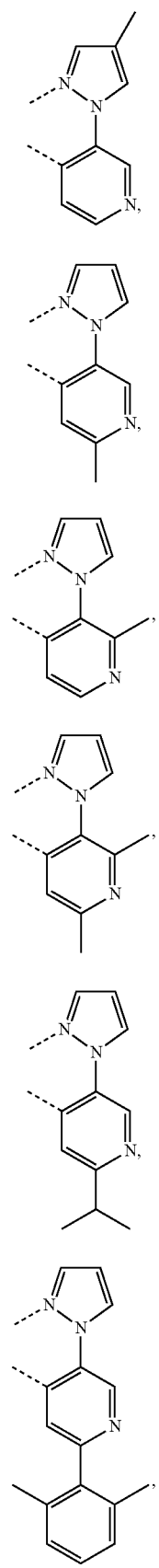
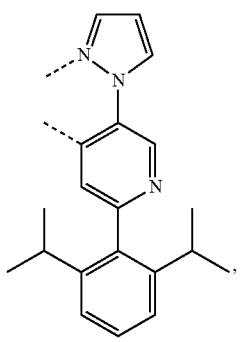
L280
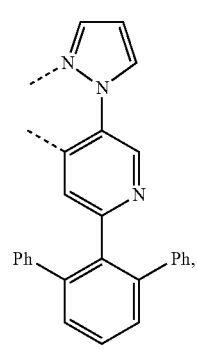
L282
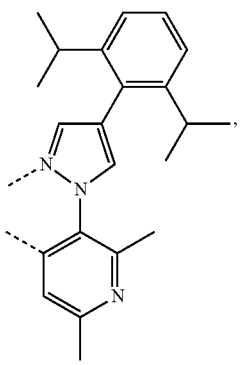
L284
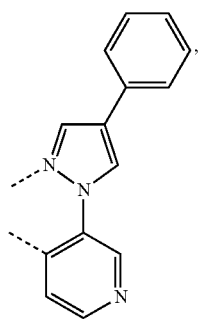
L288

L290 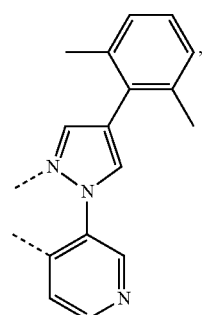
L291 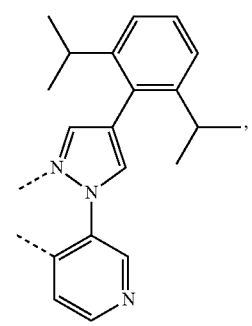
L292 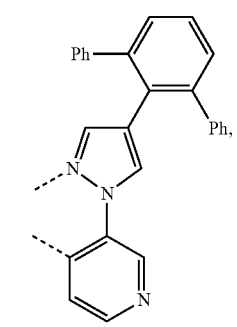
L293 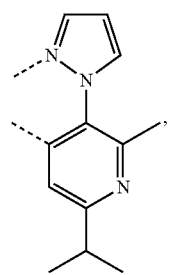
L294 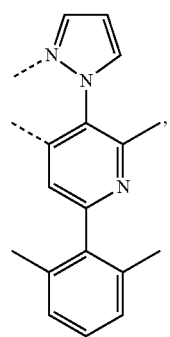
L295 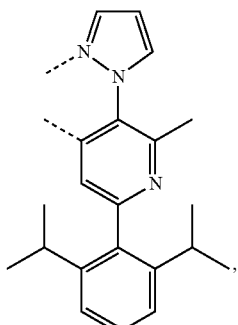
L296 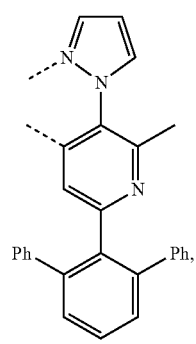
L297 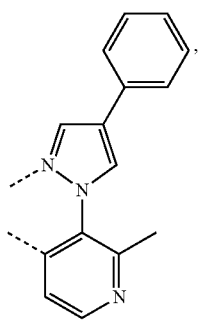
L298 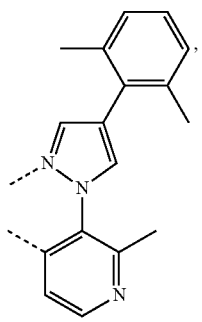
L299 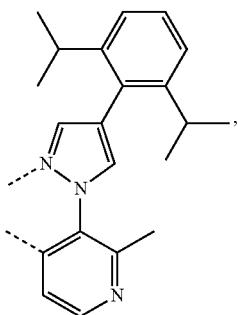

-continued

L300 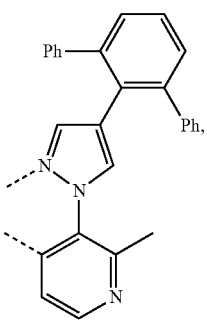

L301 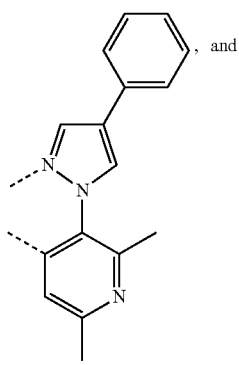, and

L302 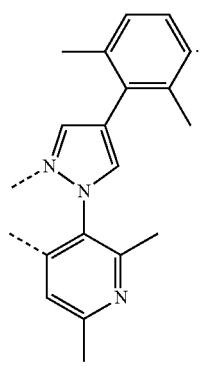

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Devices of the Invention

According to another aspect of the present disclosure, an OLED is also provided. The OLED includes an anode, a cathode, and an organic layer disposed between the anode and the cathode. The organic layer may include a host and a phosphorescent dopant. The organic layer can include a compound comprising a ligand $L_A$ of Formula I, and its variations as described herein.

The OLED can be incorporated into one or more of a consumer product, an electronic component module and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv C-C_nH_{2n+1}$, $Ar_1$, $Ar_1-Ar_2$, and $C_nH_{2n}-Ar_1$, or the host has no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. The host can be an inorganic compound. For example a Zn containing inorganic material e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be, but is not limited to, a specific compound selected from the group consisting of:

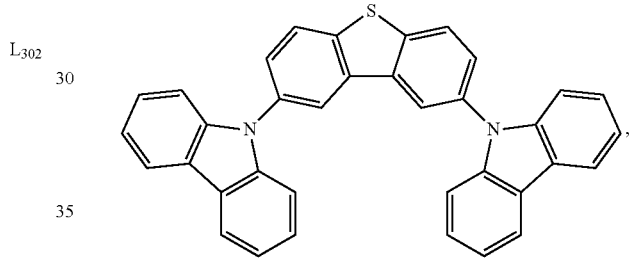

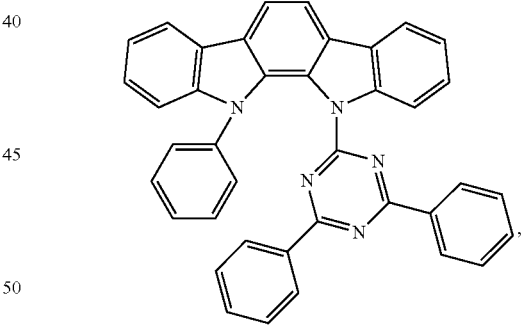

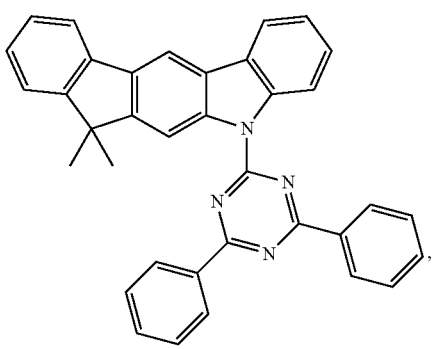

193
-continued
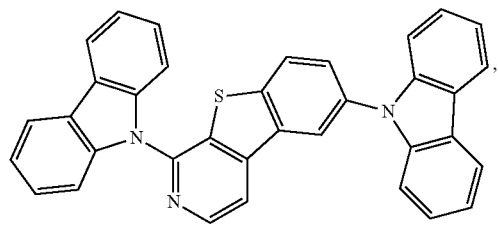
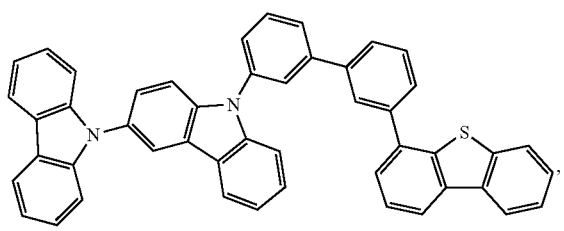
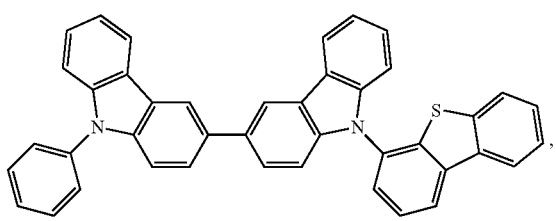
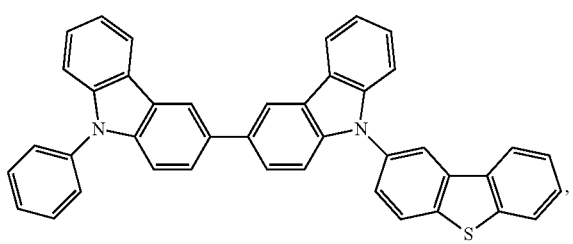
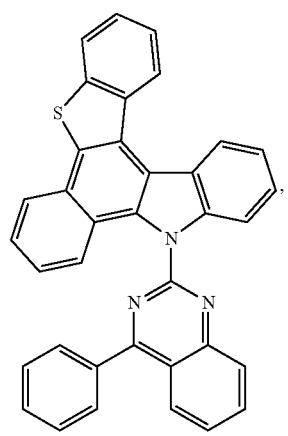
194
-continued
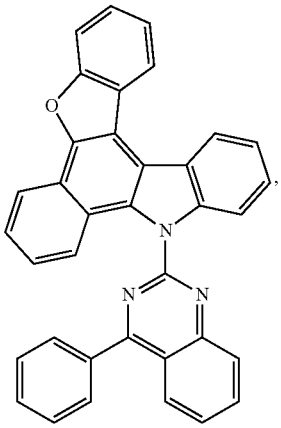
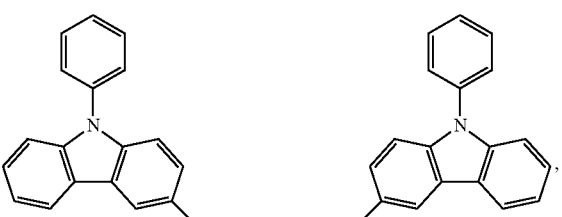
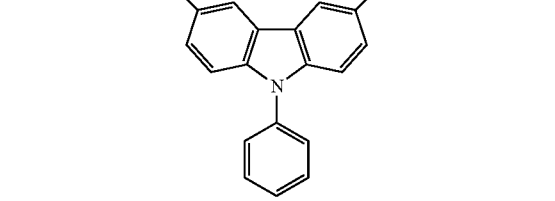
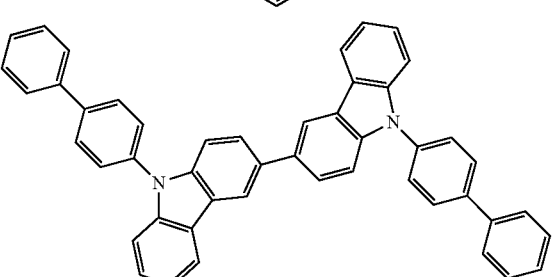
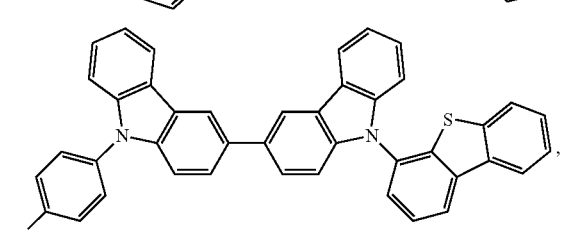
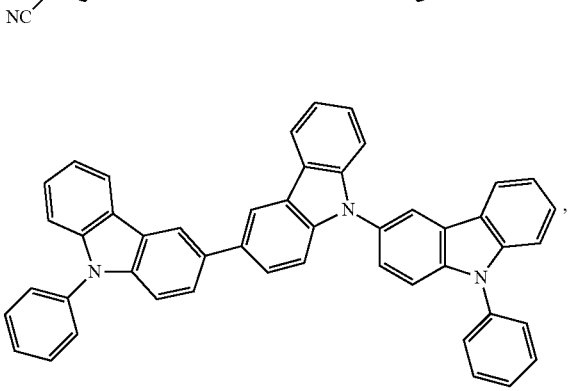

-continued

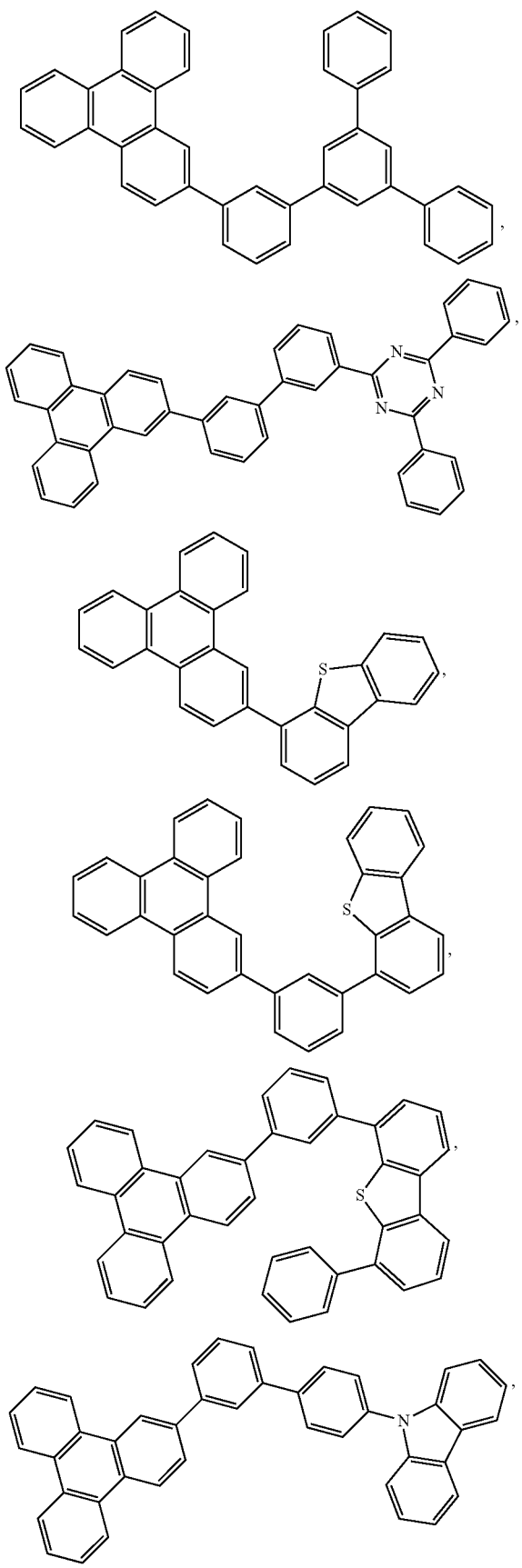

-continued

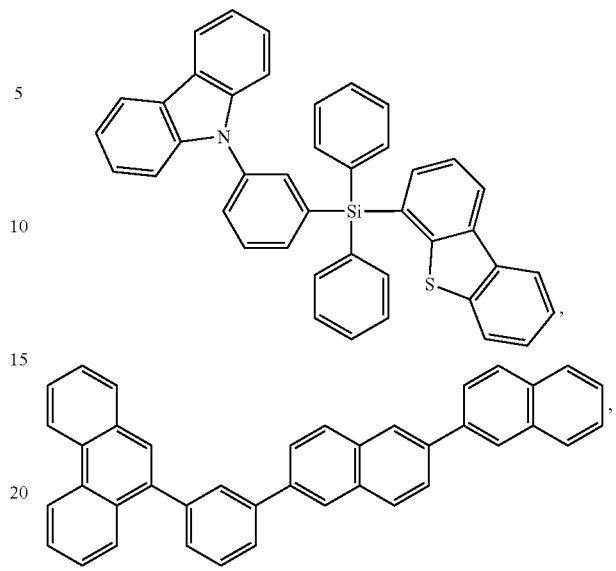

and combinations thereof.

Additional information on possible hosts is provided below.

In yet another aspect of the present disclosure, a formulation that comprises a compound according to Formula I is described. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer. Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804 and US2012146012.

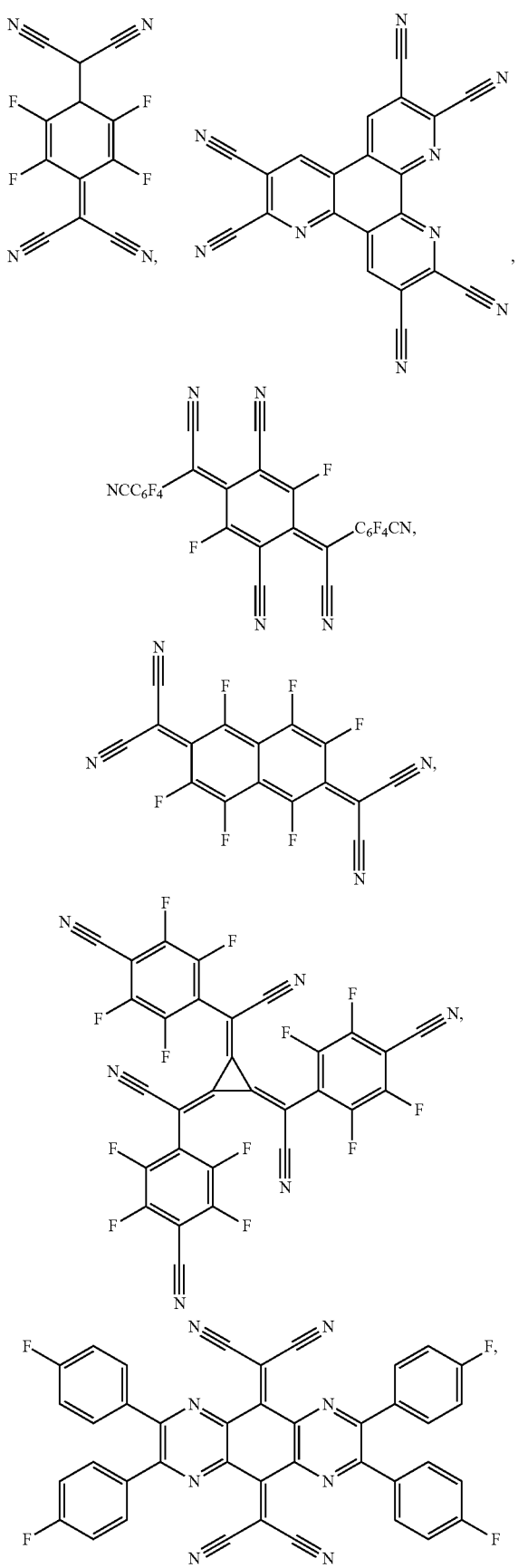
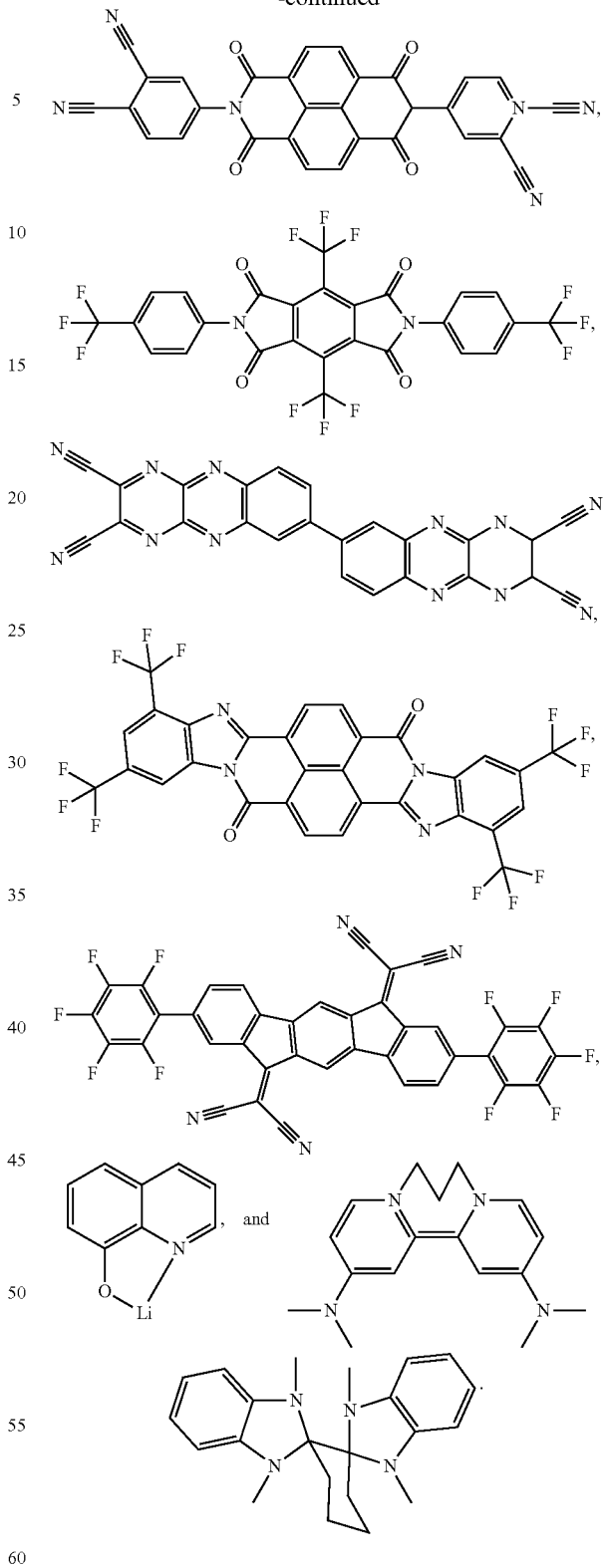
HIL/HTL:
A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

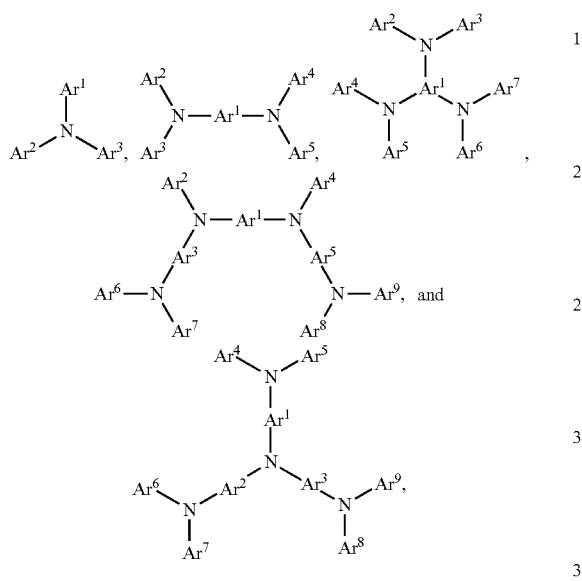

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

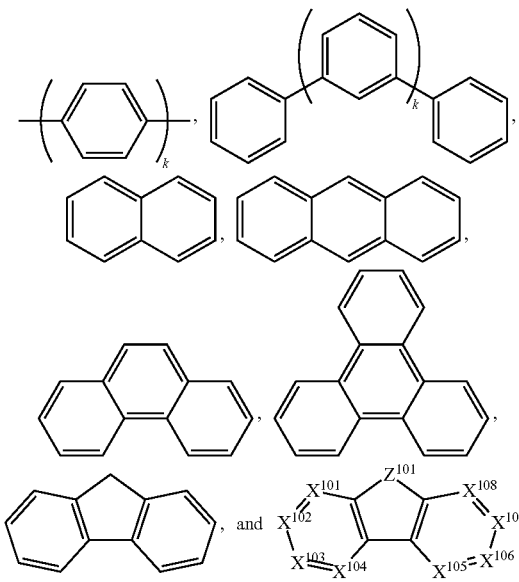

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

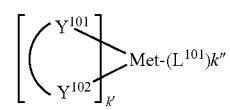

wherein Met is a metal, which can have an atomic weight greater than 40; $(Y^{101}\text{—}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{—}Y^{102})$ is a 2-phenylpyridine derivative. In another aspect, $(Y^{101}\text{—}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Pat. No. 6,517,957, US20020158242, US20030162053, US20050123751, US20060182993, US20060240279, US20070145888, US20070181874,

201
US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. No. 5,061,569, U.S. Pat. No. 5,639,914, WO05075451, WO07125714, WO2009145016, WO2012177006, WO2013087142, WO2013157367, WO2014015935, WO2014030921, WO2014157018.
202
WO08023550, WO08023759, WO2010061824, WO2011075644, WO2013018530, WO2013039073, WO2013118812, WO2013120577, WO2013175747, WO2014002873, WO2014015937, WO2014030872, WO2014034791, WO2014104514,
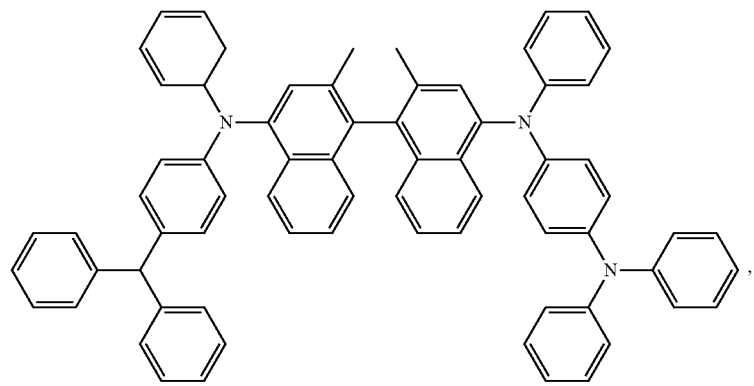
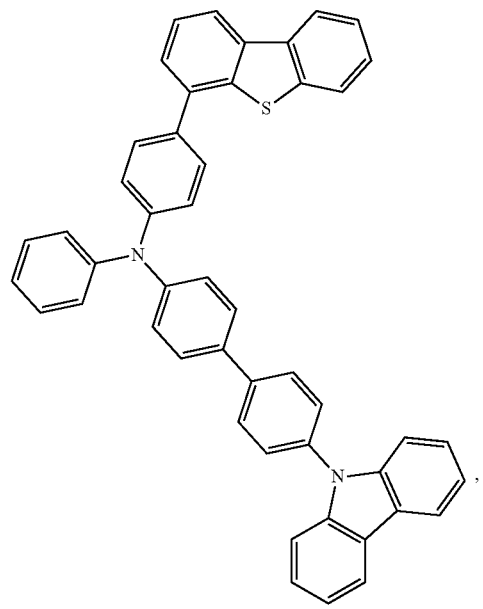

-continued
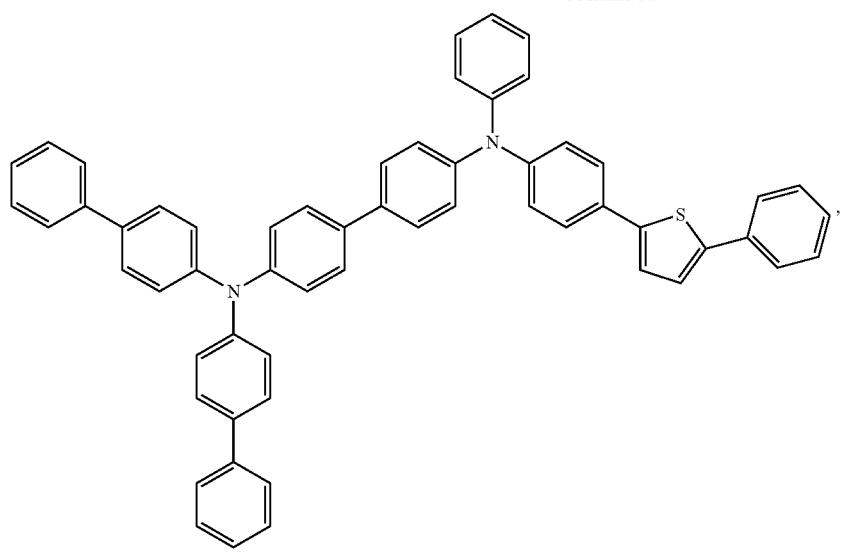
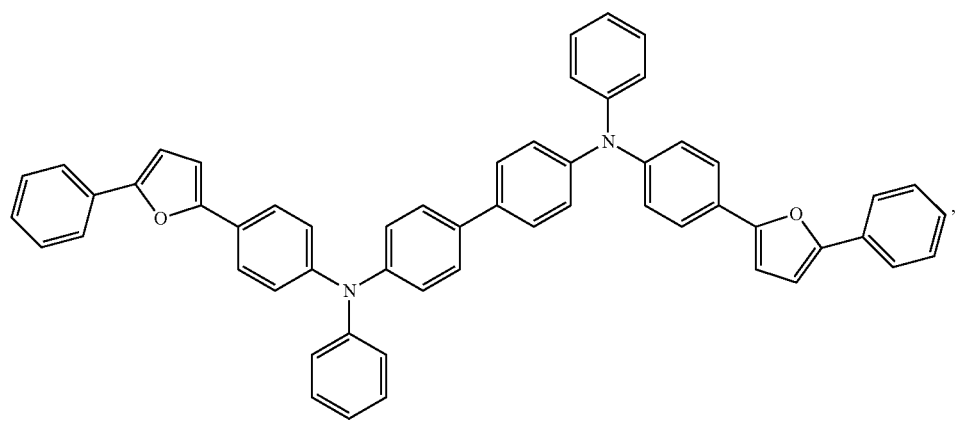
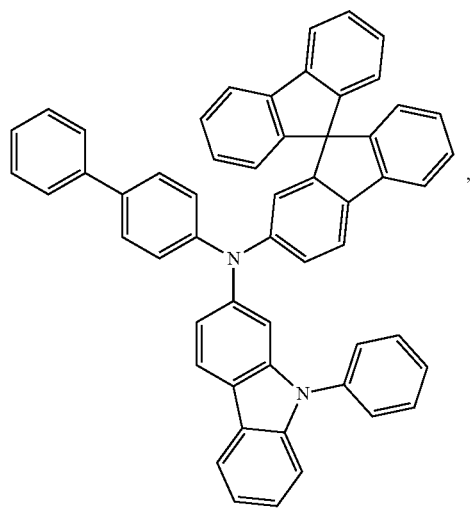

-continued
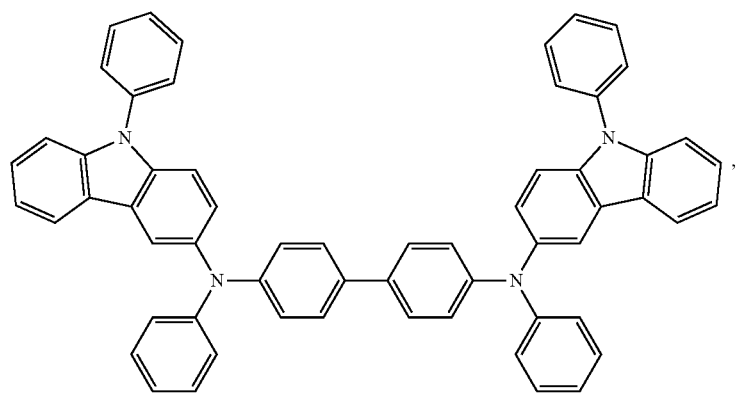
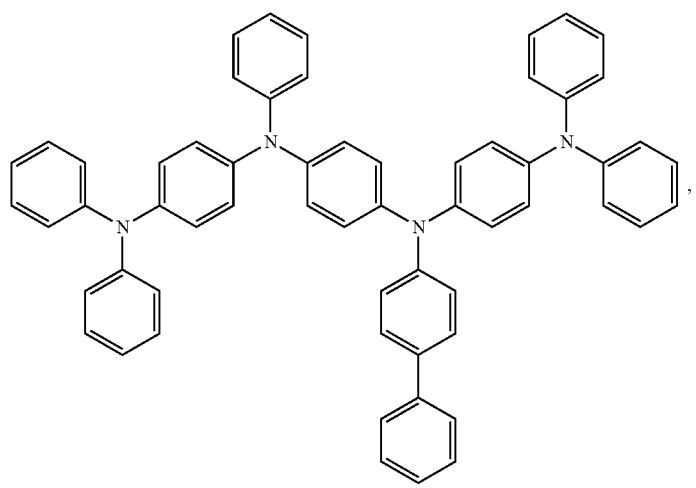
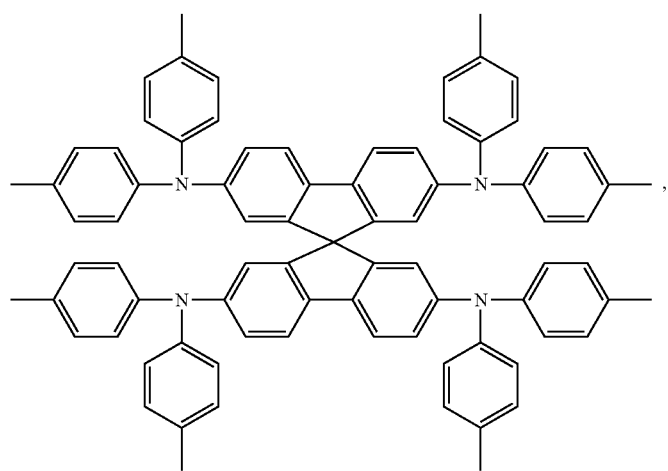

-continued
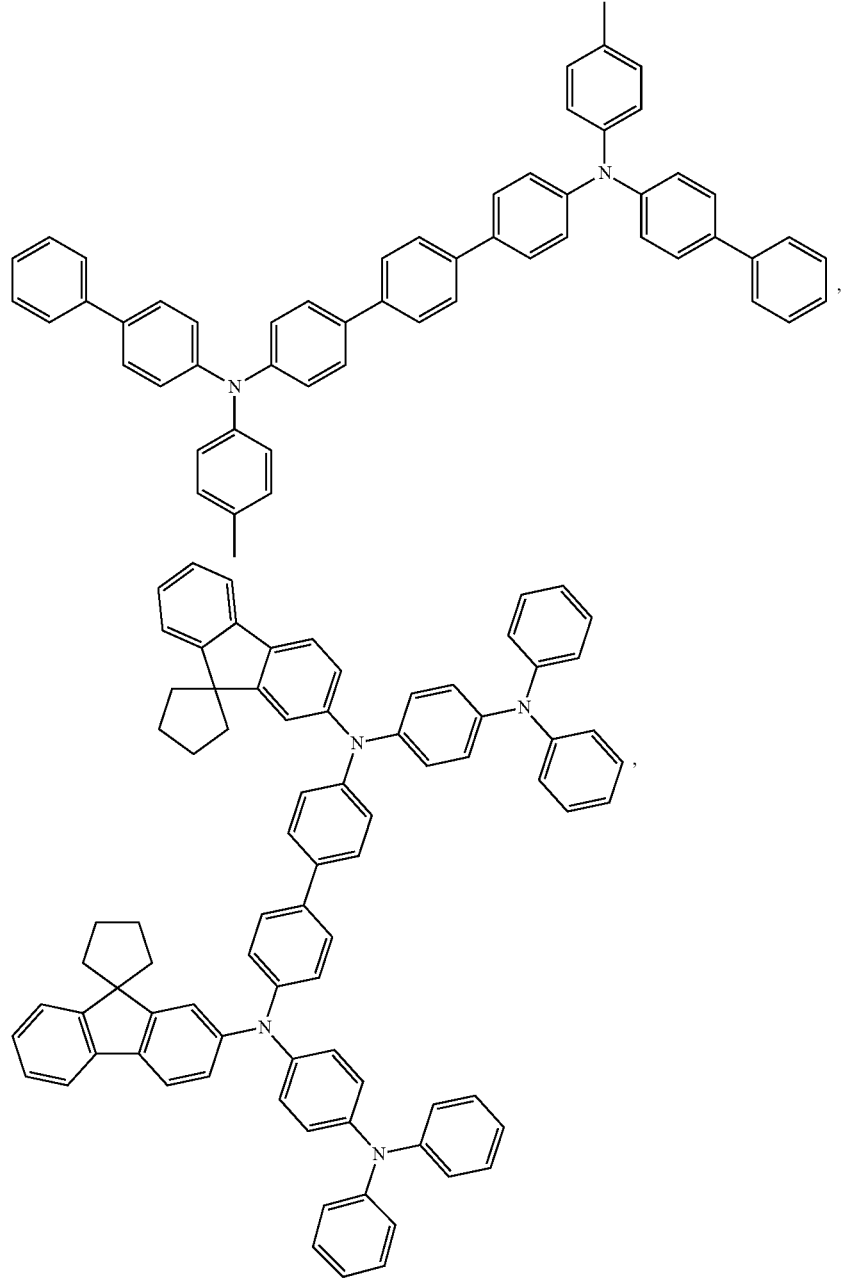
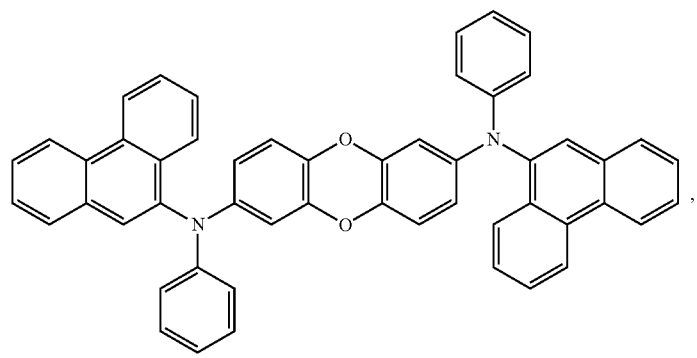

209
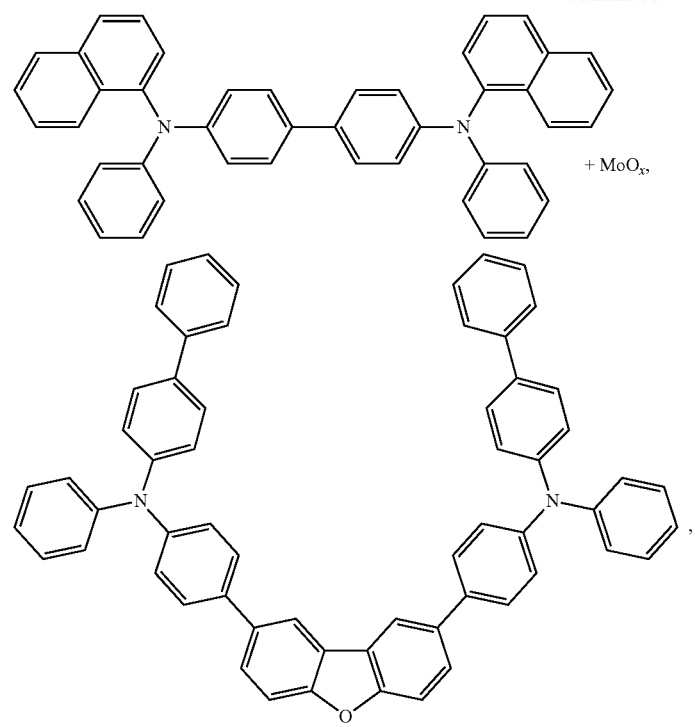
+ MoO$_x$,
210
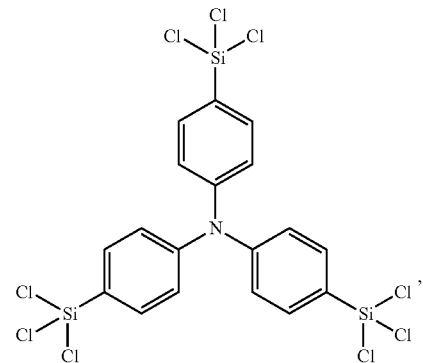
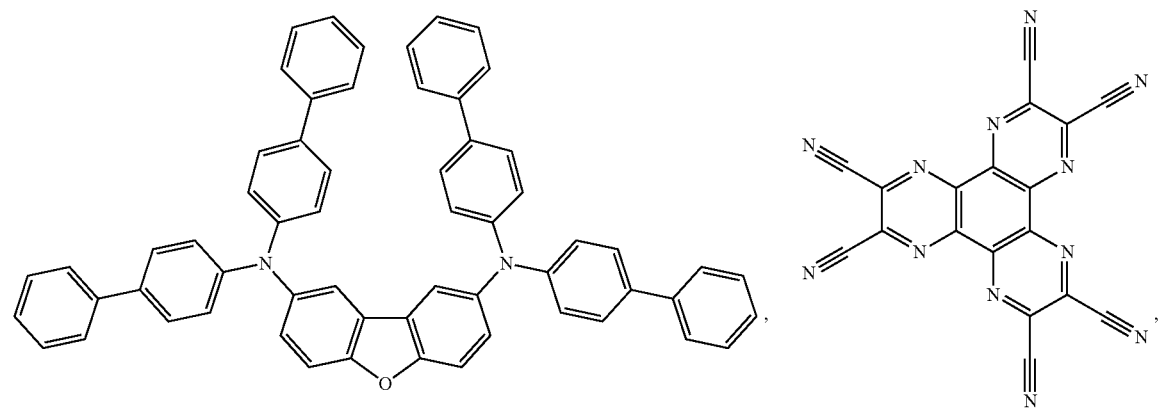
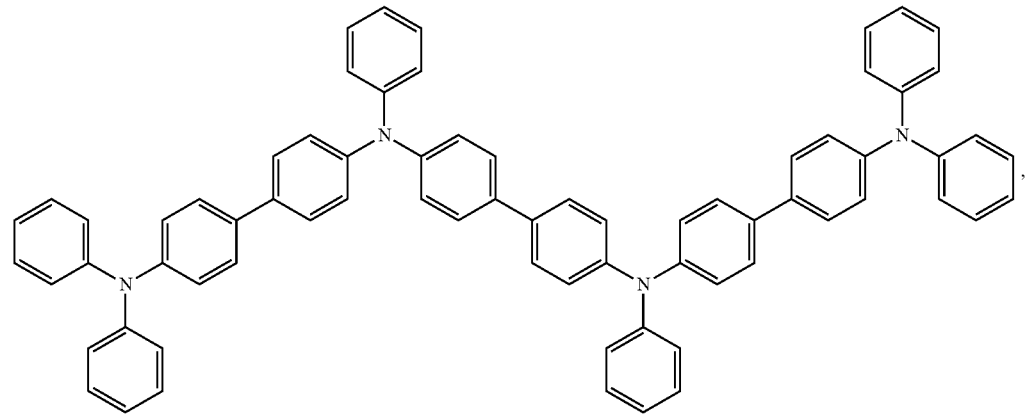

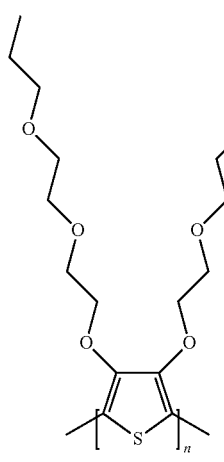
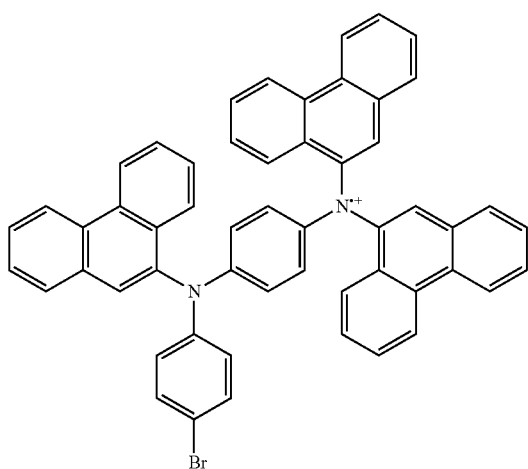
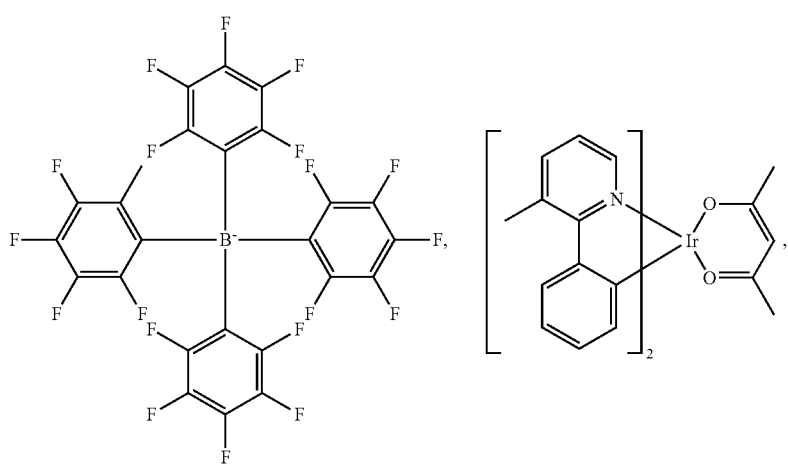
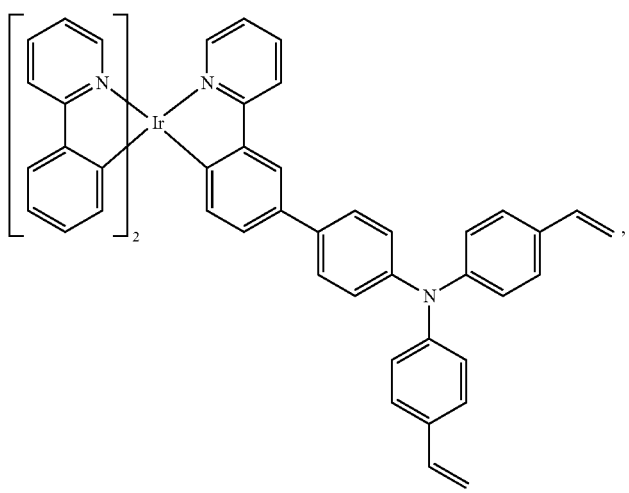

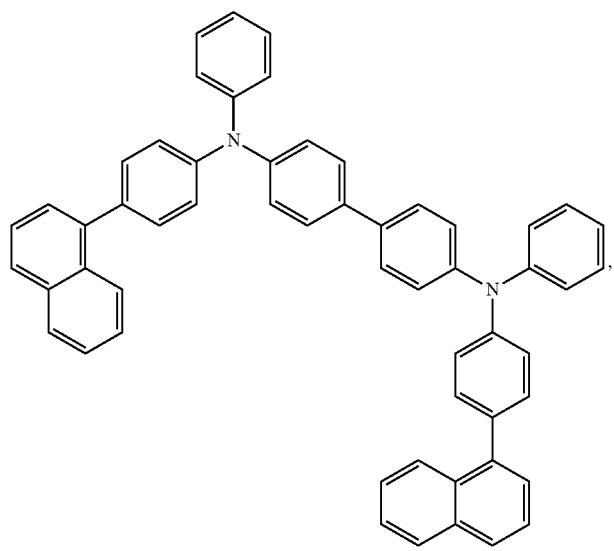
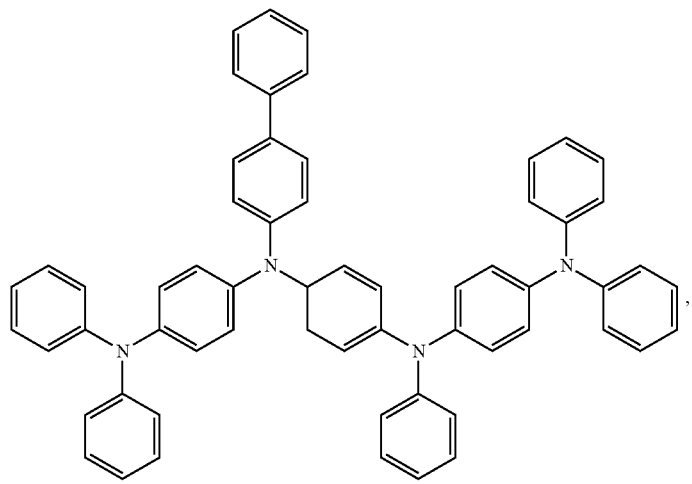
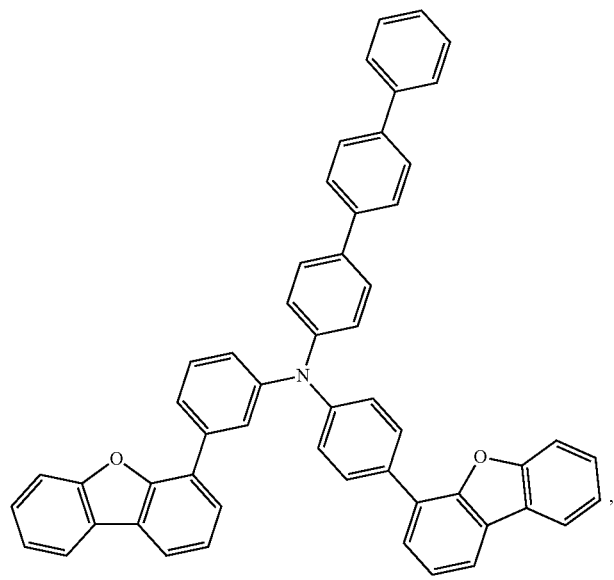

-continued
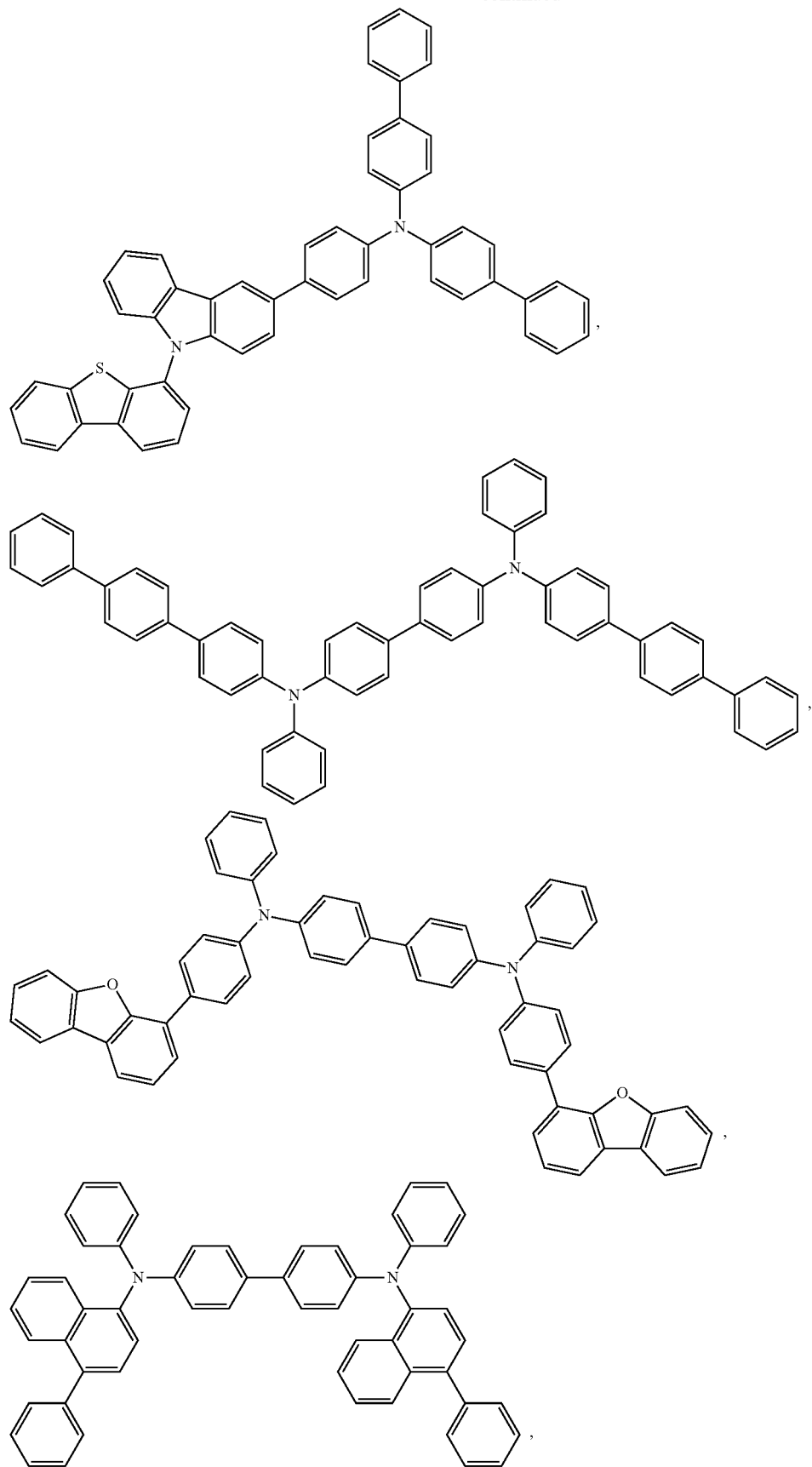

217
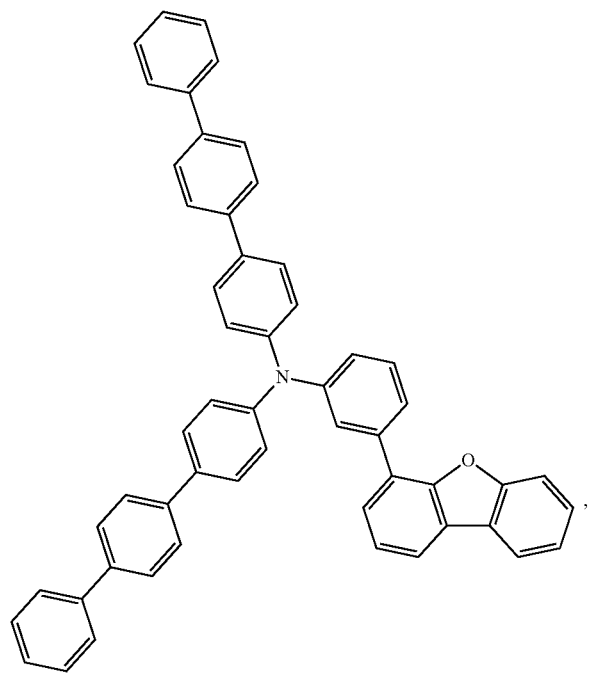
218
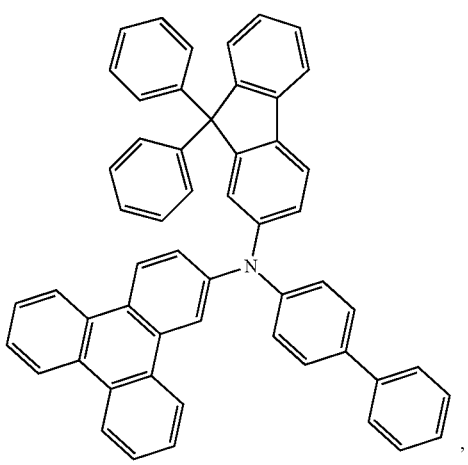
-continued
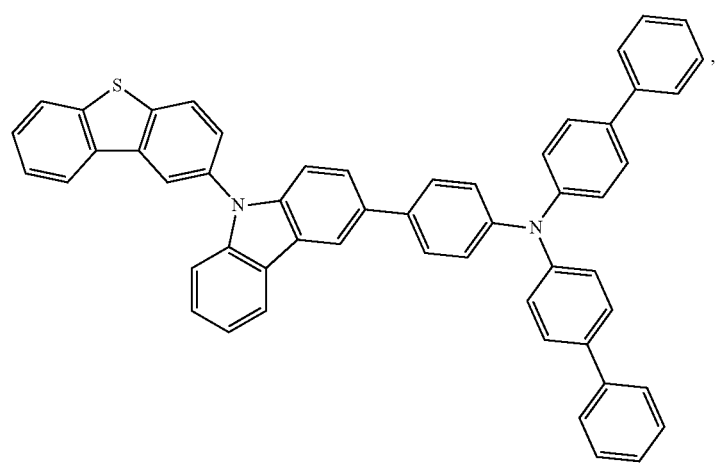

219 220
-continued
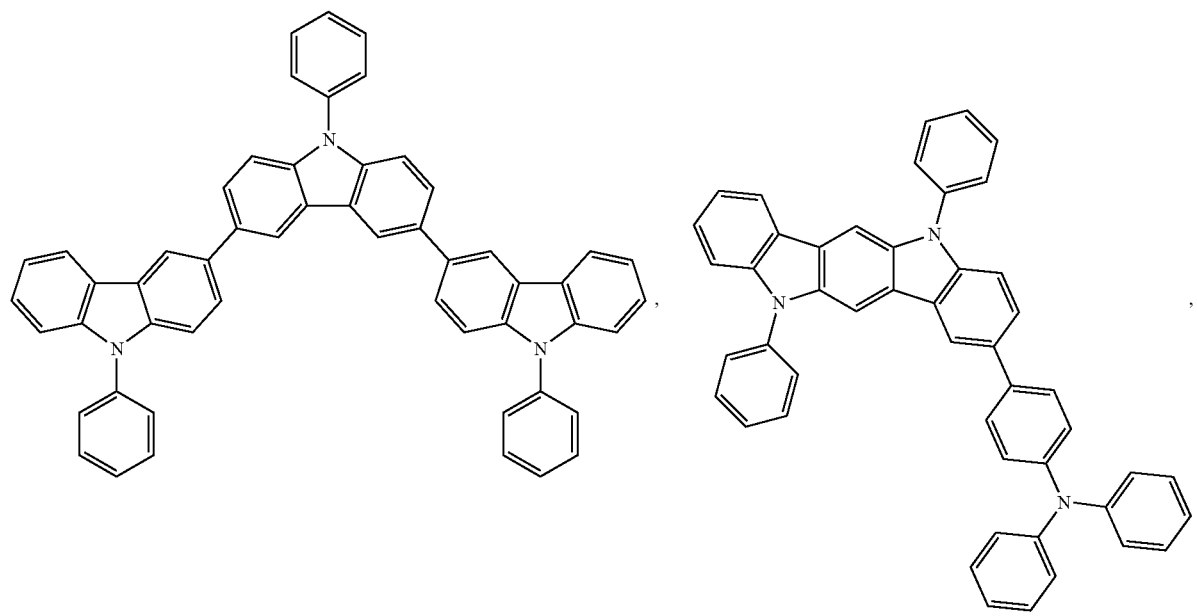
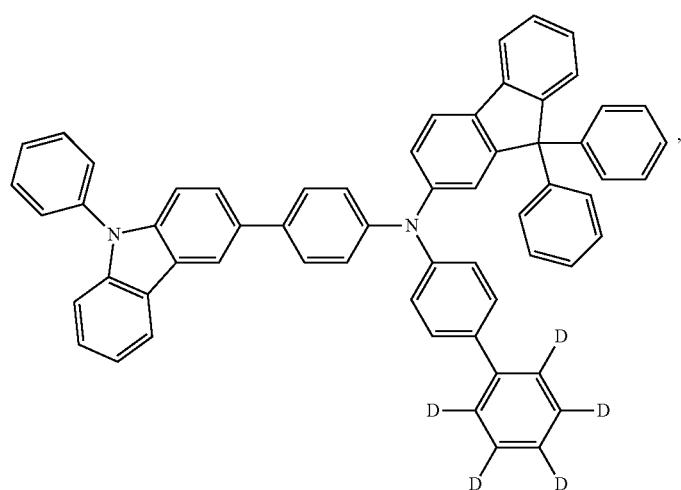
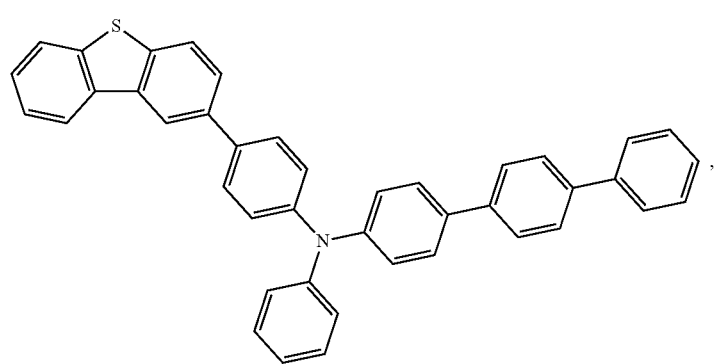

221 222
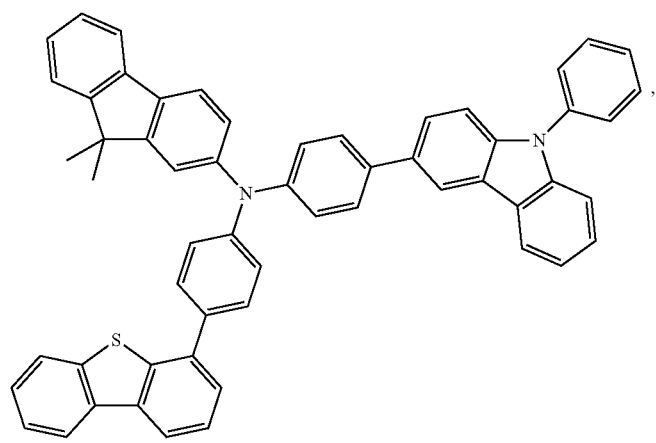
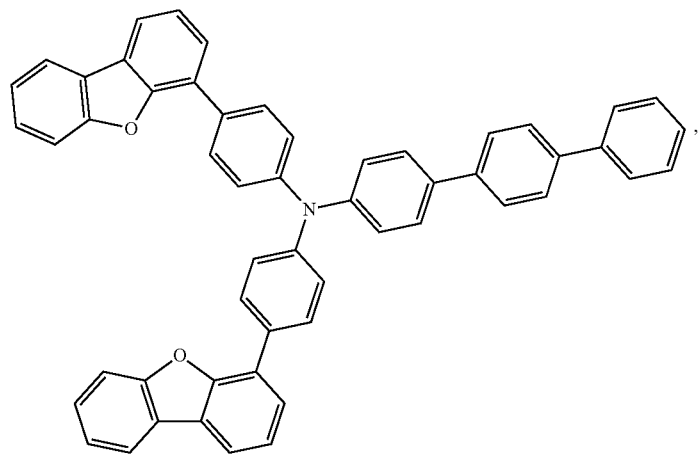
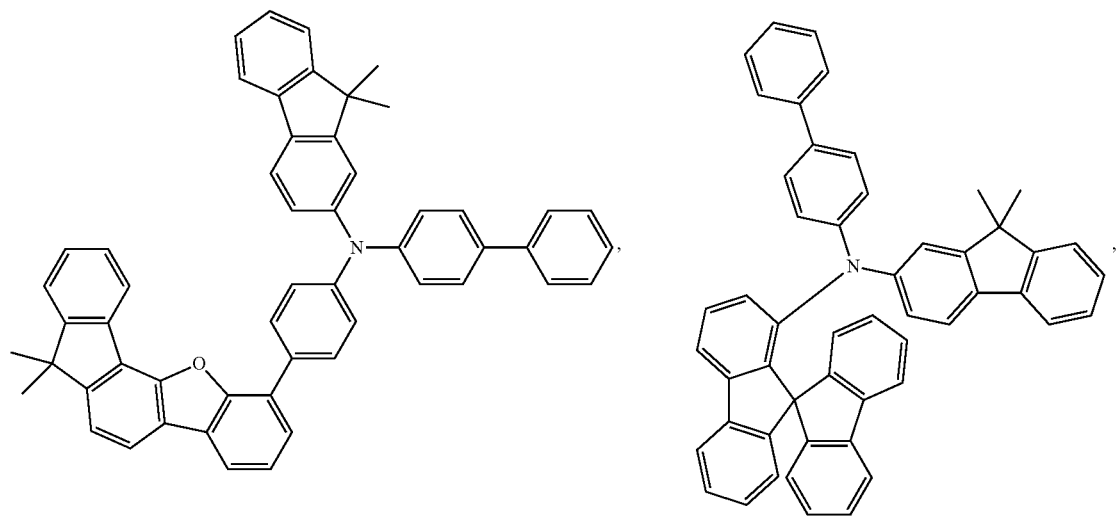

-continued
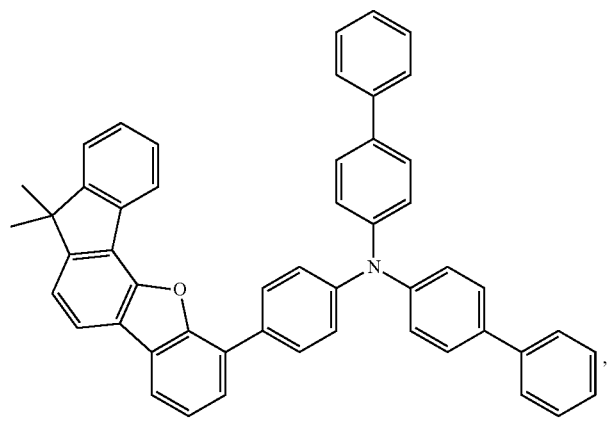
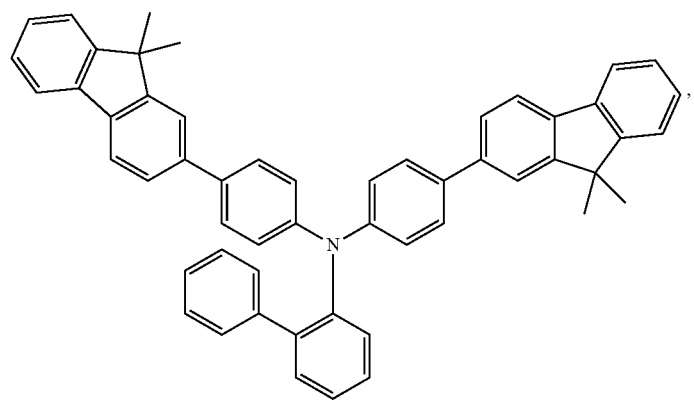
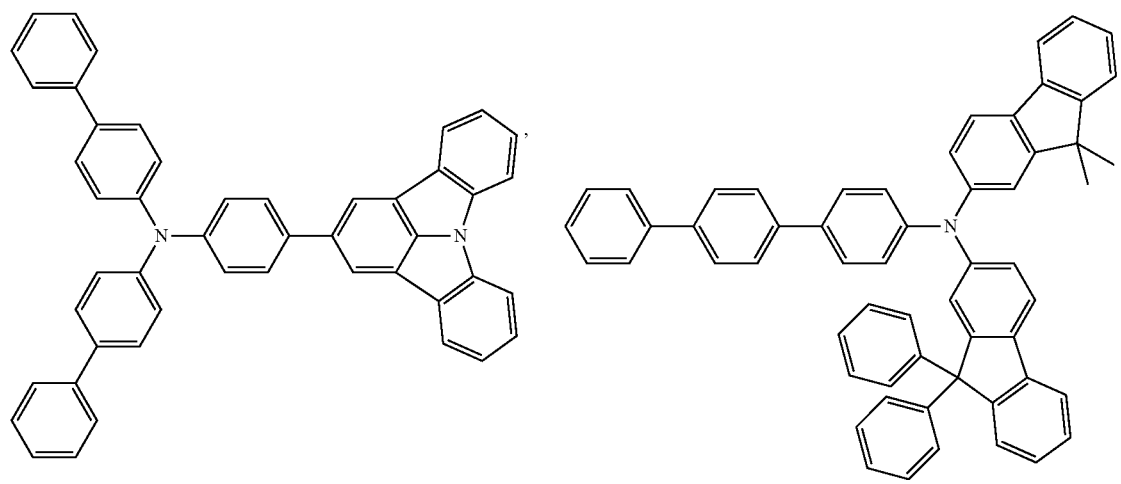

-continued
225
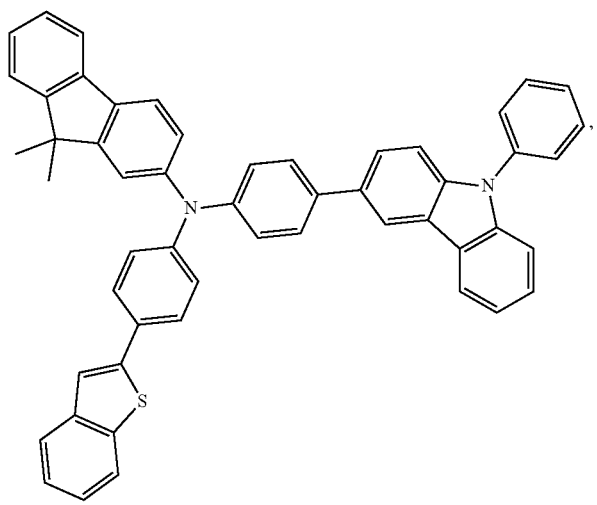
226
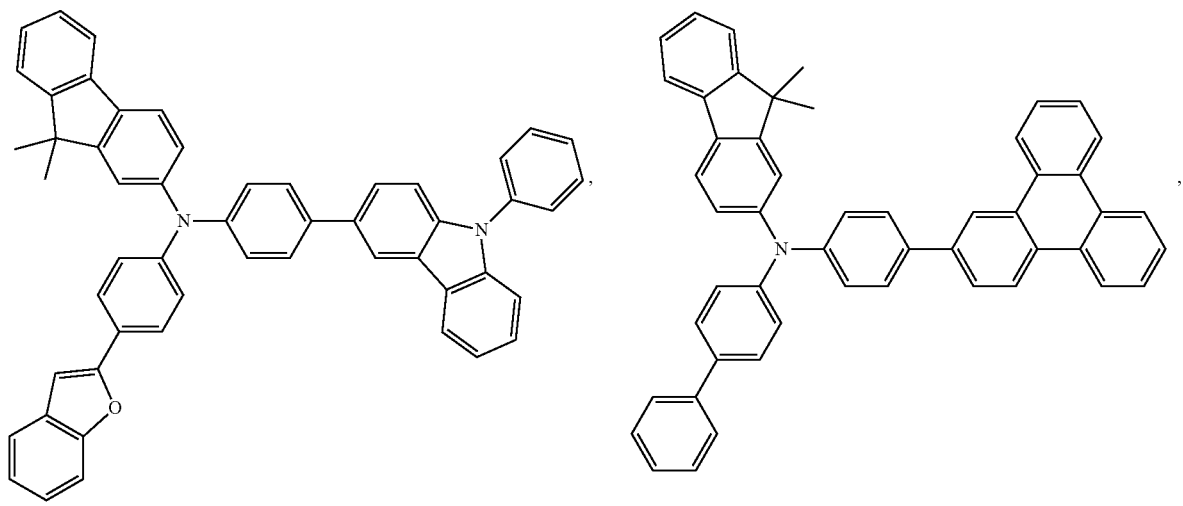
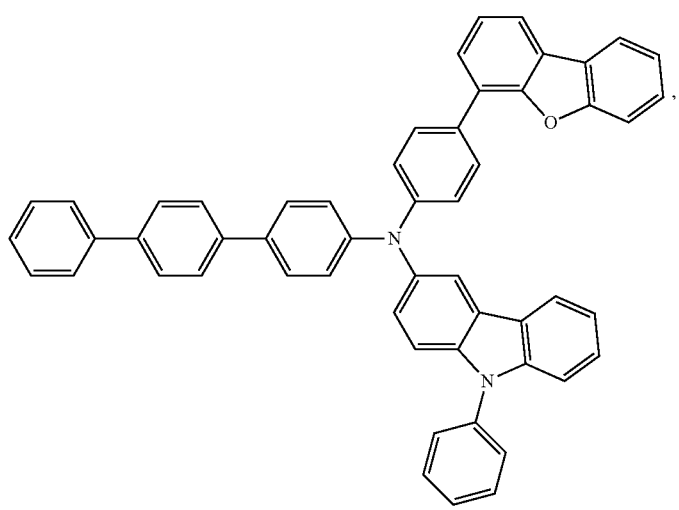

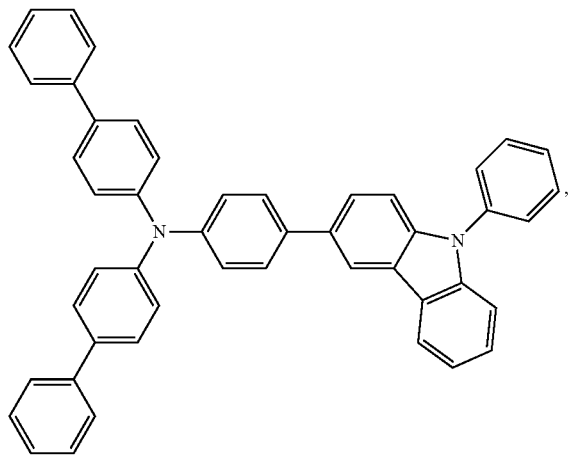
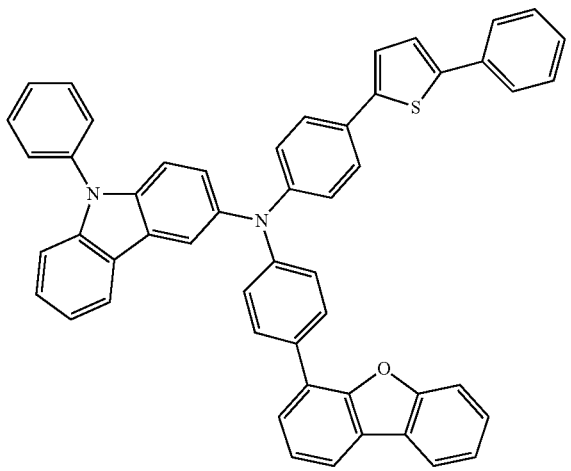
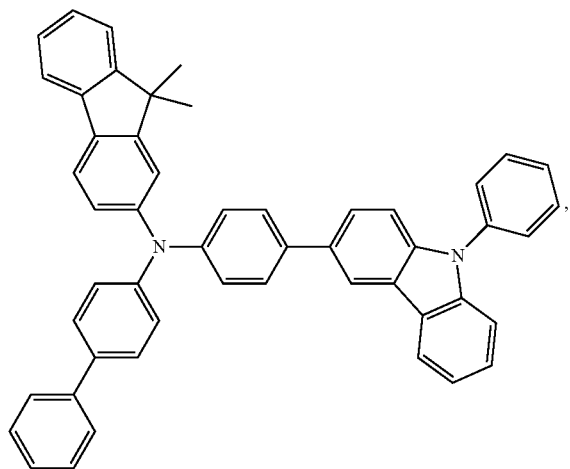
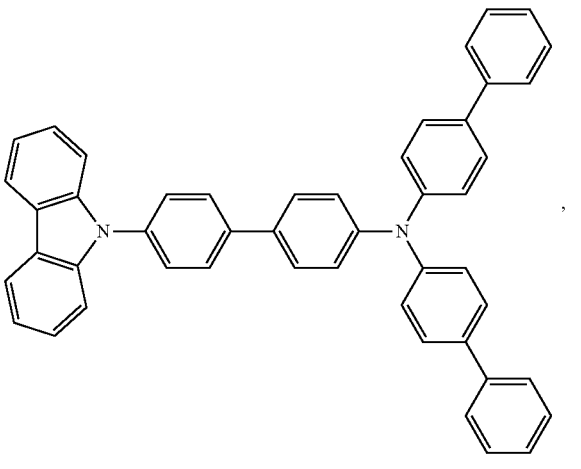
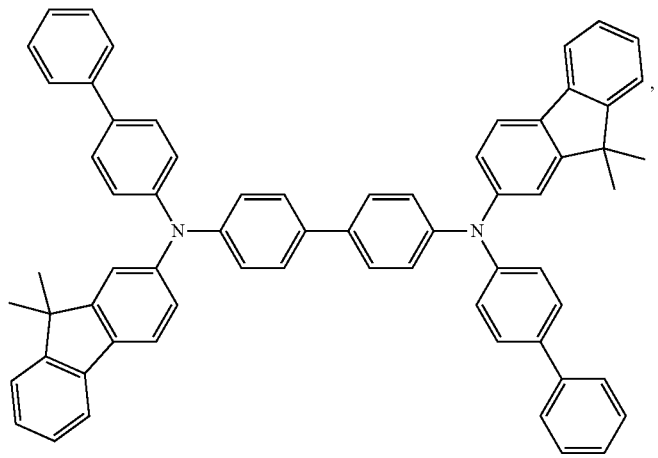

-continued
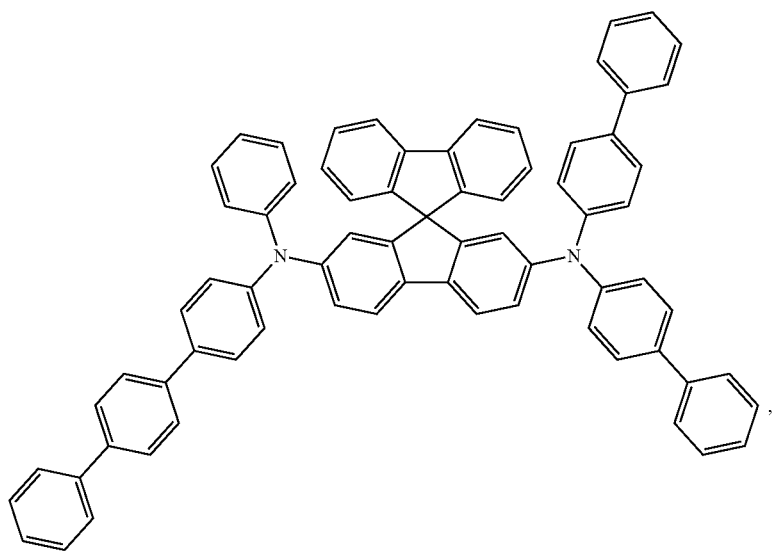
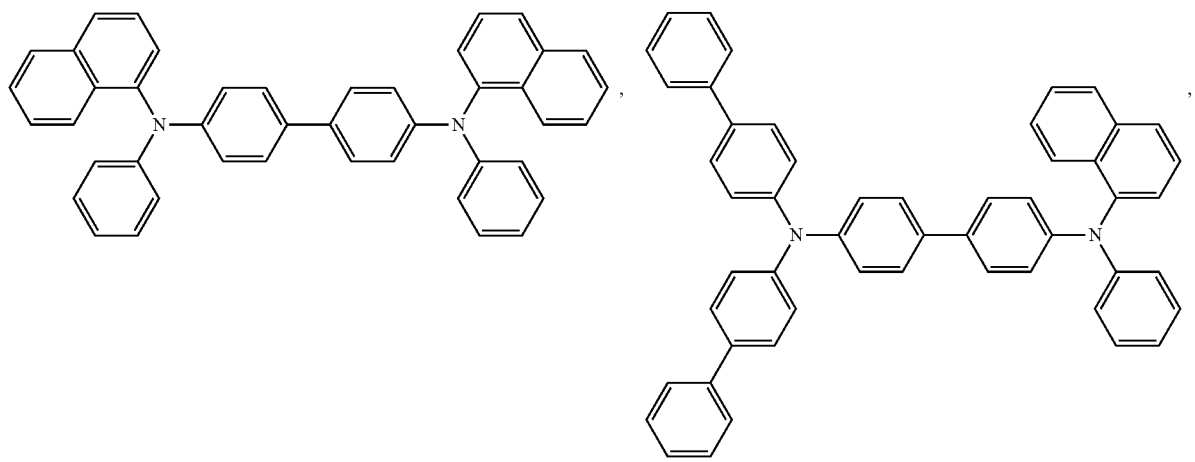
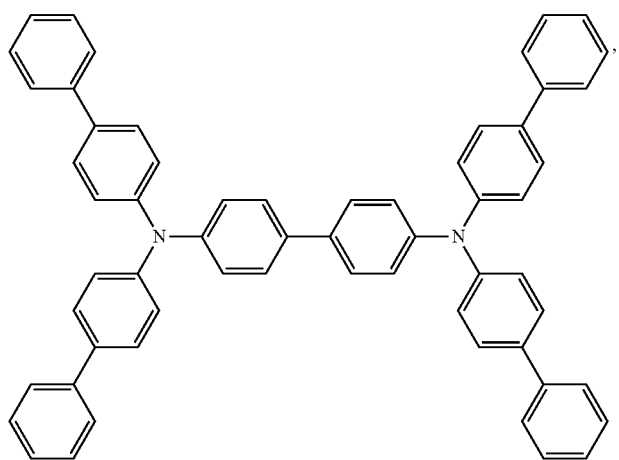

-continued
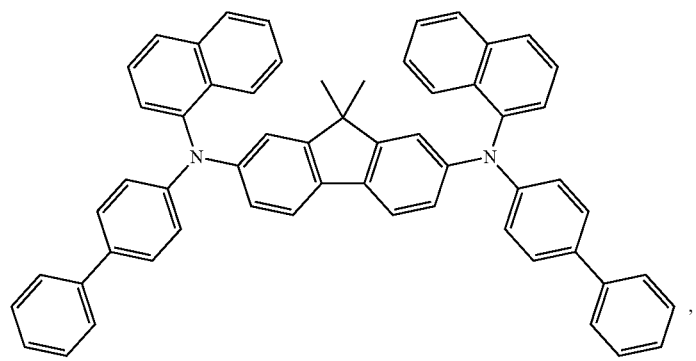
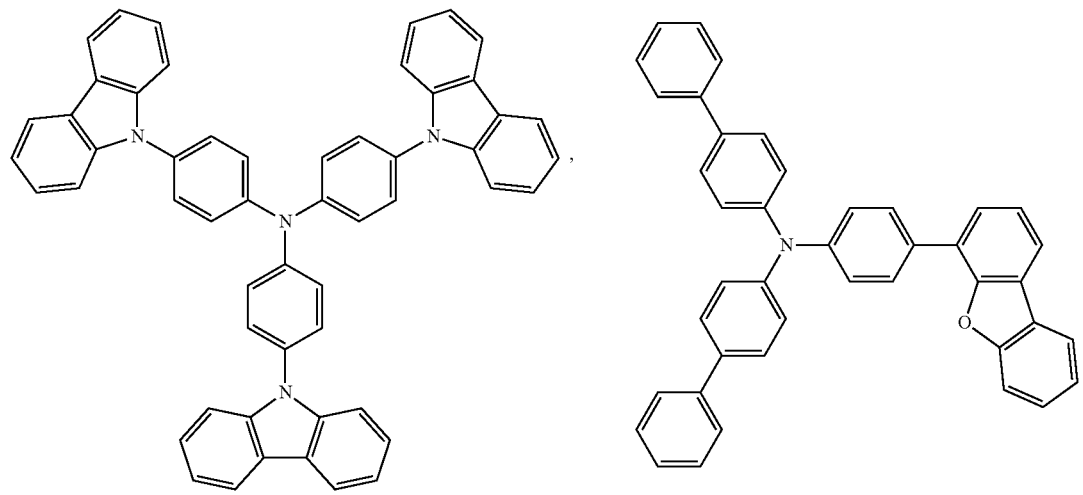
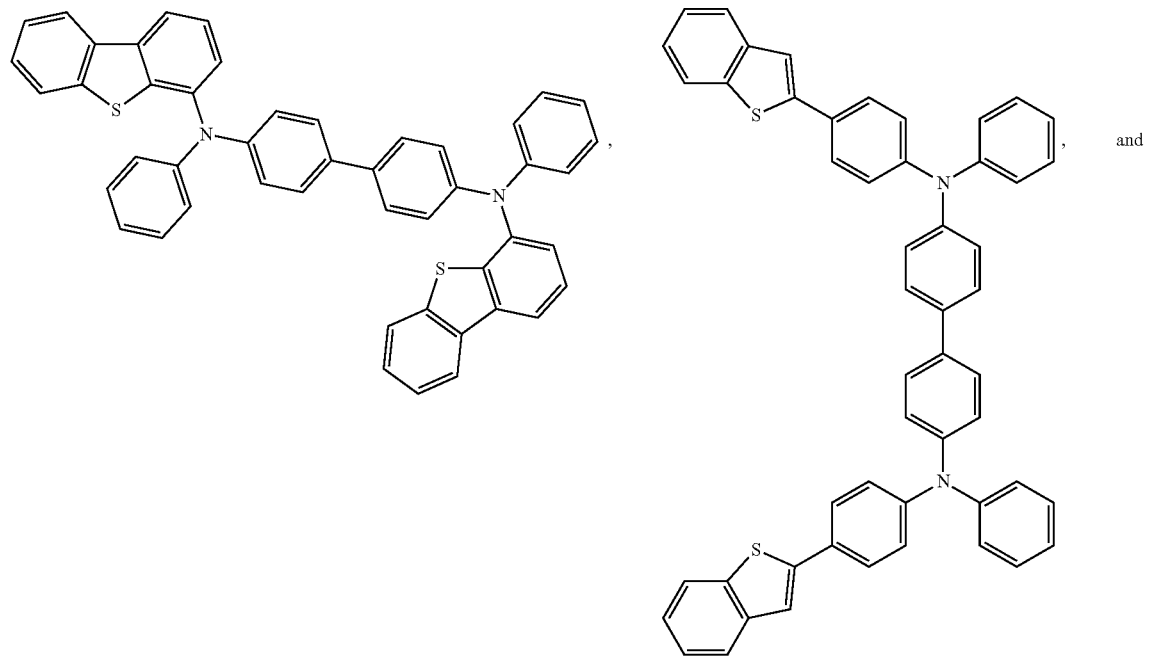
and

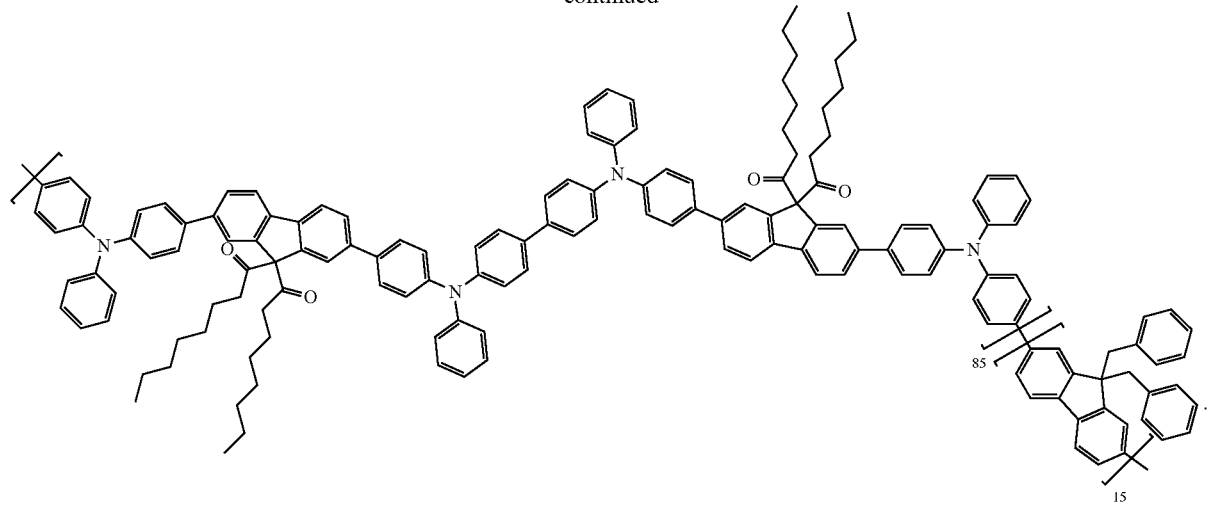

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

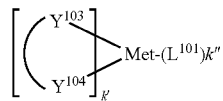

wherein Met is a metal; $(Y^{103}-Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

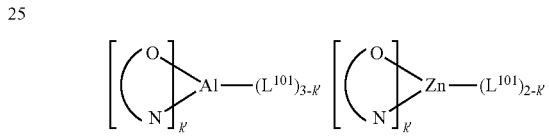

wherein (O—N) is a bidentate ligand, having metal coordinated to atoms O and N.

In another aspect, Met is selected from Ir and Pt. In a further aspect, $(Y^{103}-Y^{104})$ is a carbene ligand.

Examples of organic compounds used as host are selected from the group consisting of aromatic hydrocarbon cyclic compounds such as benzene, biphenyl, triphenyl, triphenylene, tetraphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each option within each group may be unsubstituted or may be substituted by a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

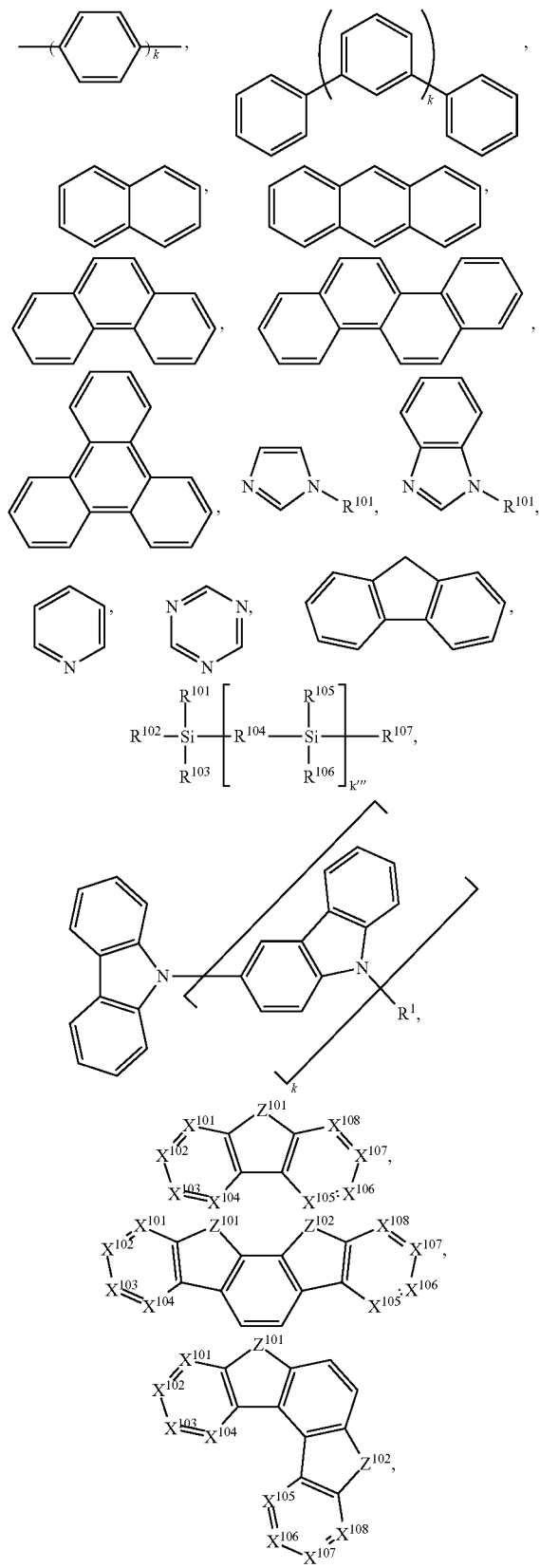

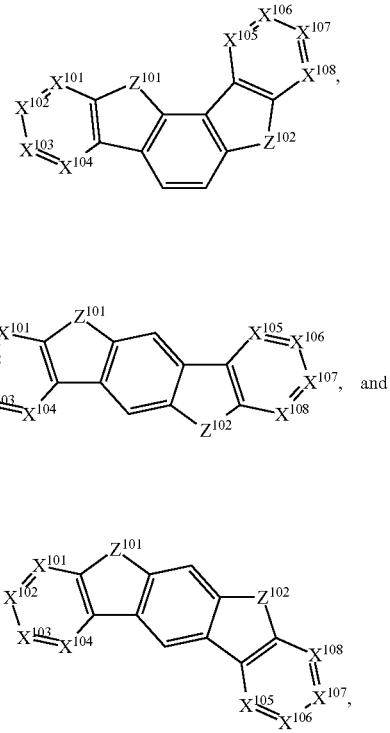

wherein each of $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, and when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.

$Z^{101}$ and $Z^{102}$ is selected from $NR^{101}$, O, or S.

Non-limiting examples of the Host materials that may be used in an OLED in combination with materials disclosed herein are exemplified below together with references that disclose those materials: EP2034538, EP2034538A, EP2757608, JP2007254297, KR20100079458, KR20120088644, KR20120129733, KR20130115564, TW201329200, US20030175553, US20050238919, US20060280965, US20090017330, US20090030202, US20090167162, US20090302743, US20090309488, US20100012931, US20100084966, US20100187984, US2010187984, US2012075273, US2012126221, US2013009543, US2013105787, US2013175519, US2014001446, US20140183503, US20140225088, US2014034914, U.S. Pat. No. 7,154,114, WO2001039234, WO2004093207, WO2005014551, WO2005089025, WO2006072002, WO2006114966, WO2007063754, WO2008056746, WO2009003898, WO2009021126, WO2009063833, WO2009066778, WO2009066779, WO2009086028, WO2010056066, WO2010107244, WO2011081423, WO2011081431, WO2011086863, WO2012128298, WO2012133644, WO2012133649, WO2013024872, WO2013035275, WO2013081315, WO2013191404, WO2014142472.

237 238
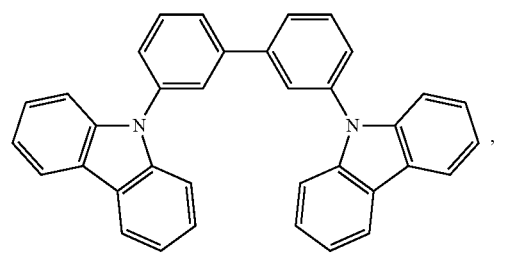
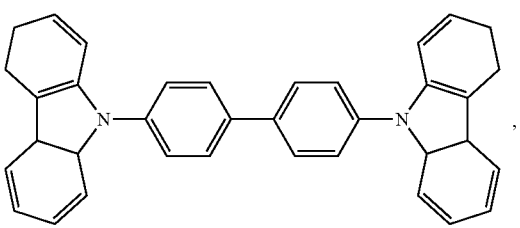
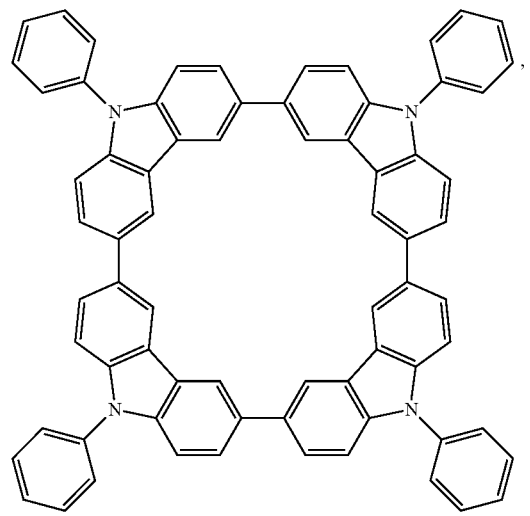
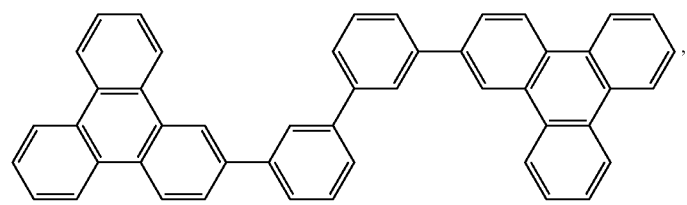
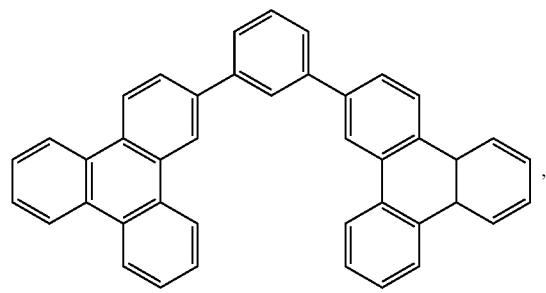
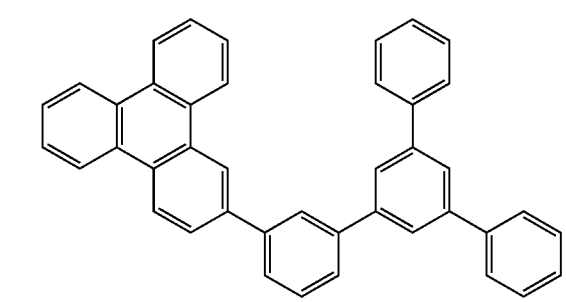
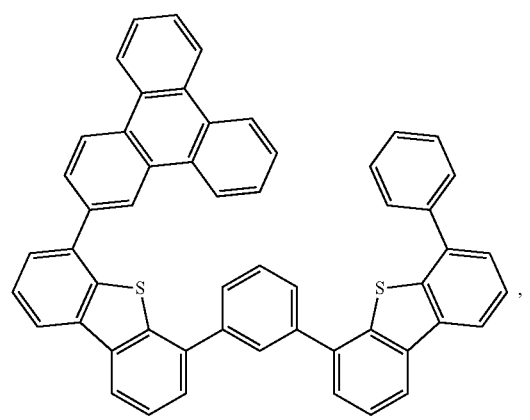
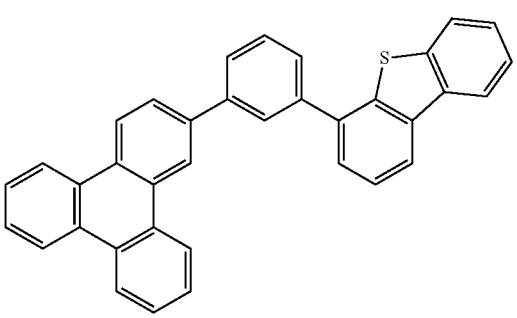

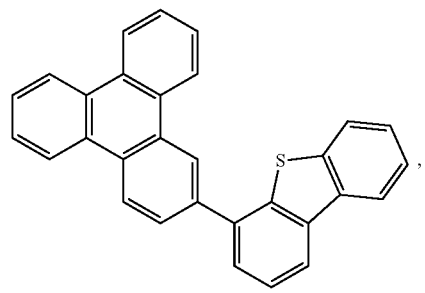,
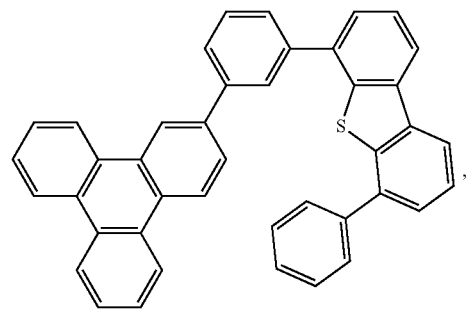,
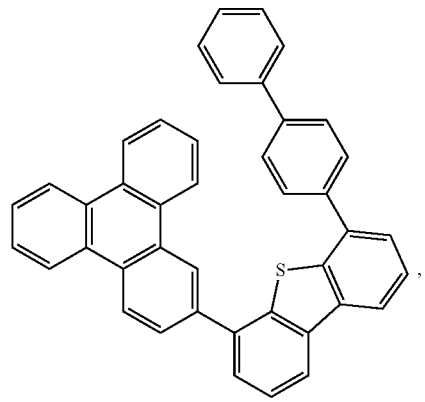,
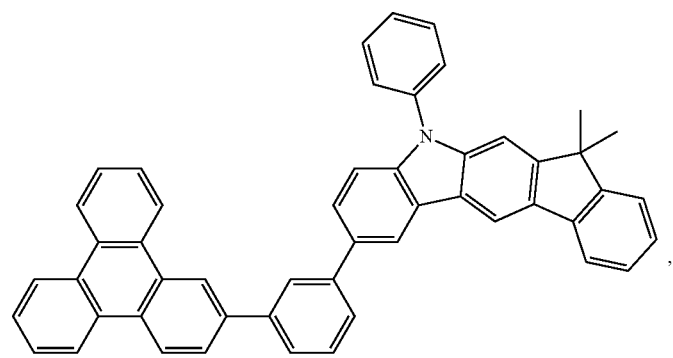,
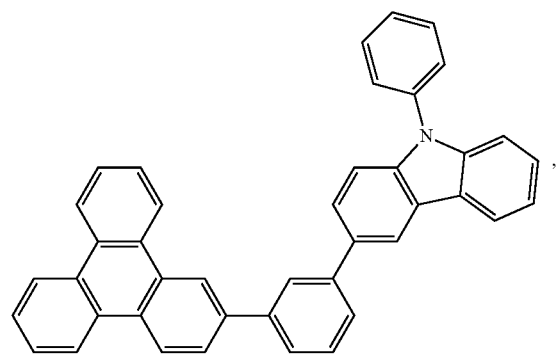,
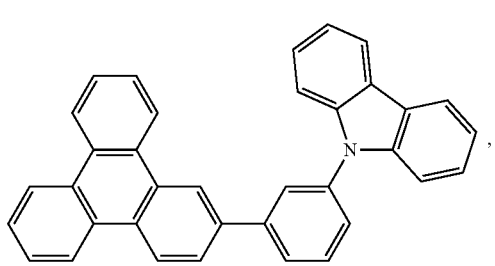,
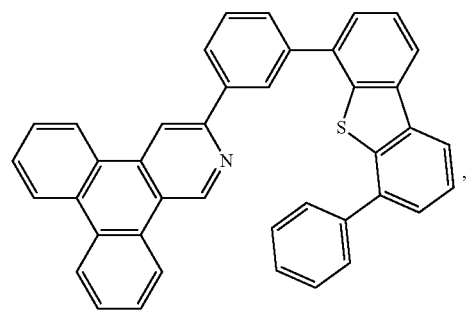,
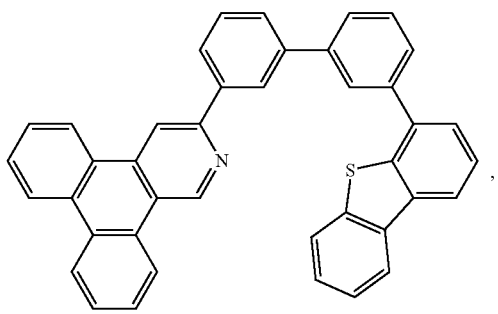,
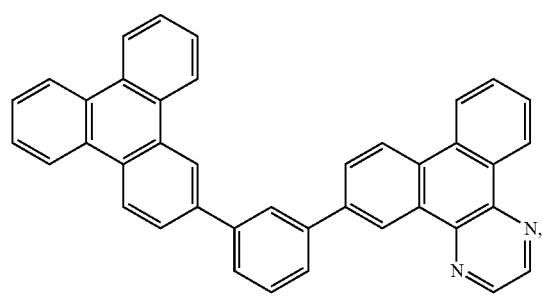,
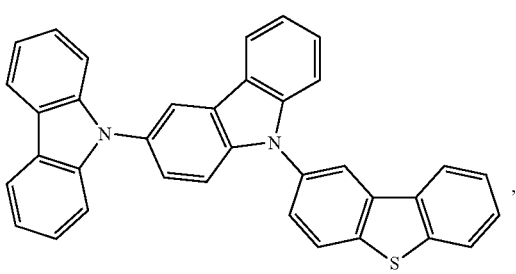,

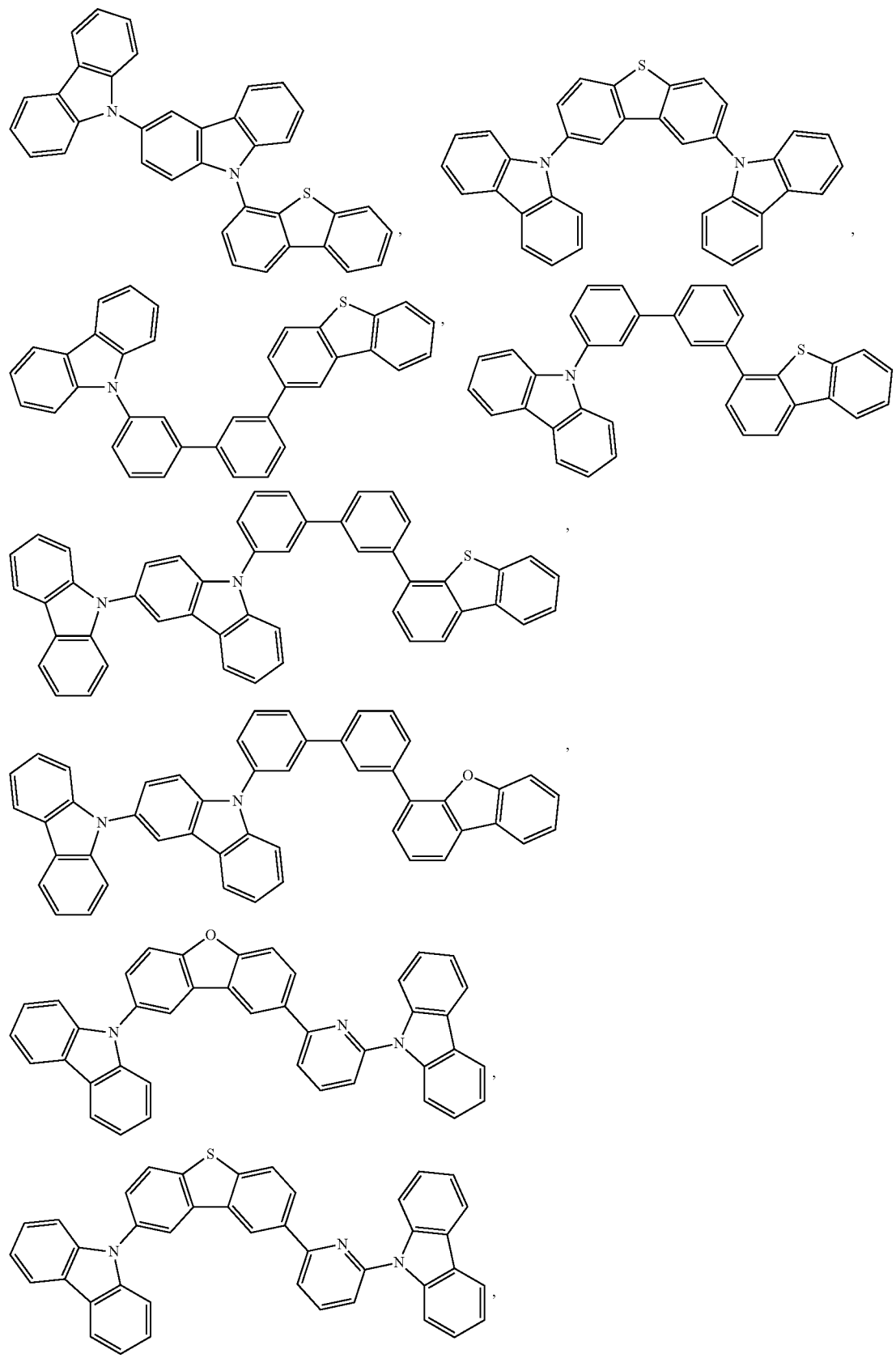

243 244
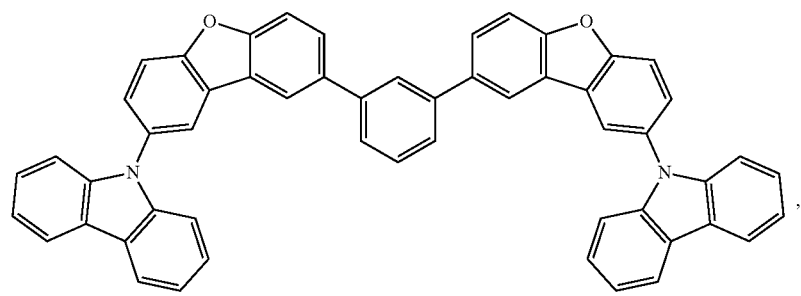
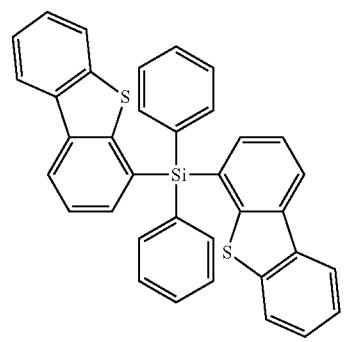
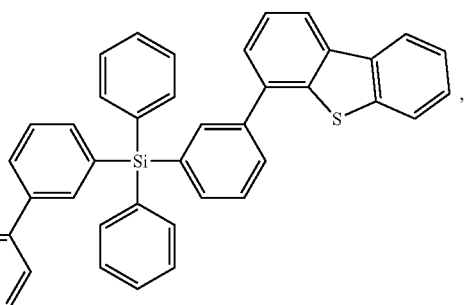
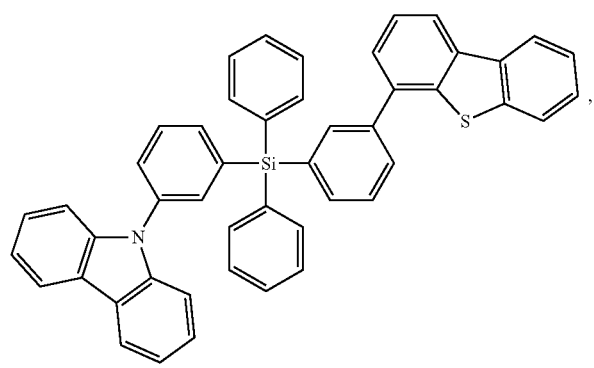
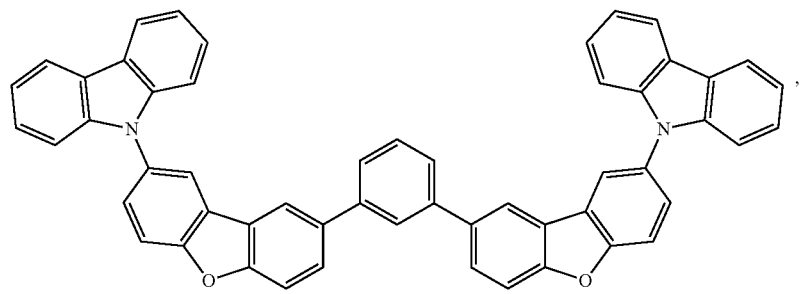
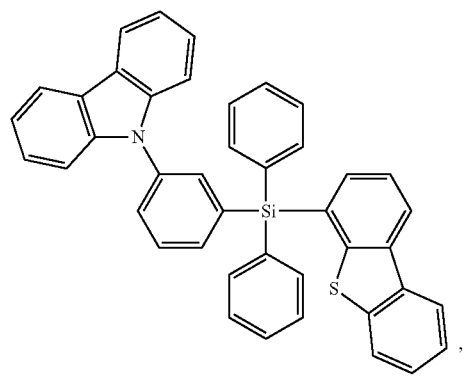
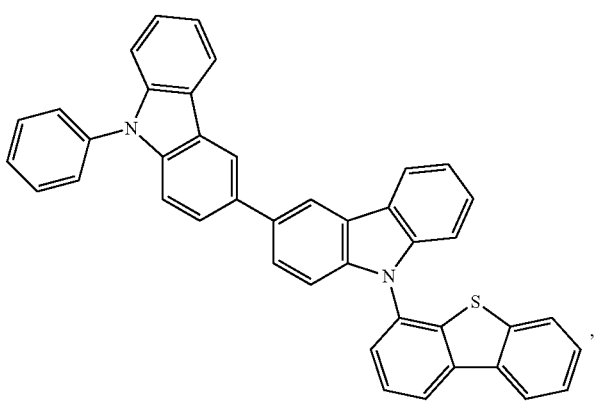

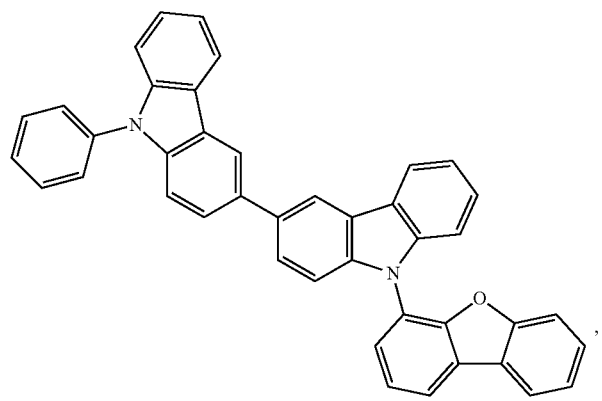
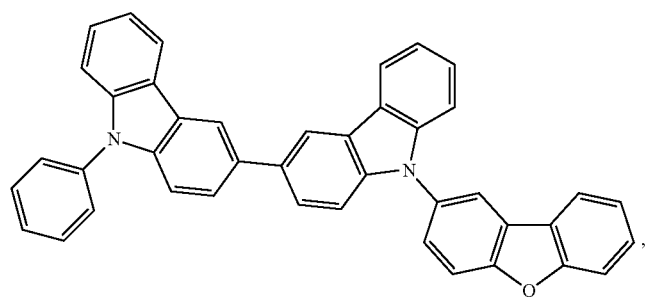
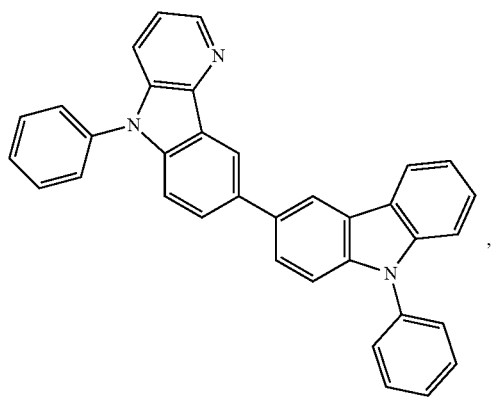
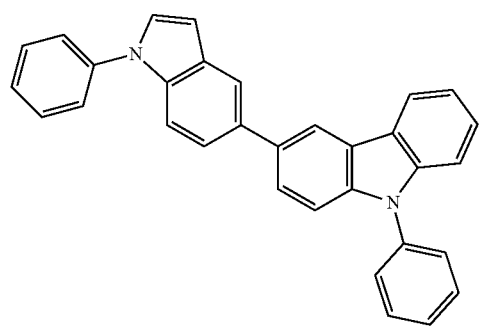
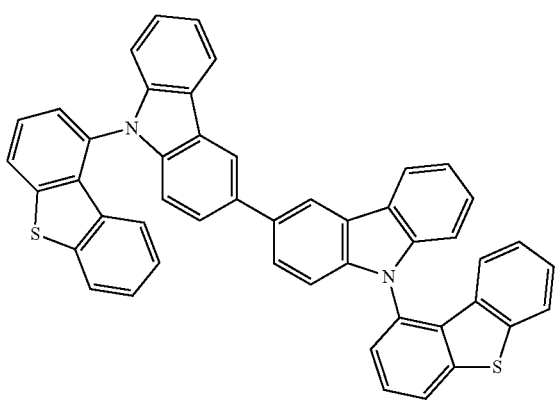
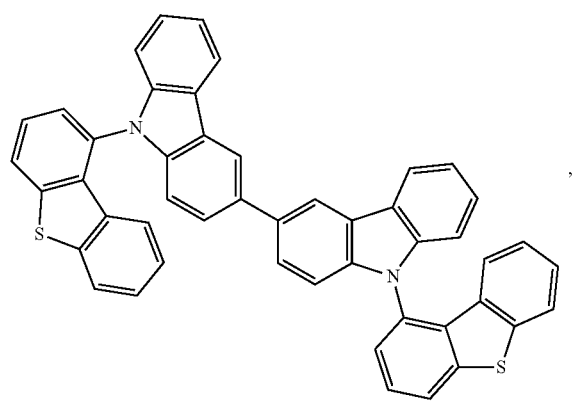

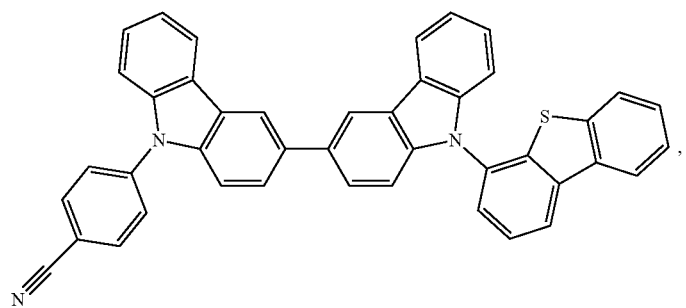
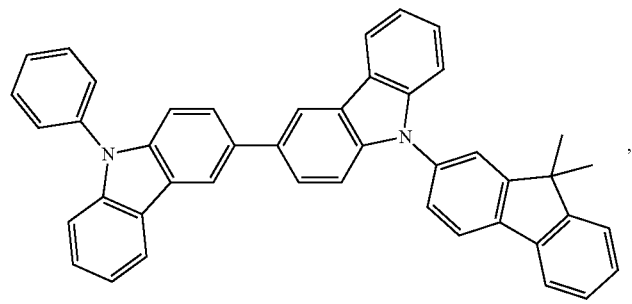
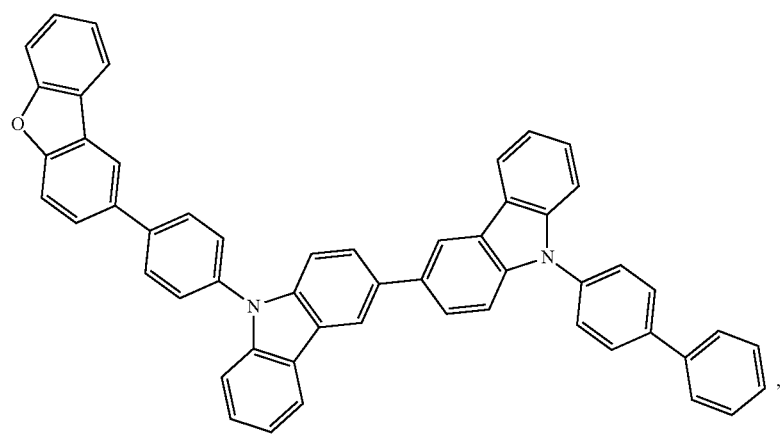
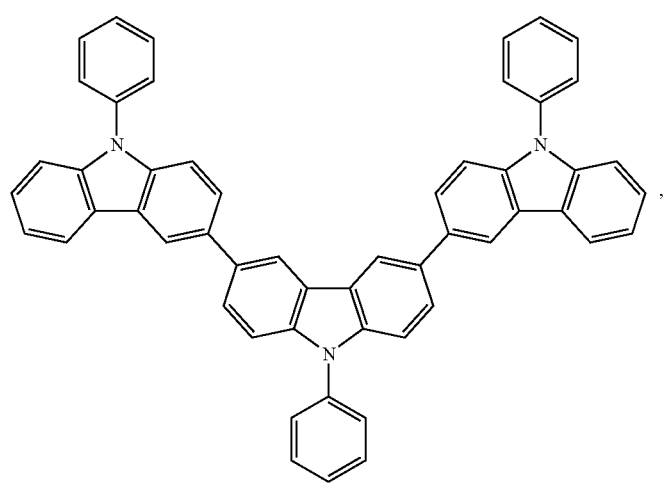

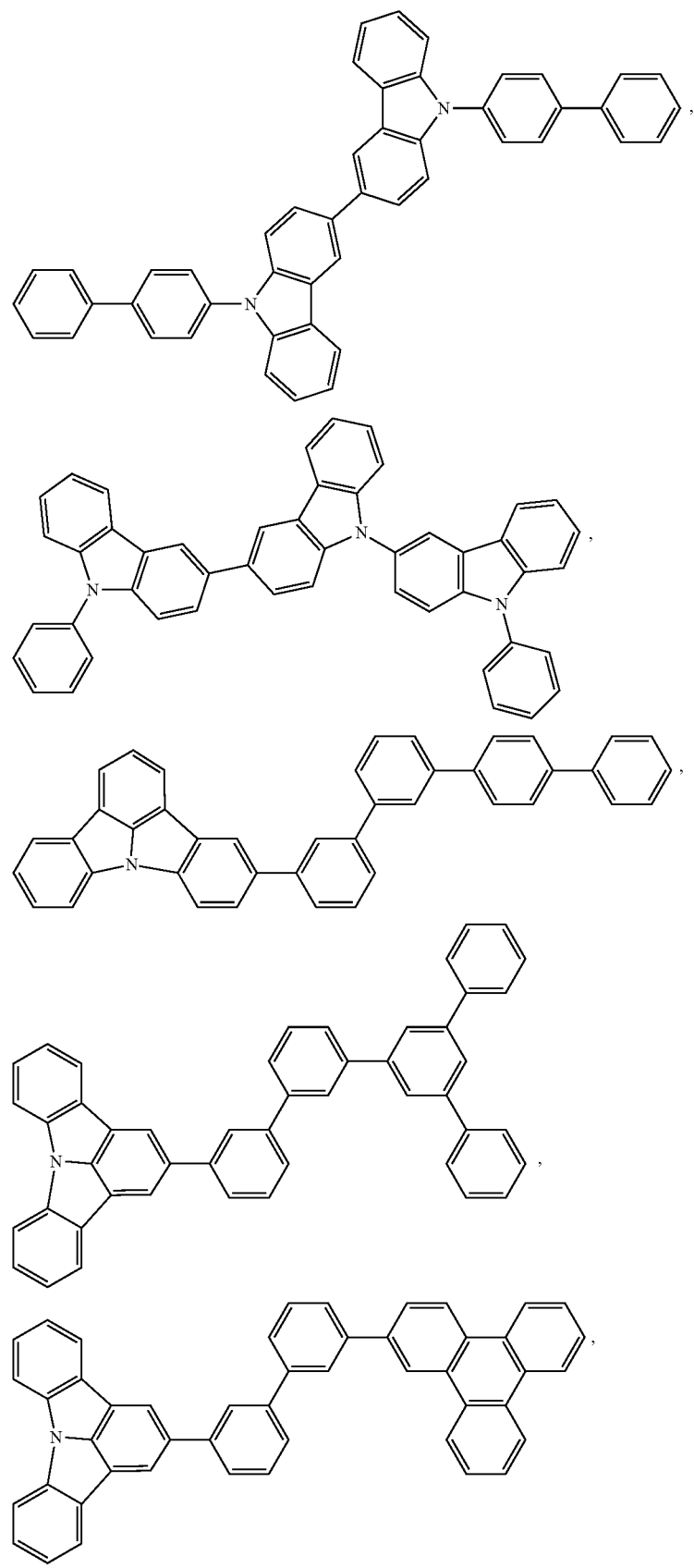

-continued
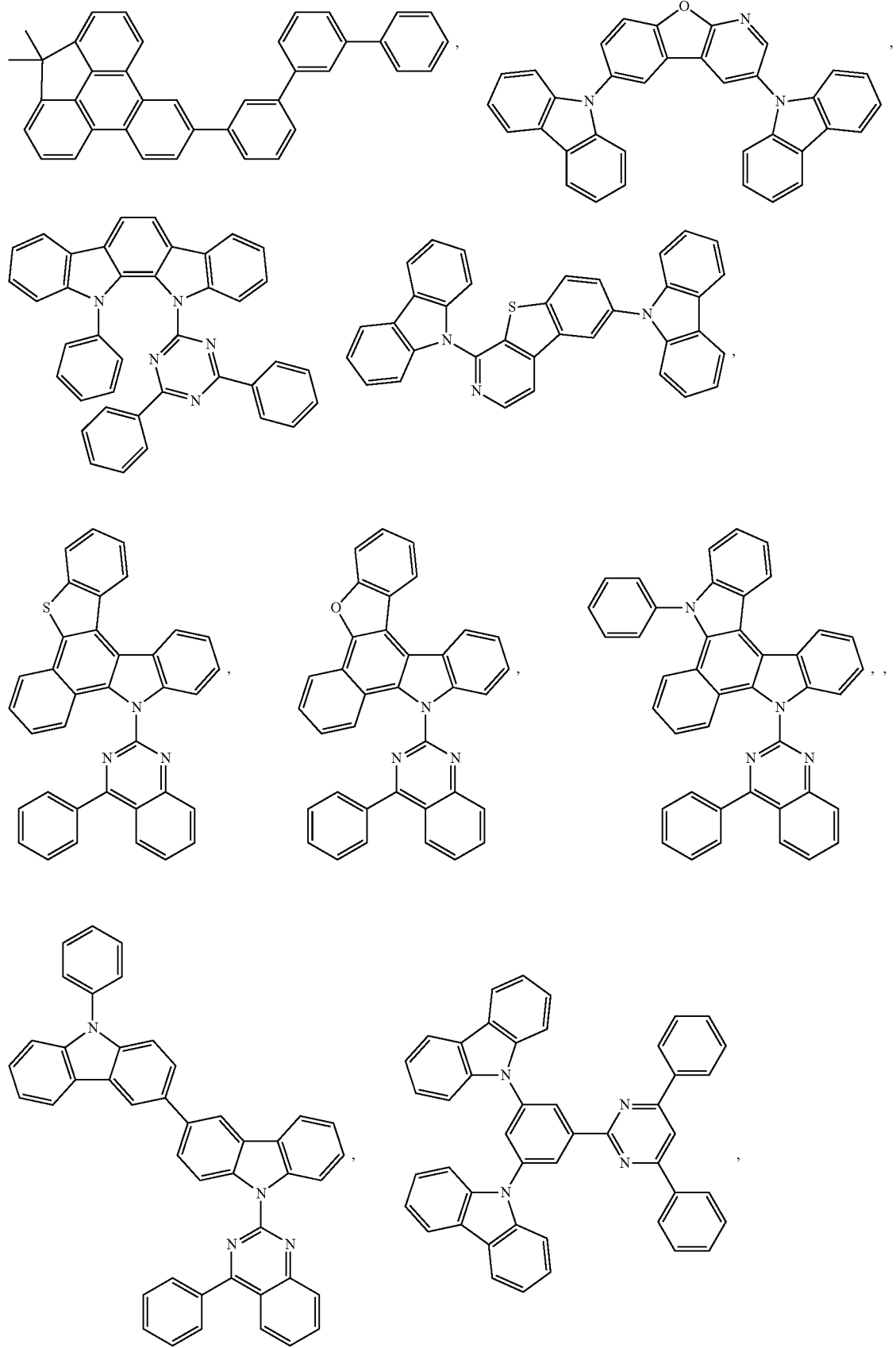

253
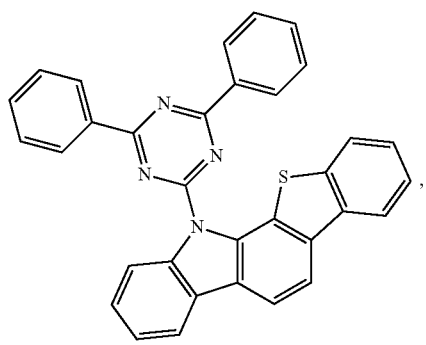
254
-continued
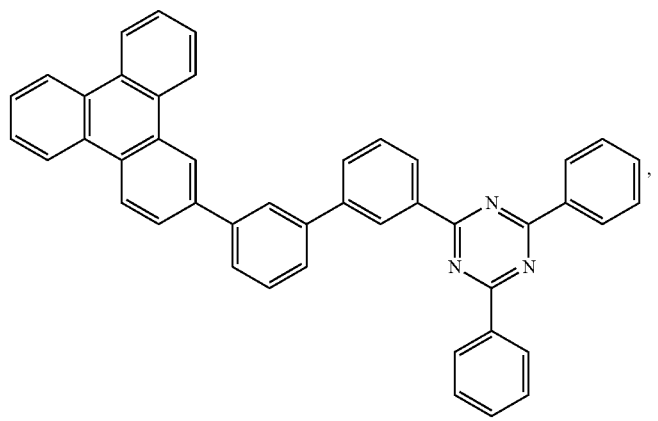
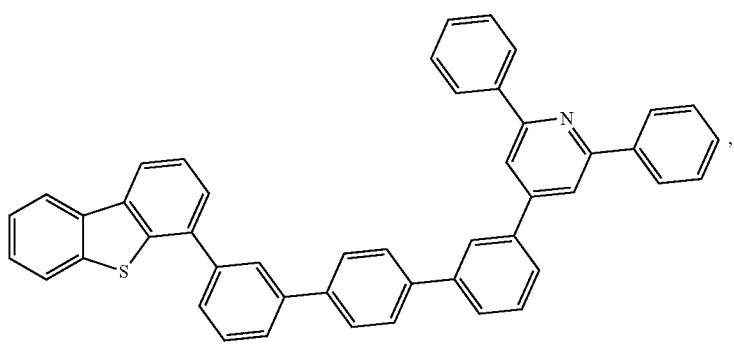
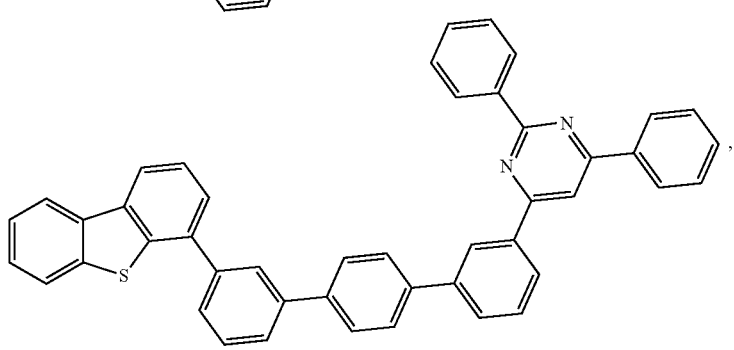
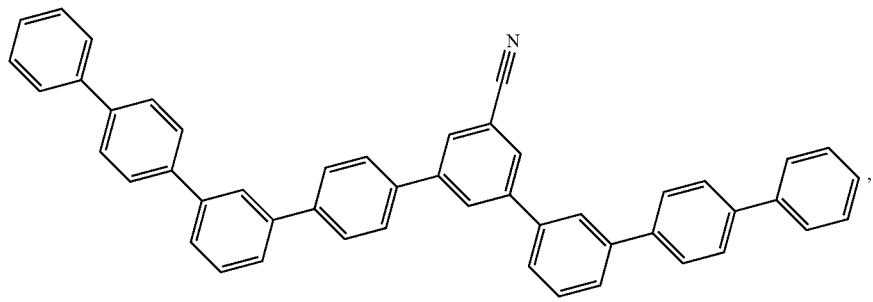
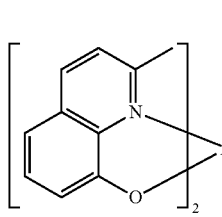
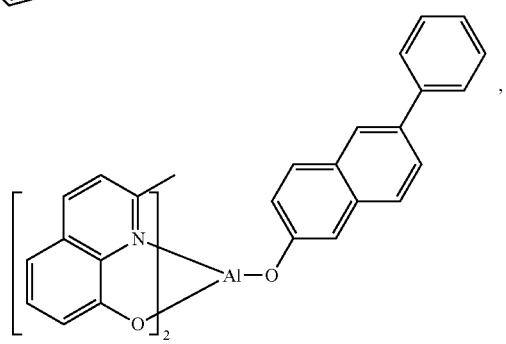

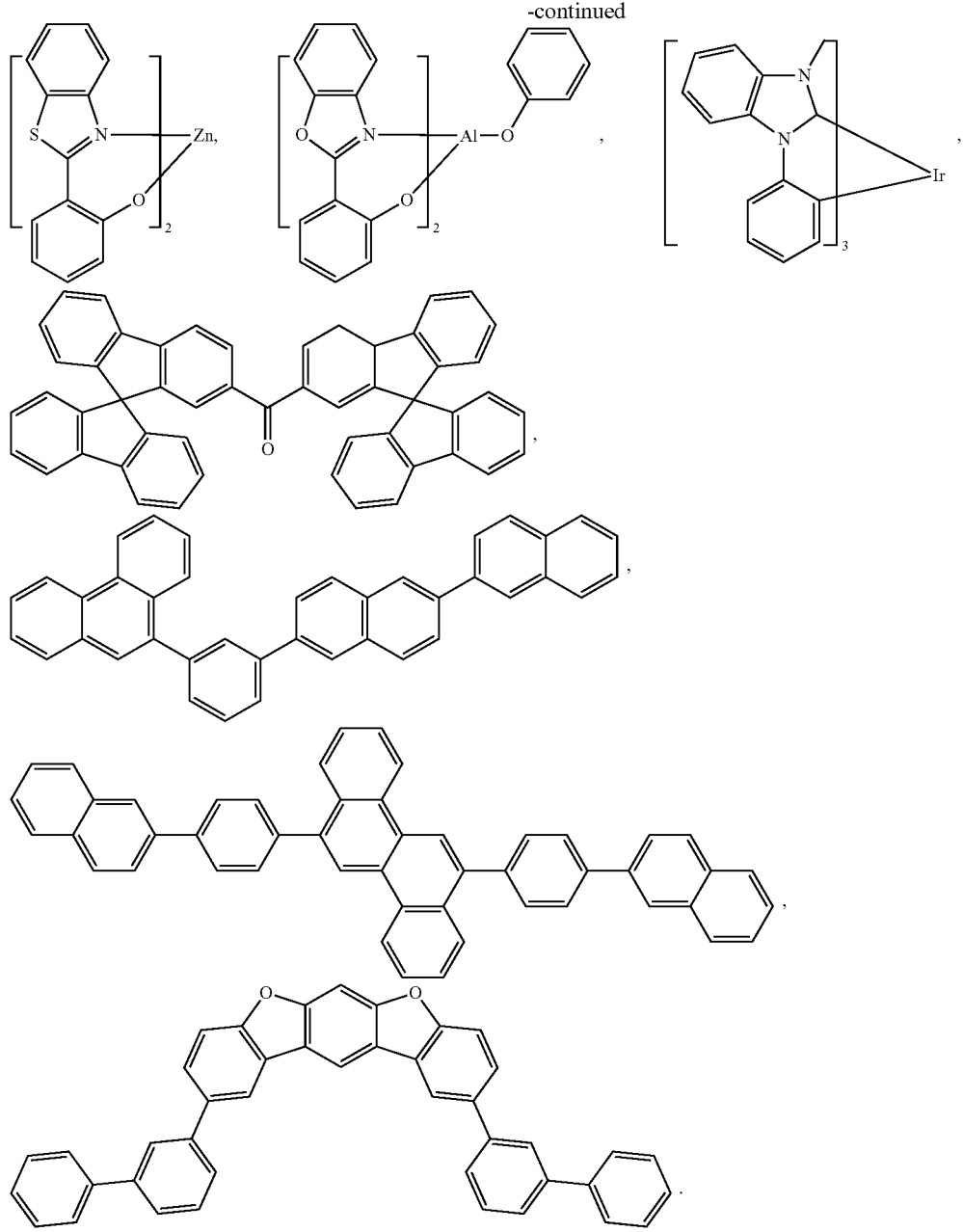

Emitter:

An emitter example is not particularly limited, and any compound may be used as long as the compound is typically used as an emitter material. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Pat. No. 6,699,599, U.S. Pat. No. 6,916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. No. 6,303,238, U.S. Pat. No. 6,413,656, U.S. Pat. No. 6,653,654, U.S. Pat. No. 6,670,645, U.S. Pat. No. 6,687,266, U.S. Pat. No. 6,835,469, U.S. Pat. No. 6,921,915, U.S. Pat. No. 7,279,704, U.S. Pat. No. 7,332,232, U.S. Pat. No. 7,378,162, U.S. Pat. No. 7,534,505, U.S. Pat. No. 7,675,228, U.S. Pat. No. 7,728,137, U.S. Pat. No. 7,740,957, U.S. Pat. No. 7,759,489, U.S. Pat. No. 7,951,947, U.S. Pat. No. 8,067,099, U.S. Pat. No. 8,592,586, U.S. Pat. No. 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.
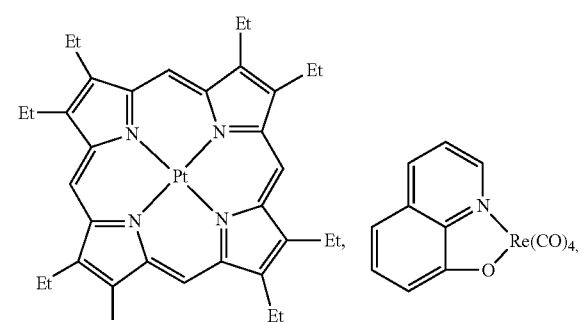
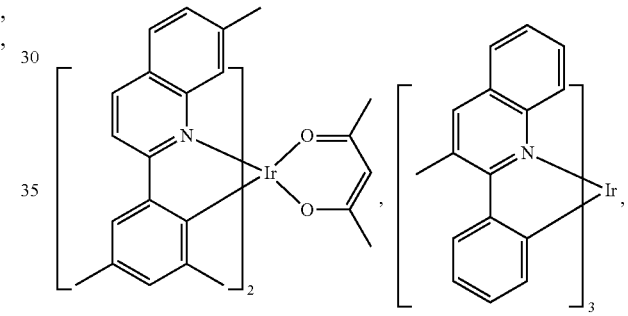
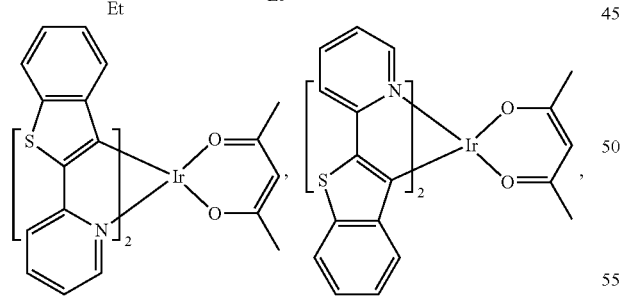
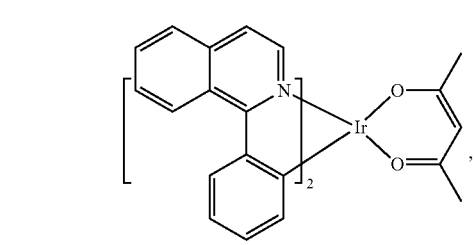
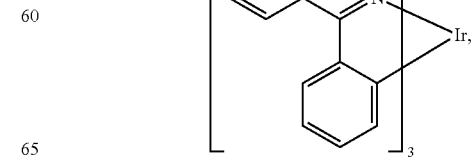
-continued
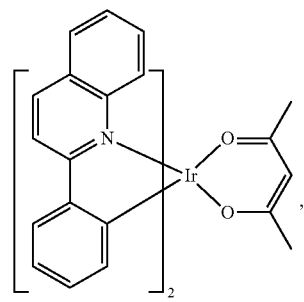
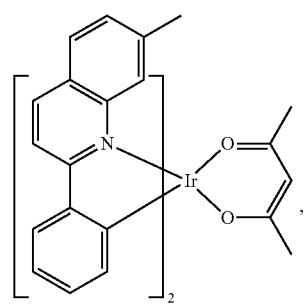
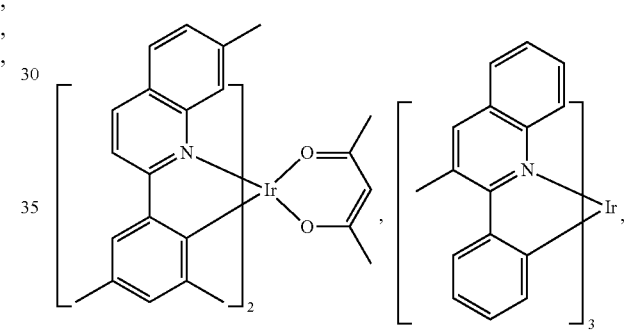
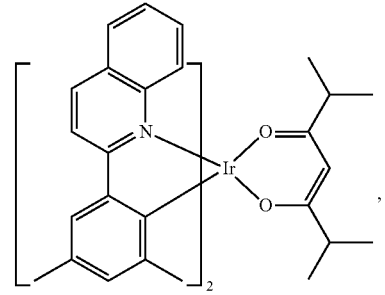
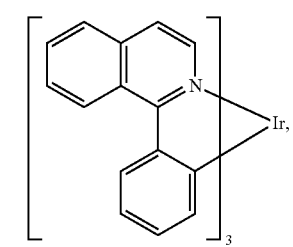

259
-continued
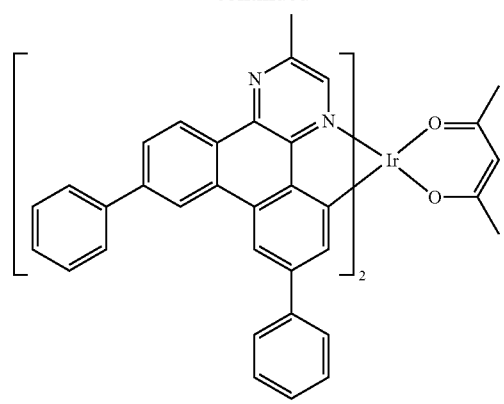
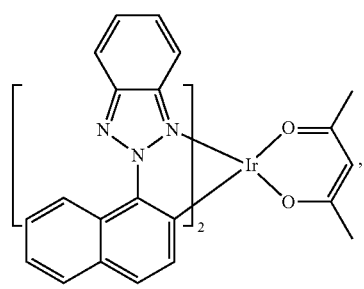
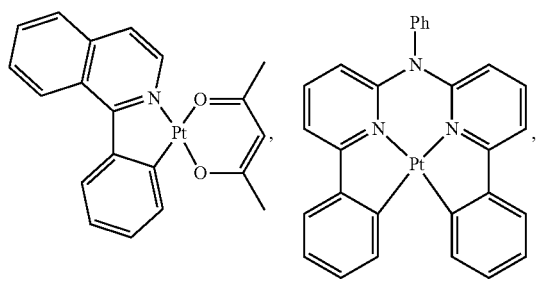
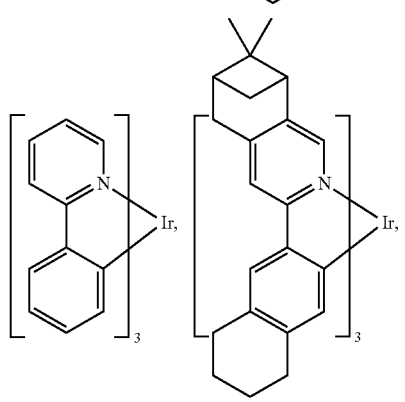
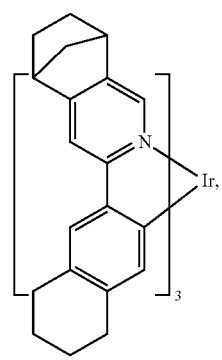
260
-continued
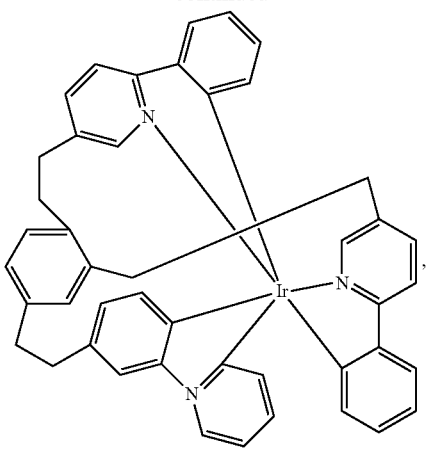
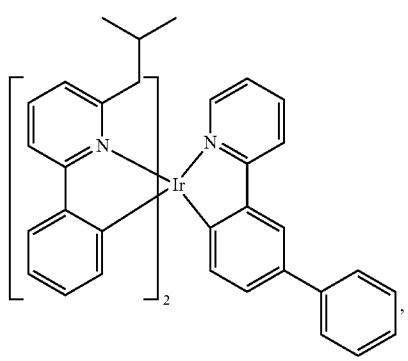
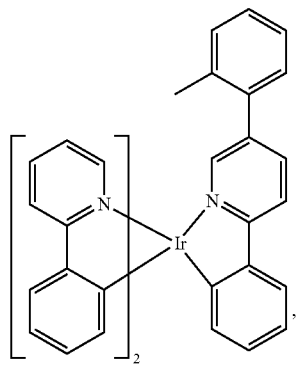
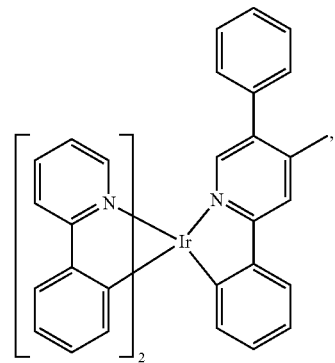

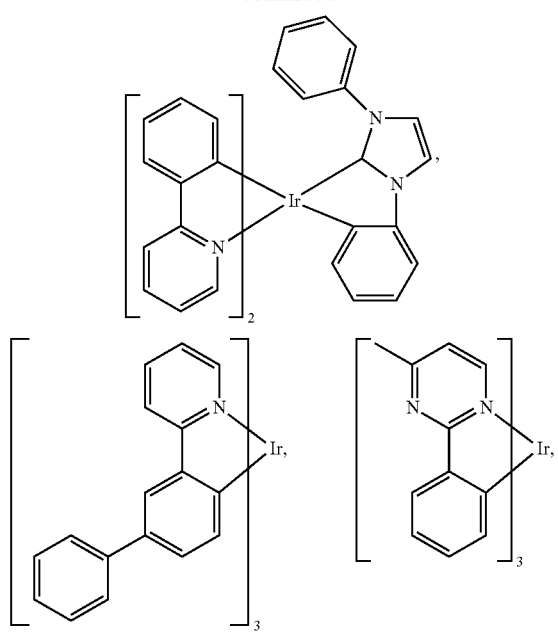
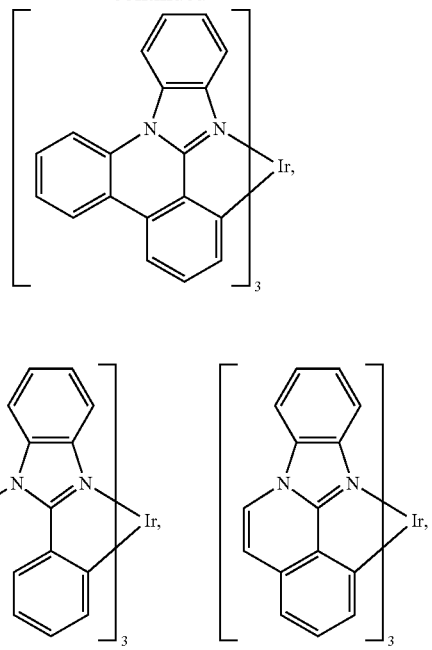
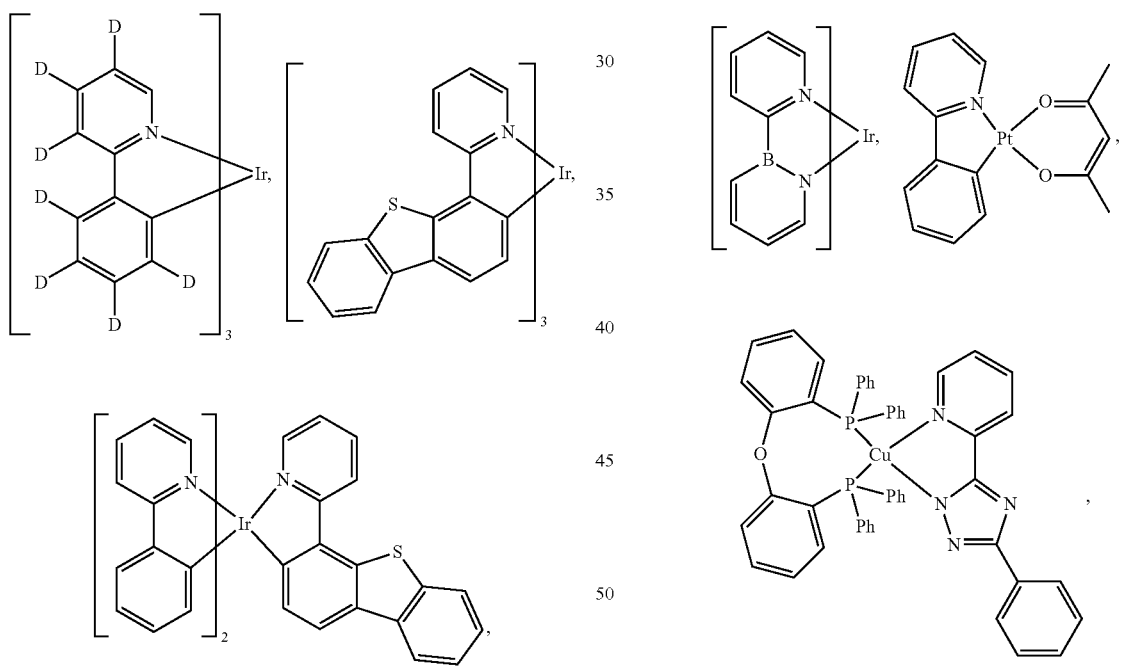
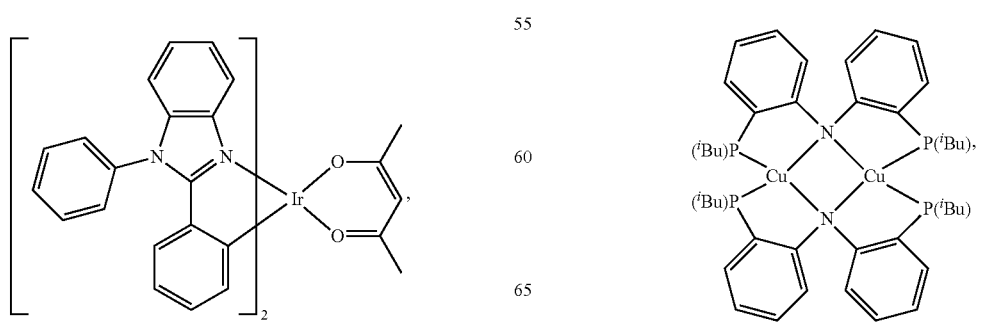

263
-continued
264
-continued
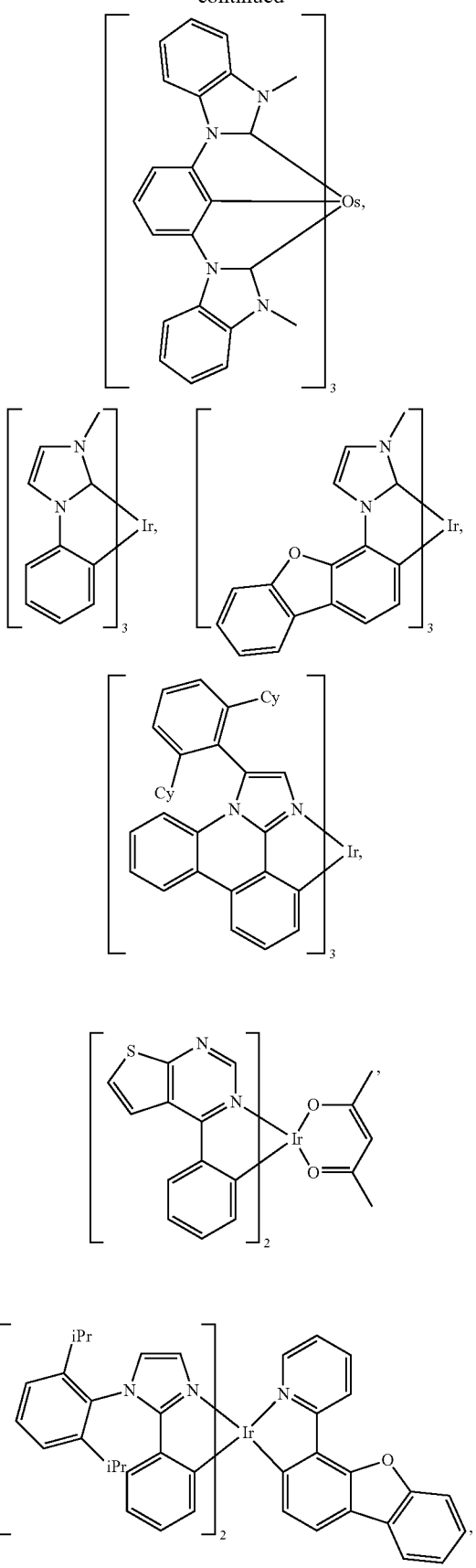
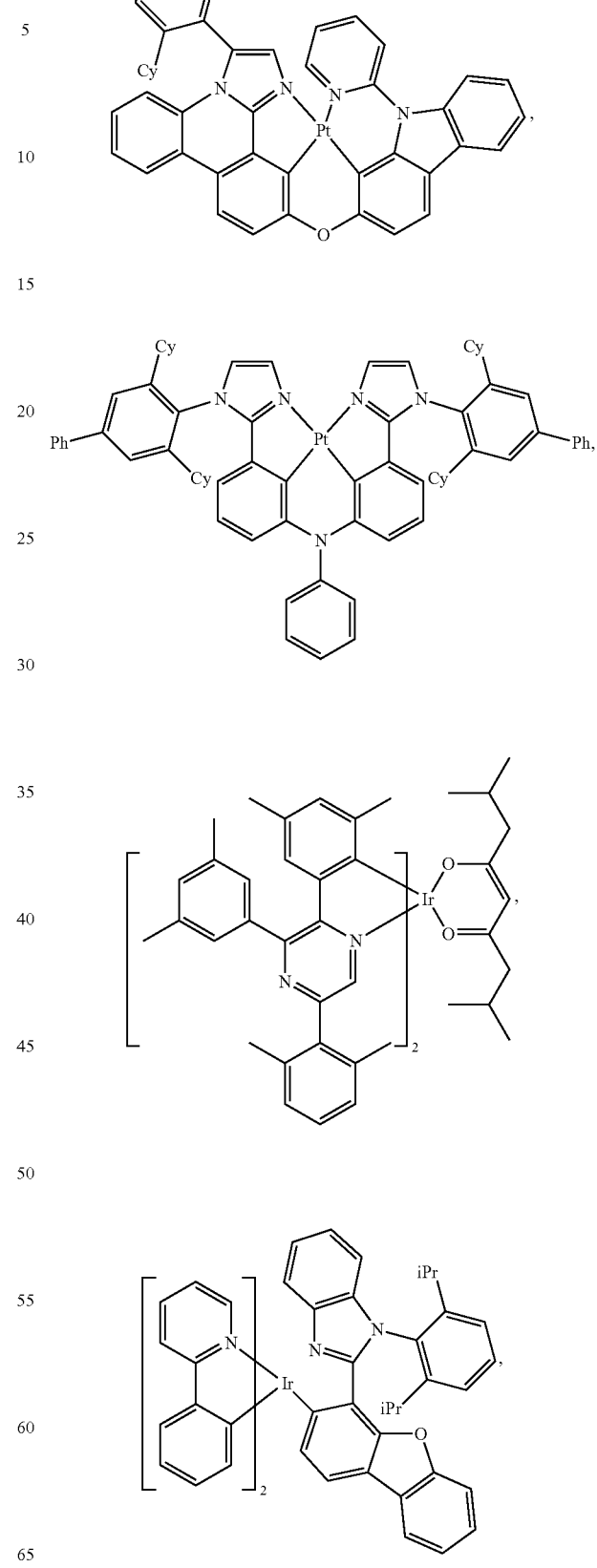

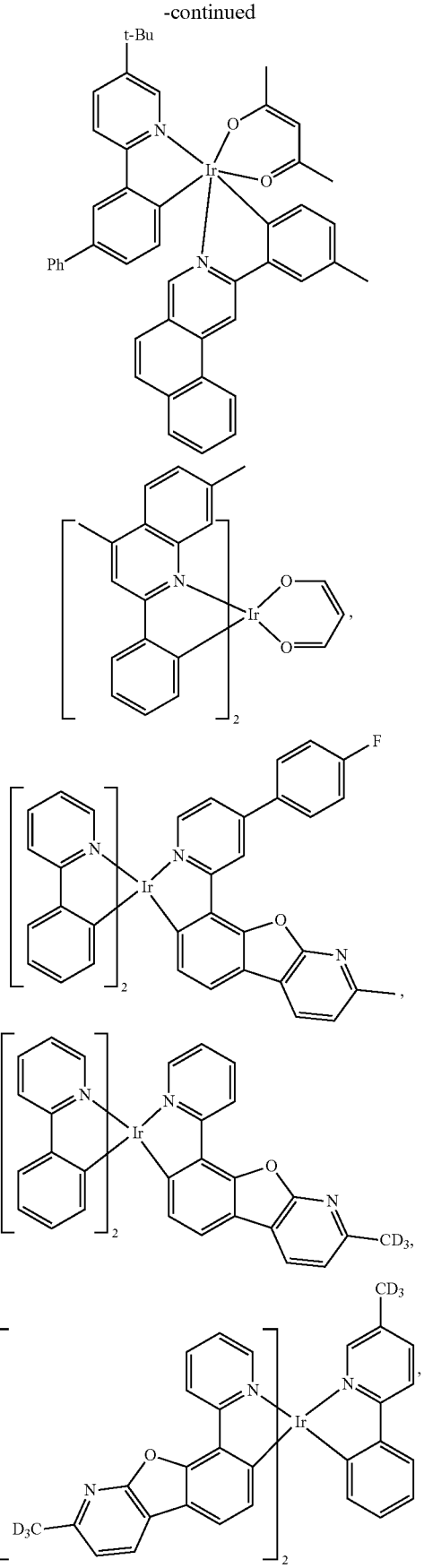
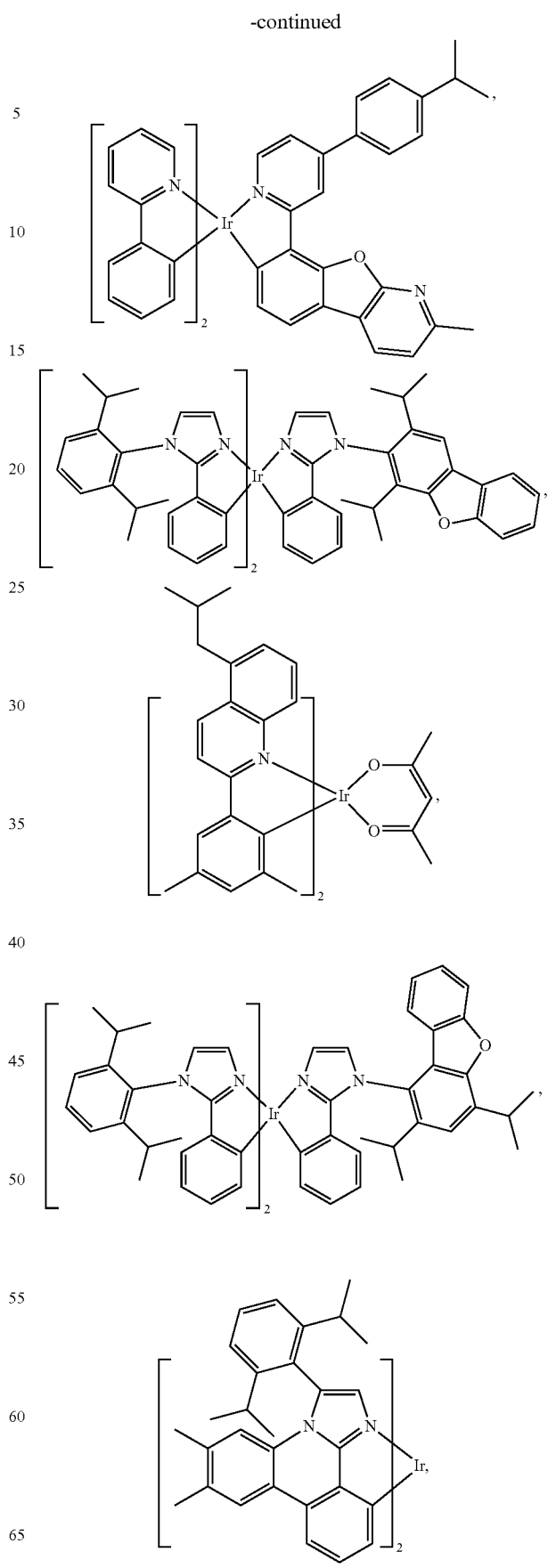

267
-continued
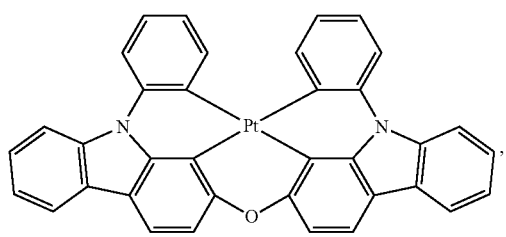
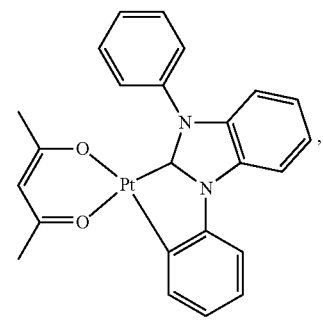
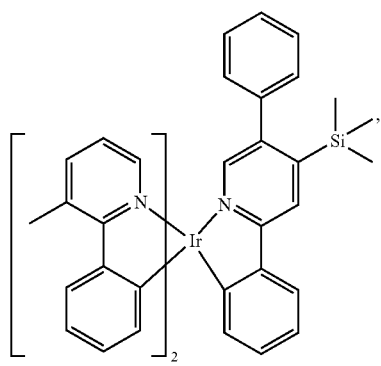
268
-continued
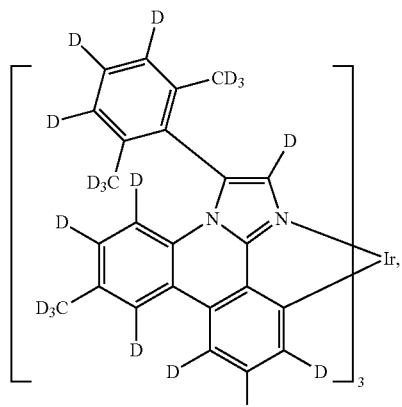
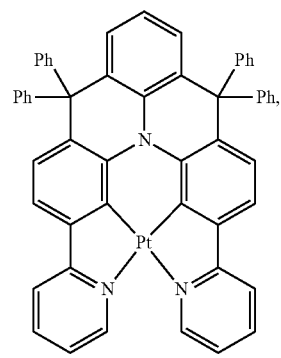
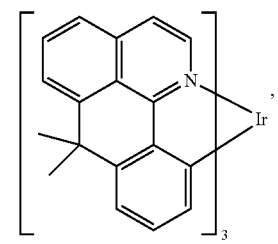
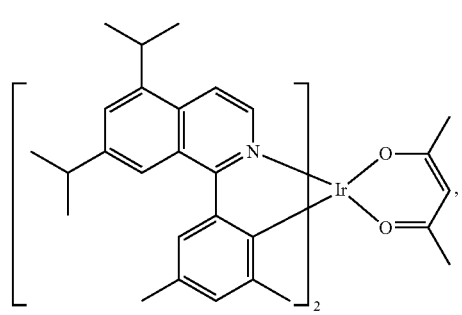
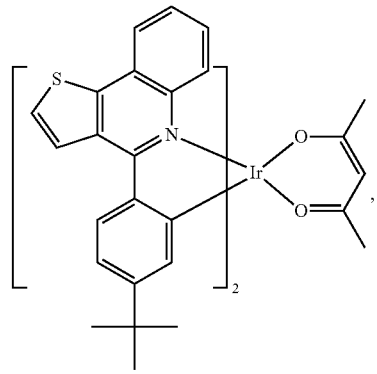
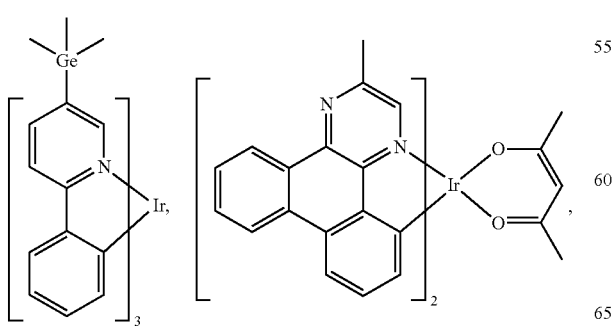
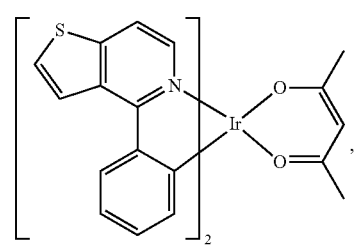

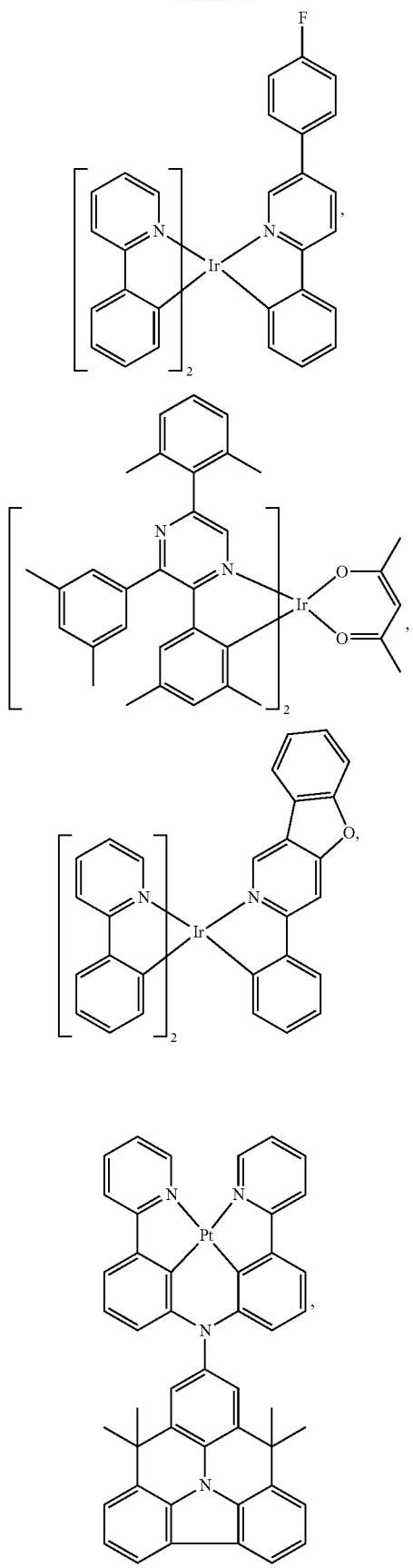
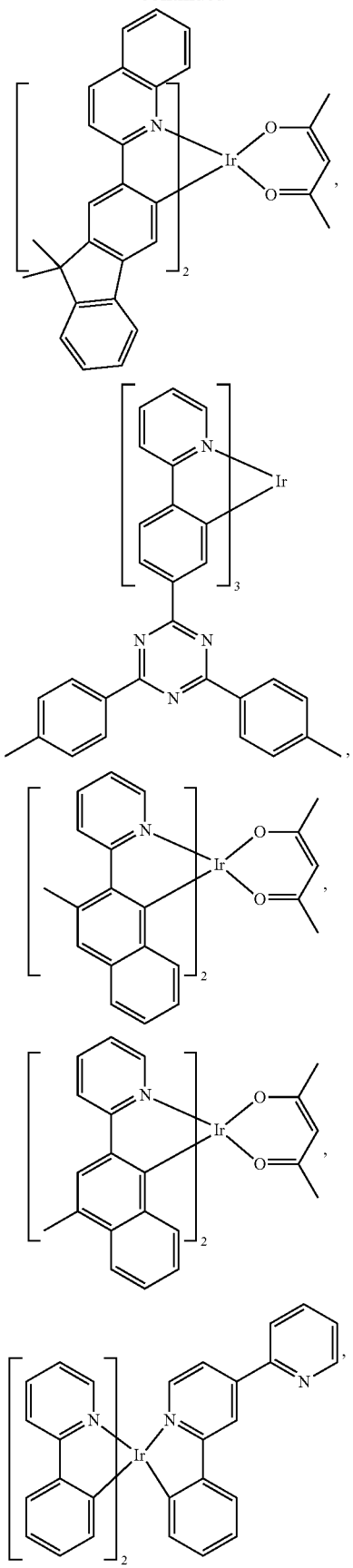

-continued
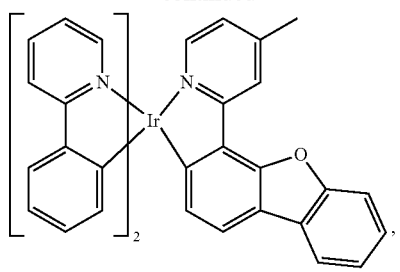
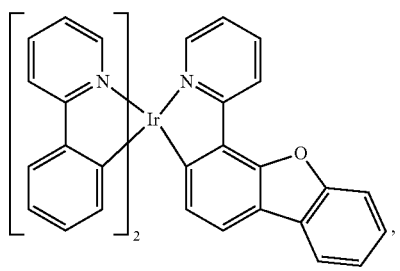
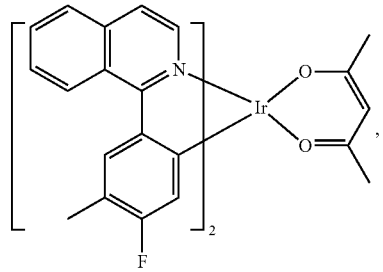
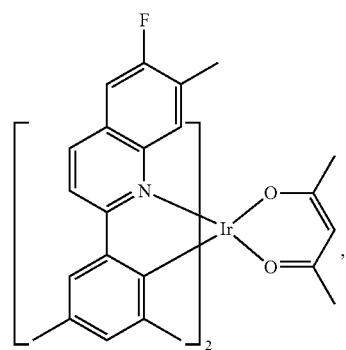
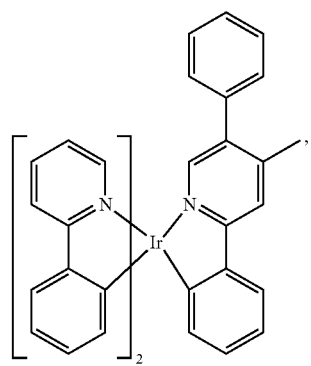
-continued
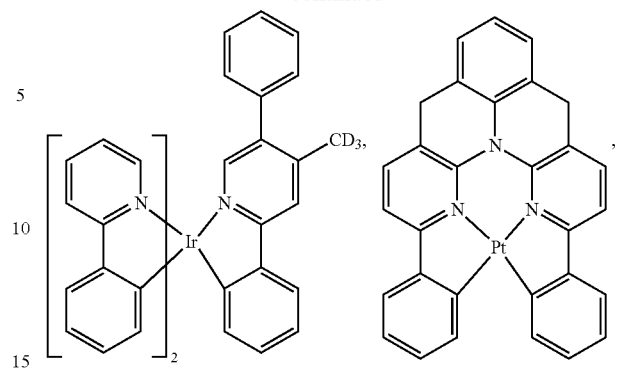
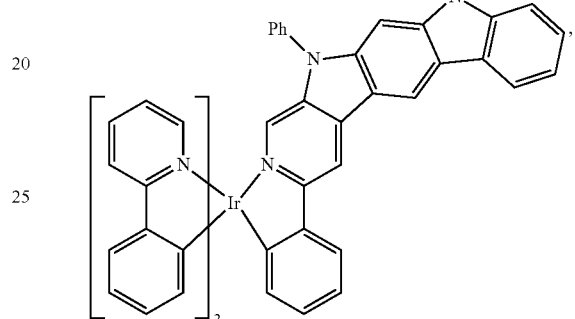
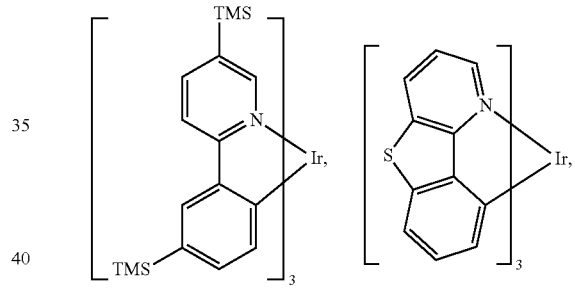
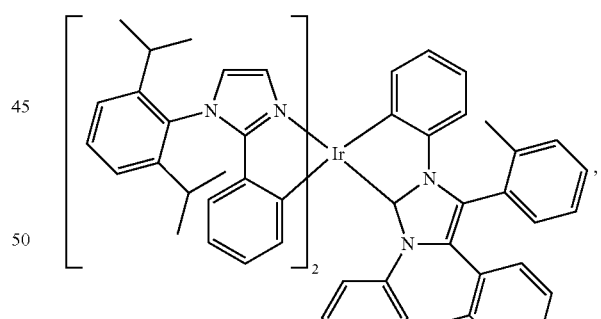
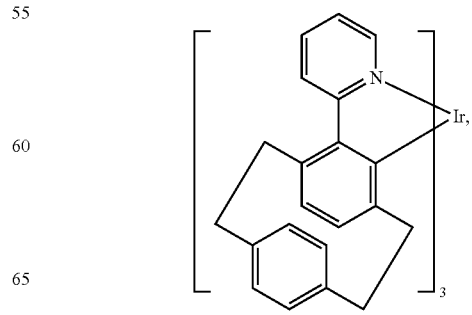

273
-continued
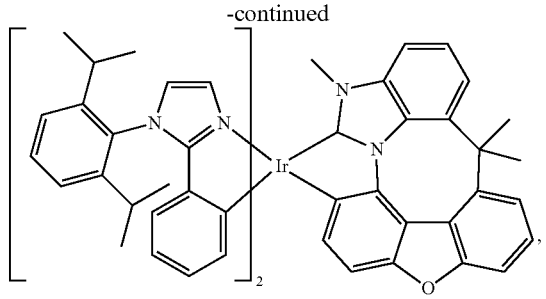
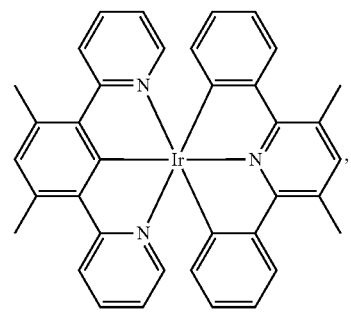
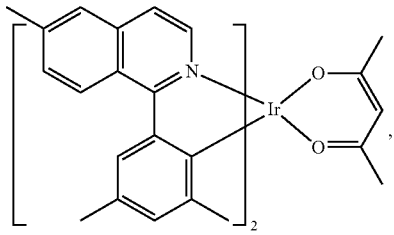
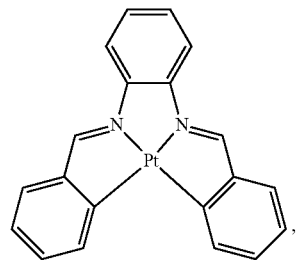
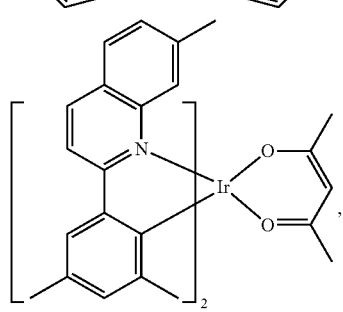
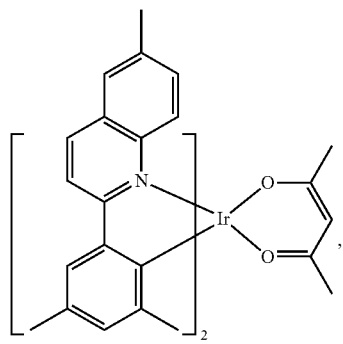
274
-continued
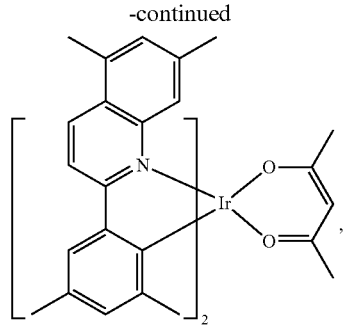
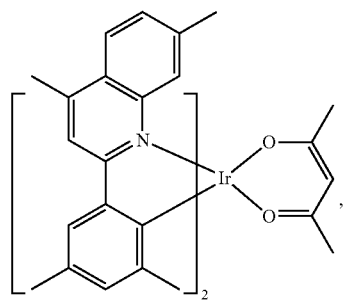
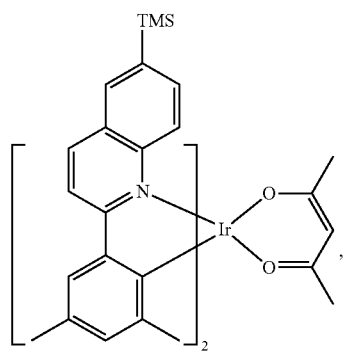
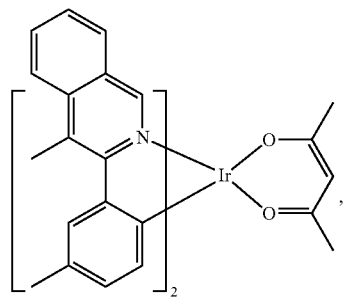
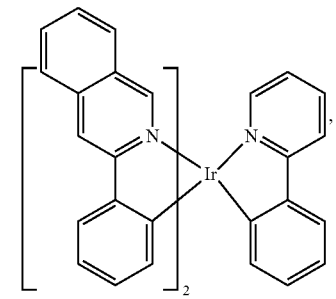

275
-continued
276
-continued
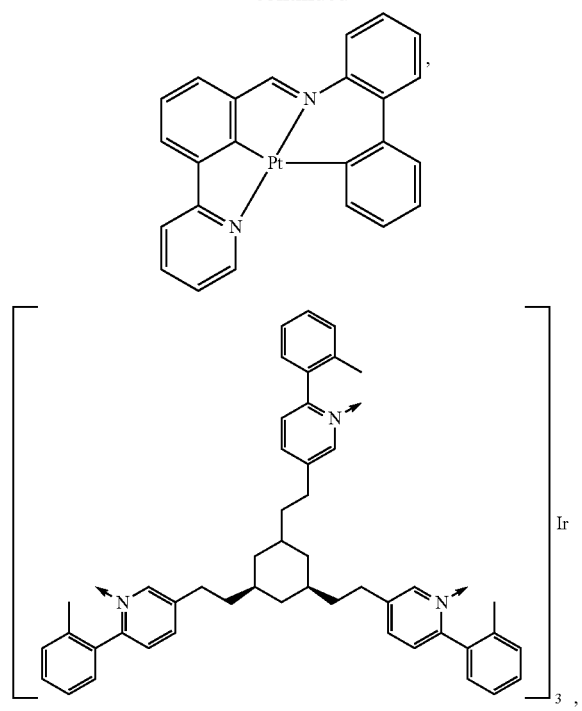
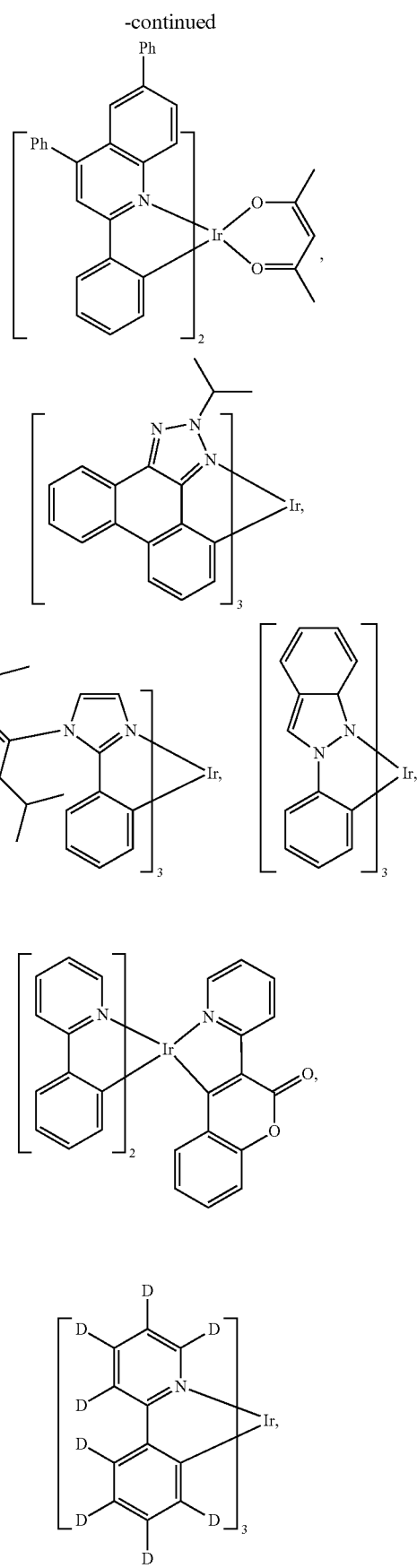

-continued

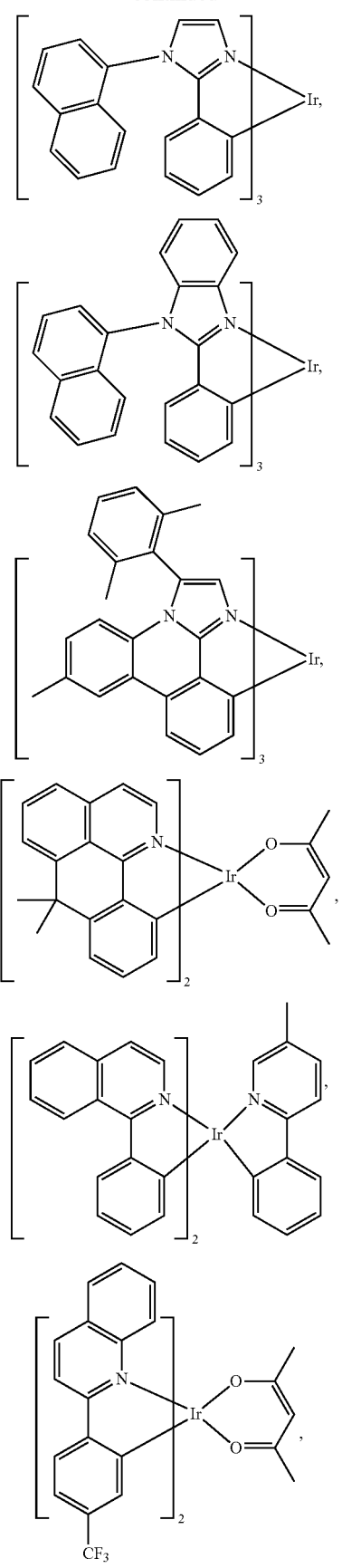

-continued

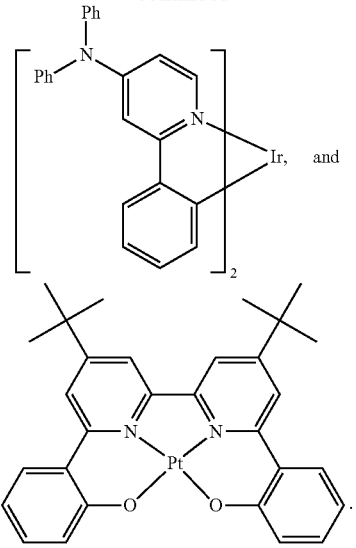

HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

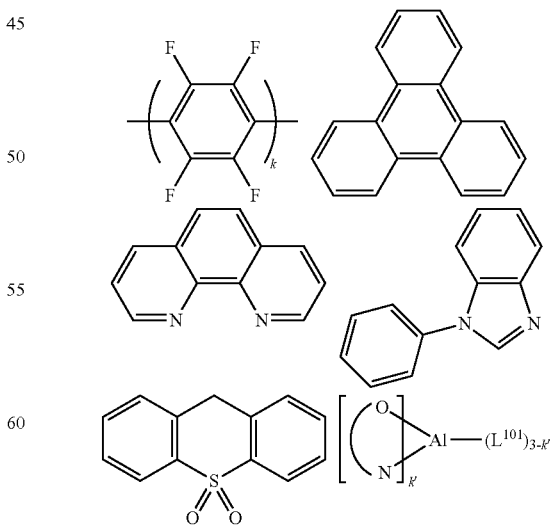

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

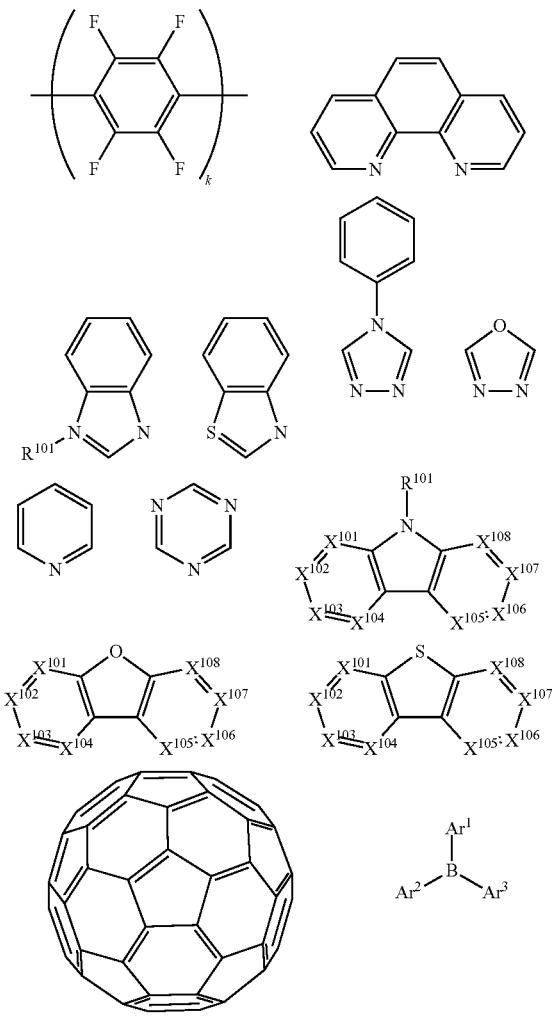

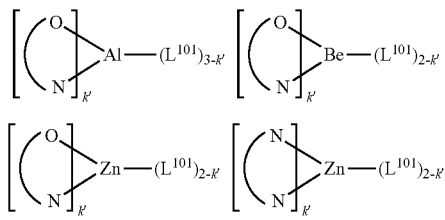

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. No. 6,656,612, U.S. Pat. No. 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535.

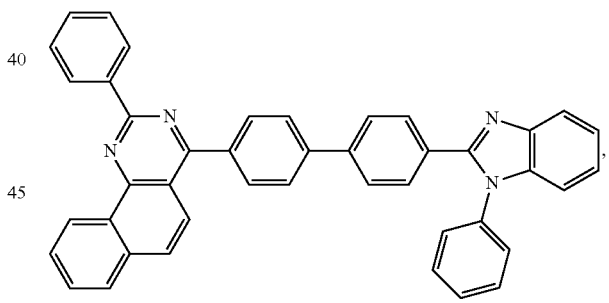

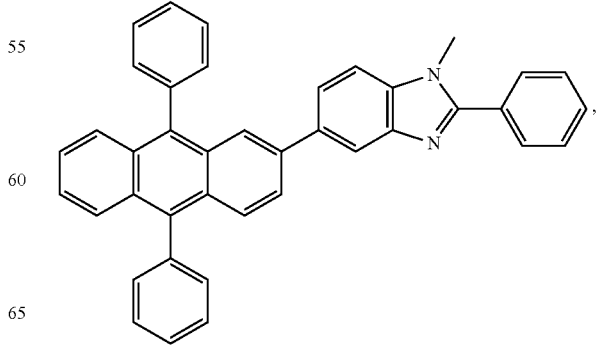

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contain, but are not limited to, the following general formulae:

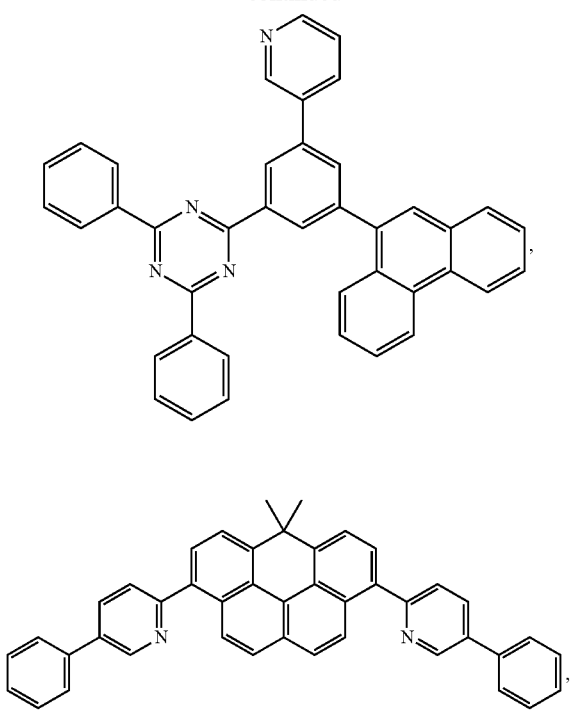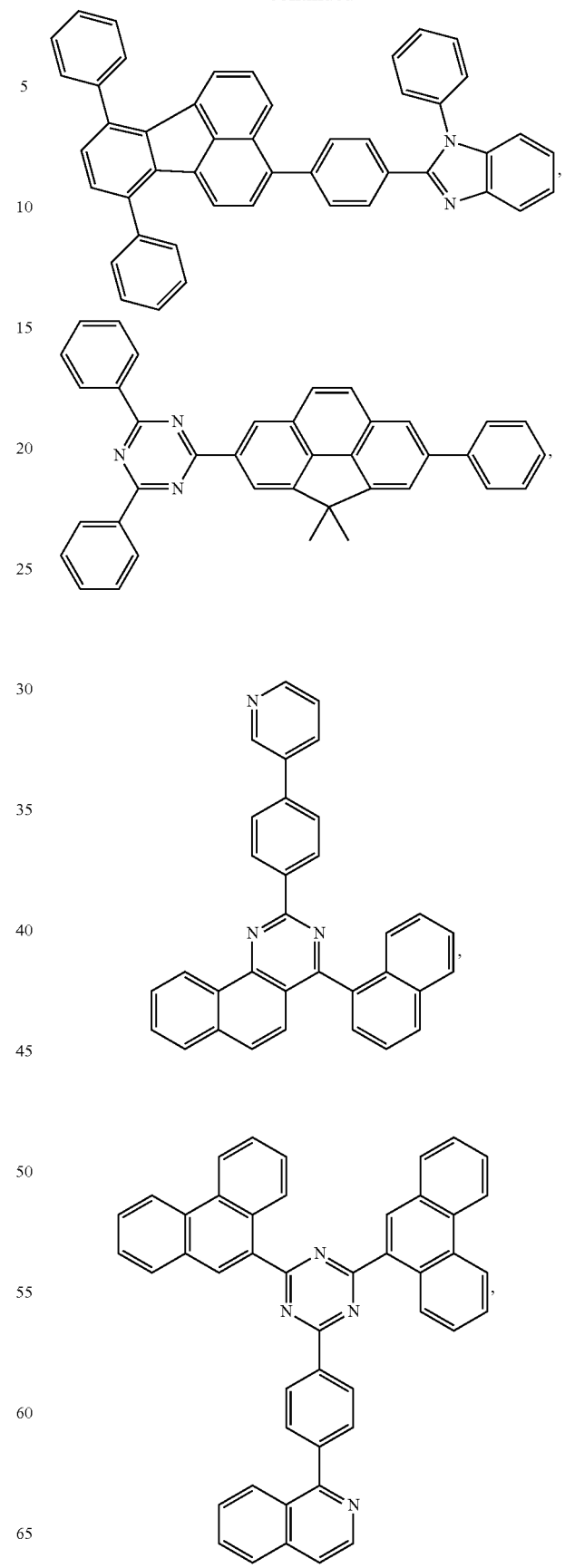

283
-continued
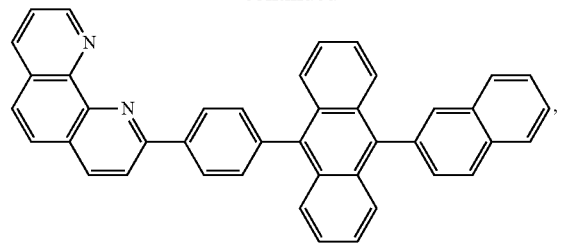
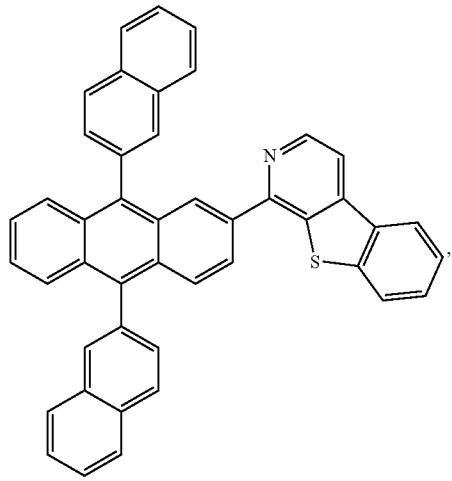
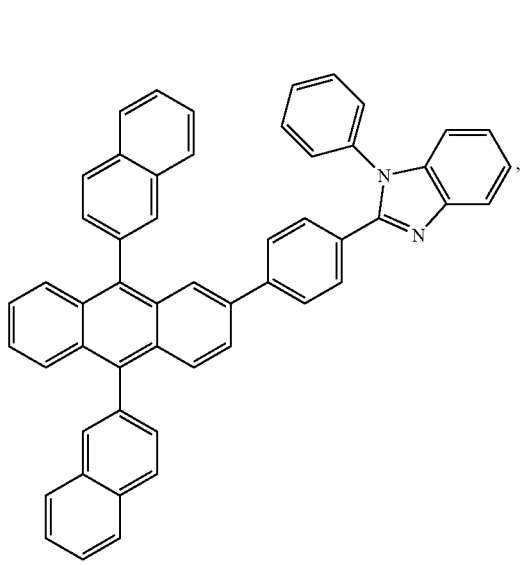
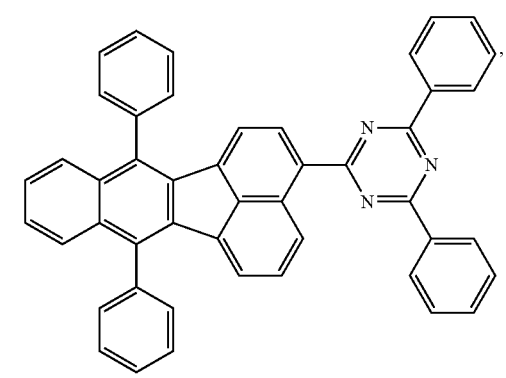
284
-continued
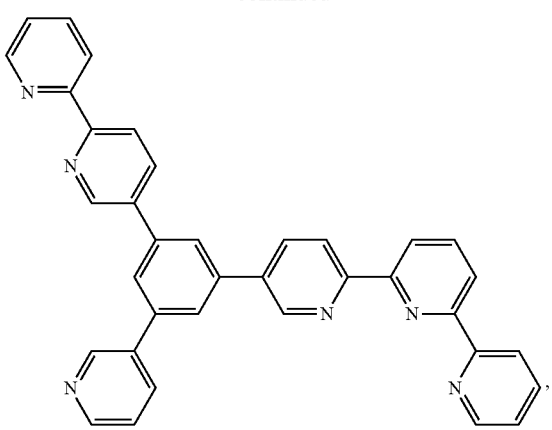
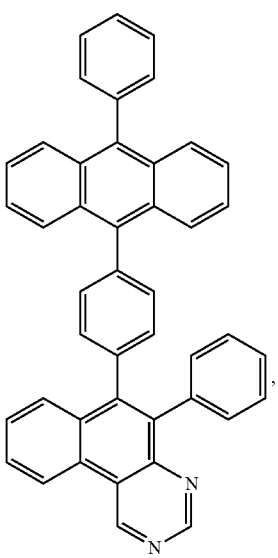
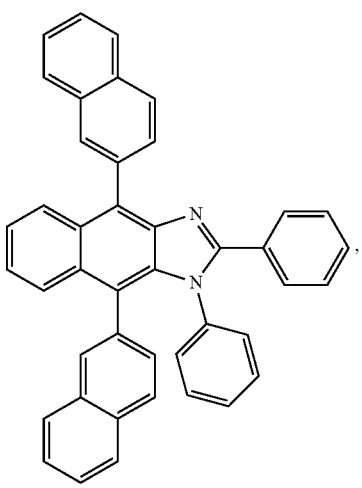

285
-continued
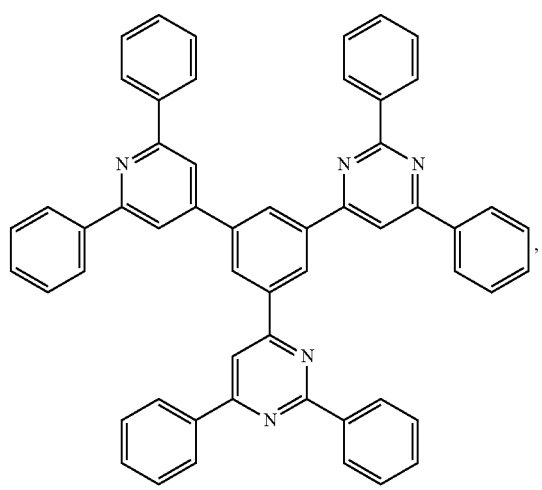
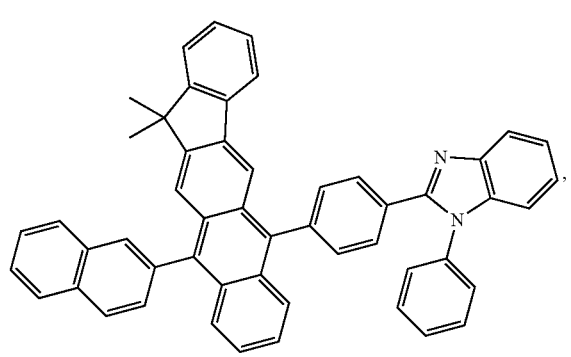
286
-continued
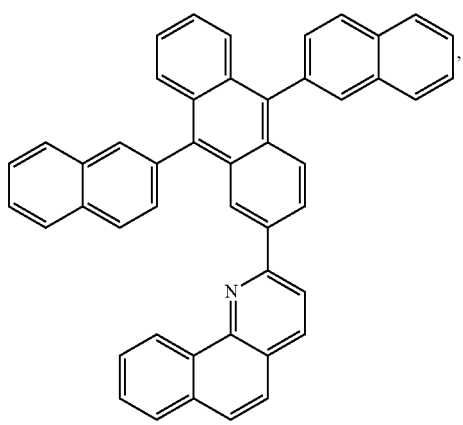
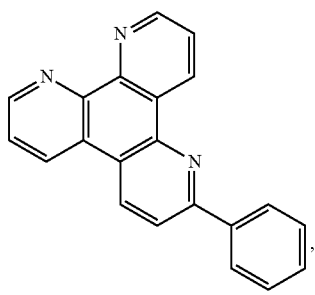
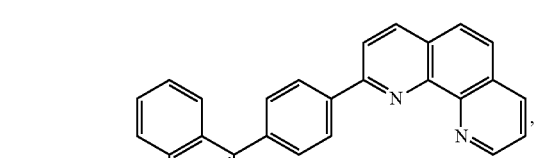
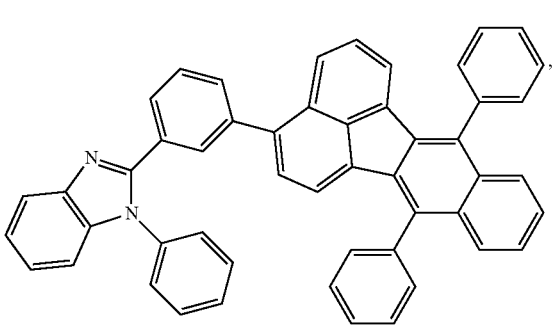

287
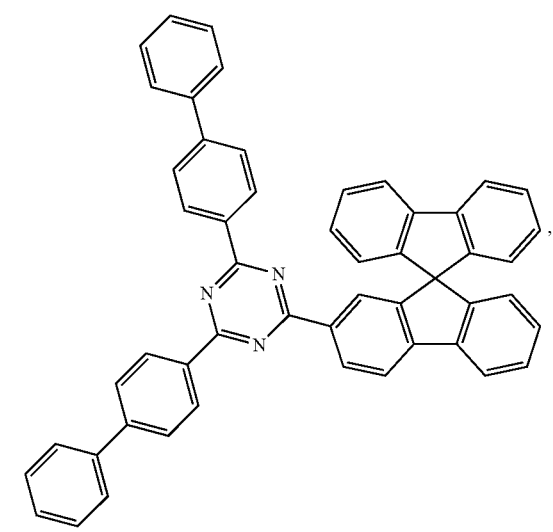
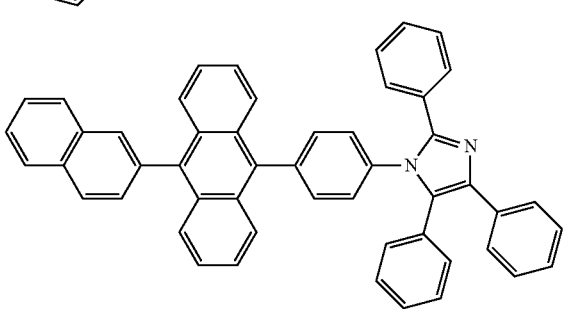
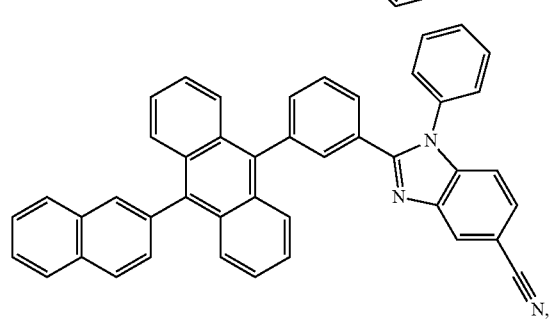
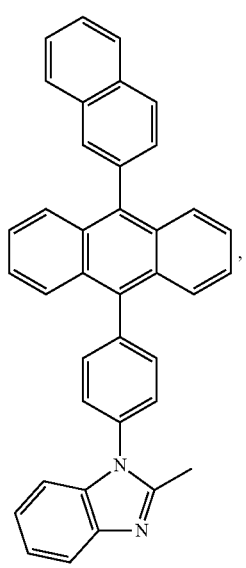
288
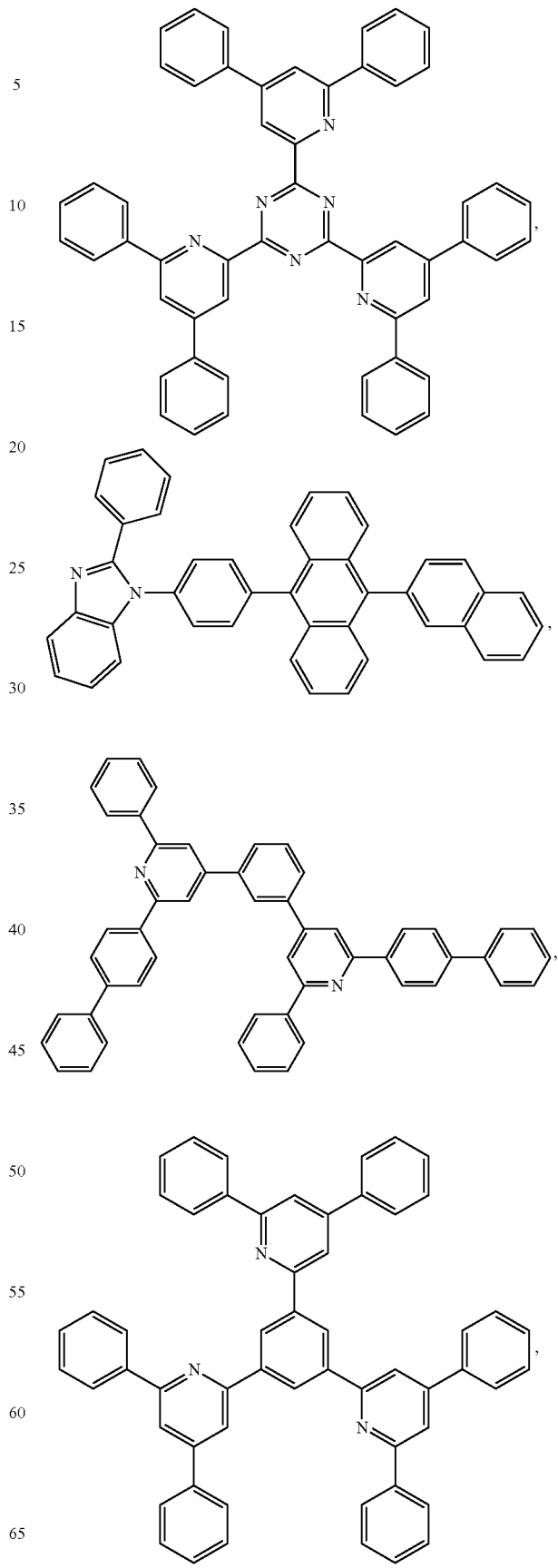

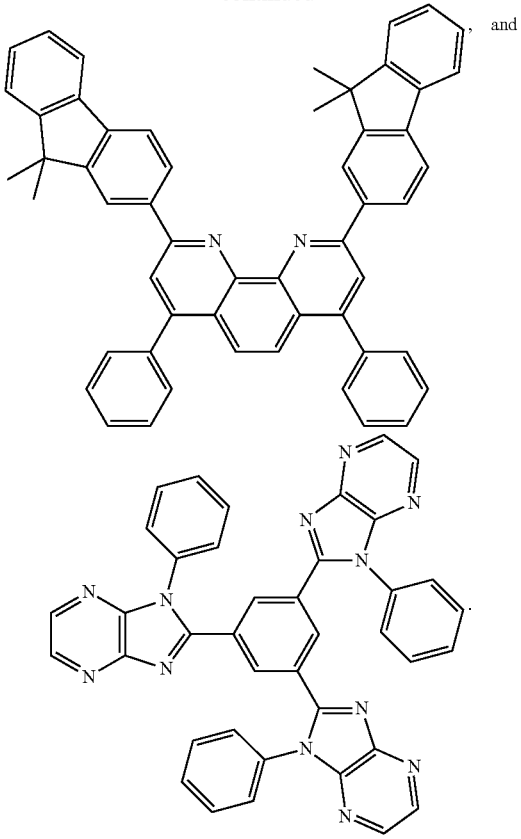

Charge Generation Layer (CGL):

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

EXPERIMENTAL

Chemical Synthesis

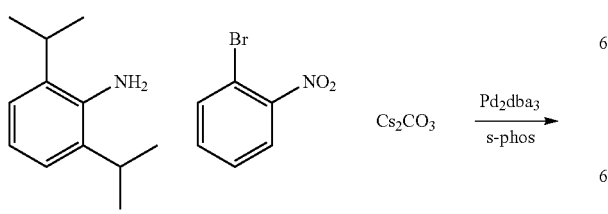

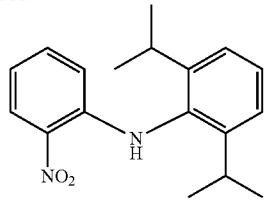

Preparation of 2,6-diisopropyl-N-(2-nitrophenyl)aniline: 2,6-diisopropylaniline (5.27 grams, 29.7 mmol), 1-bromo-2-nitrobenzene (6.00 grams, 29.7 mmol), cesium carbonate (14.5 grams, 44.6 mmol), $Pd_2dba_3$ (0.544 grams, 0.594 mmol) and s-phos (0.98 grams, 2.40 mmol) were all charged into a 1 L round bottom flask. Toluene (250 mL) was added and the reaction was stirred at reflux for 18 h. The mix was cooled to ambient temperature and diluted with ethyl acetate. The mixture was filtered through celite. The filtrate was evaporated in vacuo and used without further purification.

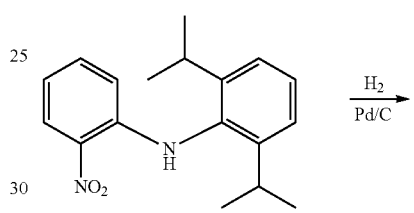

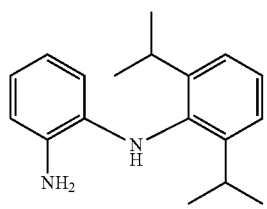

Crude 2,6-diisopropyl-N-(2-nitrophenyl)aniline was hydrogenated in ethanol with 4 grams of Pd/C 10% for 3 h. The mixture was filtered and evaporated. The product was purified on a silica gel column eluted with dichloromethane giving 7.6 grams of an oil.

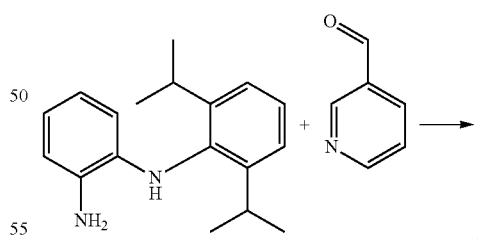

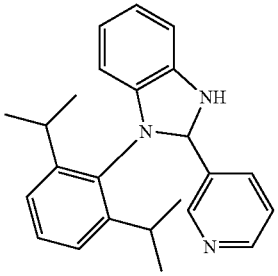

Diamine (7.5 grams, 27.9 mmol), nicotinaldehyde (4.49 grams, 41.9 mmol) and hexadecylpyridinium bromide hydrate (0.56 grams, 5%) were all added to a 500 mL flask. Tetrahydrofuran (100 mL) and water (200 mL) were added. The mixture was stirred for 2 days. The mixture was then diluted with brine and ethyl acetate. The organic layer was dried and evaporated. The crude product was used without further purification.

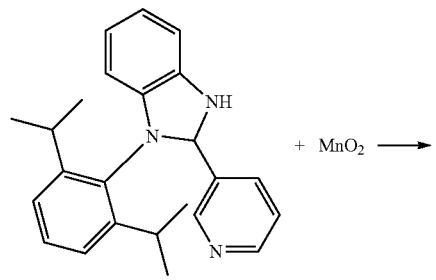

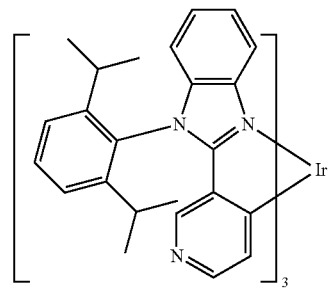

4.00 grams, 11.3 mmol of ligand was combined with 1.1 grams (2.25 mmol) of Ir(acac)$_3$ in a Schlenk tube. 4 mL of pentadecane was added, the air was evacuated, and the tube backfilled with nitrogen. The mixture was heated to reflux for 20 h. The mixture was chromatographed on a silica gel column eluted with 0-3% methanol in DCM to give 1.2 grams of product.

Dihydrobenzimidazole (10 grams, (28.0 mmol) and manganese (IV) oxide (13.5 grams, 140 mmol) were combined in a 1 L flask. Toluene (400 mL) was added and the mixture was stirred at reflux overnight. The mixture was then filtered through celite and the filtrate was chromatographed on a silica gel column eluted with 0-3% methanol in dichloromethane to give 7 grams of product. 1H NMR δ 0.86 (d, 6H), 0.98 (d, 6H), 2.28 (m, 2H).

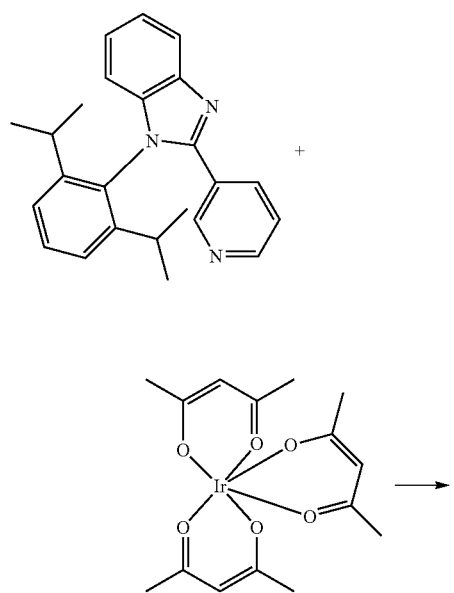

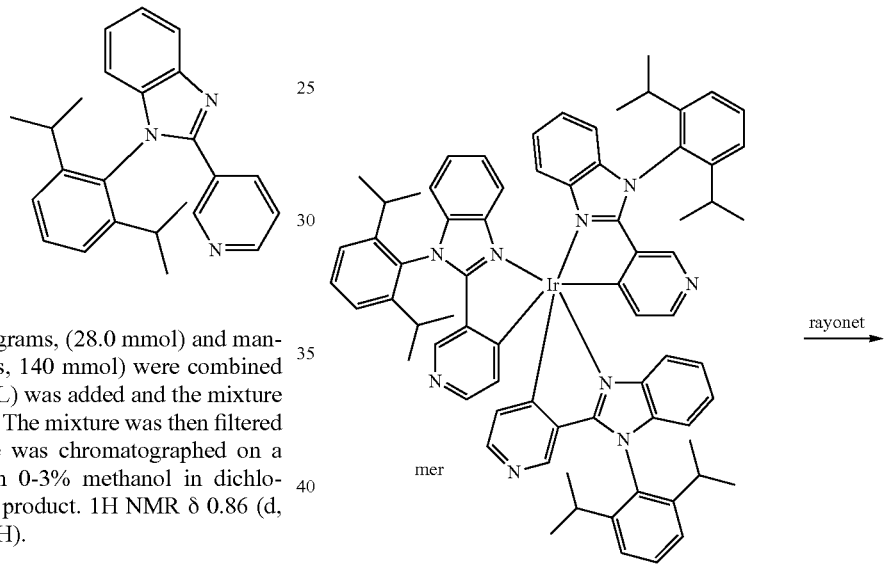

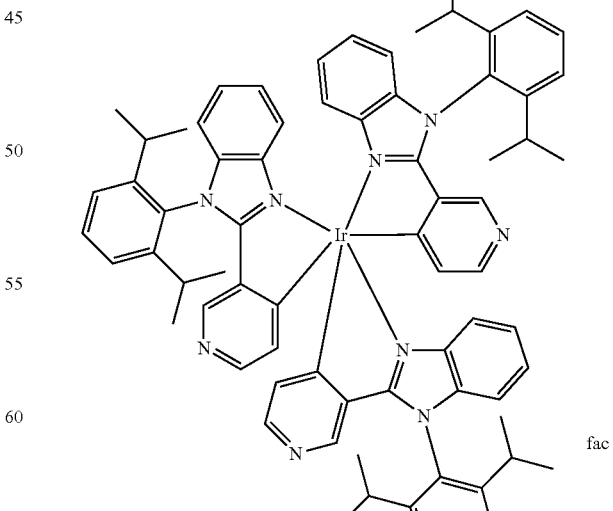

1.3 grams of mer complex was dissolved in DMSO (500 mL) and irradiated in the rayonet for 20 h. The solvent was removed and the complex purified on silica gel column eluted with 0-3% methanol in DCM.

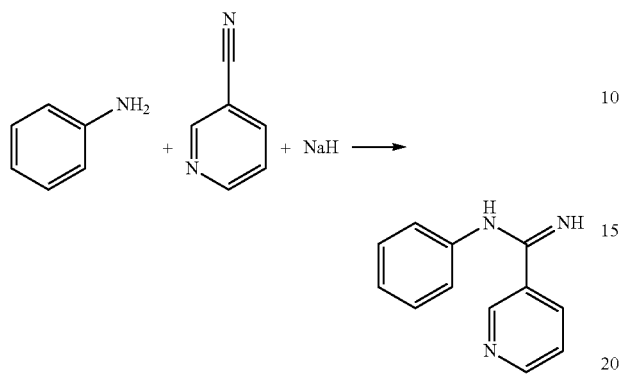

A 250 mL flask was charged with DMSO (55 mL), aniline (9.80 mL, 107 mmol) and nitrile (11.2 grams, 107 mmol). This was stirred in an ice water bath before addition of sodium hydride (4.72 grams, 118 mmol). The reaction was stirred to ambient temperature overnight. The mixture was then poured into ice and filtered. The product was washed with water then heptane to give 12.4 grams of product (59%) as a yellow solid.

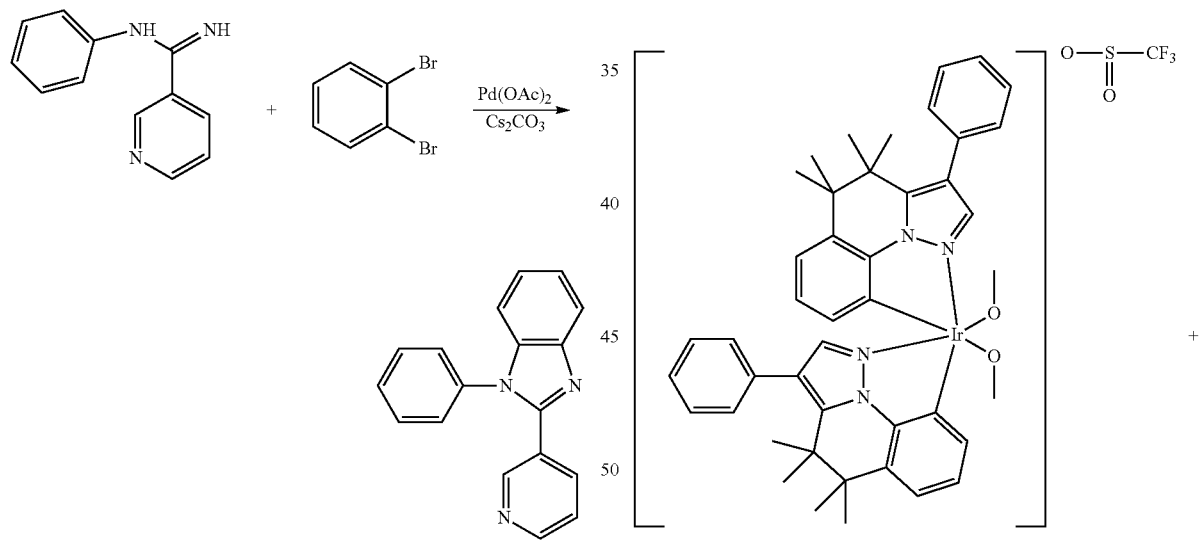

Amidine (3.0 grams, 15.2 mmol), 1,2-dibromobenzene (4.66 grams, 19.8 mmol), Pd(OAc)$_2$ (0.171 grams, 0.76 mmol), xantphos (0.44 grams, 0.76 mmol) and cesium carbonate (19.8 grams, 60.8 mmol) were added to a 250 mL flask. Toluene (120 mL) was added and the mixture was stirred under an atmosphere of nitrogen for 20 h. The reaction mixture was then filtered through celite and the cake was washed with DCM. Column chromatography using a mobile phase gradient of 0-2% methanol in DCM gave 1.4 grams of product.

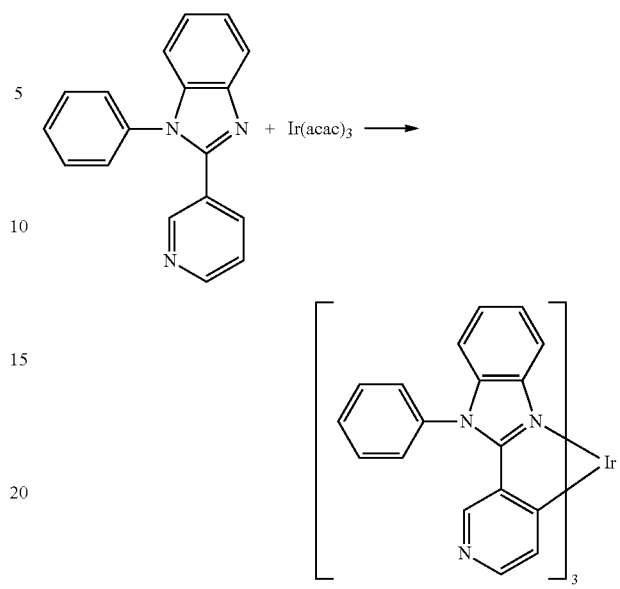

Ligand (0.2 grams, 0.737 mmol) and Ir(acac)$_3$ (72 mg, 0.147 mmol) were place in a Schlenk tube. Pentadecane (0.5 mL) was added and the mixture was stirred at reflux in a sand bath for 18 h. The product was chromatographed on a silica gel column eluted with 0-4% methanol in DCM to give the product.

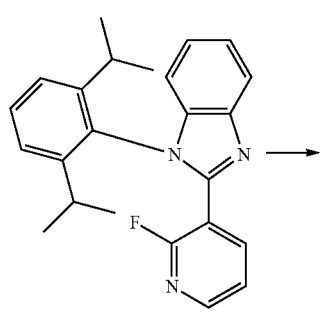

-continued

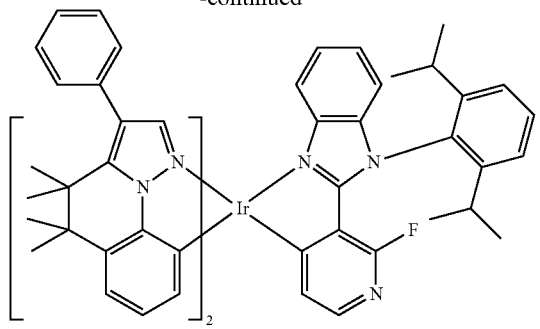

The triflate (0.8 grams, 0.8 mmol) and 1-(2,6-diisopropylphenyl)-2-(2-fluoropyridin-3-yl)-1H-benzo[d]imidazole (0.74 grams, 1.98 mmol) were combined in a Schlenk tube. 2-ethoxyethanol (10 mL) was added and the mixture was stirred at reflux for 4 h. The mixture was diluted with dichloromethane and washed with aqueous sodium bicarbonate. The organic layer was concentrated and chromatographed using a gradient of 70-100% DCM in heptane to give 150 mg of product. LCMS 1168.

Device Examples

All example devices were fabricated by high vacuum ($<10^{-7}$ Torr) thermal evaporation. The anode electrode was 1150 Å of indium tin oxide (ITO). The cathode consisted of 10 Å of Liq (8-hydroxyquinoline lithium) followed by 1,000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package. The organic stack of the device examples consisted of sequentially, from the ITO surface, HIL1 (100 Å)/HTL1 (250 Å)/Host1: Host2 40%: Ir($L_A$4)$_3$ 10% (300 Å)/EBL1 (50 Å)/ETL1 (300 Å)/LiF (5 Å)/Al (1000 Å). The materials used in the device fabrication have the following structure:

HIL 1

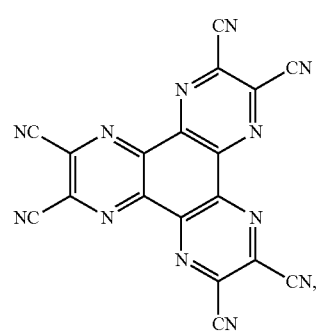

HTL1

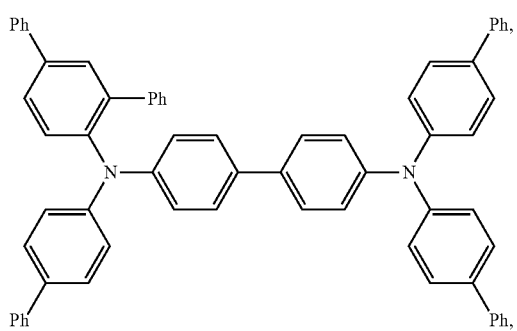

-continued

Host 1

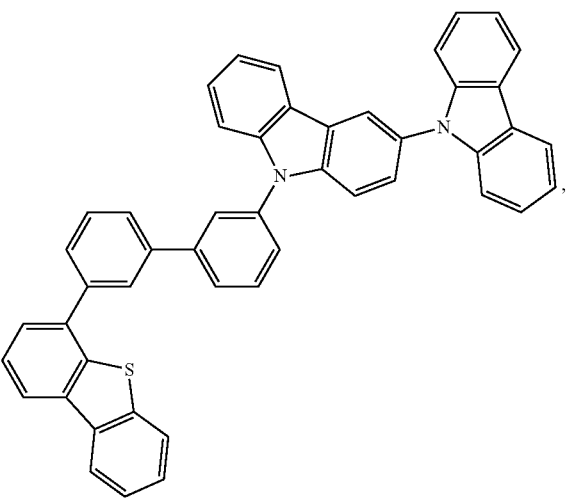

Host 2

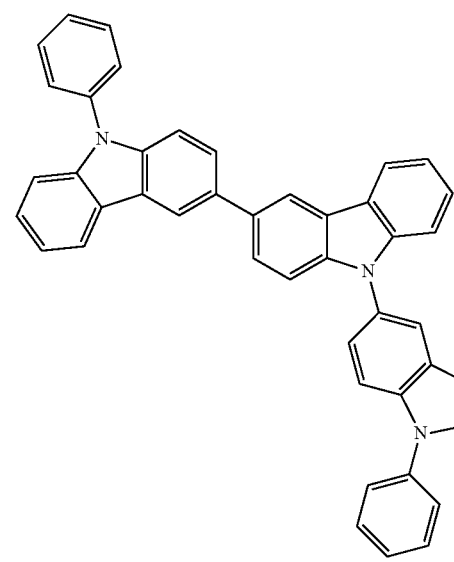

EBL 1

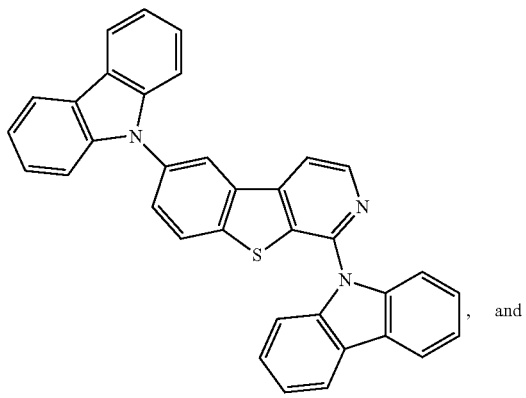

, and

-continued

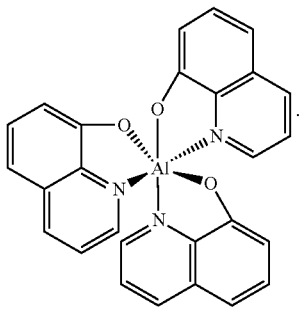

ETL 1

The device performance data are summarized in the following table. In general, the inventive compound emits blue color with high LE, EQE, PE and low voltage:

| 1931 CIE | | λ max | FWHM | Voltage | LE | EQE | PE |
|---|---|---|---|---|---|---|---|
| | | | | At 10 mA/cm² | | | |
| x | y | [nm] | [nm] | [V] | [cd/A] | [%] | [lm/W] |
| 0.1837 | 0.4113 | 476 | 58.2 | 4.8 | 34.3 | 14.8 | 22.4 |

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound comprising a ligand $L_A$ of Formula I:

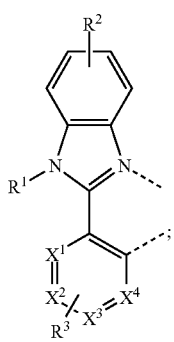

Formula I wherein $R^1$ is a substituted aryl or substituted heteroaryl with at least one substitution on at least one ortho position;
wherein $R^2$ represents mono, di, tri, or tetra substitution, or no substitution;
wherein $R^3$ represents from mono to the maximum number of substitutions it may represent, or no substitution, or any adjacent $R^2$ and $R^3$ are optionally joined or fused into a ring;

wherein $X^1$, $X^2$, $X^3$, and $X^4$ are each independently selected from the group consisting of carbon and nitrogen, and at least one of $X^1$, $X^2$, $X^3$, and $X^4$ is nitrogen; and when any of $X^1$, $X^2$, $X^3$, and $X^4$ is nitrogen, there is no substitution on that nitrogen;
wherein $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acid, ester, nitrile, and isonitrile;
wherein the ligand $L_A$ is coordinated to a metal M; and
wherein the ligand $L_A$ is optionally linked with other ligands to form a tridentate, or tetradentate ligand.
2. The compound of claim 1, wherein $R^1$ has substitutions on both ortho positions.
3. The compound of claim 1, wherein $R^1$ is a substituted aryl.
4. The compound of claim 1, wherein only one of $X^1$, $X^2$, $X^3$, and $X^4$ is nitrogen.
5. The compound of claim 1, wherein M is selected from the group consisting of Ir, Rh, Re, Ru, Os, Pt, Au, and Cu.
6. The compound of claim 1, wherein the ligand $L_A$ has the formula:

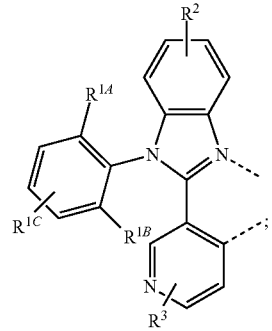

wherein $R^{1C}$ represents mono, di, or tri substitution, or no substitution;
wherein $R^{1A}$, $R^{1B}$ and $R^{1C}$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, and isonitrile;
or any adjacent $R^{1A}$, $R^{1B}$ and $R^{1C}$ are optionally joined or fused into a ring; and
at least one of $R^{1A}$, and $R^{1B}$ is not hydrogen or deuterium.
7. The compound of claim 1, wherein the ligand $L_A$ is selected from the group consisting of:

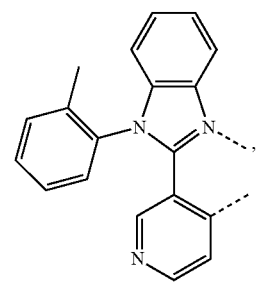

$L_A1$

-continued
L$_A$2
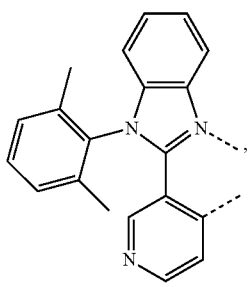
L$_A$3
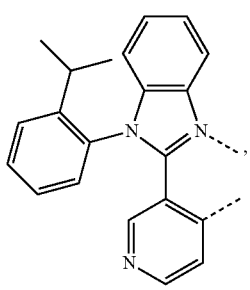
L$_A$4
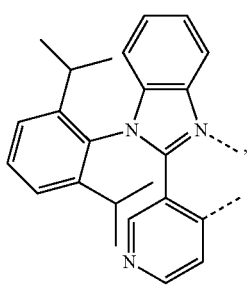
L$_A$5
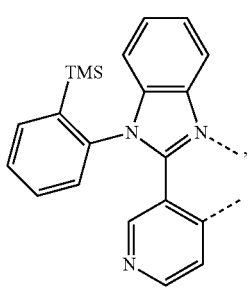
L$_A$6
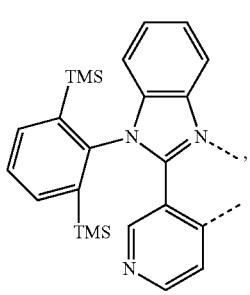
-continued
L$_A$7
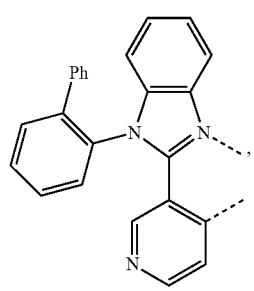
L$_A$8
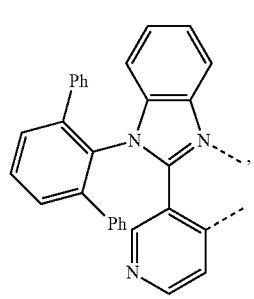
L$_A$9
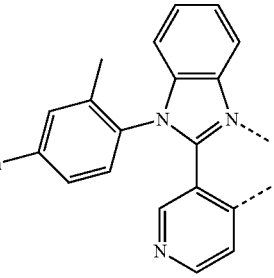
L$_A$10
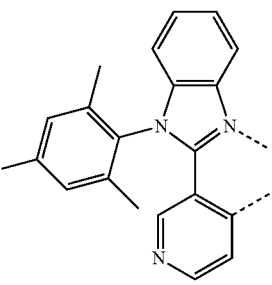
L$_A$11
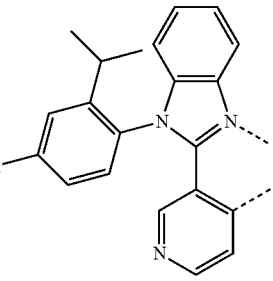

| | |
|---|---|
| L$_A$12 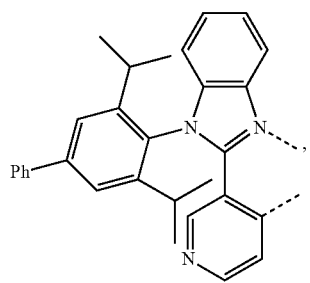 | L$_A$17 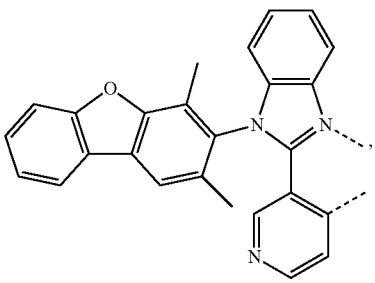 |
| L$_A$13 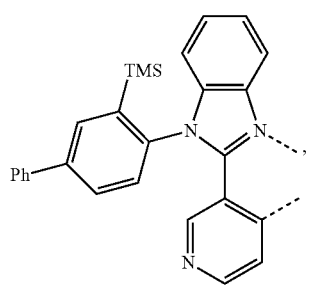 | L$_A$18 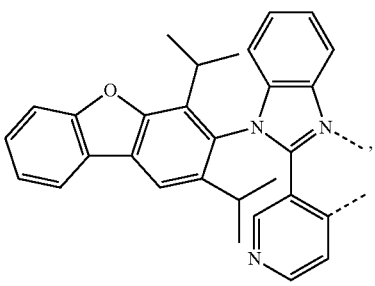 |
| L$_A$14 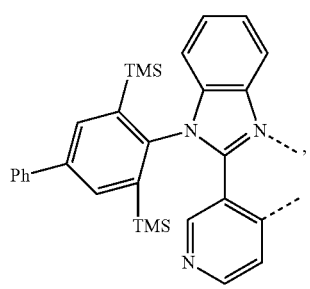 | L$_A$19 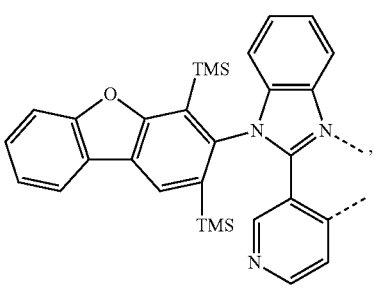 |
| L$_A$15 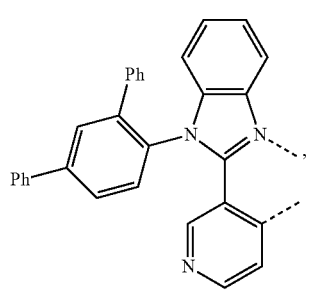 | L$_A$20 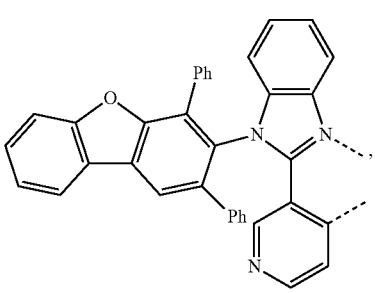 |
| L$_A$16 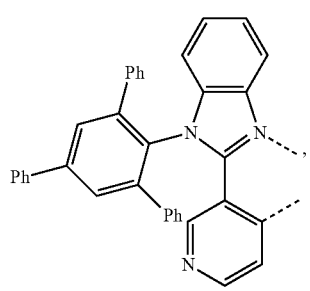 | L$_A$21 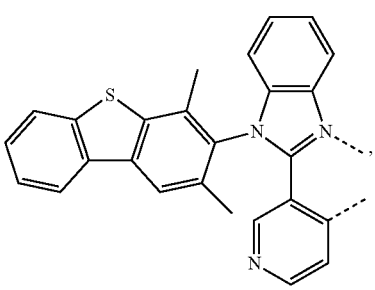 |

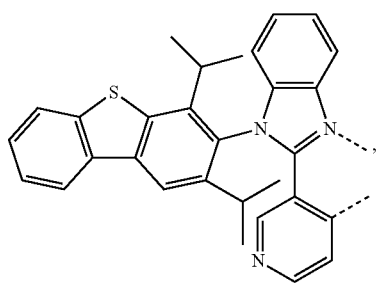 L_A22
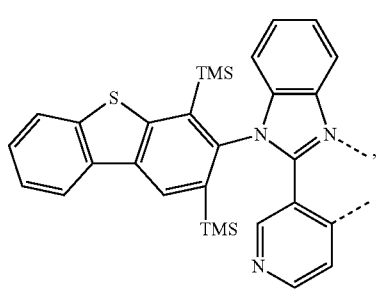 L_A23
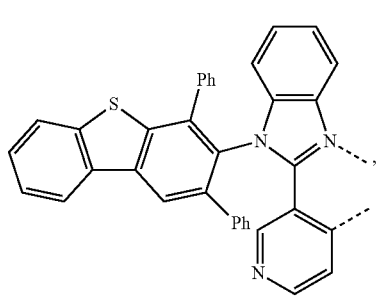 L_A24
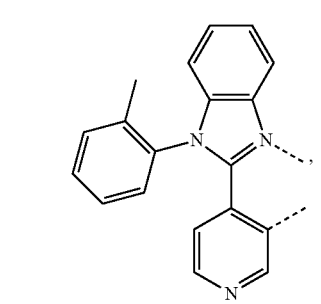 L_A25
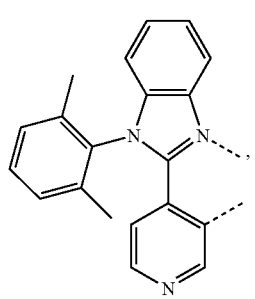 L_A26
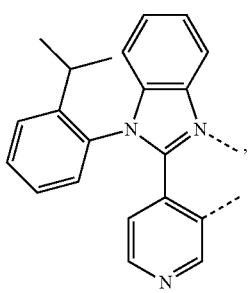 L_A27
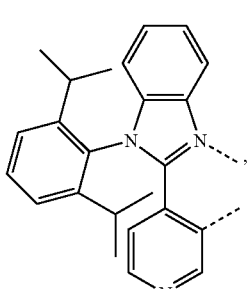 L_A28
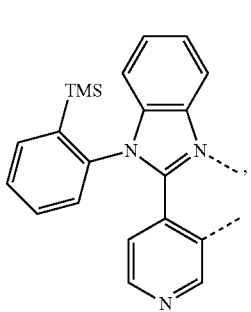 L_A29
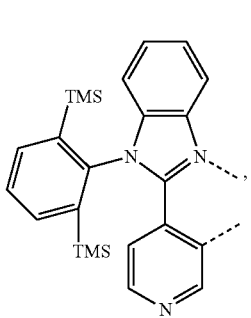 L_A30
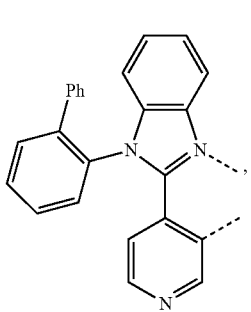 L_A31

L_A32 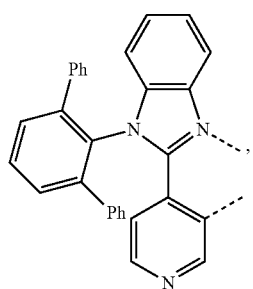
L_A33 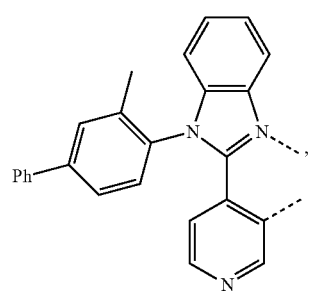
L_A34 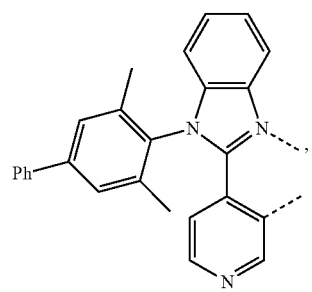
L_A35 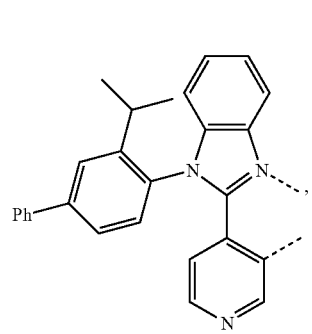
L_A36 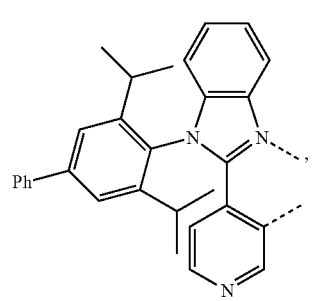
L_A37 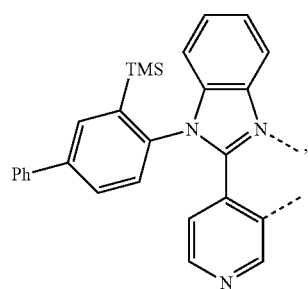
L_A38 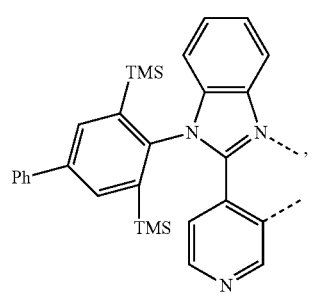
L_A39 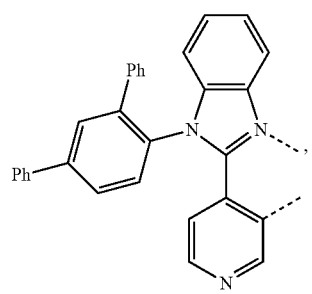
L_A40 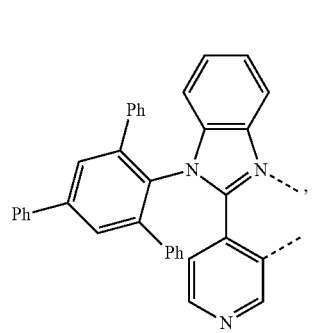
L_A41 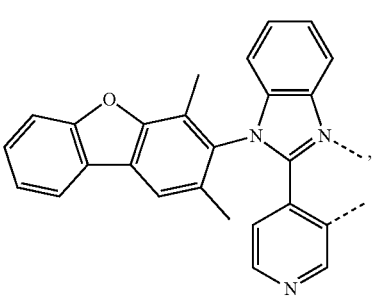

-continued
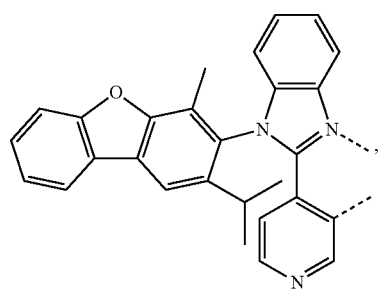
L_A42
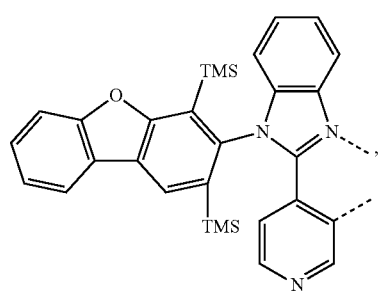
L_A43
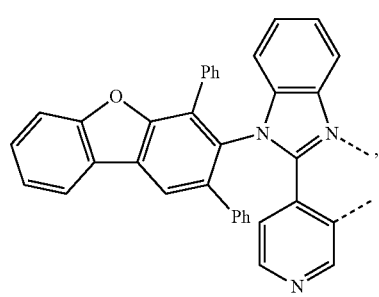
L_A44
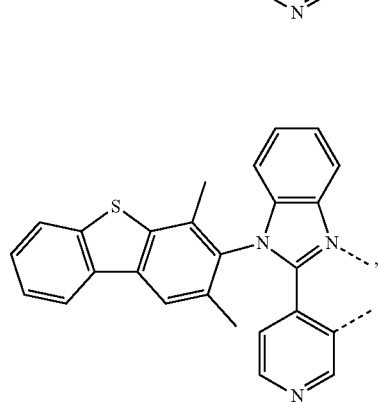
L_A45
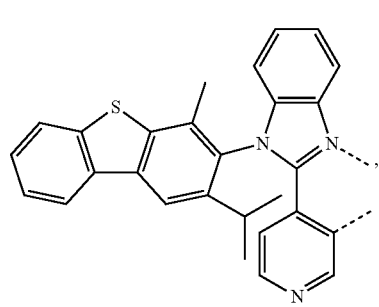
L_A46
-continued
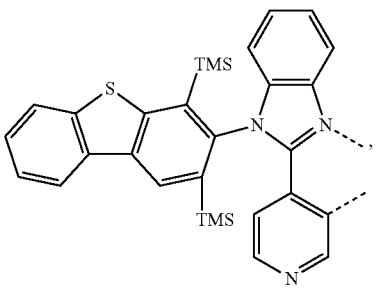
L_A47
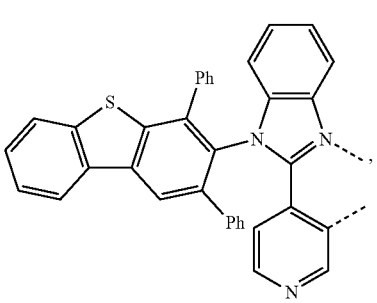
L_A48
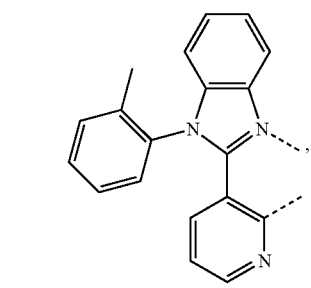
L_A49
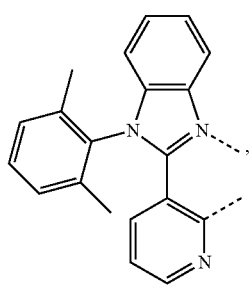
L_A50
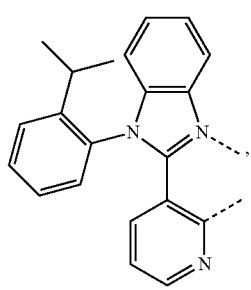
L_A51

L_A52 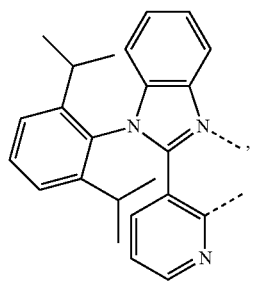
L_A53 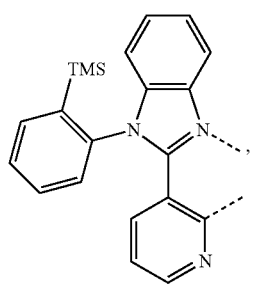
L_A54 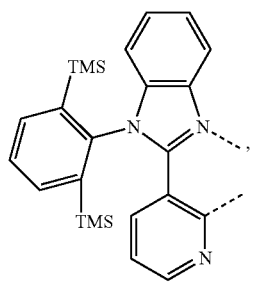
L_A55 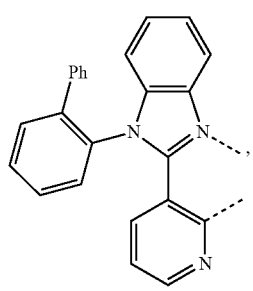
L_A56 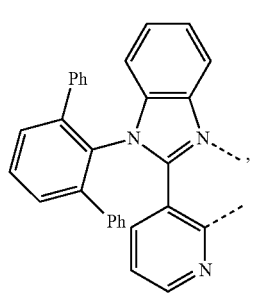
L_A57 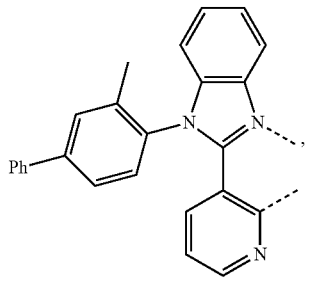
L_A58 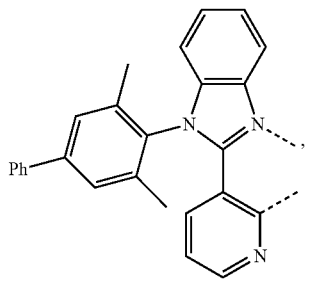
L_A59 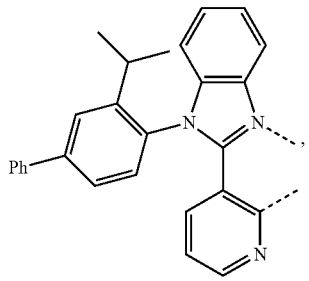
L_A60 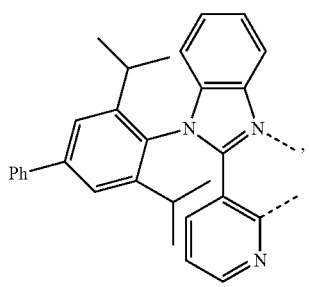
L_A61 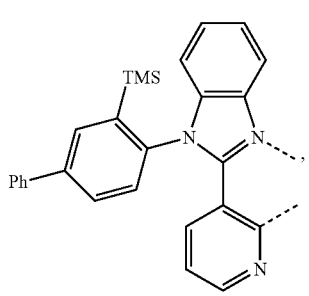

L_A62
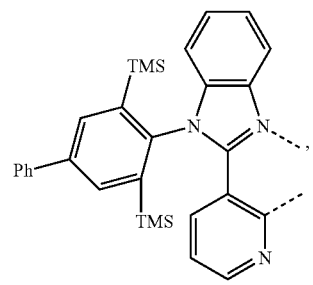
L_A63
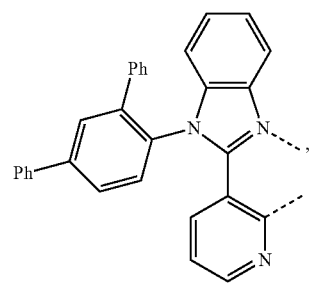
L_A64
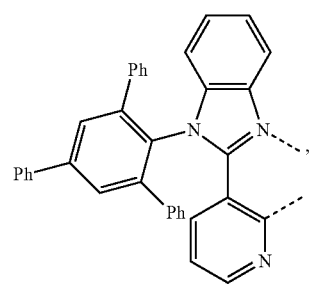
L_A65
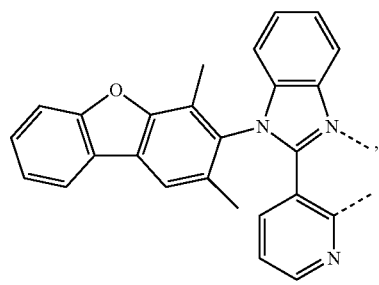
L_A66
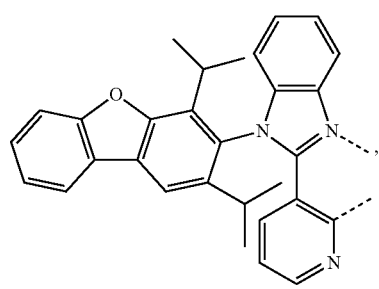
L_A67
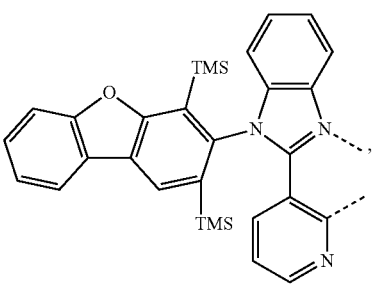
L_A68
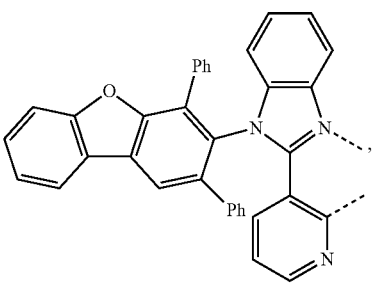
L_A69
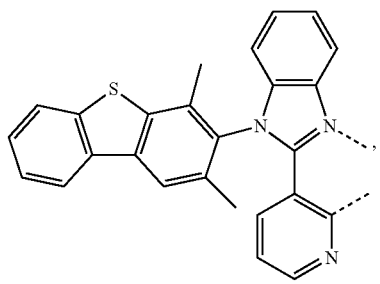
L_A70
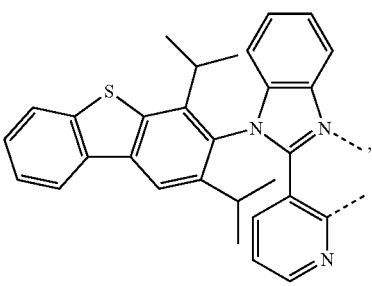
L_A71
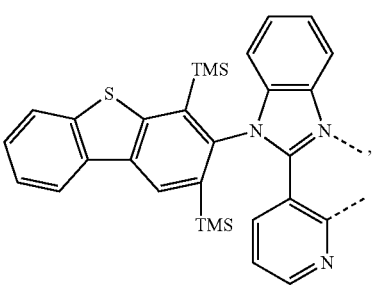

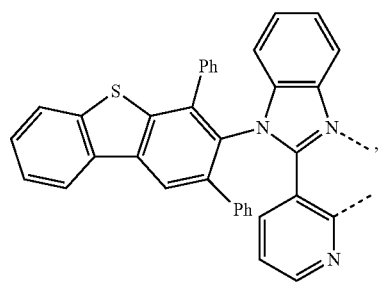 L$_A$72
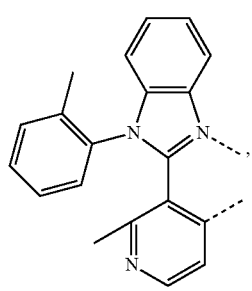 L$_A$73
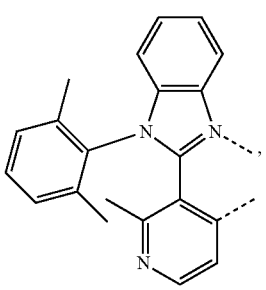 L$_A$74
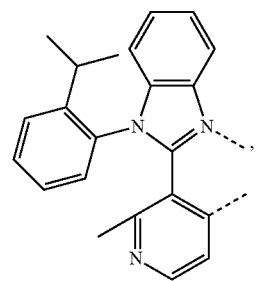 L$_A$75
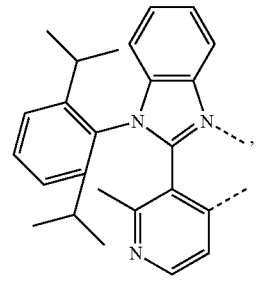 L$_A$76
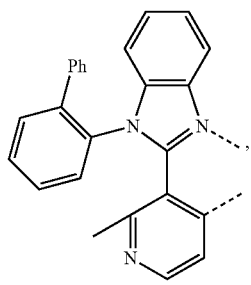 L$_A$77
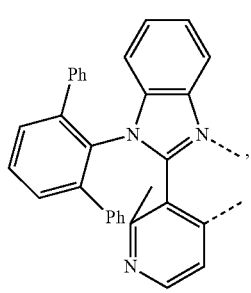 L$_A$78
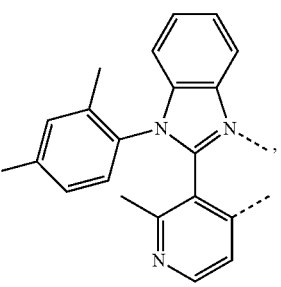 L$_A$79
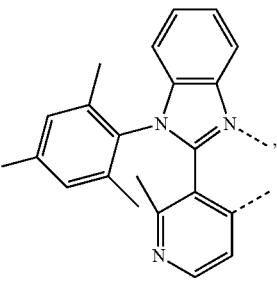 L$_A$80
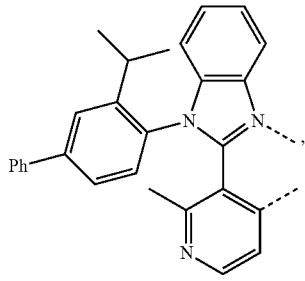 L$_A$81

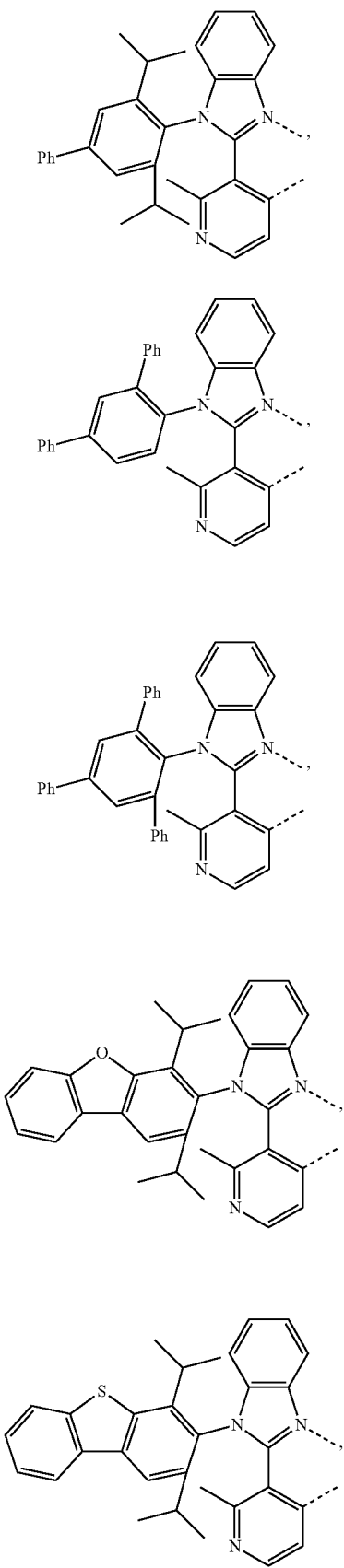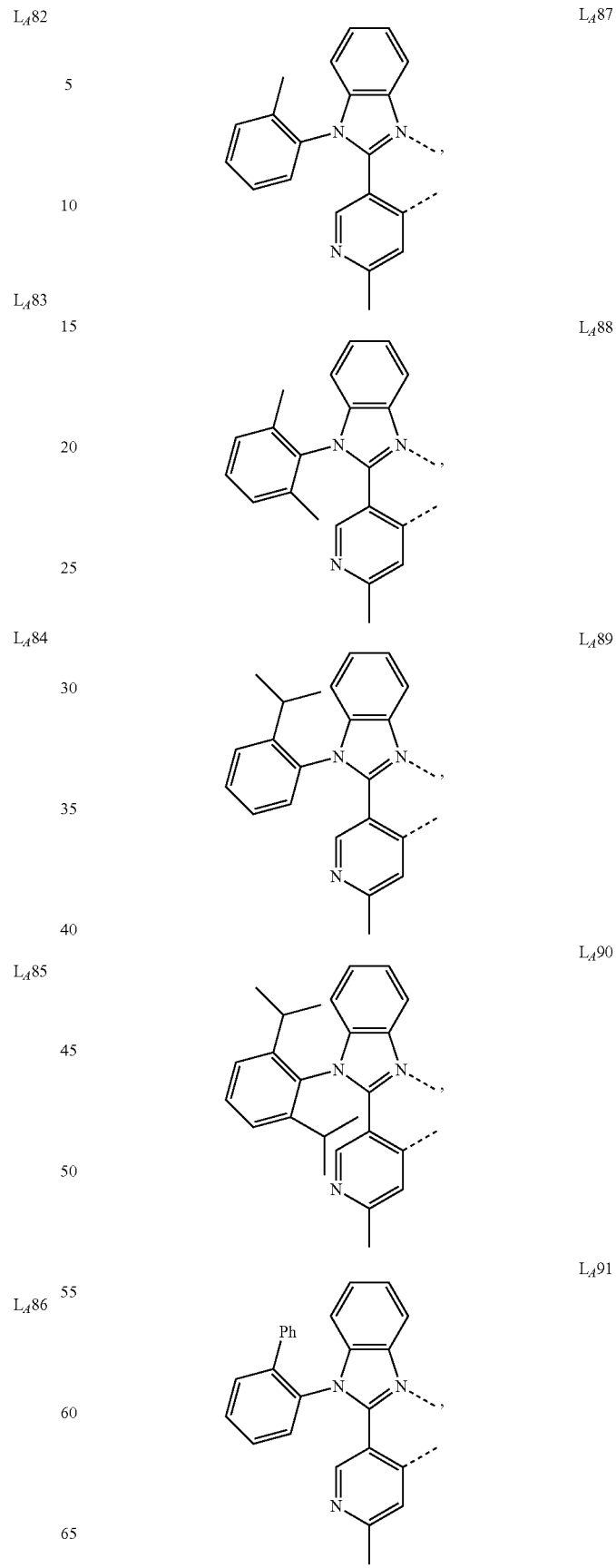

L_A92 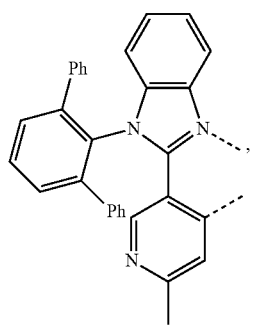
L_A93 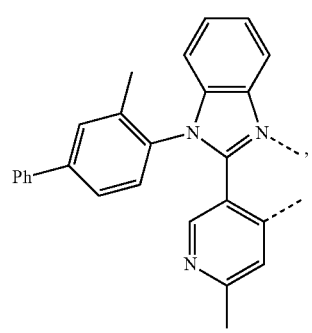
L_A94 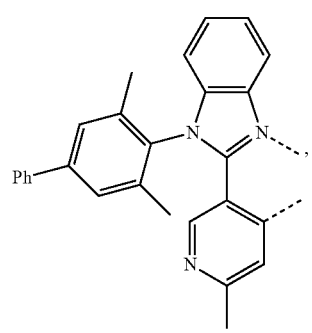
L_A95 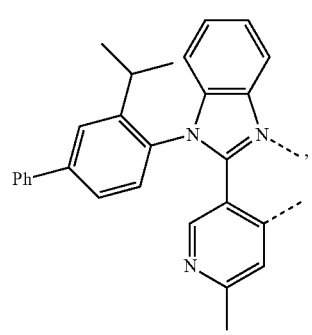
L_A96 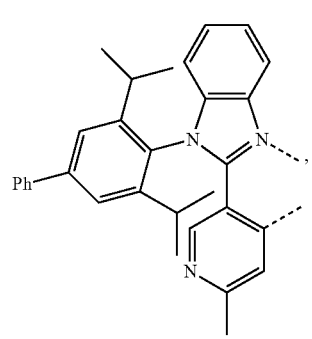
L_A97 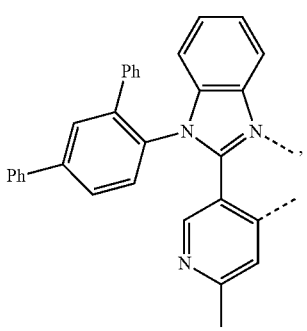
L_A98 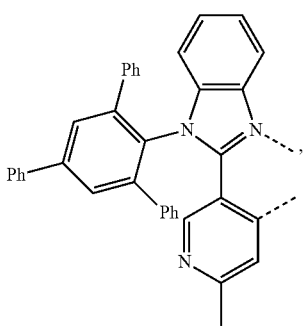
L_A99 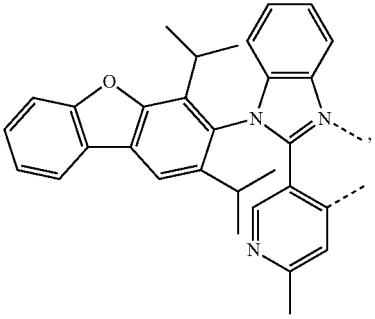
L_A100 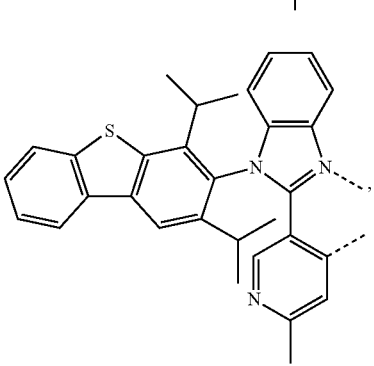
L_A101 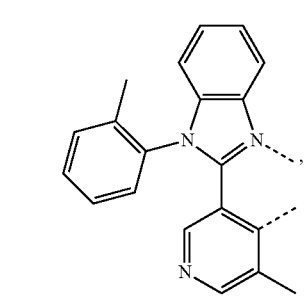

L<sub>A</sub>102
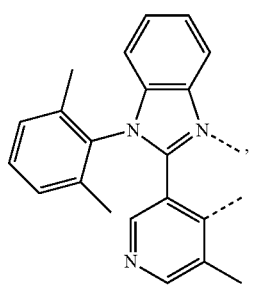
L<sub>A</sub>103
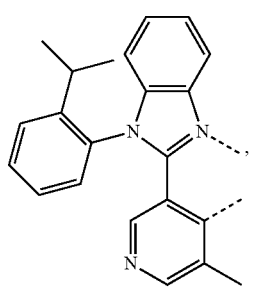
L<sub>A</sub>104
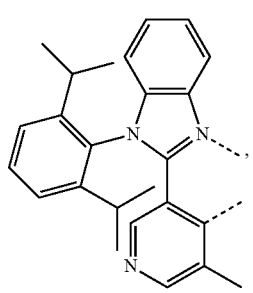
L<sub>A</sub>105
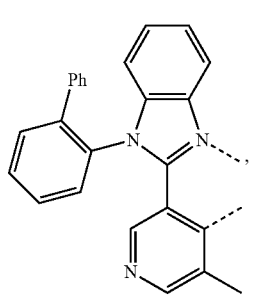
L<sub>A</sub>106
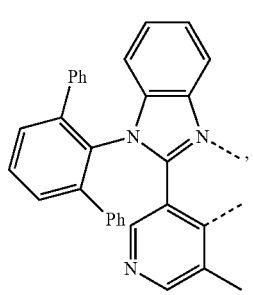
L<sub>A</sub>107
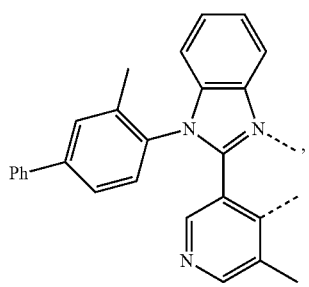
L<sub>A</sub>108
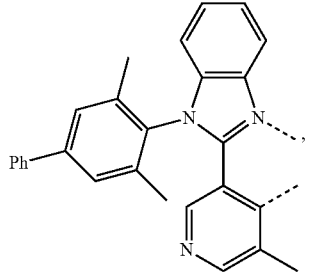
L<sub>A</sub>109
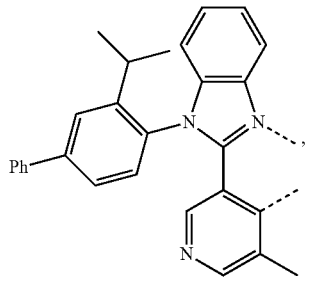
L<sub>A</sub>110
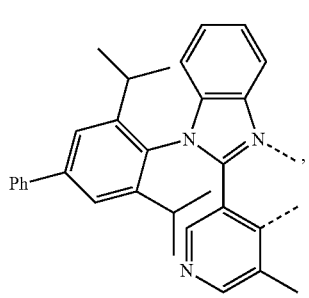
L<sub>A</sub>111
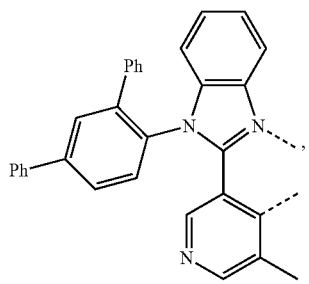

321
-continued
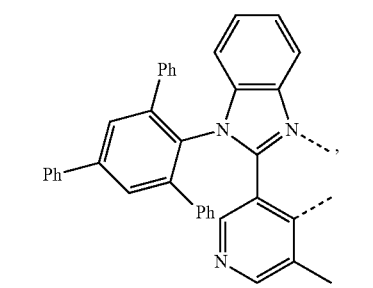
L<sub>A</sub>112
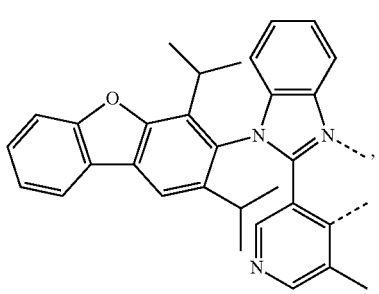
L<sub>A</sub>113
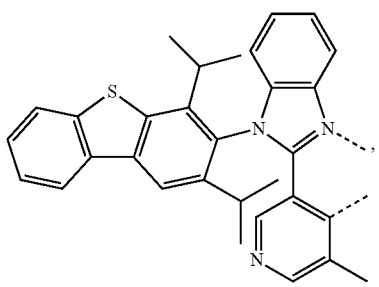
L<sub>A</sub>114
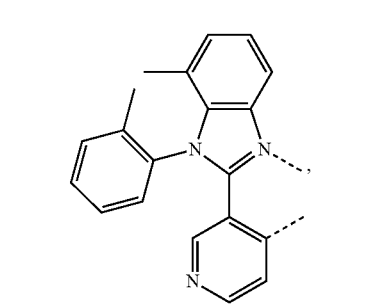
L<sub>A</sub>115
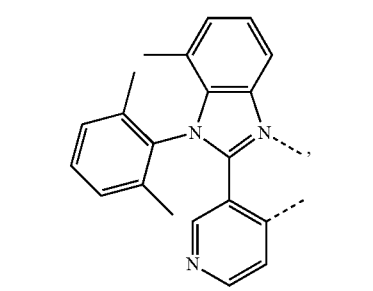
L<sub>A</sub>116
322
-continued
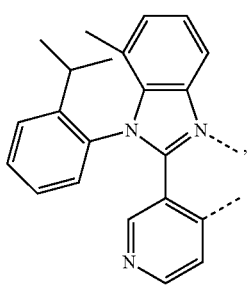
L<sub>A</sub>117
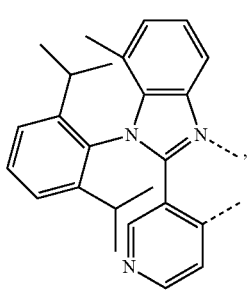
L<sub>A</sub>118
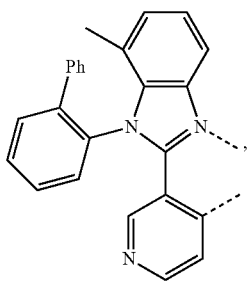
L<sub>A</sub>119
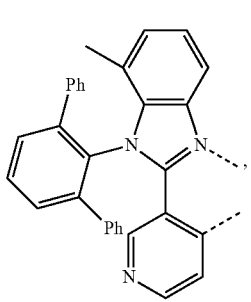
L<sub>A</sub>120
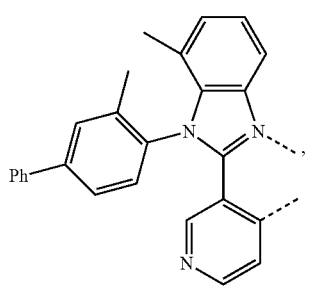
L<sub>A</sub>121

-continued
L<sub>A</sub>122
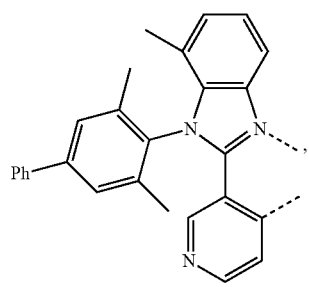
L<sub>A</sub>123
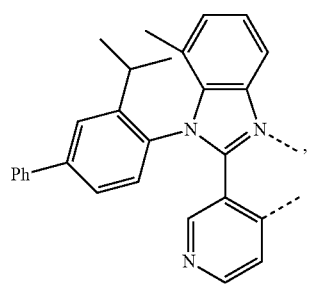
L<sub>A</sub>124
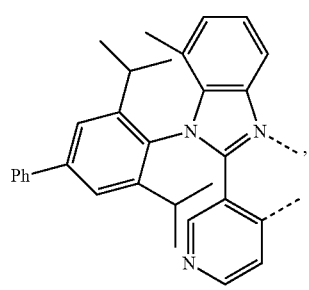
L<sub>A</sub>125
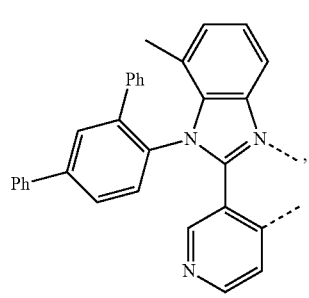
L<sub>A</sub>126
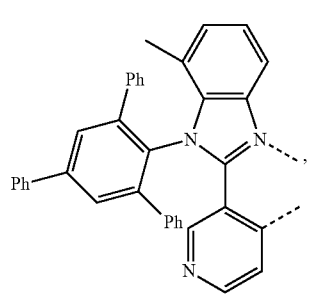
-continued
L<sub>A</sub>127
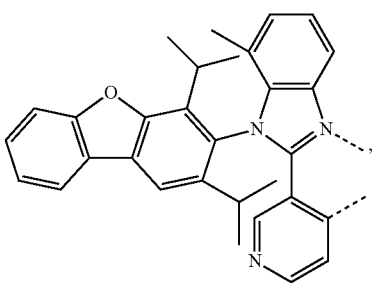
L<sub>A</sub>128
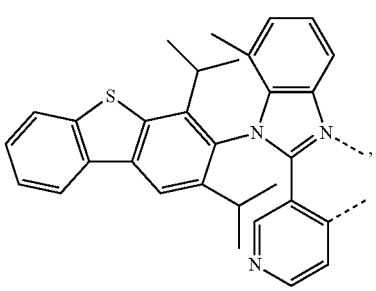
L<sub>A</sub>129
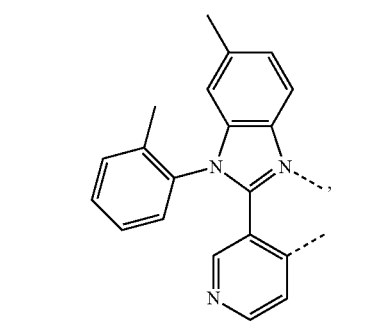
L<sub>A</sub>130
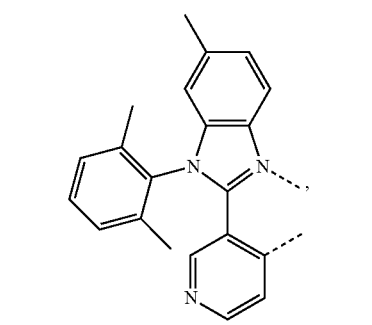
L<sub>A</sub>131
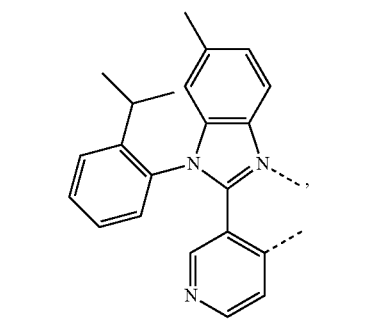

325
-continued
L_A132
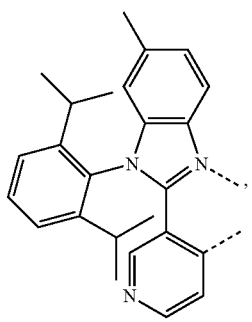
L_A133
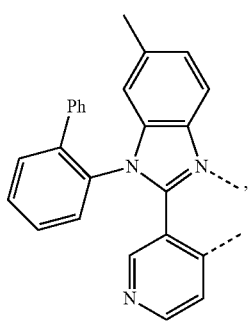
L_A134
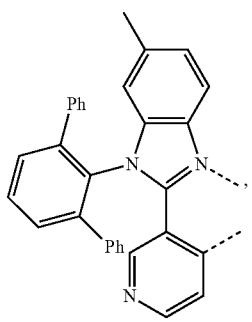
L_A135
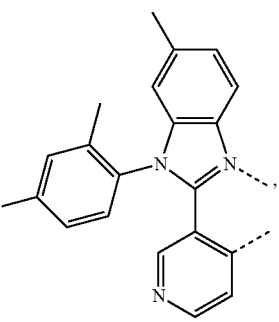
L_A136
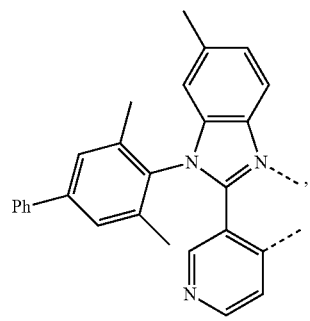
326
-continued
L_A137
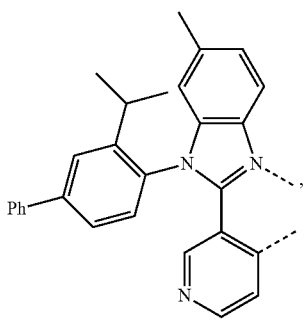
L_A138
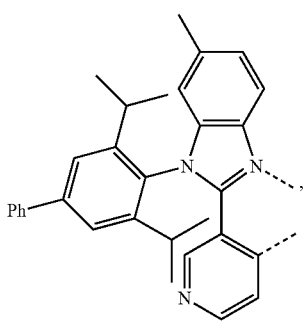
L_A139
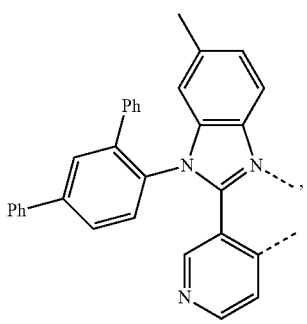
L_A140
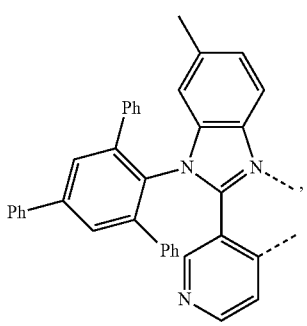
L_A141
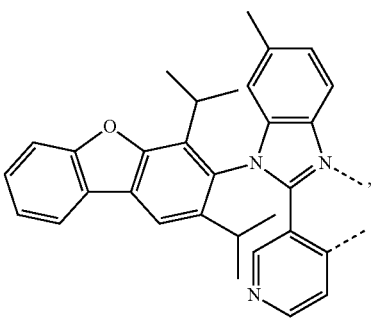

L_A142 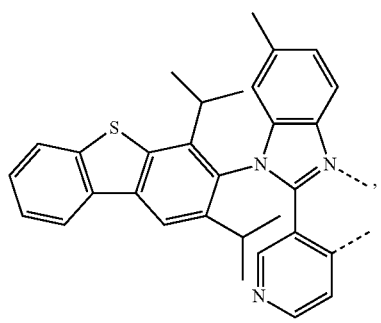
L_A143 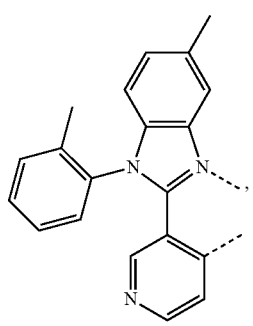
L_A144 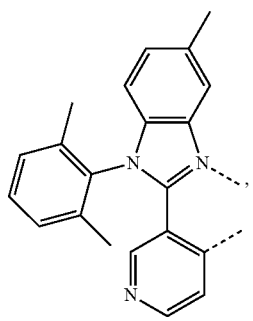
L_A145 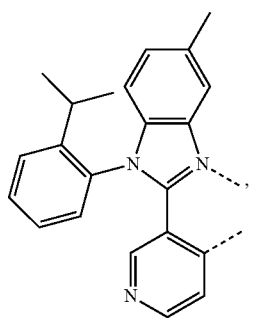
L_A146 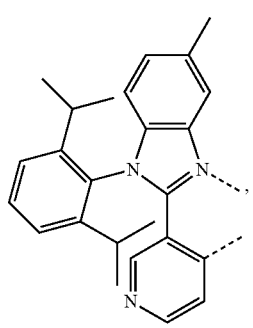
L_A147 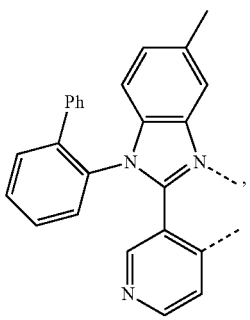
L_A148 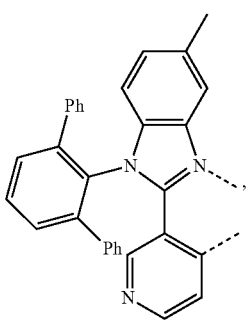
L_A149 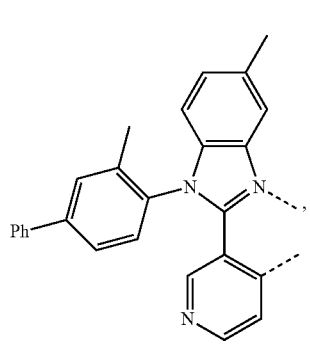
L_A150 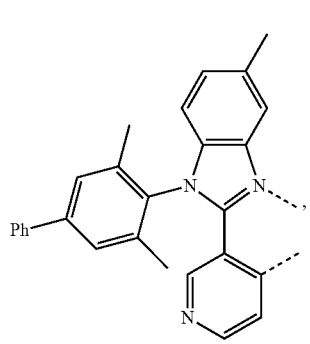
L_A151 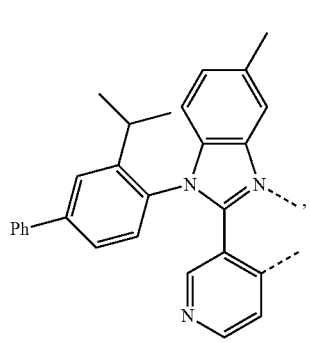

L_A152
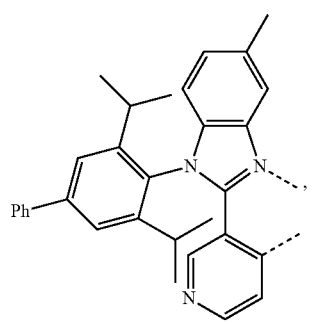
L_A153
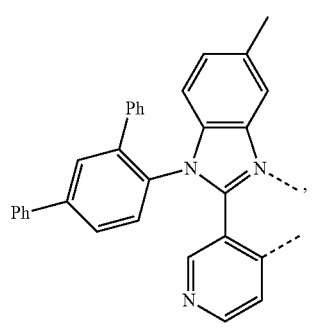
L_A154
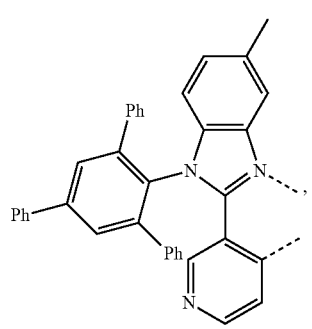
L_A155
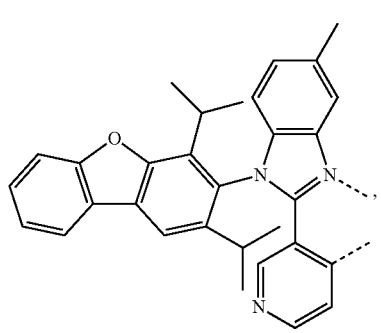
L_A156
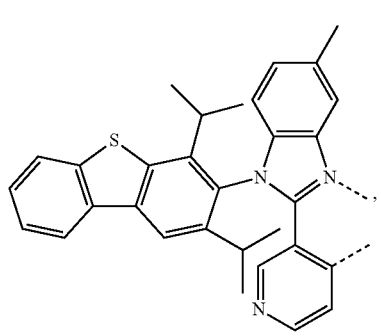
L_A157
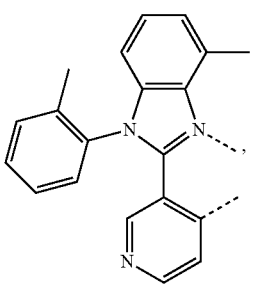
L_A158
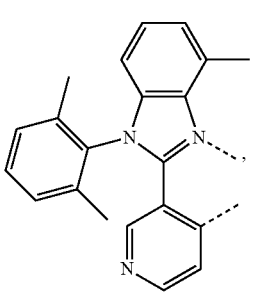
L_A159
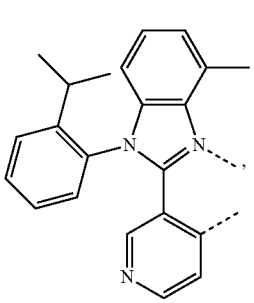
L_A160
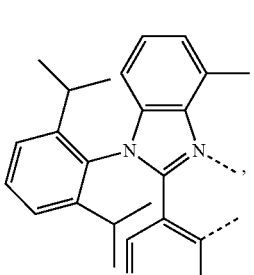
L_A161
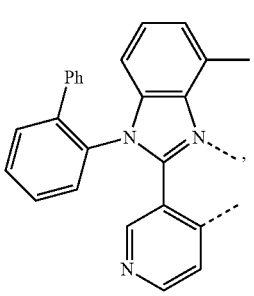

L<sub>A</sub>162
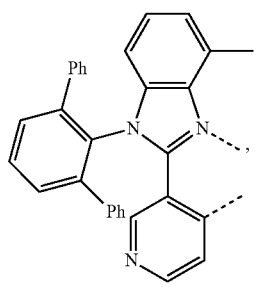
L<sub>A</sub>163
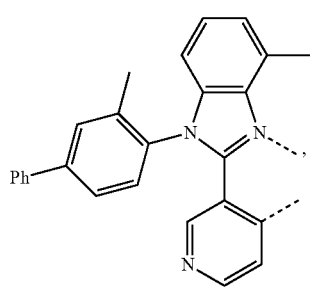
L<sub>A</sub>164
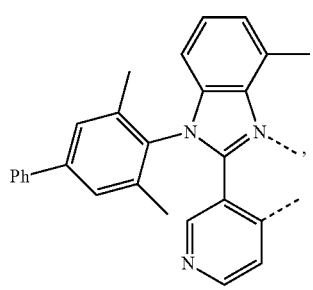
L<sub>A</sub>165
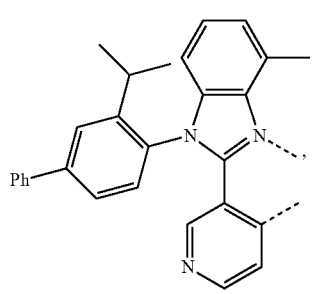
L<sub>A</sub>166
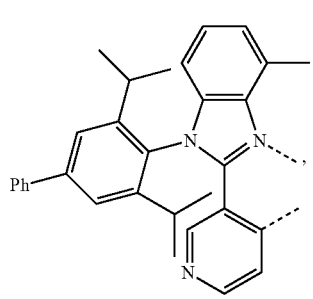
L<sub>A</sub>167
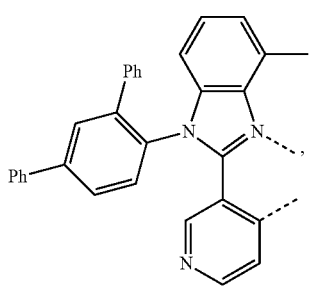
L<sub>A</sub>168
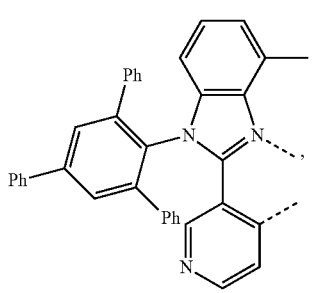
L<sub>A</sub>169
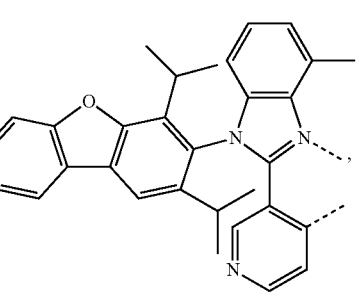
L<sub>A</sub>170
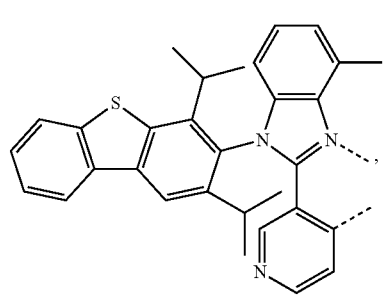
L<sub>A</sub>171
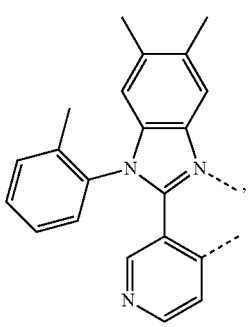

L<sub>A</sub>172
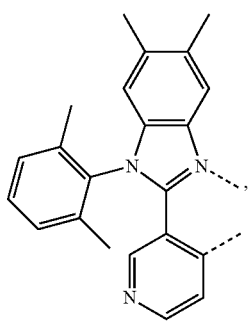
L<sub>A</sub>173
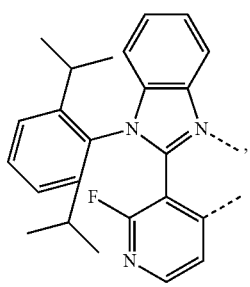
L<sub>A</sub>174
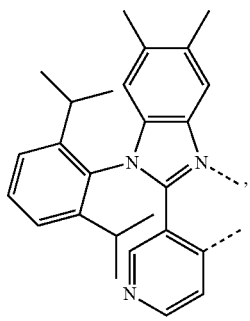
P<sub>A</sub>175
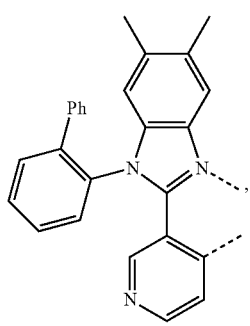
P<sub>A</sub>176
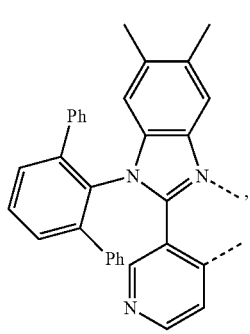
P<sub>A</sub>177
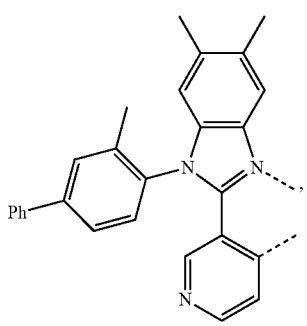
P<sub>A</sub>178
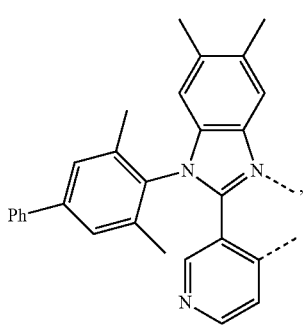
P<sub>A</sub>179
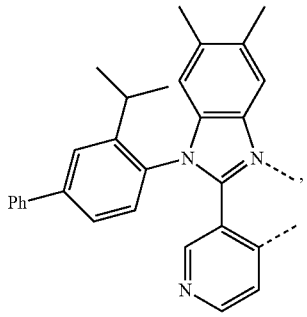
L<sub>A</sub>180
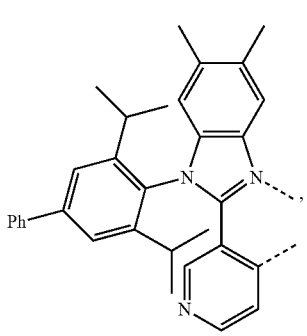
L<sub>A</sub>181
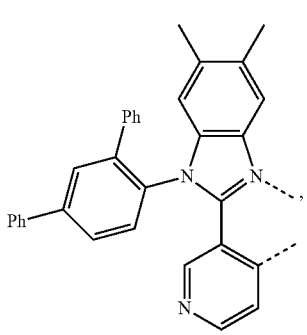

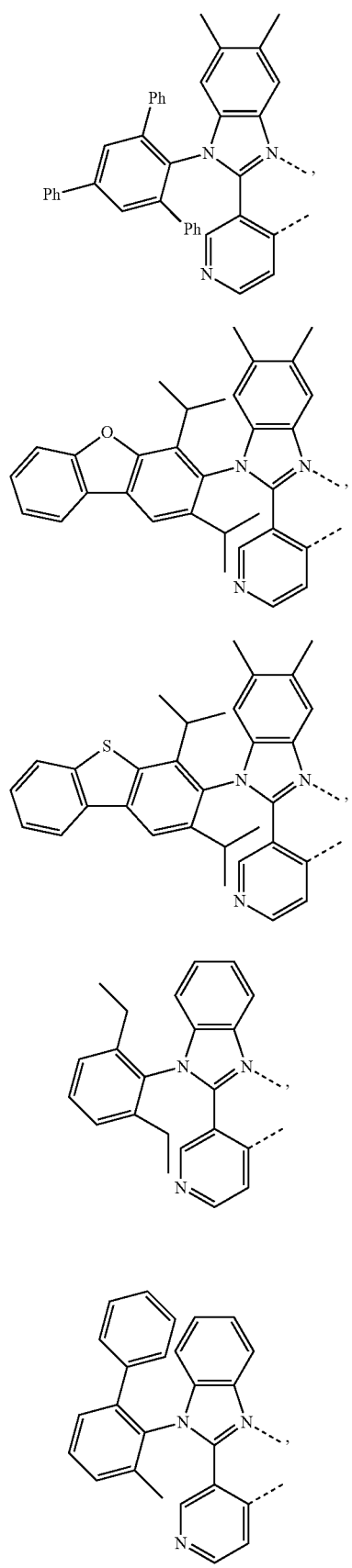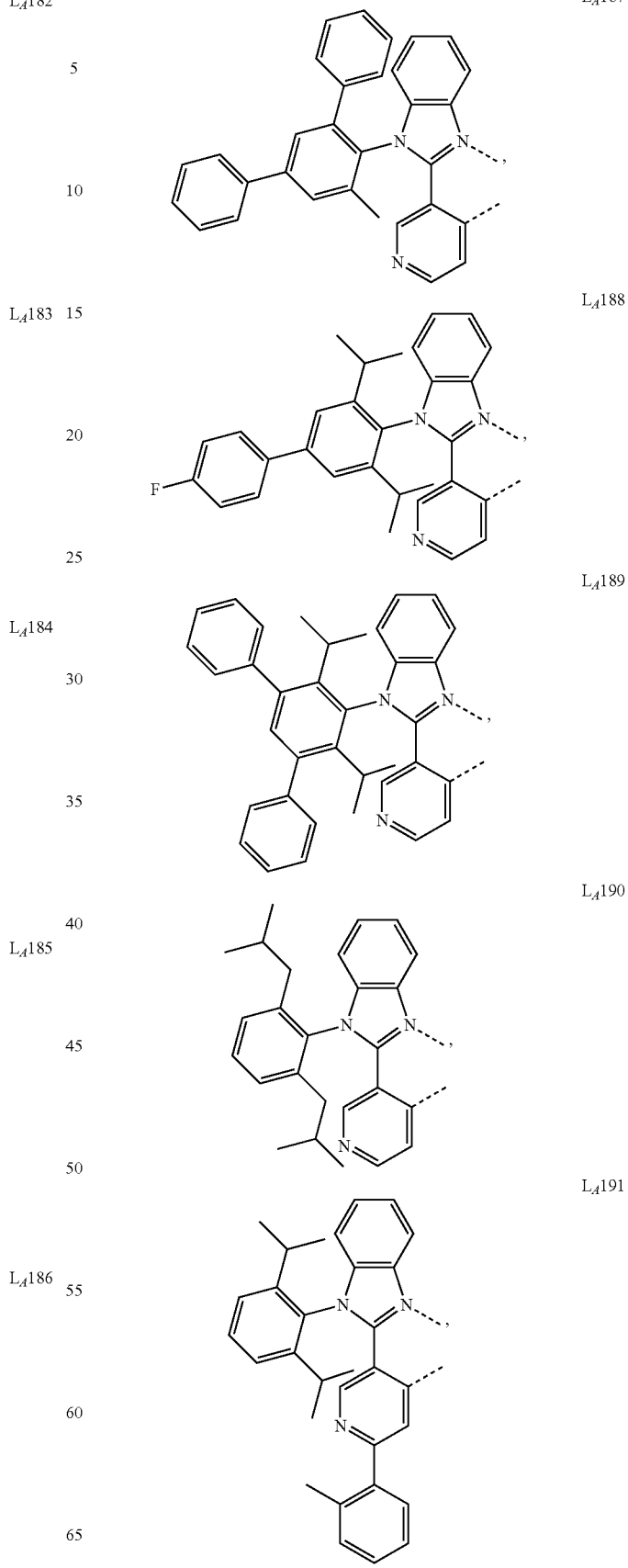

-continued

L$_A$192
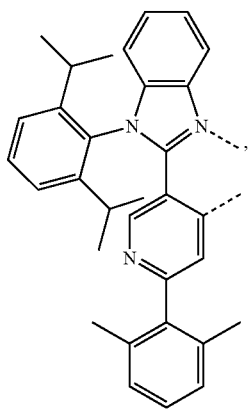

L$_A$193
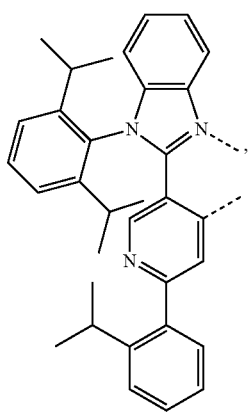

L$_A$194
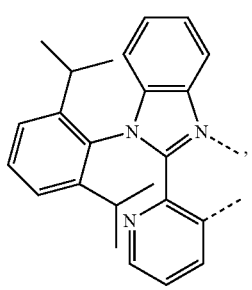

L$_A$195
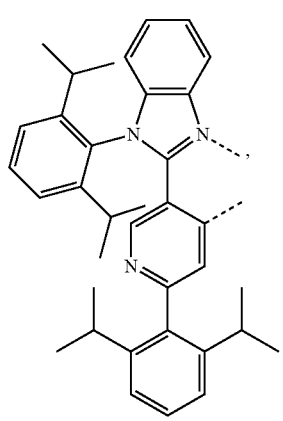

-continued

L$_A$196
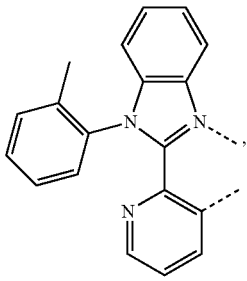

L$_A$197
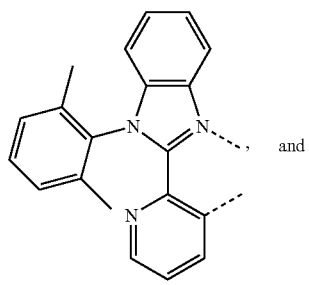

and

L$_A$198
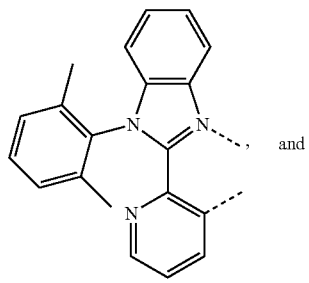

8. The compound of claim 7, wherein the compound is Compound Ax having the formula Ir(L$_A$i)$_3$, or Compound By having the formula Ir(L$_A$i)(L$_j$)$_2$ or Compound Cz having the formula Ir(L$_A$i)$_2$(L$_j$);

wherein x=i; i is an integer from 1 to 198;

wherein y=302i+j−302; i is an integer from 1 to 198, and j is an integer from 1 to 302;

wherein z=302i+j−302; i is an integer from 1 to 198, and j is an integer from 1 to 302; and wherein L$_1$ to L$_{302}$ have the following structure L$_1$
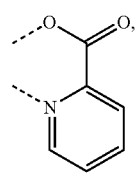

L$_2$
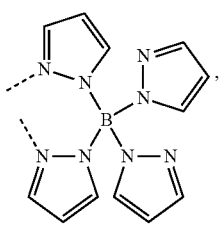

-continued
| | |
|---|---|
| L3 | 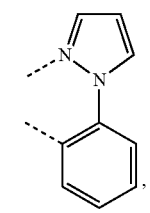 |
| L4 | 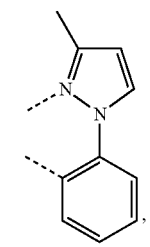 |
| L5 | 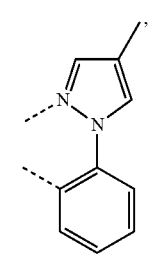 |
| L6 | 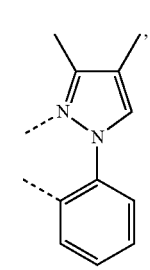 |
| L7 | 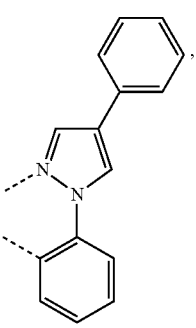 |
| L8 | 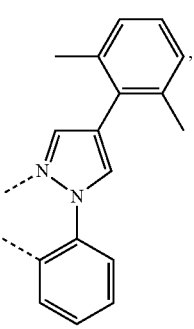 |
-continued
| | |
|---|---|
| L9 | 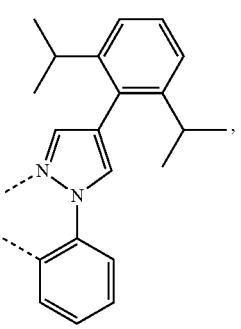 |
| L10 | 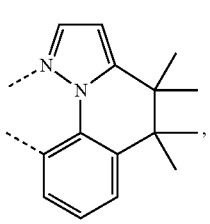 |
| L11 | 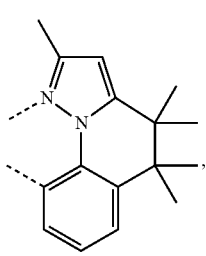 |
| L12 | 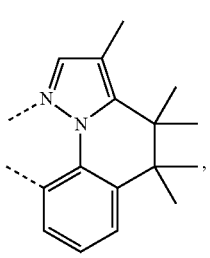 |
| L13 | 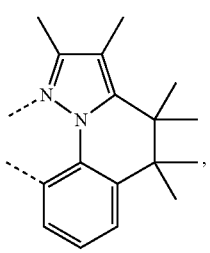 |
| L14 | 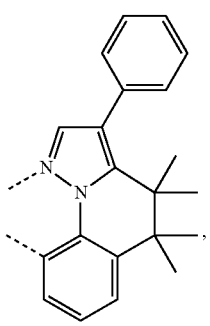 |

-continued
L15 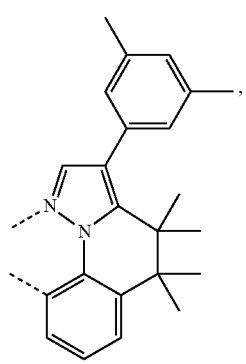
L16 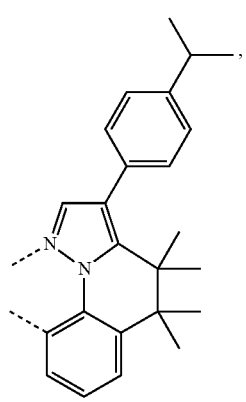
L17 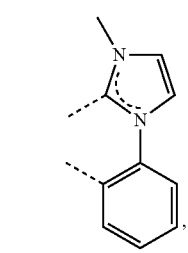
L18 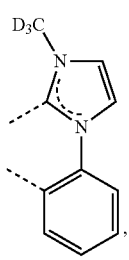
L19 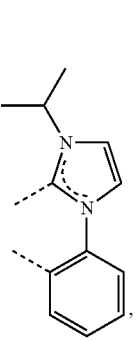
-continued
L20 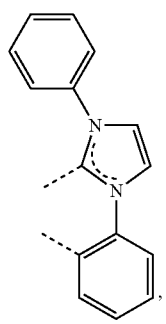
L21 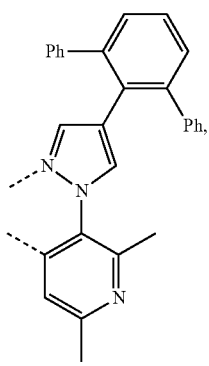
L22 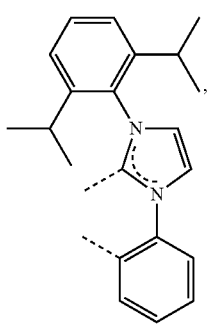
L23 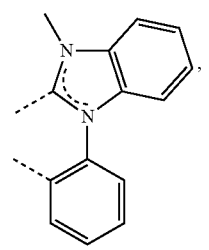
L24 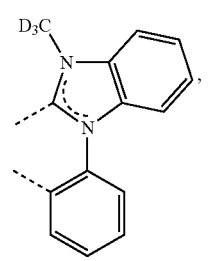

L25 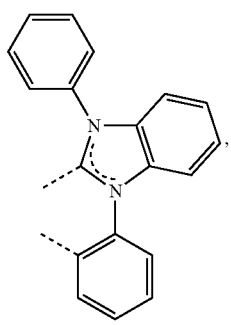
L26 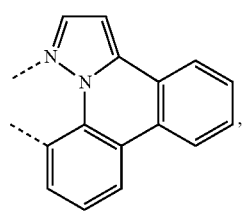
L27 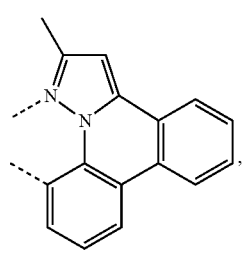
L28 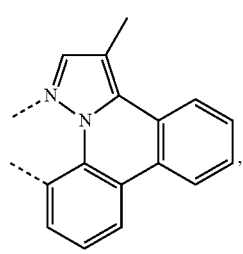
L29 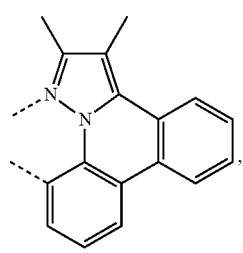
L30 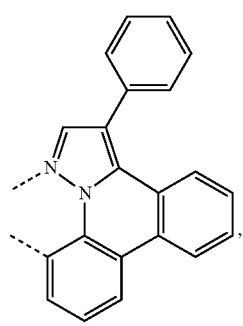
L31 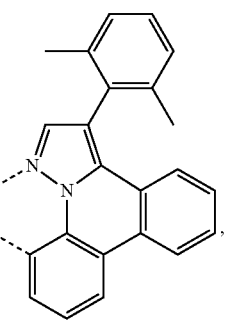
L32 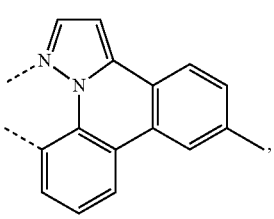
L33 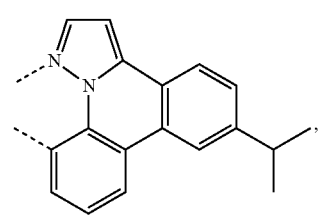
L34 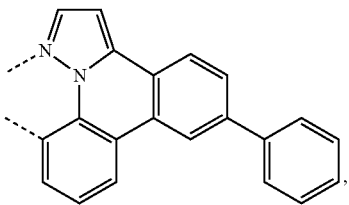
L35 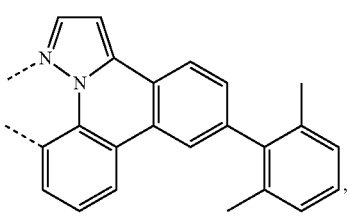
L36 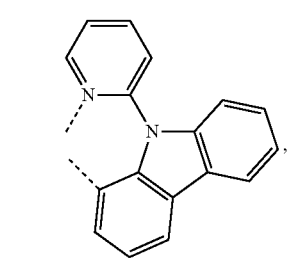

| | |
|---|---|
| 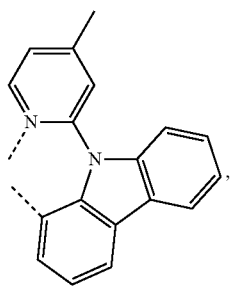 | $L_{37}$ |
| 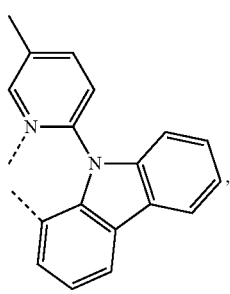 | $L_{38}$ |
| 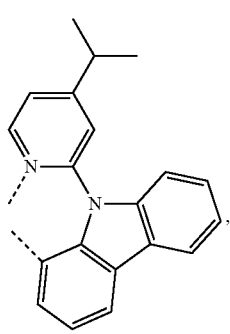 | $L_{39}$ |
| 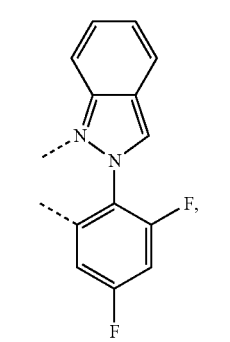 | $L_{40}$ |
| 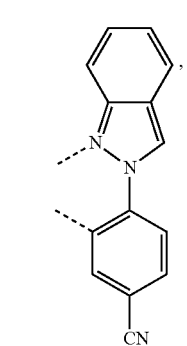 | $L_{41}$ |
| 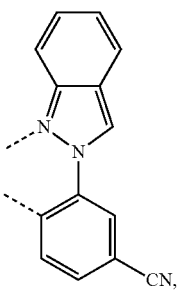 | $L_{42}$ |
| 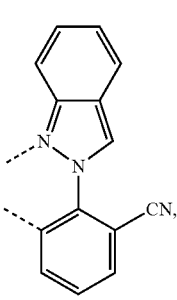 | $L_{43}$ |
| 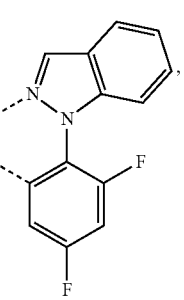 | $L_{44}$ |
| 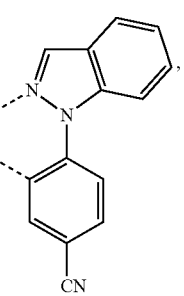 | $L_{45}$ |
| 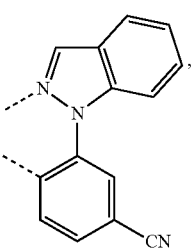 | $L_{46}$ |

-continued
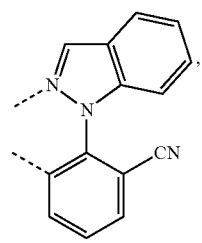 L47
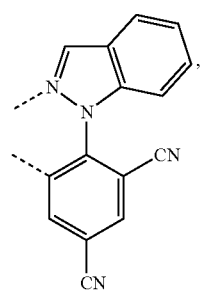 L48
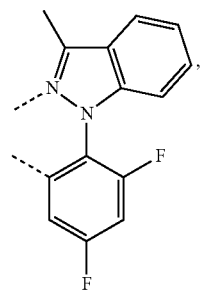 L49
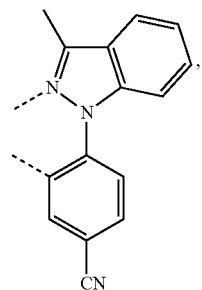 L50
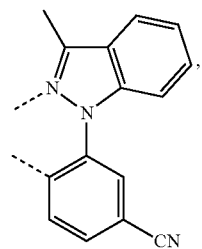 L51
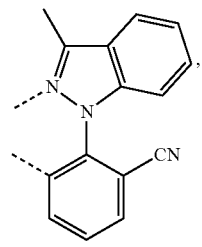 L52
-continued
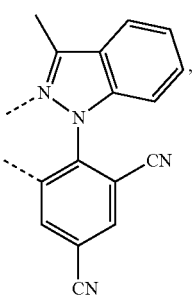 L53
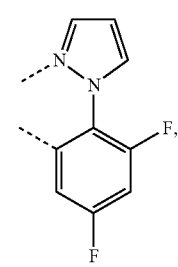 L54
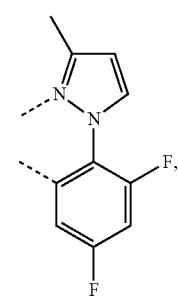 L55
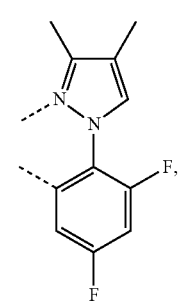 L56
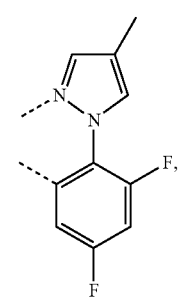 L57

L<sub>58</sub>
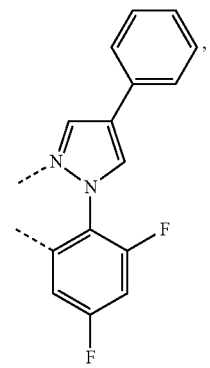
L<sub>59</sub>
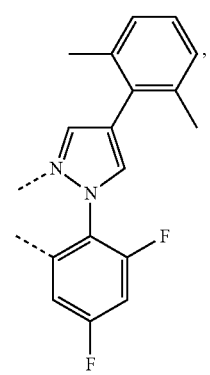
L<sub>60</sub>
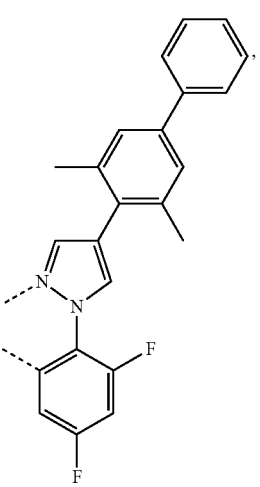
L<sub>61</sub>
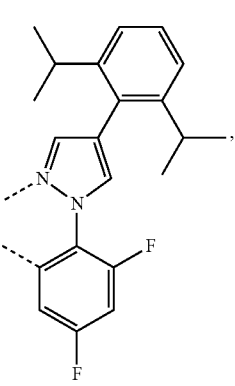
L<sub>62</sub>
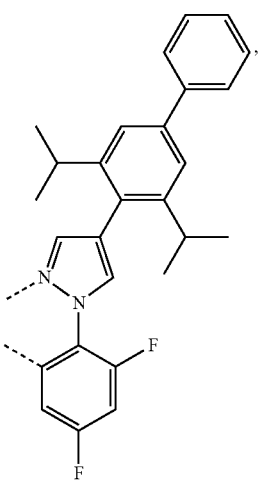
L<sub>63</sub>
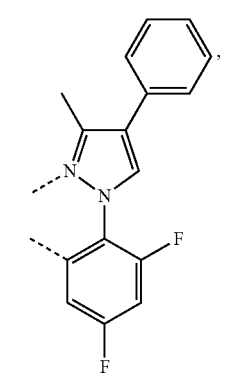
L<sub>64</sub>
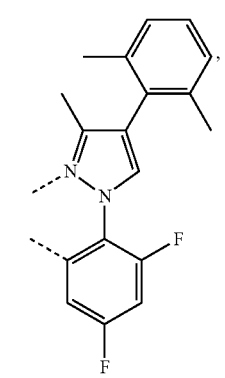

351
-continued
L$_{65}$
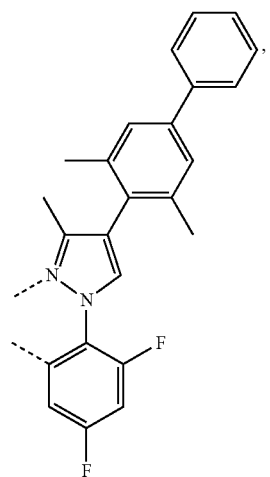
L$_{66}$
L$_{67}$
L$_{68}$
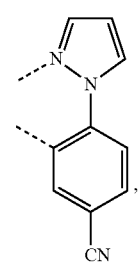
352
-continued
L$_{69}$
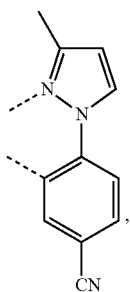
L$_{70}$
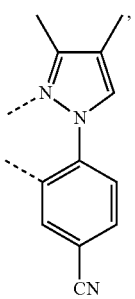
L$_{71}$
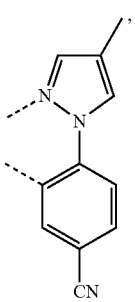
L$_{72}$
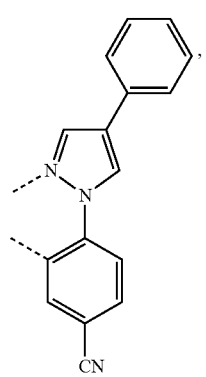

353
-continued
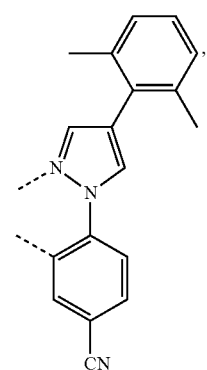
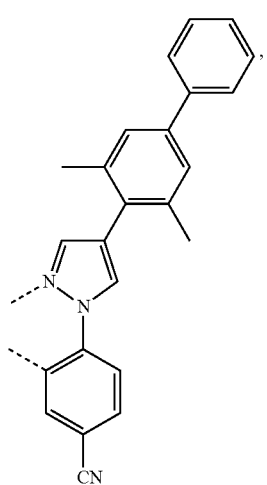
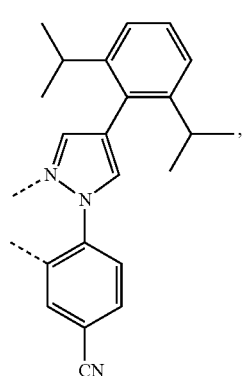
354
-continued
L73
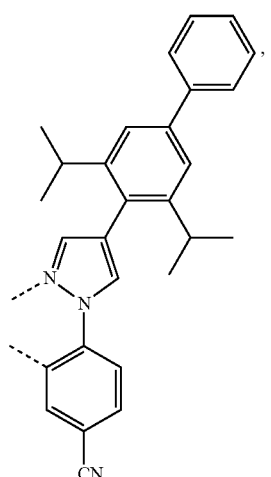
L74
L75
L76
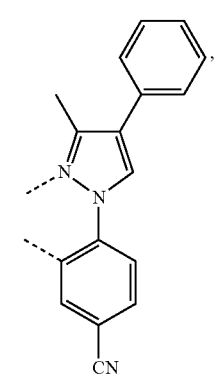
L77
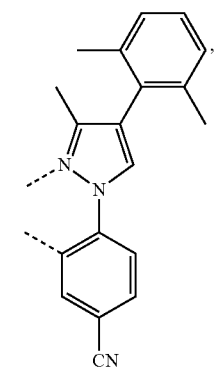
L78

L79 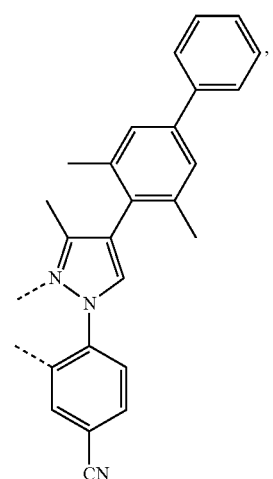
L80 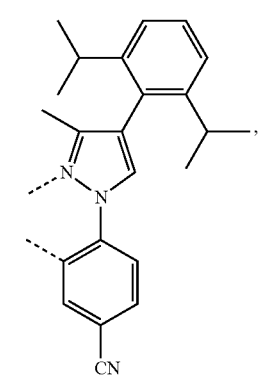
L81 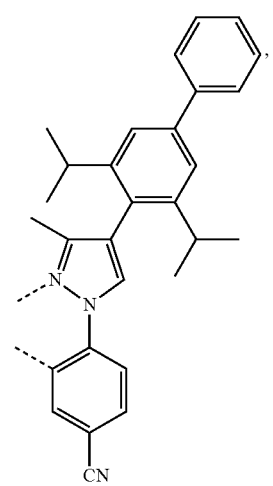
L82 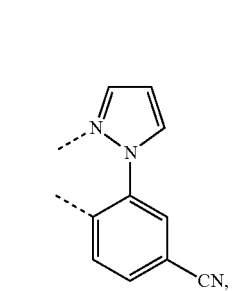
L83 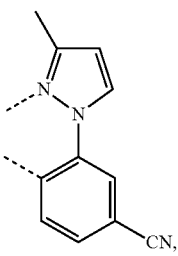
L84 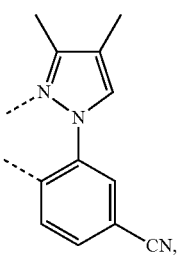
L85 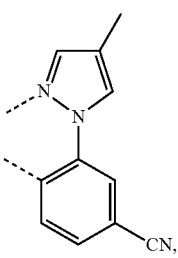
L86 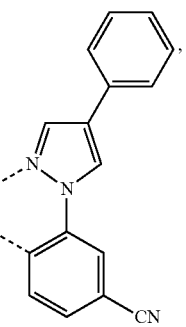
L87 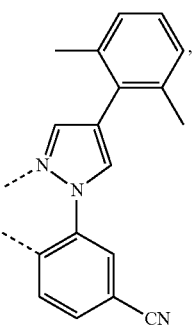

357
-continued
L<sub>88</sub>
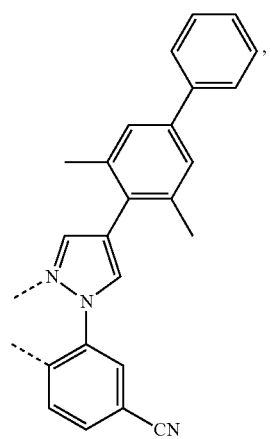
L<sub>89</sub>
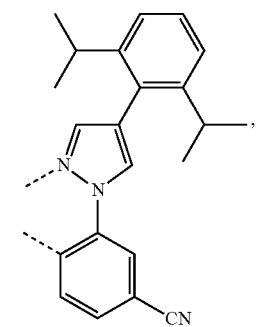
L<sub>90</sub>
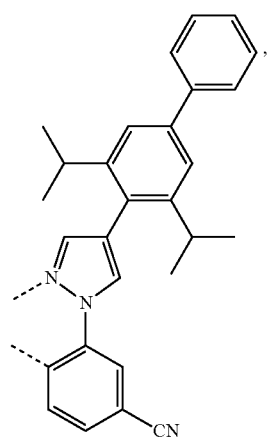
L<sub>91</sub>
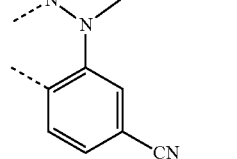
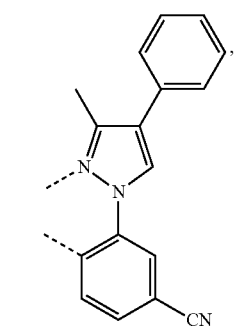
358
-continued
L<sub>92</sub>
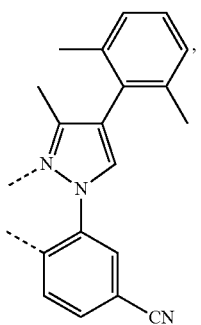
L<sub>93</sub>
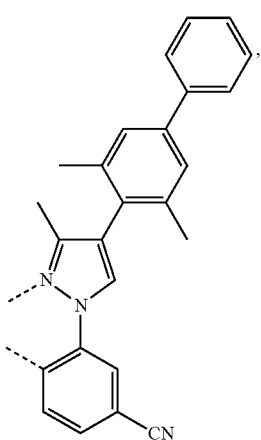
L<sub>94</sub>
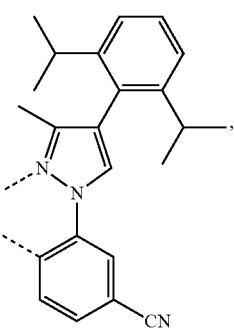
L<sub>95</sub>
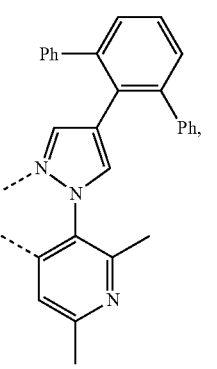

L₉₆ 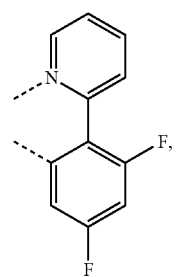
L₉₇ 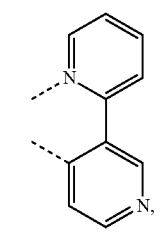
L₉₈ 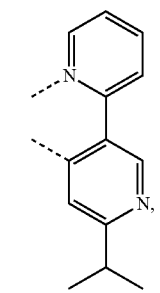
L₉₉ 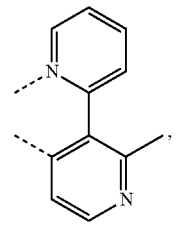
L₁₀₀ 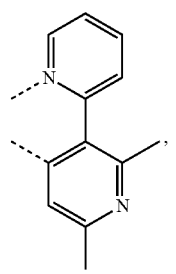
L₁₀₁ 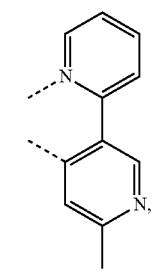
L₁₀₂ 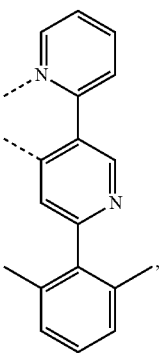
L₁₀₃ 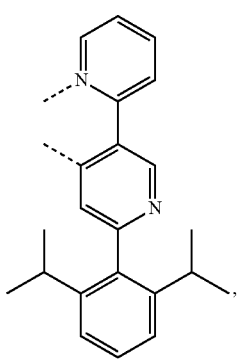
L₁₀₄ 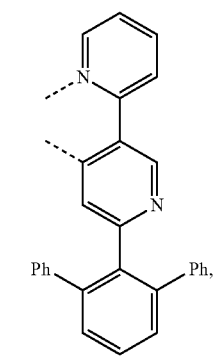
L₁₀₅ 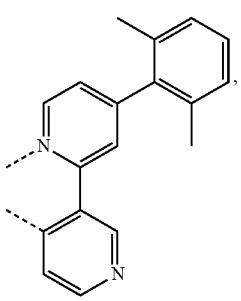

L106 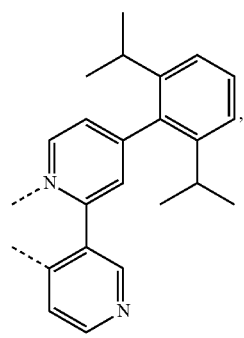
L107 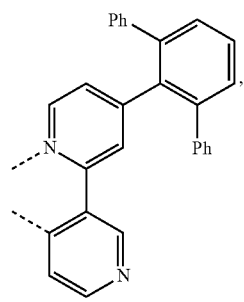
L108 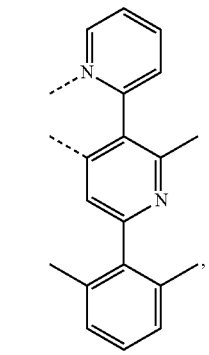
L109 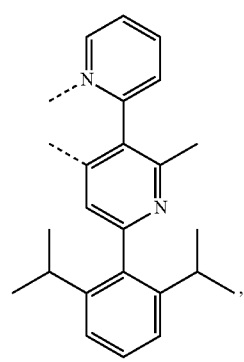
L110 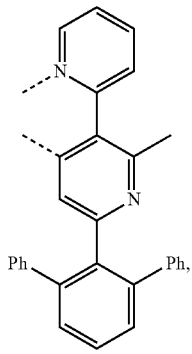
L111 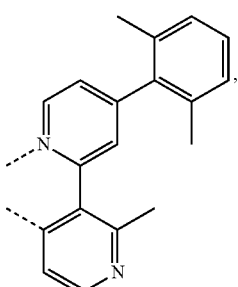
L112 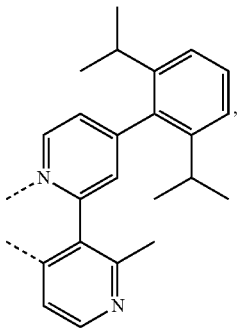
L113 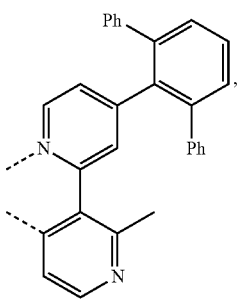
L114 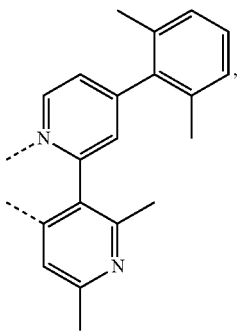

-continued
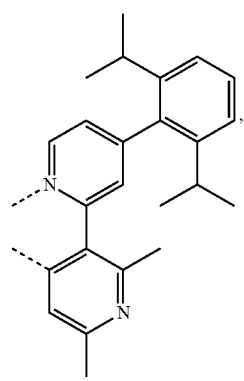 L115
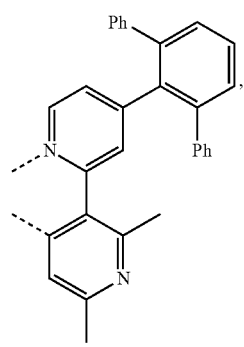 L116
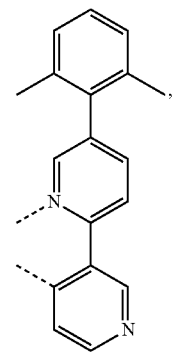 L117
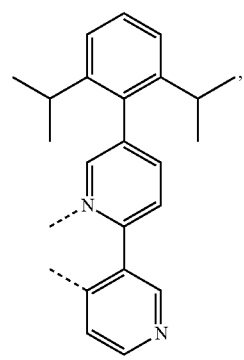 L118
-continued
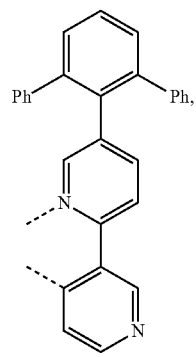 L119
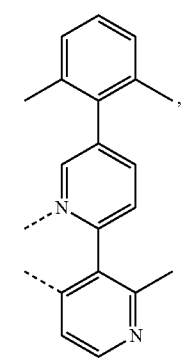 L120
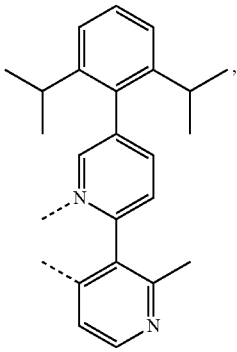 L121
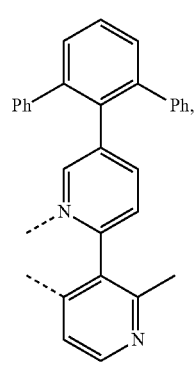 L122

-continued
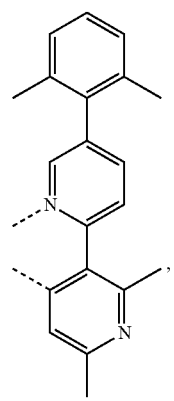
L123
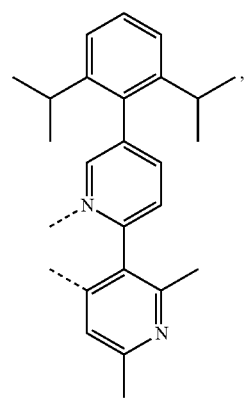
L124
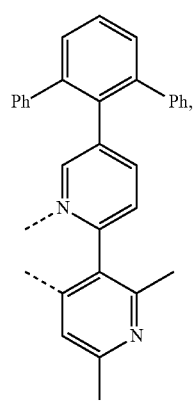
L125
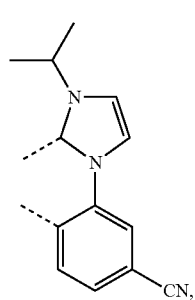
L126
-continued
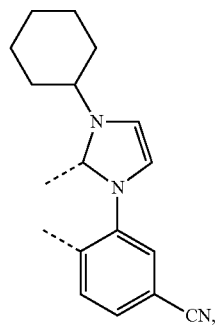
L127
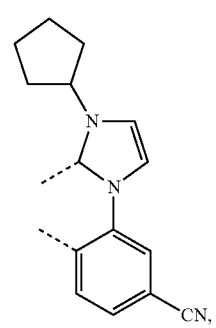
L128
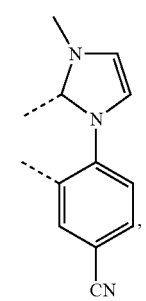
L129
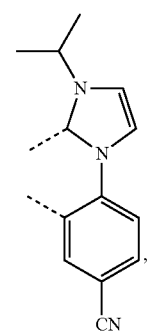
L130

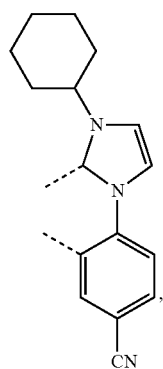 L131
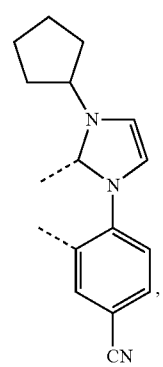 L132
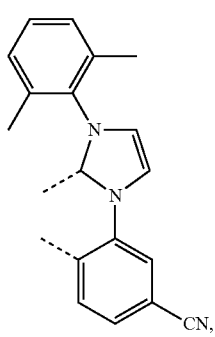 L133
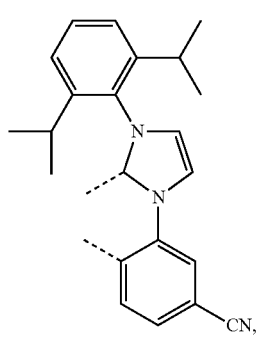 L134
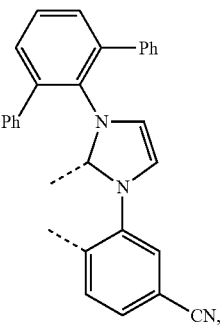 L135
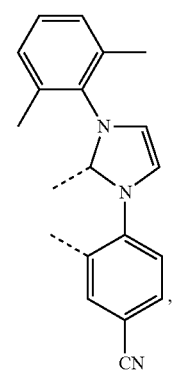 L136
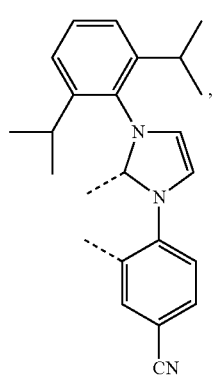 L137
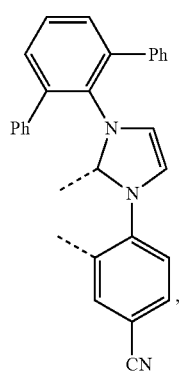 L138

-continued
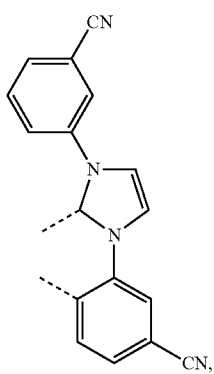
L139
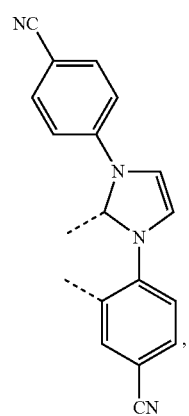
L140
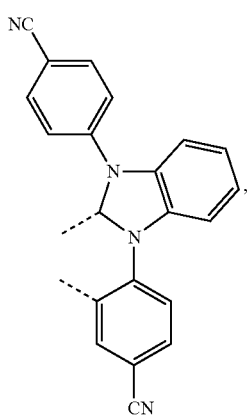
L141
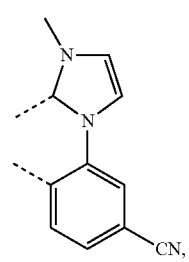
L142
-continued
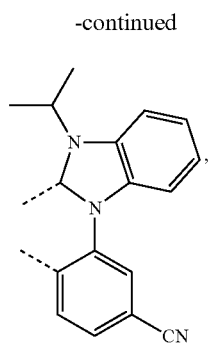
L143
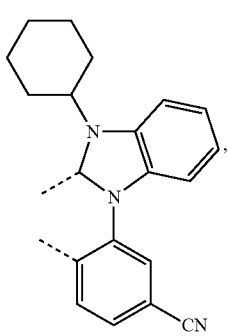
L144
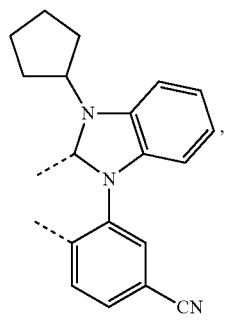
L145
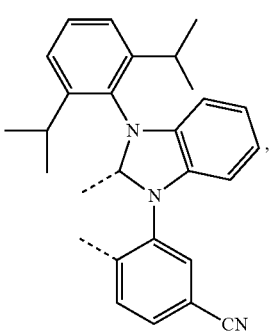
L146
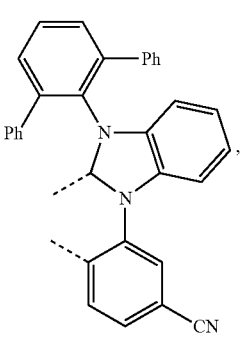
L147

371
-continued
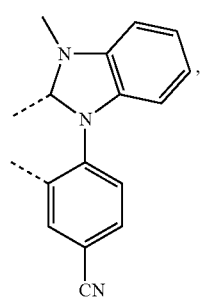
L148
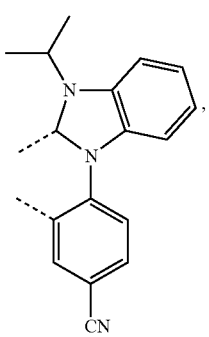
L149
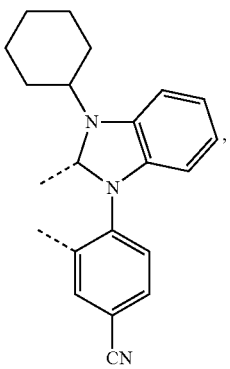
L150
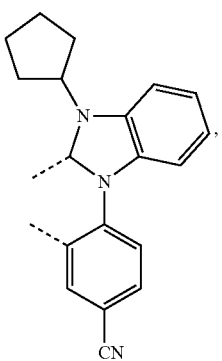
L151
372
-continued
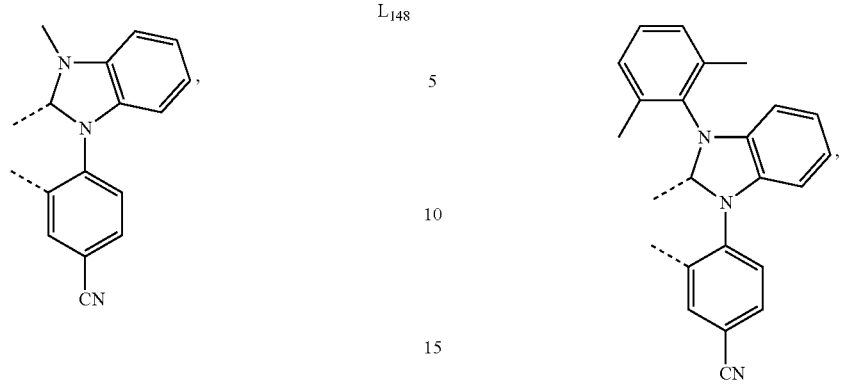
L152
L153
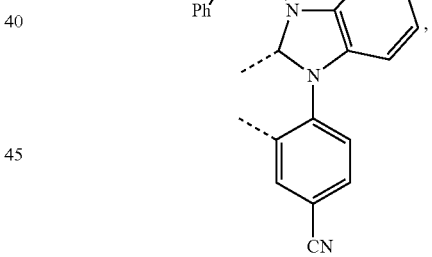
L154
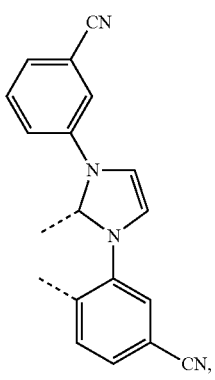
L155

-continued
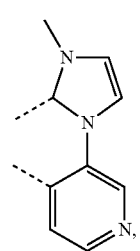   L156
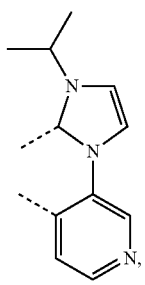   L157
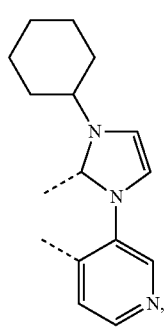   L158
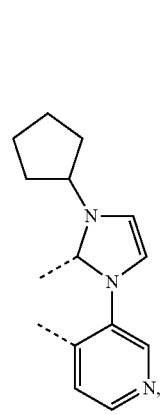   L159
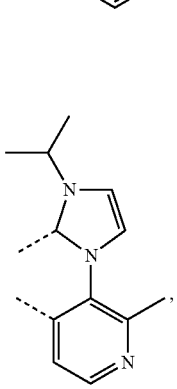   L160
-continued
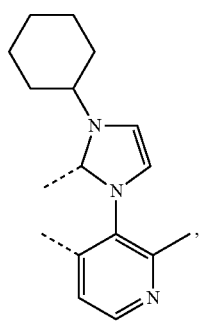   L161
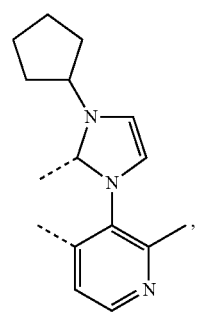   L162
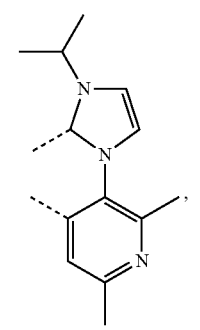   L163
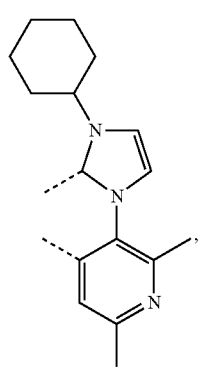   L164

-continued
L165 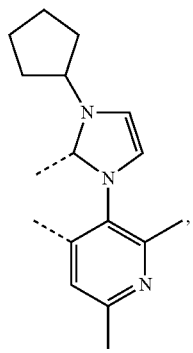
L166 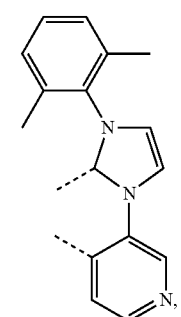
L167 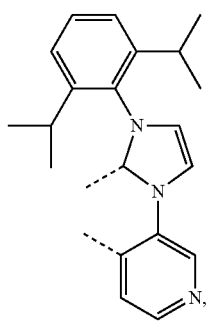
L168 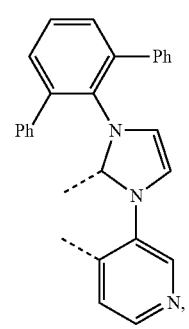
L169 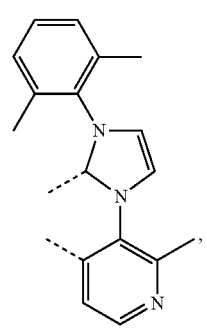
-continued
L170 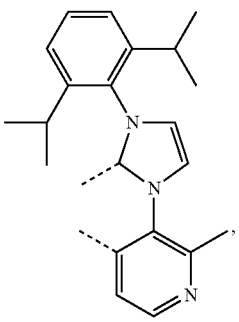
L171 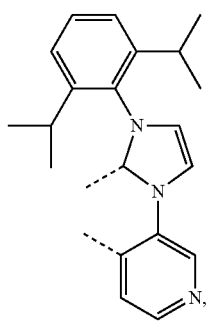
L172 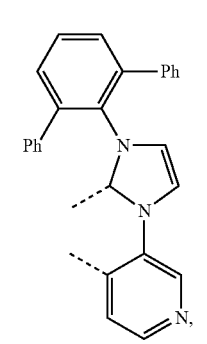
L173 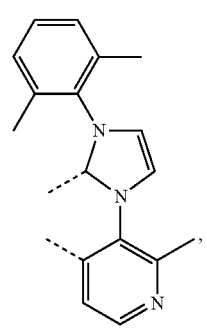

377
-continued
L174 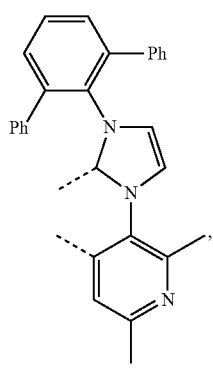
L175 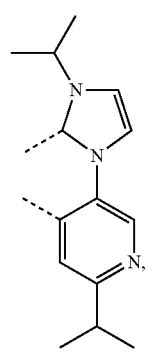
L176 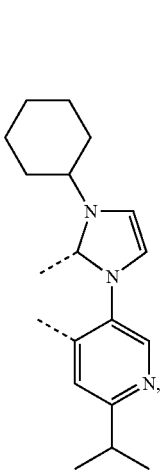
L177 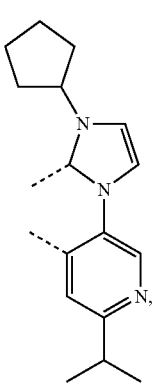
378
-continued
L178 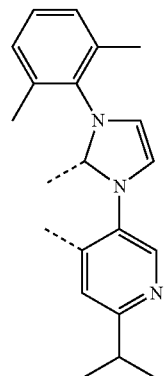
L179 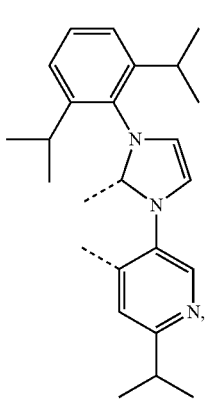
L180 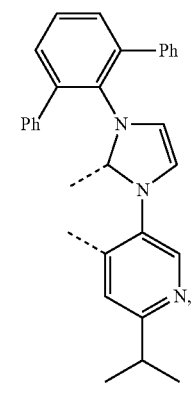
L181 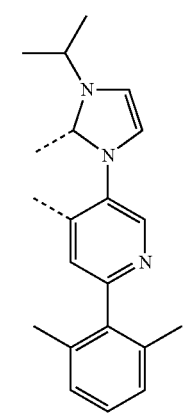

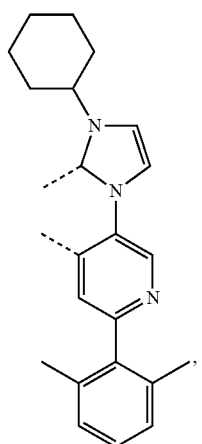 L₁₈₂
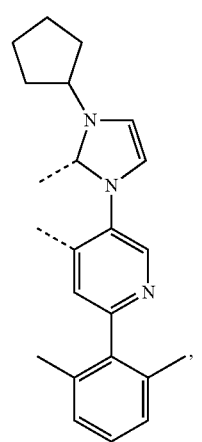 L₁₈₃
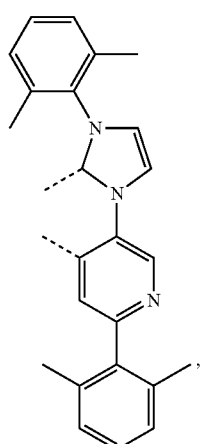 L₁₈₄
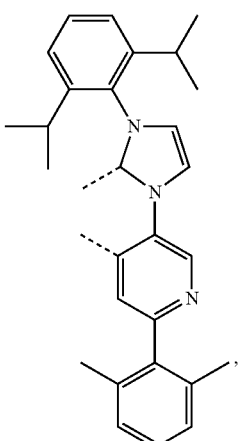 L₁₈₅
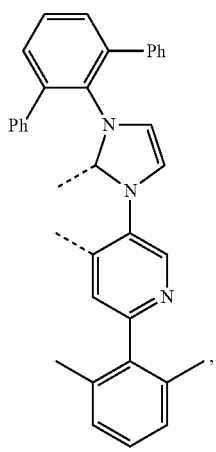 L₁₈₆
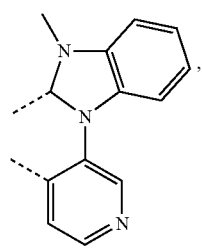 L₁₈₇
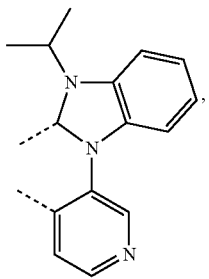 L₁₈₈

-continued
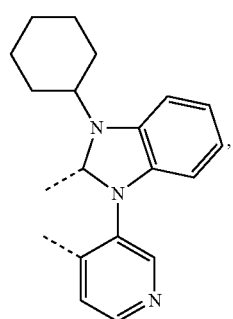 L189
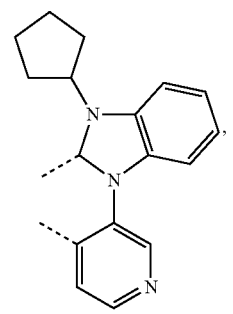 L190
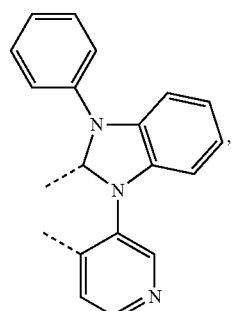 L191
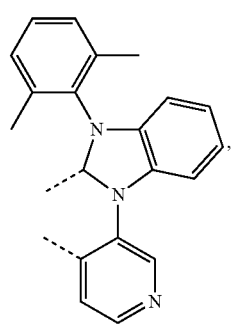 L192
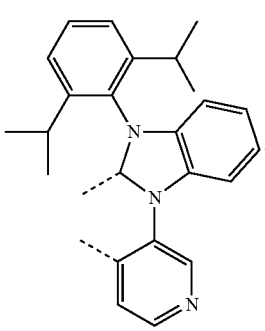 L193
-continued
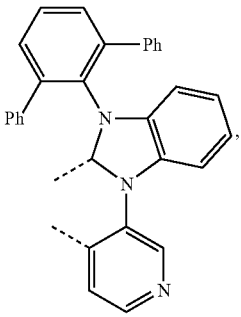 L194
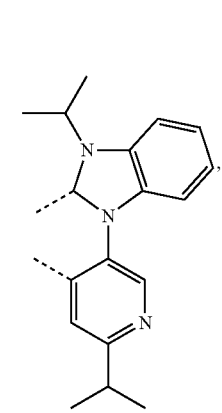 L195
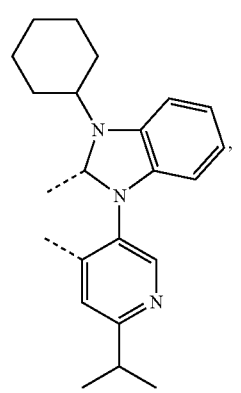 L196
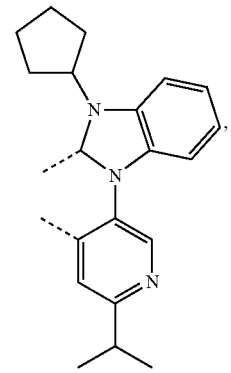 L197

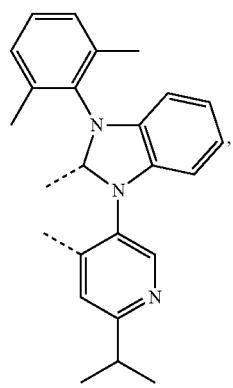 L198
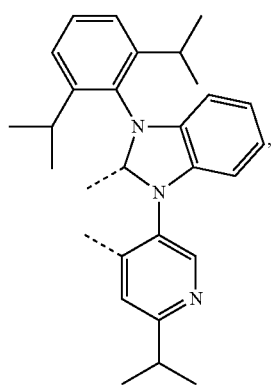 L199
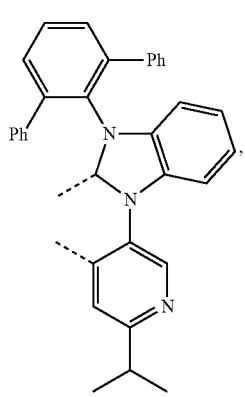 L200
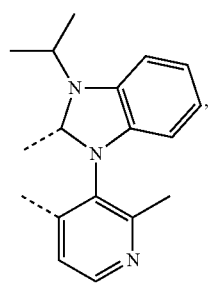 L201
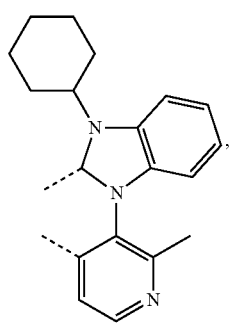 L202
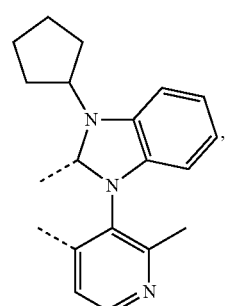 L203
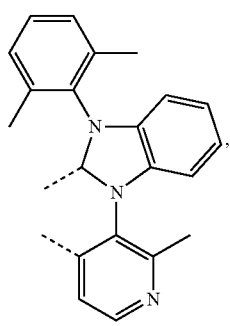 L204
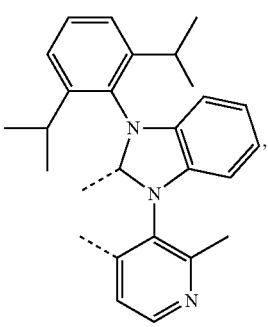 L205
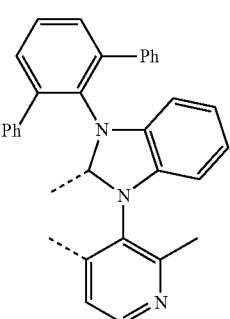 L206

L207
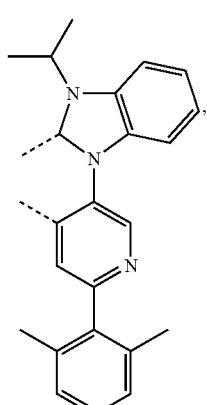
L208
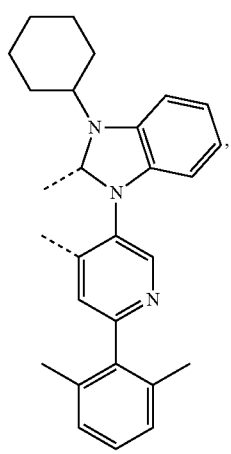
L209
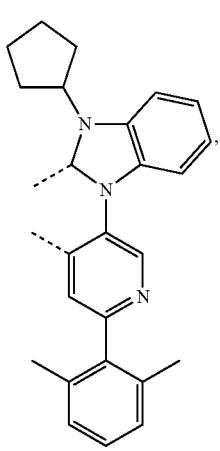
L210
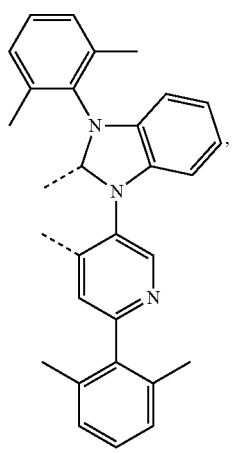
L211
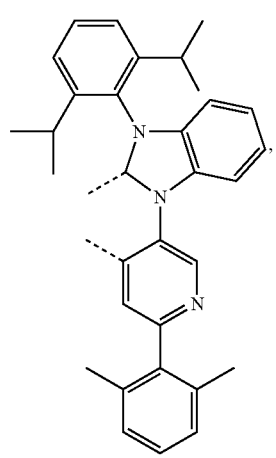
L212
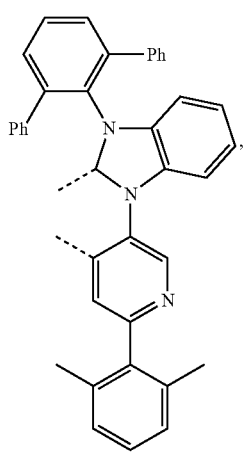

L213
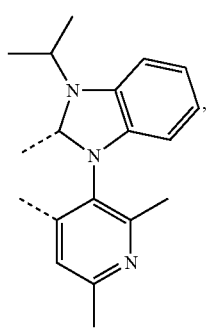
L214
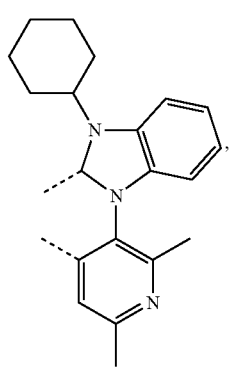
L215
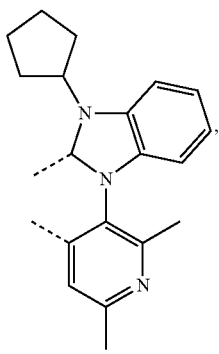
L216
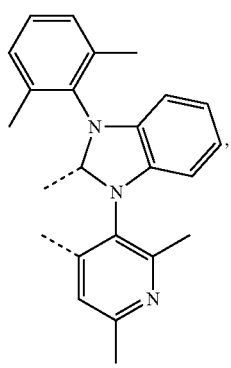
L217
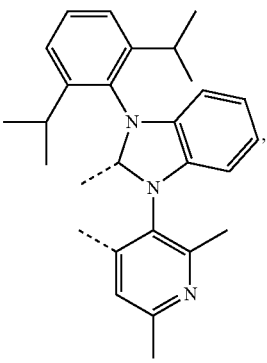
L218
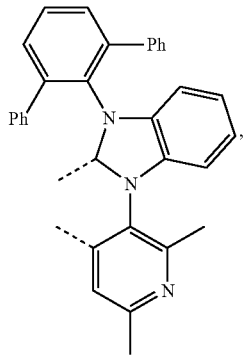
L219
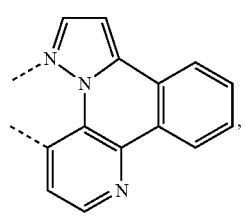
L220
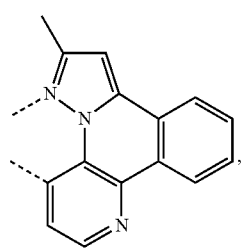
L221
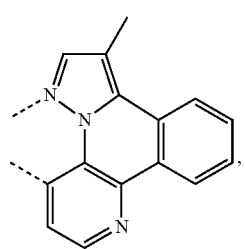

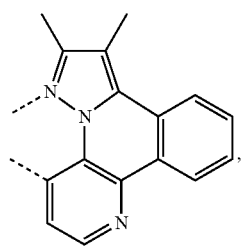 L222,
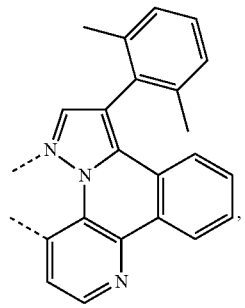 L223,
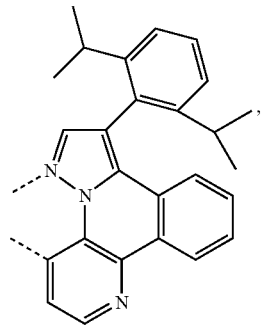 L224,
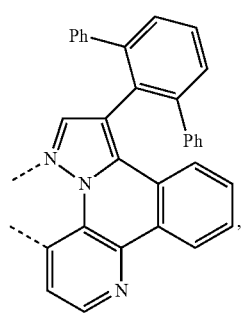 L225,
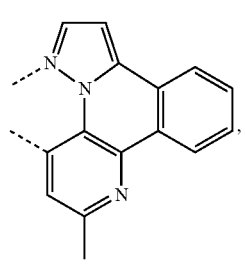 L226,
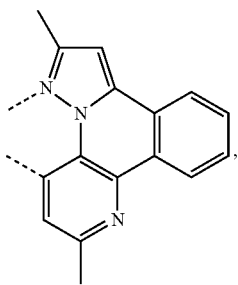 L227,
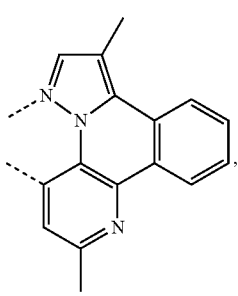 L228,
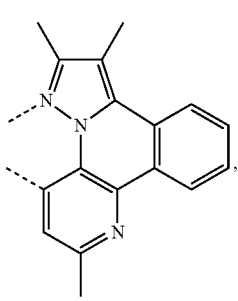 L229,
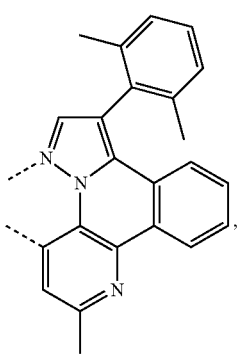 L230,
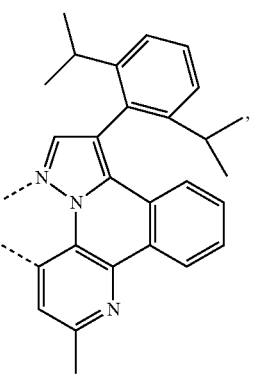 L231, -continued
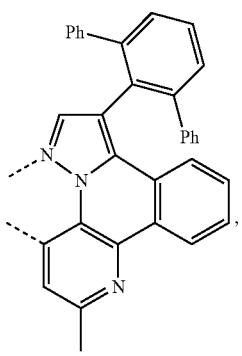 L232
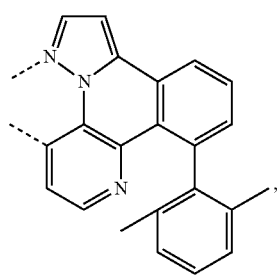 L233
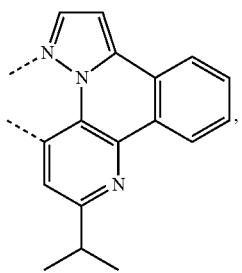 L234
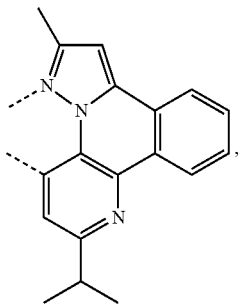 L235
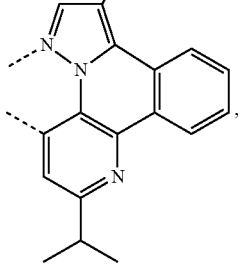 L236
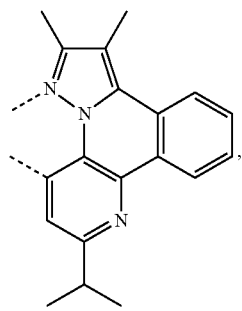 L237
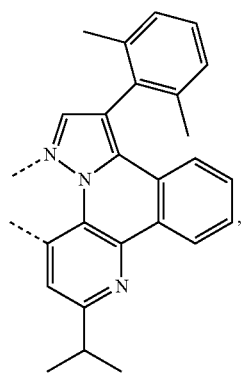 L238
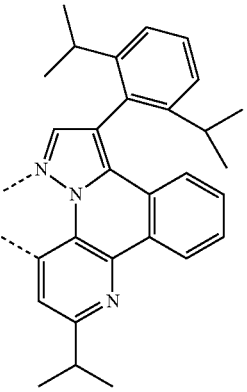 L239
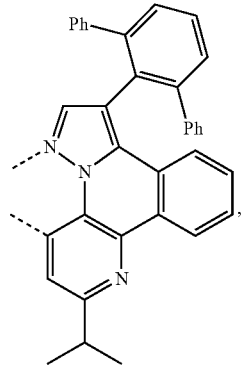 L240

-continued
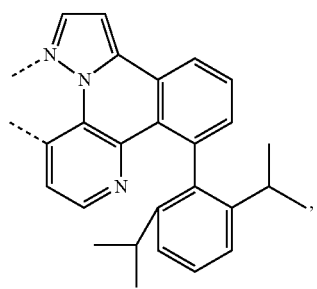 L241
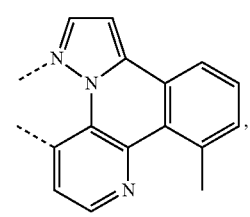 L242
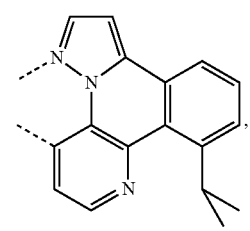 L243
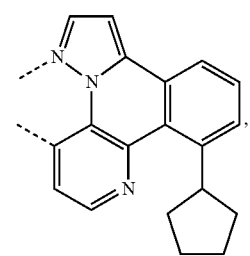 L244
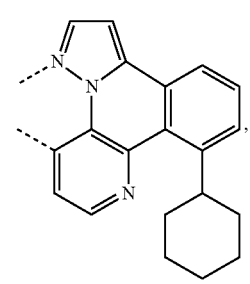 L245
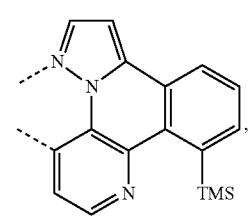 L246
-continued
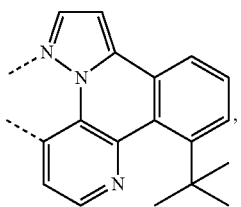 L247
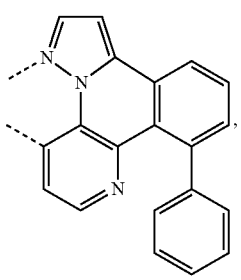 L248
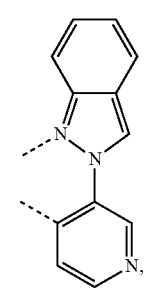 L249
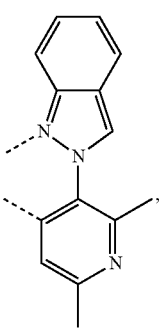 L250
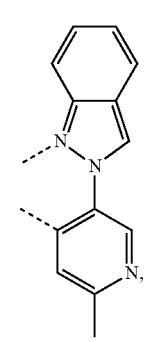 L251

| | |
|---|---|
| 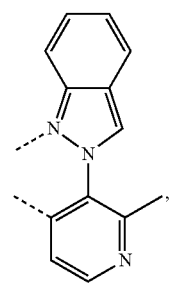 L252 | 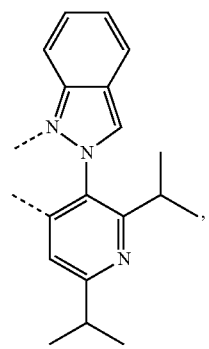 L256 |
| 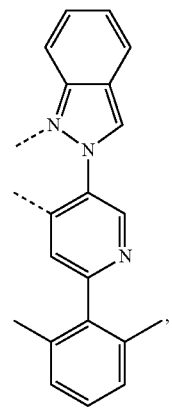 L253 | 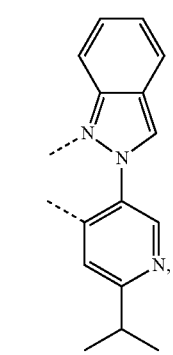 L257 |
| 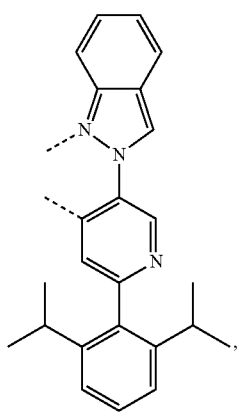 L254 | 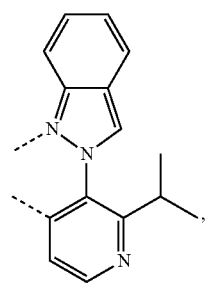 L258 |
| 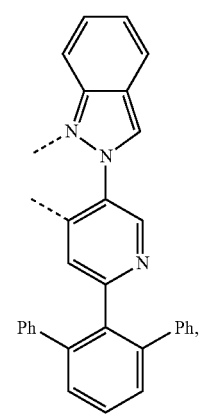 L255 | 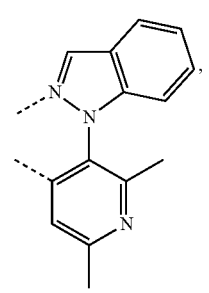 L259 |
| | 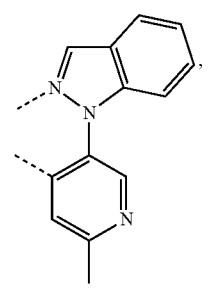 L260 |

| | |
|---|---|
| 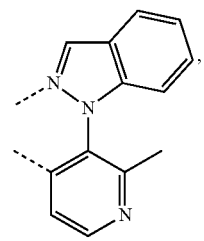 | L<sub>261</sub> |
| 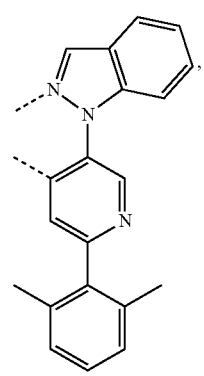 | L<sub>262</sub> |
| 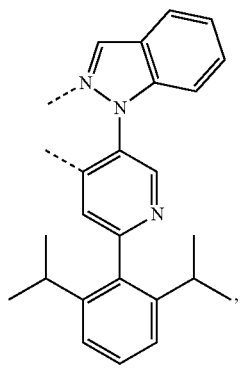 | L<sub>263</sub> |
| 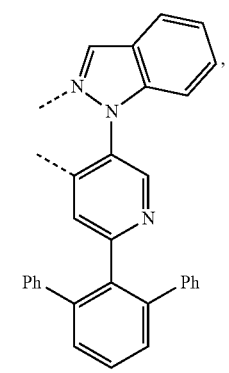 | L<sub>264</sub> |
| | |
|---|---|
| 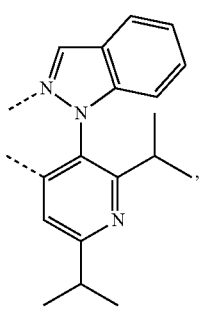 | L<sub>265</sub> |
| 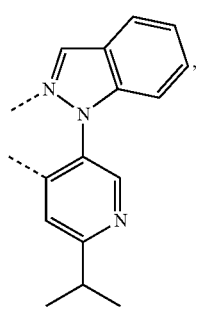 | L<sub>266</sub> |
| 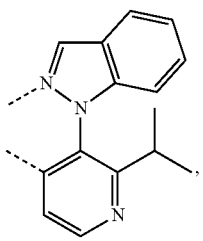 | L<sub>267</sub> |
| 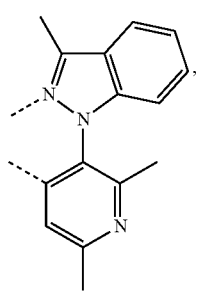 | L<sub>268</sub> |
| 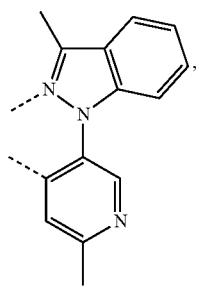 | L<sub>269</sub> |

| | |
|---|---|
| 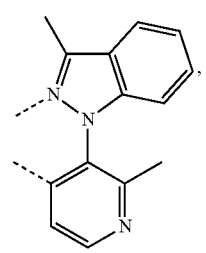 L270 | 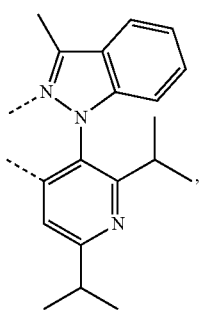 L274 |
| 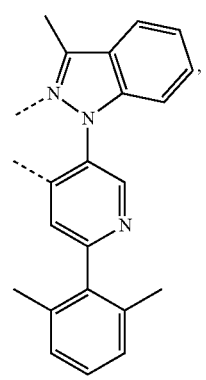 L271 | 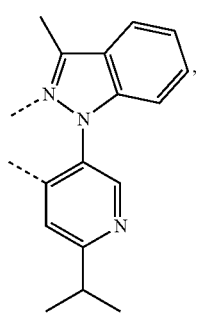 L275 |
| | 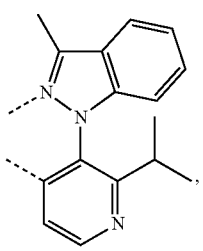 L276 |
| 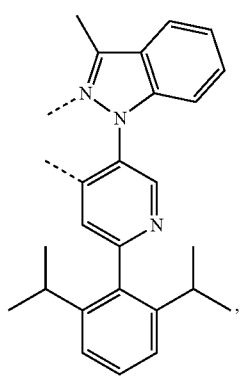 L272 | 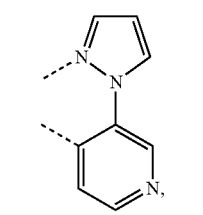 L277 |
| 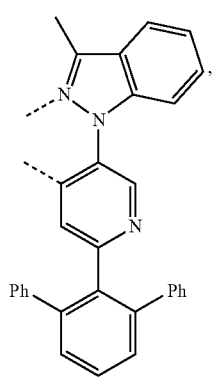 L273 | 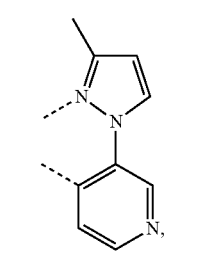 L278 |
| | 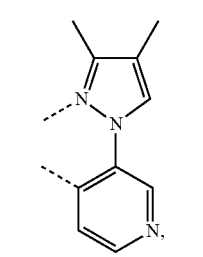 L279 |

| | |
|---|---|
| L280 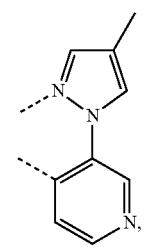 | L286 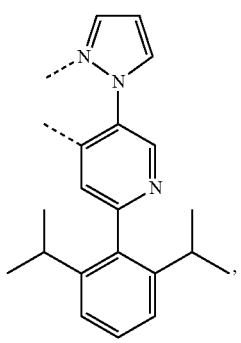 |
| L281 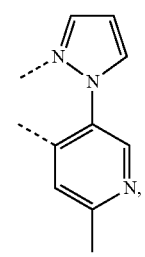 | |
| L282 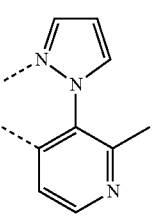 | L287 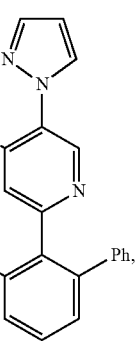 |
| L283 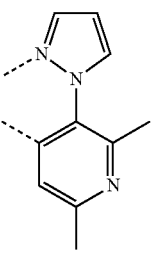 | |
| L284 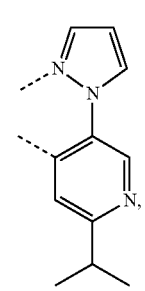 | L288 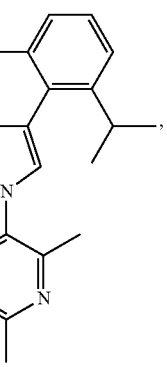 |
| L285 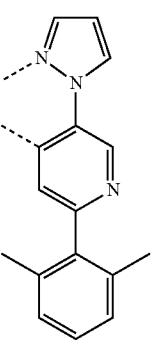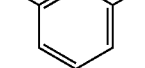 | L289 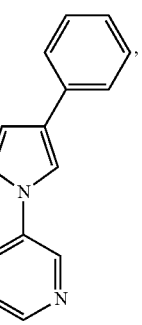 |

L<sub>290</sub> 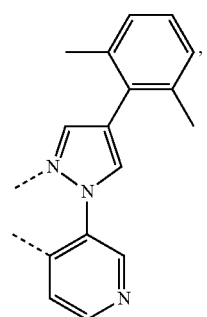
L<sub>291</sub> 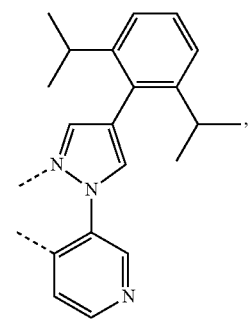
L<sub>292</sub> 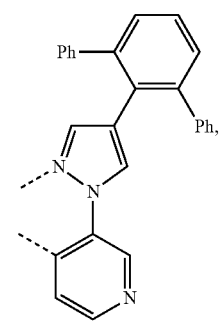
L<sub>293</sub> 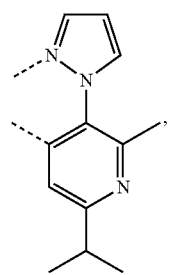
L<sub>294</sub> 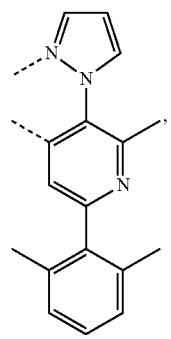
L<sub>295</sub> 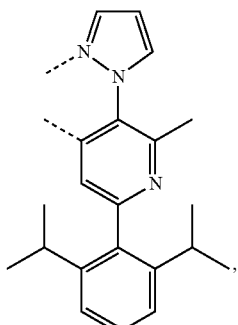
L<sub>296</sub> 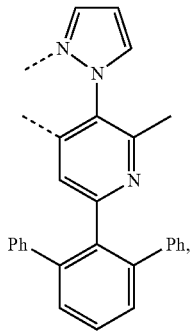
L<sub>297</sub> 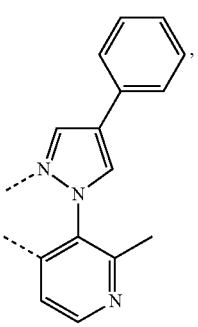
L<sub>298</sub> 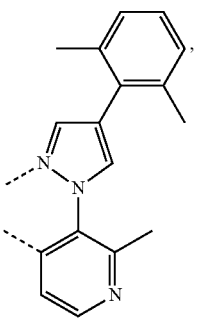
L<sub>299</sub> 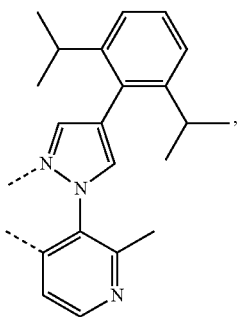

405
-continued
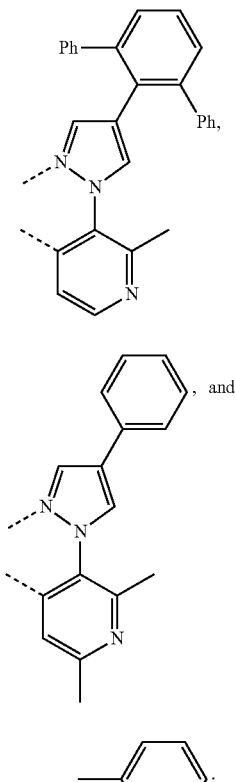
, and
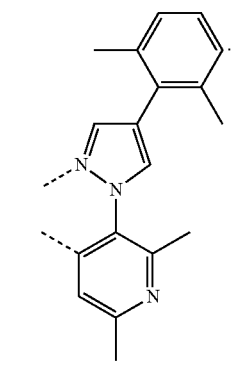
9. The compound of claim 1, wherein the compound has a formula of $M(L_A)_n(L_B)_{m-n}$;
wherein M is Ir or Pt; $L_B$ is a bidentate ligand; and
wherein when M is Ir, m is 3, and n is 1, 2, or 3; when M is Pt, m is 2, and n is 1, or 2.
10. The compound of claim 9, wherein $L_B$ is selected from the group consisting of:
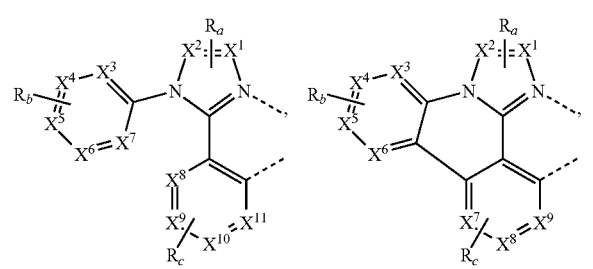
406
-continued
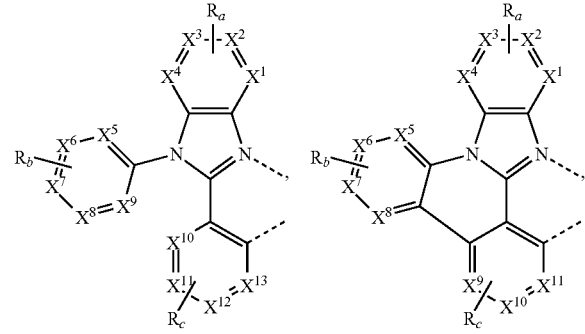
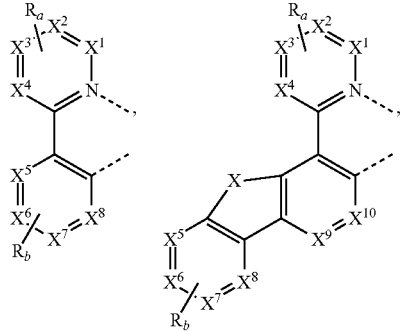
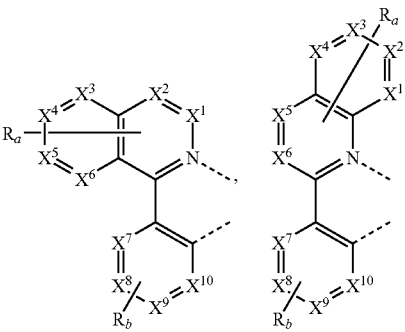
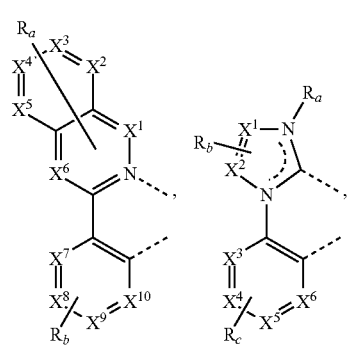
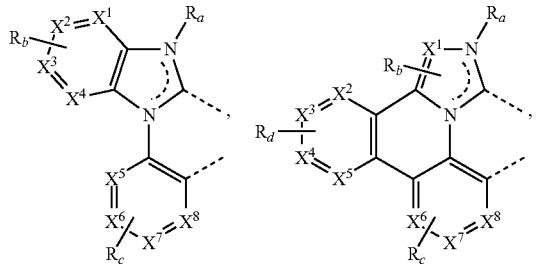

-continued

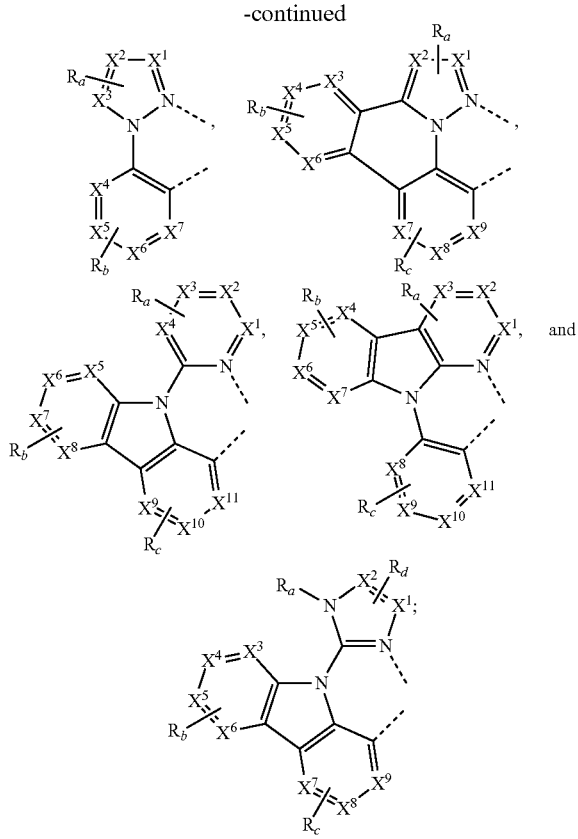

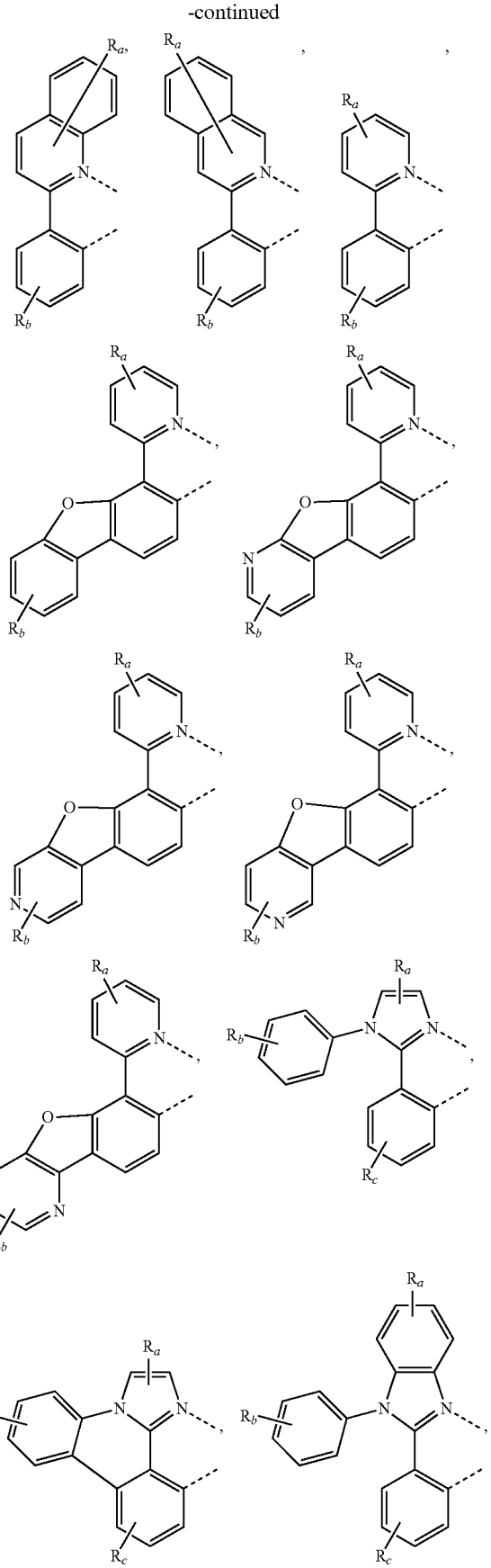

wherein each $X^1$ to $X^{13}$ are independently selected from the group consisting of carbon and nitrogen;
wherein X is selected from the group consisting of BR', NR', PR', O, S, Se, C=O, S=O, SO$_2$, CR'R", SiR'R", and GeR'R";
wherein R' and R" are optionally fused or joined to form a ring;
wherein each $R_a$, $R_b$, $R_c$, and $R_d$ may represent from mono substitution to the possible maximum number of substitution, or no substitution;
wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acid, ester, nitrile, and isonitrile; and
wherein any two adjacent substituents of $R_a$, $R_b$, $R_c$, and $R_d$ are optionally fused or joined to form a ring or form a multidentate ligand.

11. The compound of claim 10, wherein $L_B$ is selected from the group consisting of:

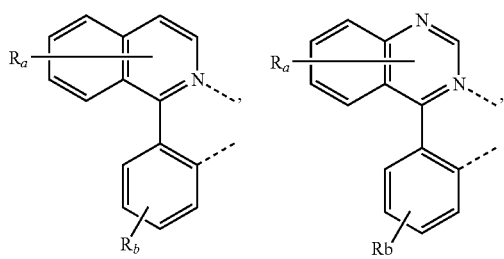

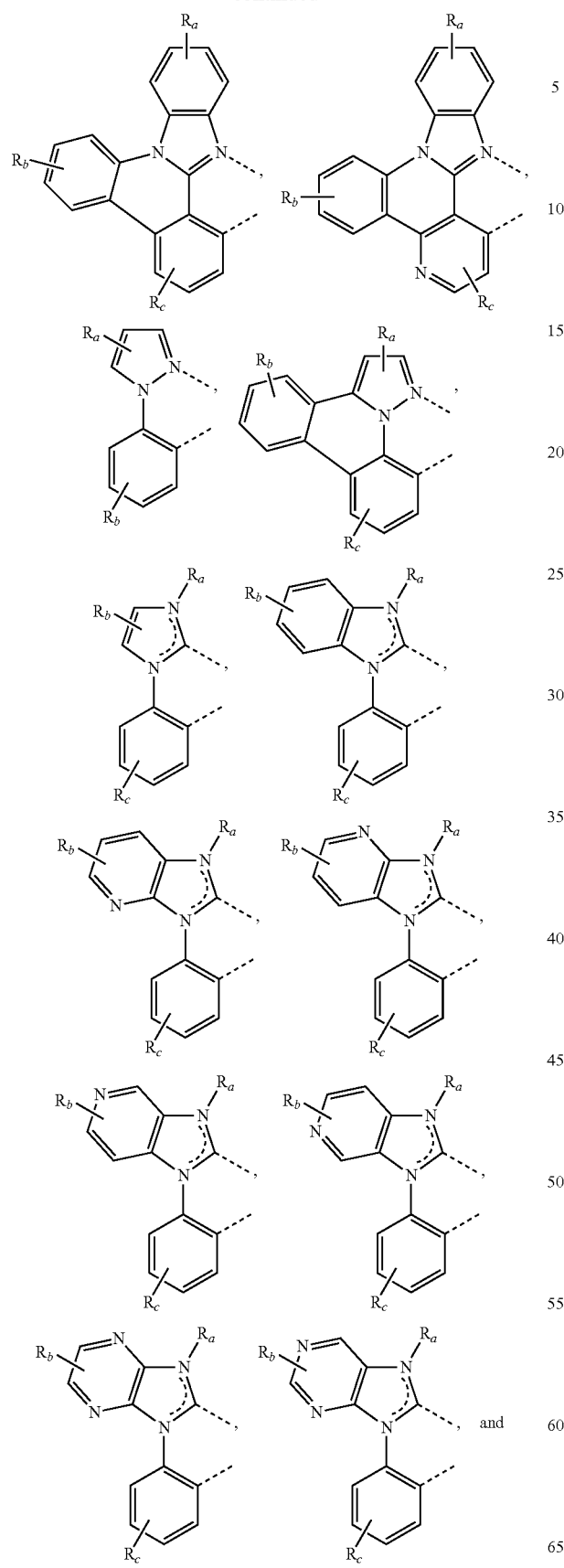
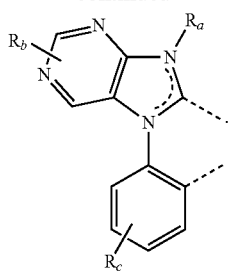
12. The compound of claim 10, wherein $L_B$ is selected from the group consisting of:
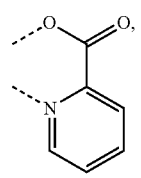  L₁
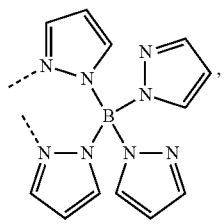  L₂
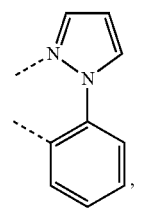  L₃
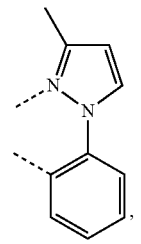  L₄
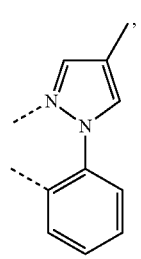  L₅

411
-continued
412
-continued
L6 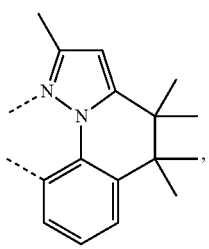
L11 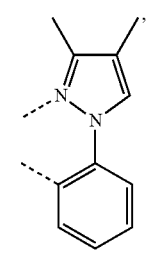
L7 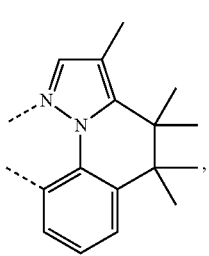
L12 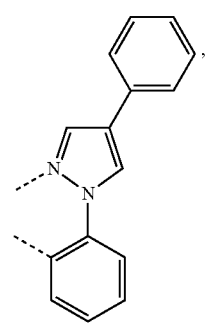
L8 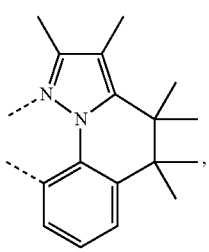
L13 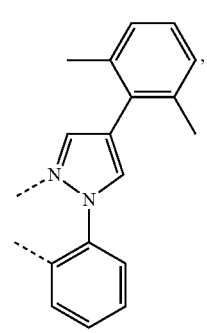
L9 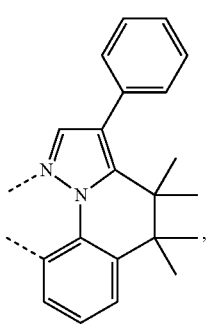
L14 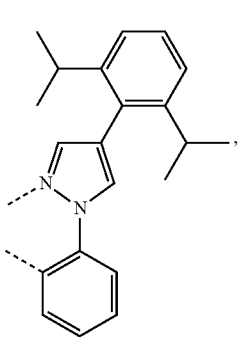
L10 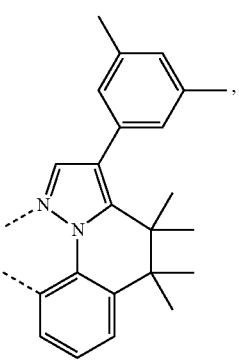
L15 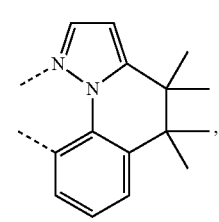

413 -continued
L16 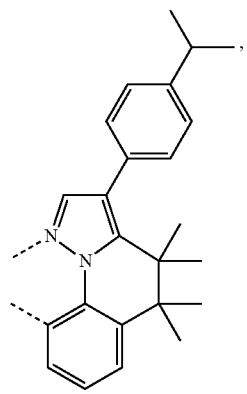
L17 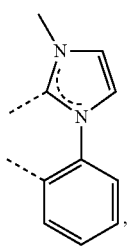
L18 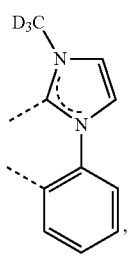
L19 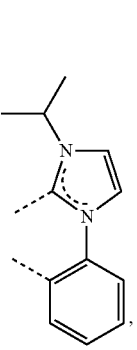
L20 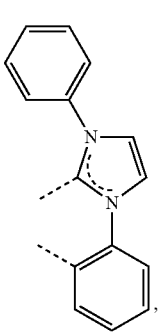
414 -continued
L21 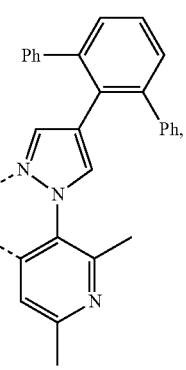
L22 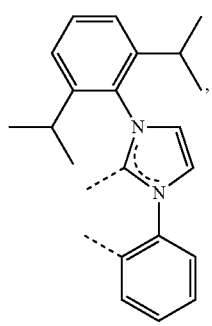
L23 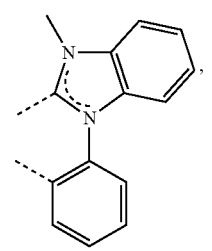
L24 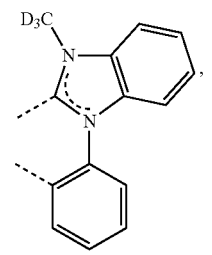
L25 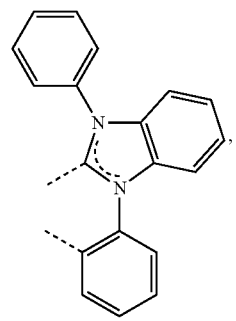

415
-continued
| | |
|---|---|
| 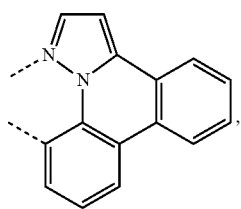 | L26 |
| 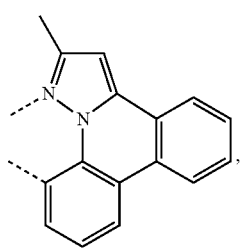 | L27 |
| 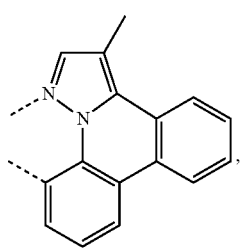 | L28 |
| 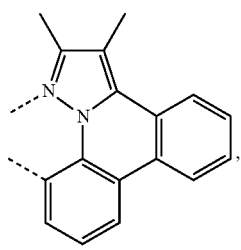 | L29 |
| 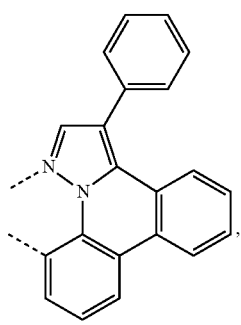 | L30 |
| 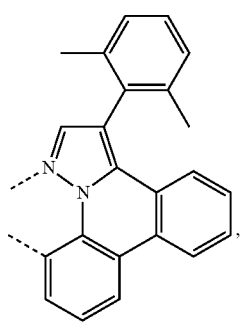 | L31 |
416
-continued
| | |
|---|---|
| 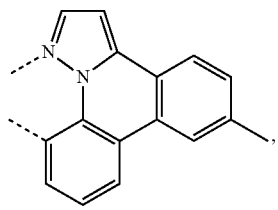 | L32 |
| 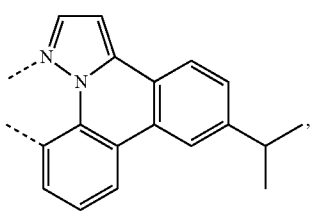 | L33 |
| 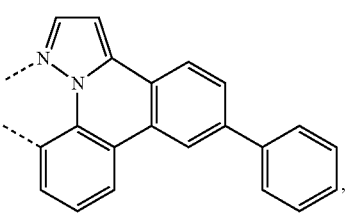 | L34 |
| 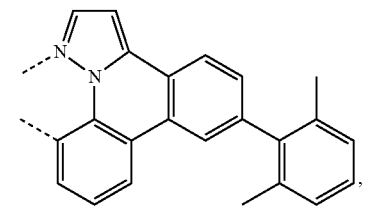 | L35 |
| 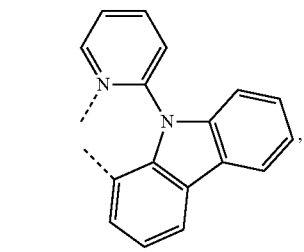 | L36 |
| 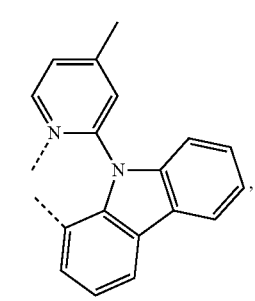 | L37 |

L38 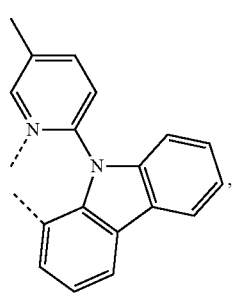
L39 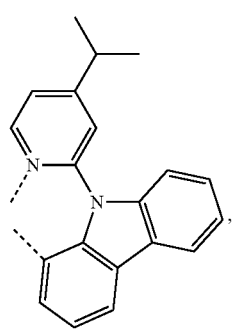
L40 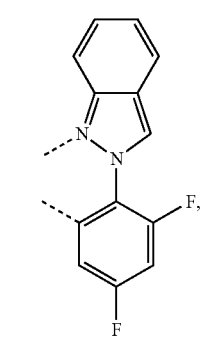
L41 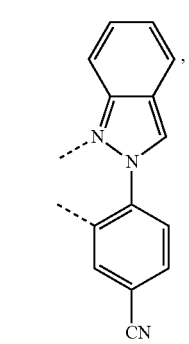
L42 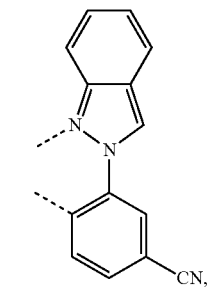
L43 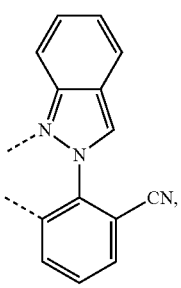
L44 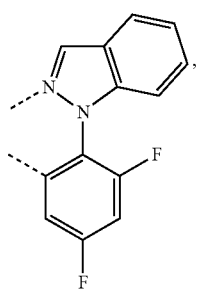
L45 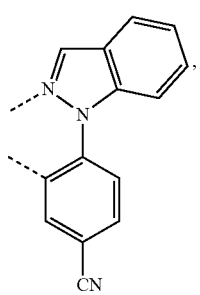
L46 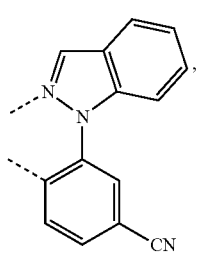
L47 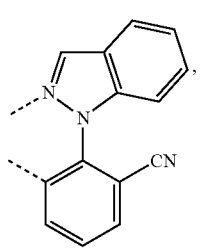

| | | | |
|---|---|---|---|
| $L_{48}$ | 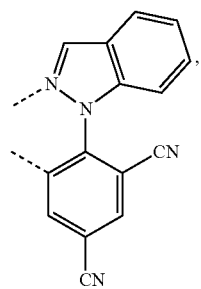 | $L_{53}$ | 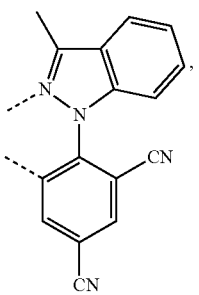 |
| $L_{49}$ | 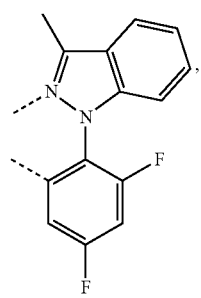 | $L_{54}$ | 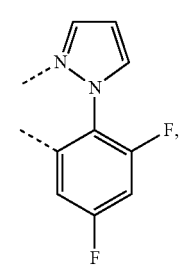 |
| $L_{50}$ | 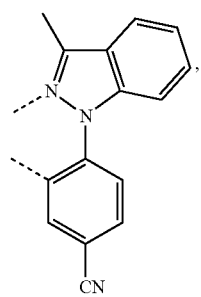 | $L_{55}$ | 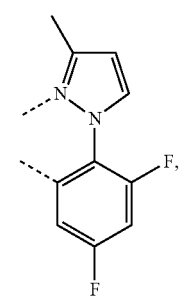 |
| $L_{51}$ | 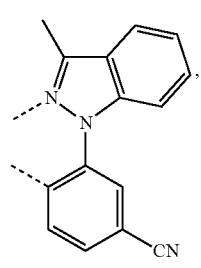 | $L_{56}$ | 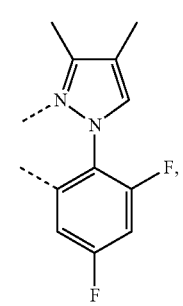 |
| $L_{52}$ | 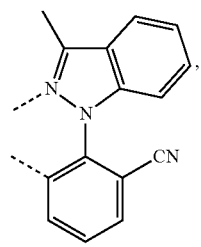 | $L_{57}$ | 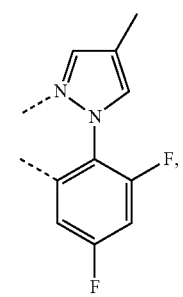 |

421
-continued
422
-continued
L58
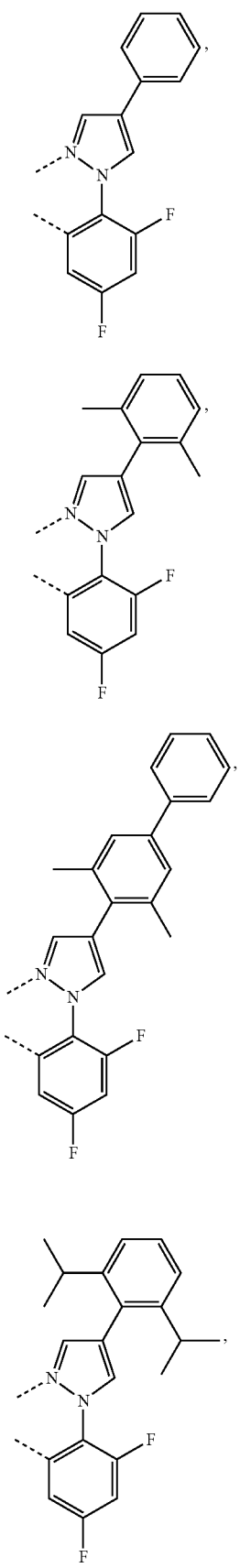
L59
L60
L61
L62 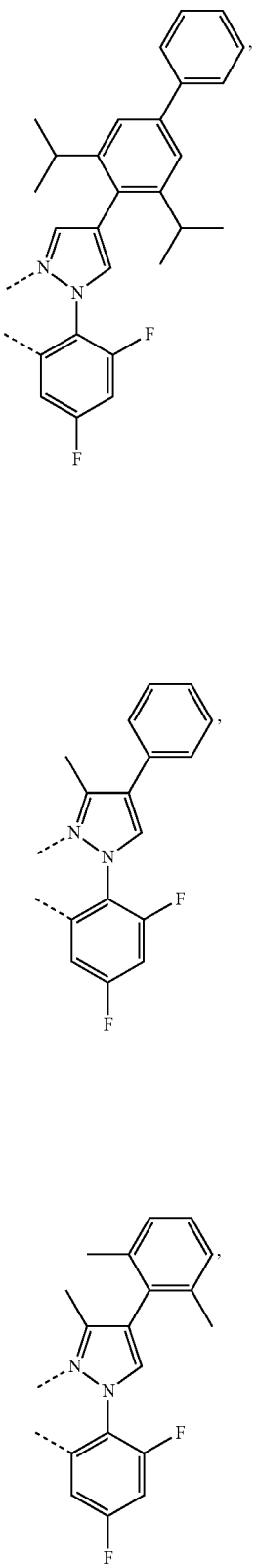
L63
L64

-continued
L65 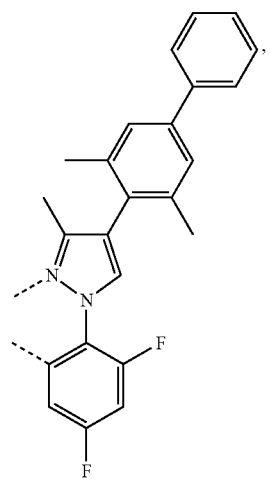
L66 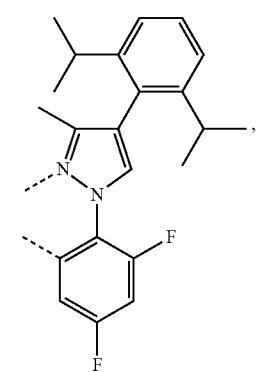
L67 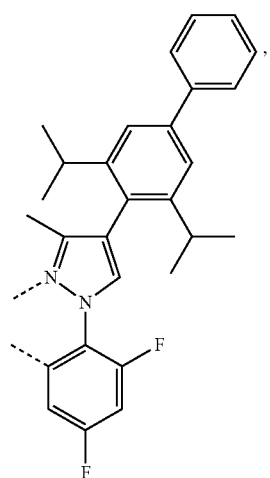
L68 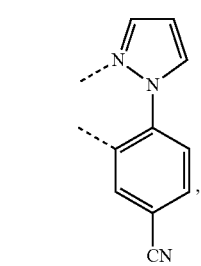
-continued
L69 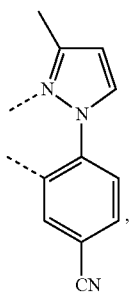
L70 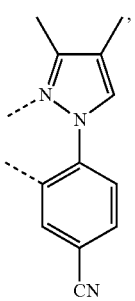
L71 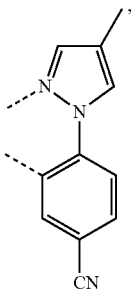
L72 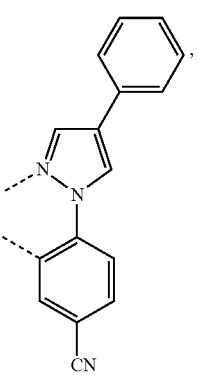

-continued
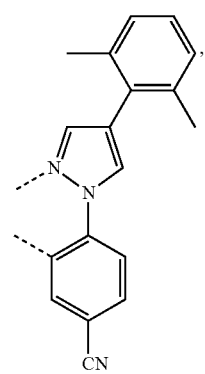
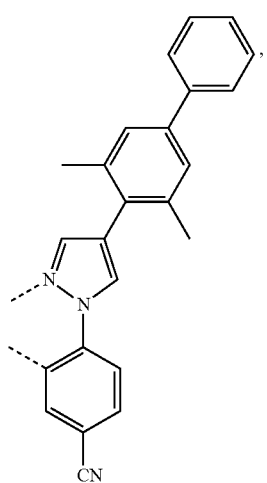
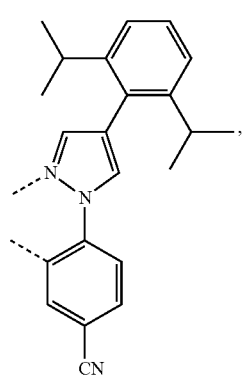
L73
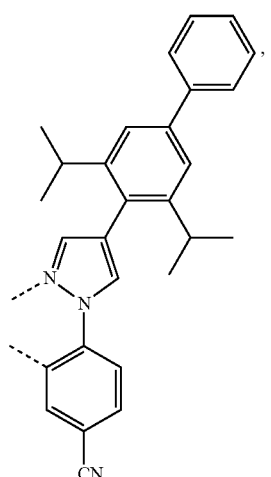
L74
L75
-continued
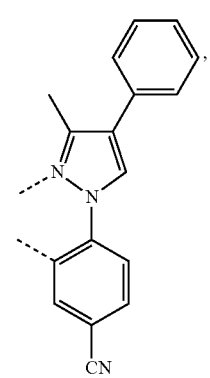
L76
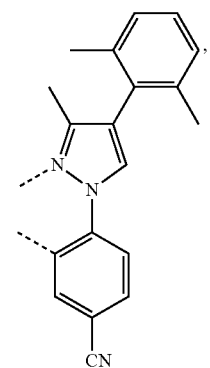
L77
L78

427
-continued
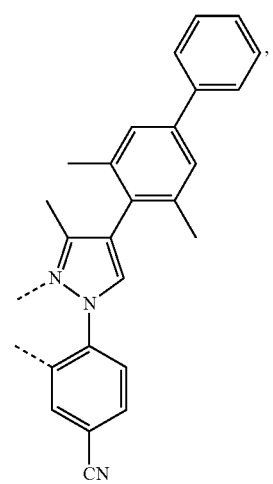
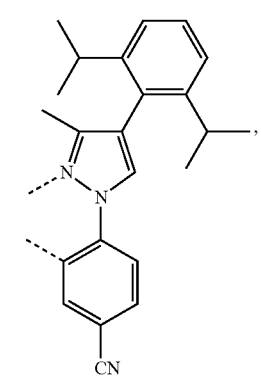
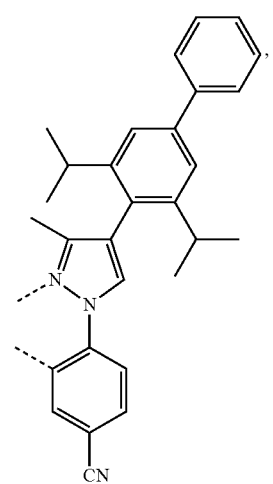
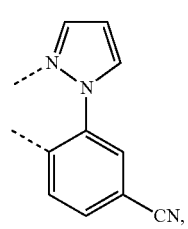
428
-continued
L79
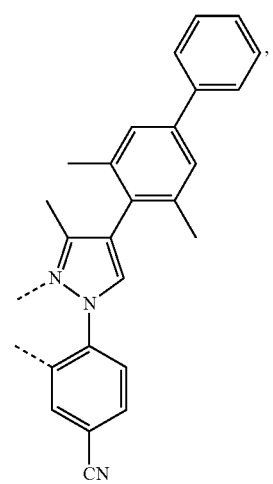
L80
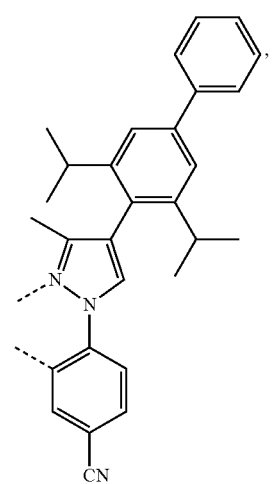
L81
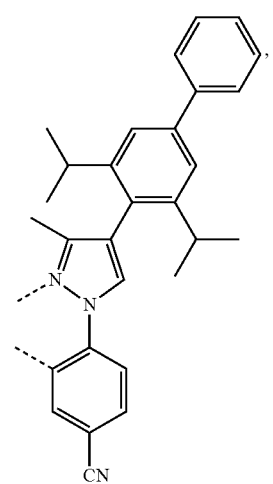
L82
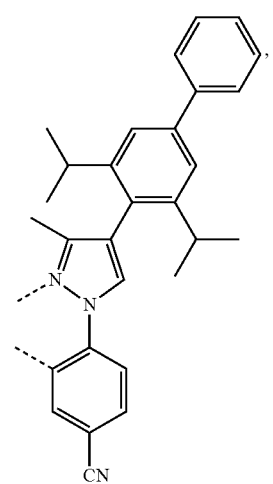
L83
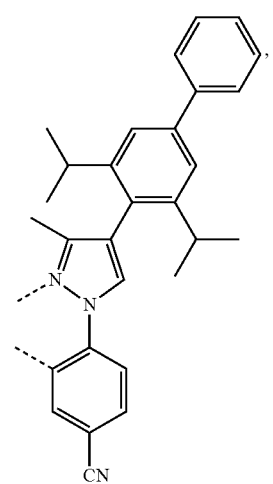
L84
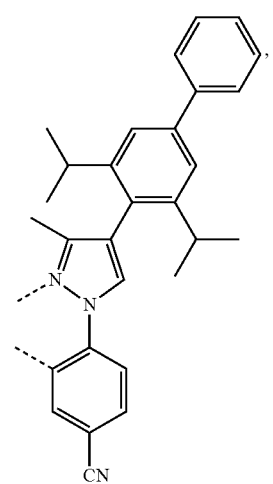
L85
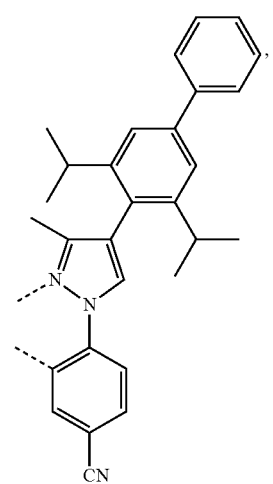
L86
L87

-continued
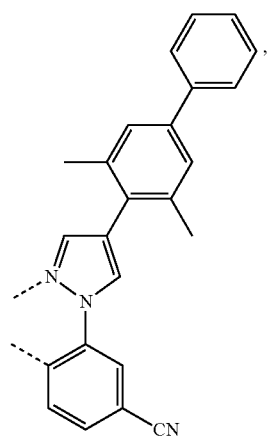 L88
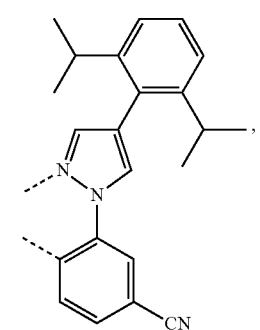 L89
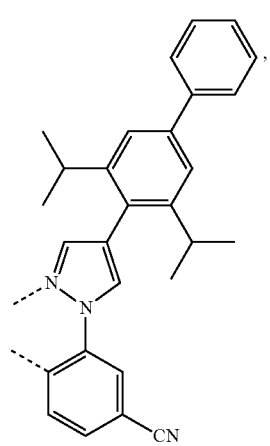 L90
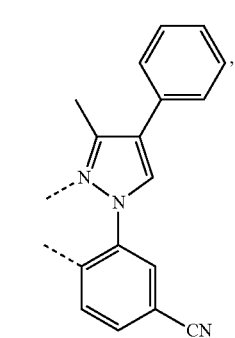 L91
-continued
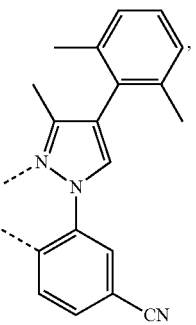 L92
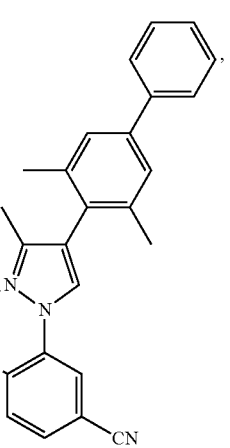 L93
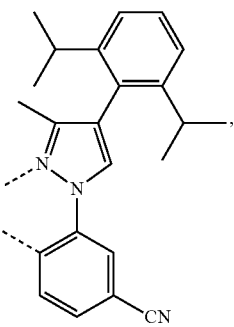 L94
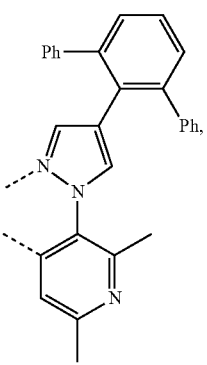 L95

| | |
|---|---|
| 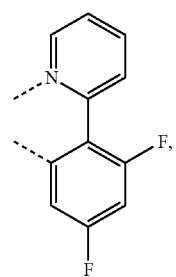 | L96 |
| 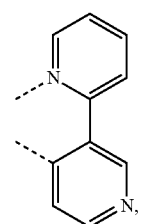 | L97 |
| 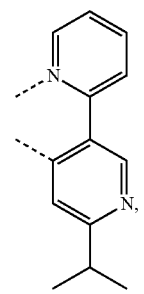 | L98 |
| 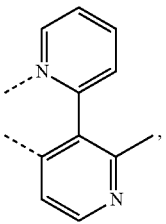 | L99 |
| 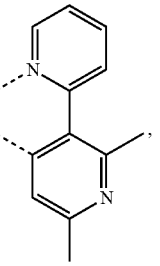 | L100 |
| 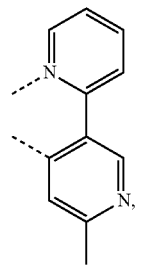 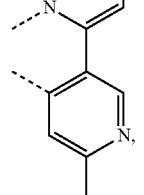 | L101 |
| 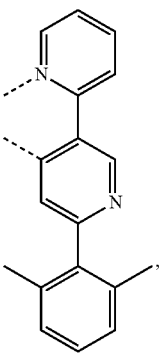 | L102 |
| 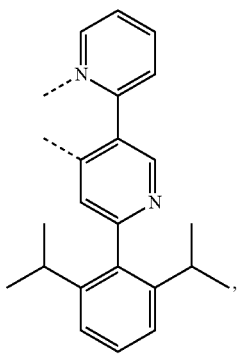 | L103 |
| 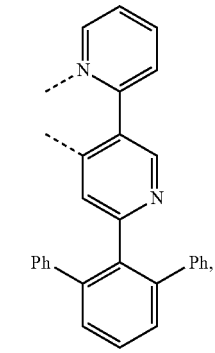 | L104 |

-continued
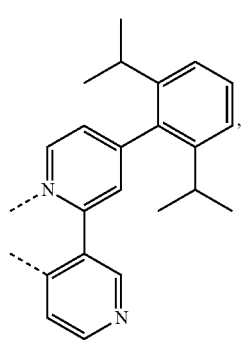 L106,
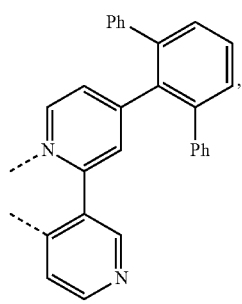 L107,
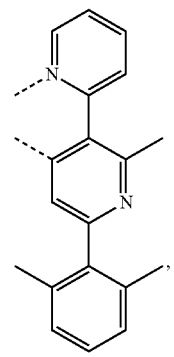 L108
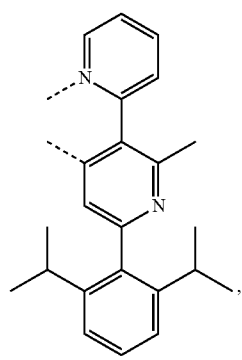 L109
-continued
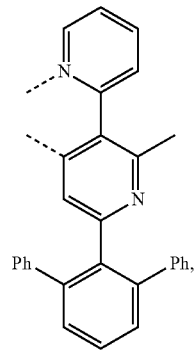 L110,
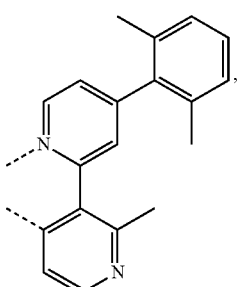 L111,
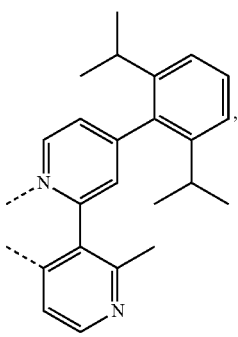 L112,
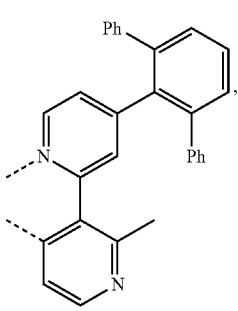 L113,
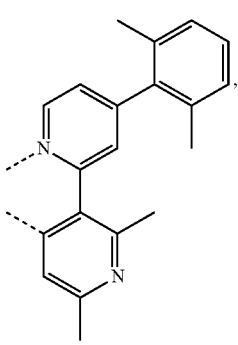 L114,

| | |
|---|---|
| 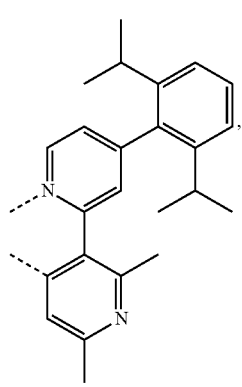 | L115 |
| 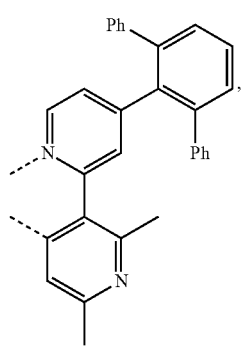 | L116 |
| 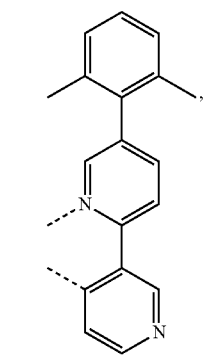 | L117 |
| 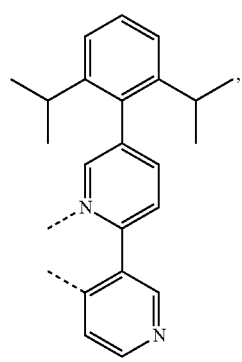 | L118 |
| 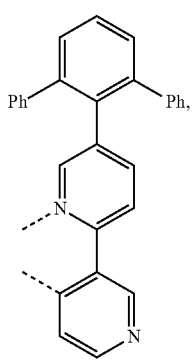 | L119 |
| 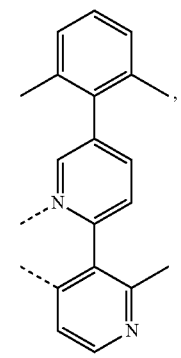 | L120 |
| 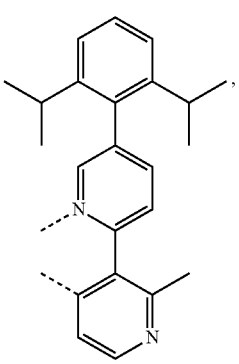 | L121 |
| 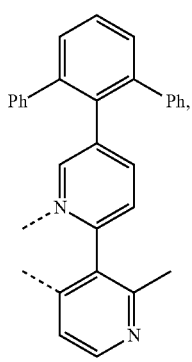 | L122 |

| | |
|---|---|
| 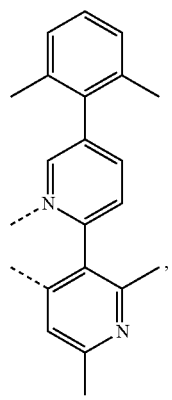 | $L_{123}$ |
| 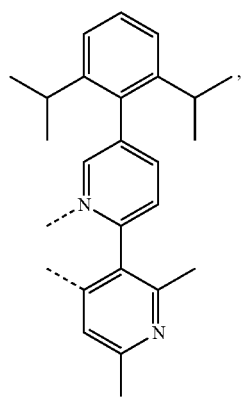 | $L_{124}$ |
| 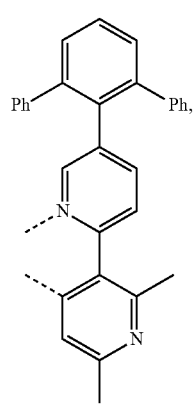 | $L_{125}$ |
| 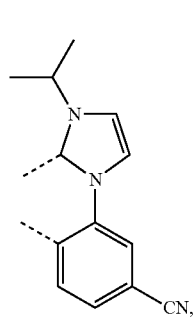 | $L_{126}$ |
| 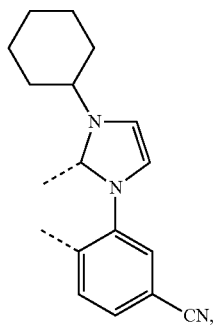 | $L_{127}$ |
| 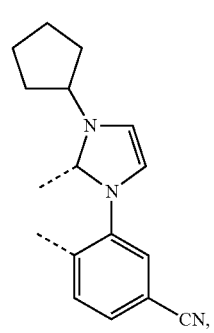 | $L_{128}$ |
| 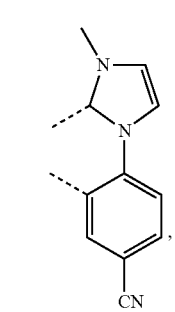 | $L_{129}$ |
| 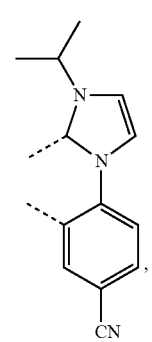 | $L_{130}$ |

-continued
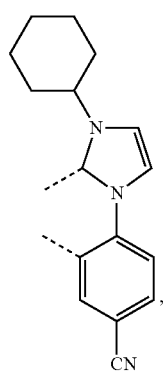
L131
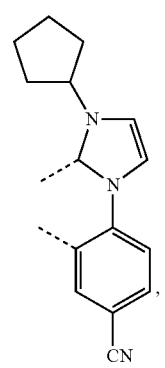
L132
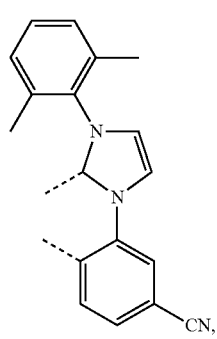
L133
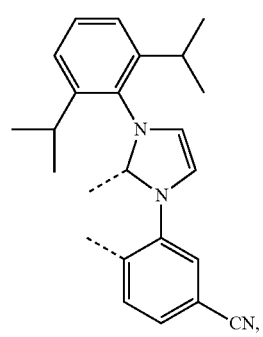
L134
-continued
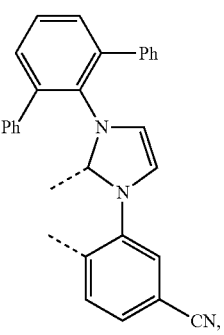
L135
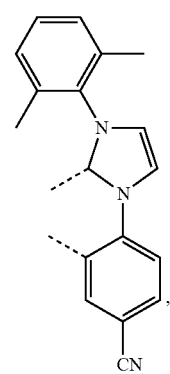
L136
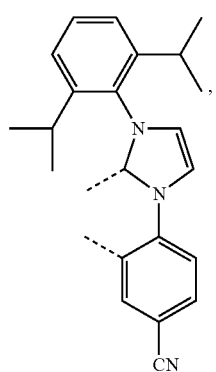
L137
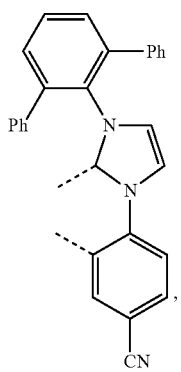
L138

L139 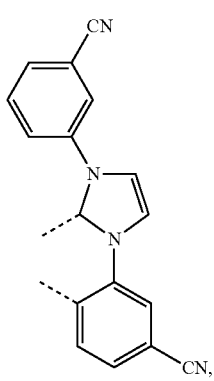
L140 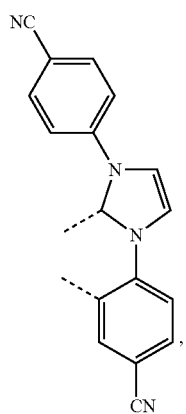
L141 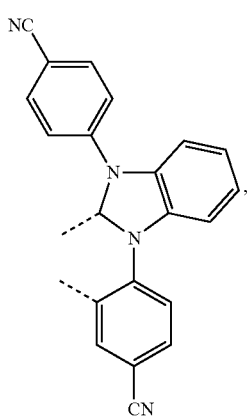
L142 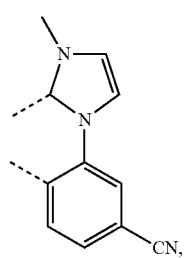
L143 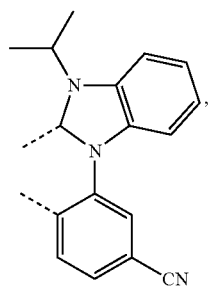
L144 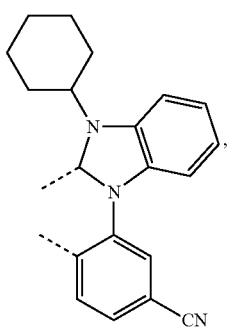
L145 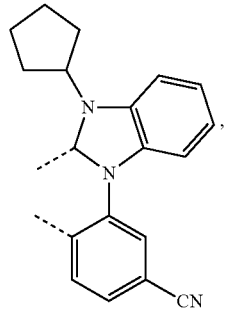
L146 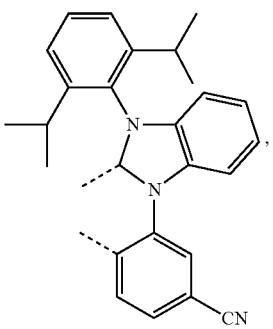
L147 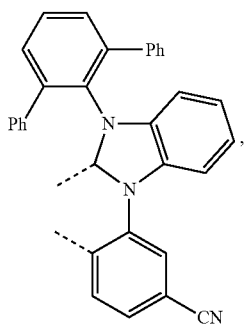

443 -continued
L148 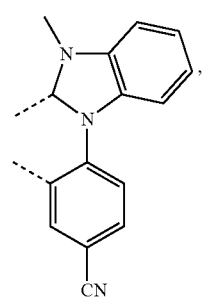
L149 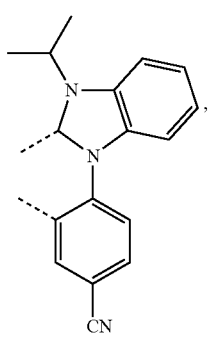
L150 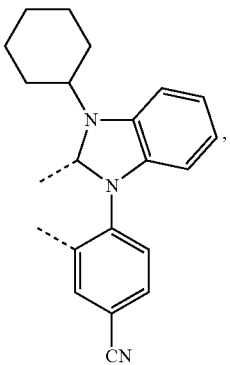
L151 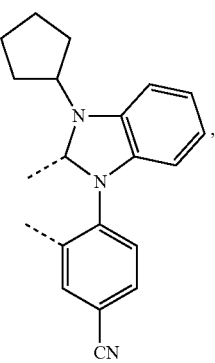
444 -continued
L152 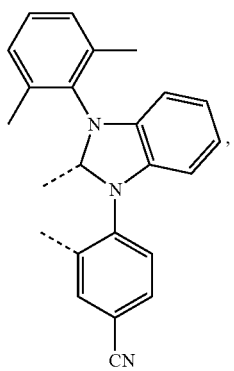
L153 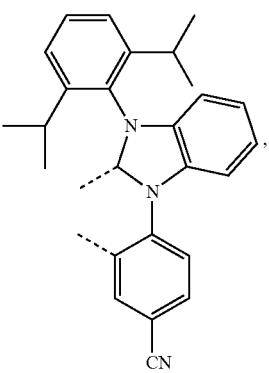
L154 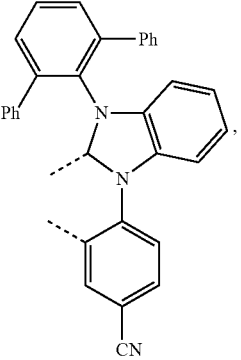
L155 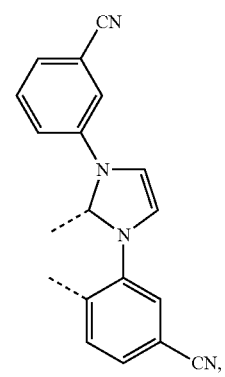

| | |
|---|---|
| 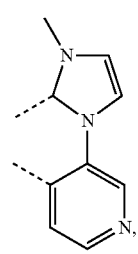 | $L_{156}$ |
| 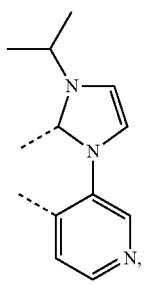 | $L_{157}$ |
| 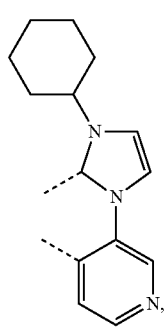 | $L_{158}$ |
| 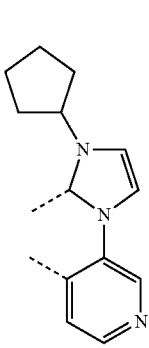 | $L_{159}$ |
| 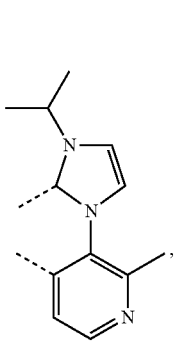 | $L_{160}$ |
| 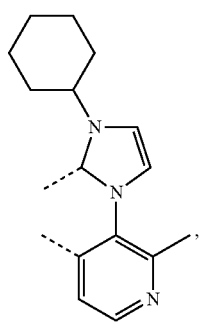 | $L_{161}$ |
| 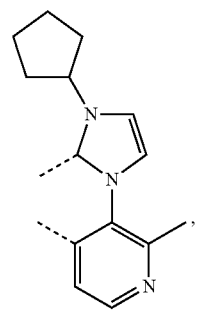 | $L_{162}$ |
| 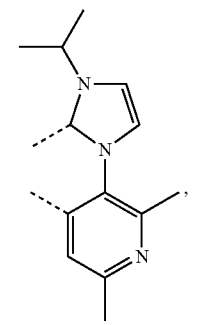 | $L_{163}$ |
| 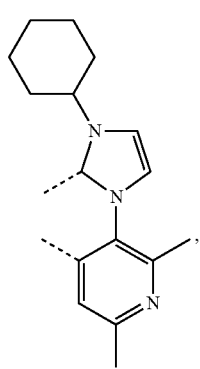 | $L_{164}$ |

| | |
|---|---|
| 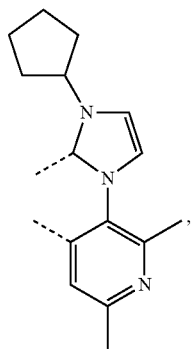 | L165 |
| 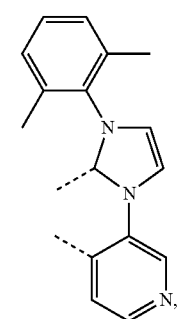 | L166 |
| 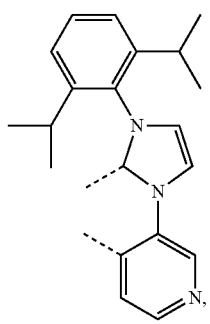 | L167 |
| 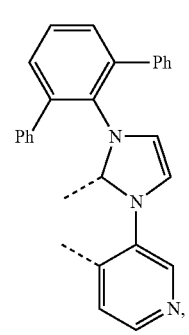 | L168 |
| 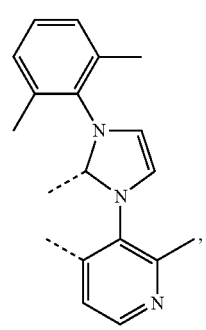 | L169 |
| | |
|---|---|
| 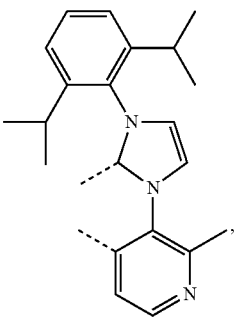 | L170 |
| 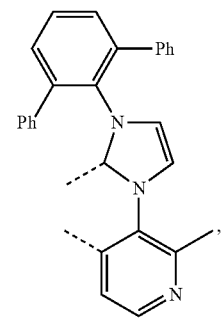 | L171 |
| 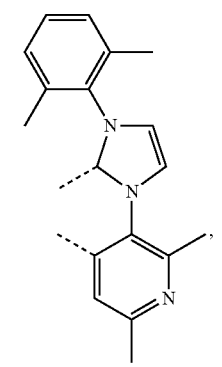 | L172 |
| 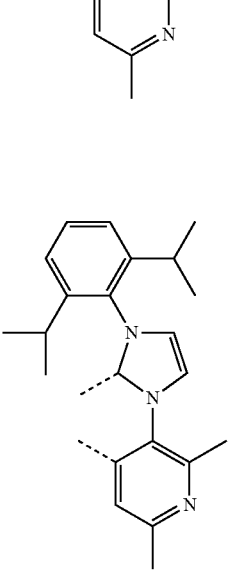 | L173 |

-continued
L₁₇₄ 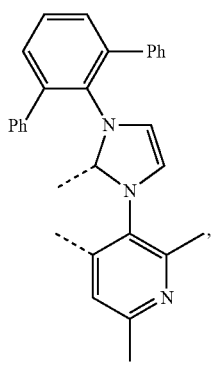
L₁₇₅ 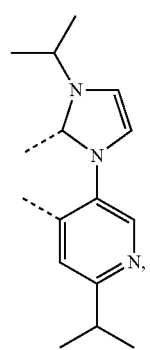
L₁₇₆ 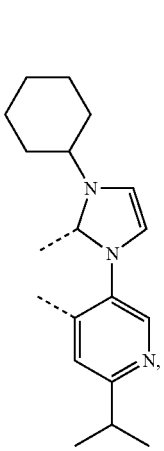
L₁₇₇ 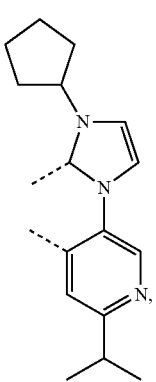
-continued
L₁₇₈ 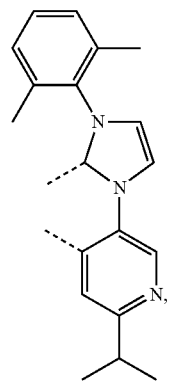
L₁₇₉ 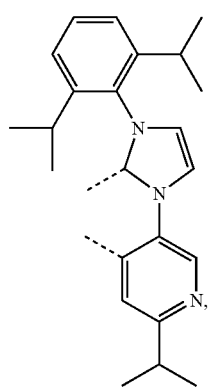
L₁₈₀ 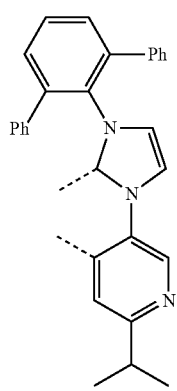
L₁₈₁ 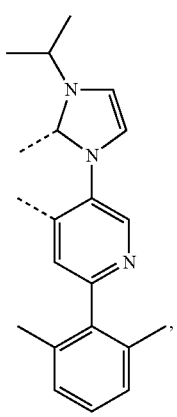

| | |
|---|---|
| 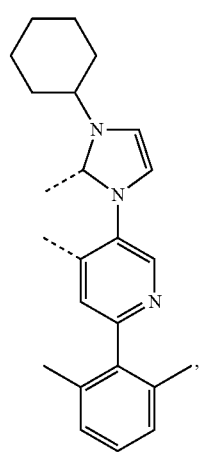 L<sub>182</sub> | 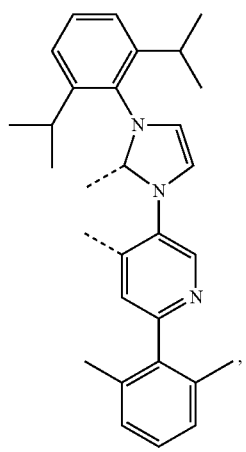 L<sub>185</sub> |
| 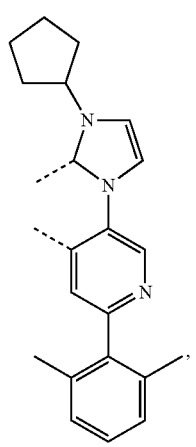 L<sub>183</sub> | 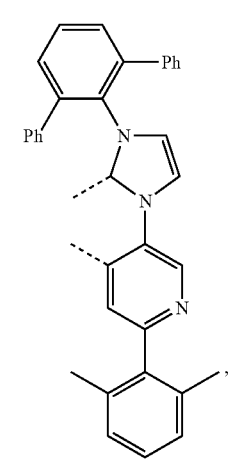 L<sub>186</sub> |
| 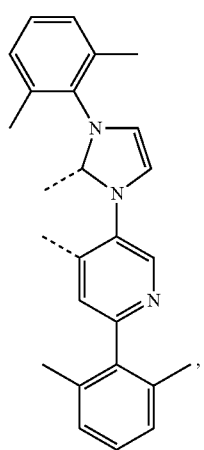 L<sub>184</sub> | 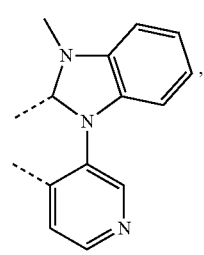 L<sub>187</sub> |
| | 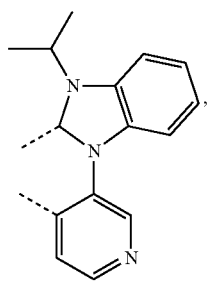 L<sub>188</sub> |

-continued
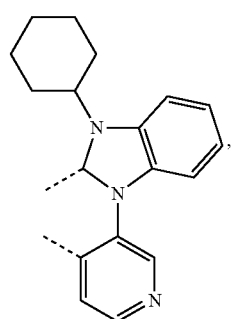 L189
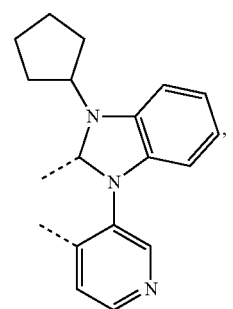 L190
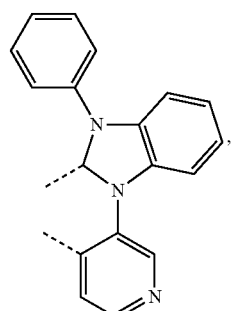 L191
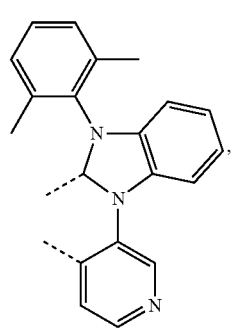 L192
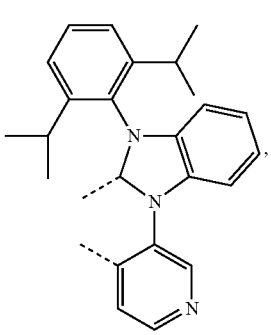 L193
-continued
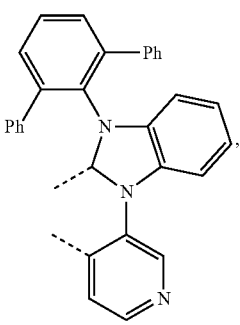 L194
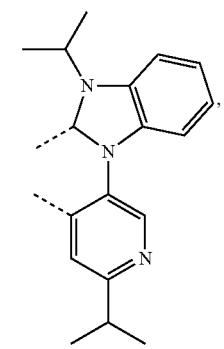 L195
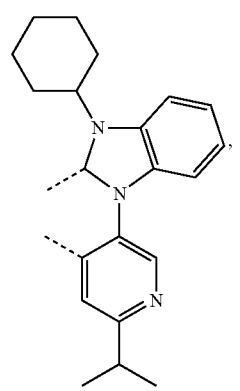 L196
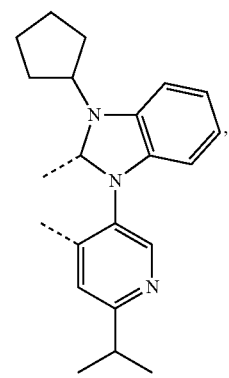 L197

455
-continued
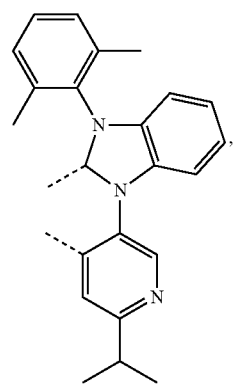
L198
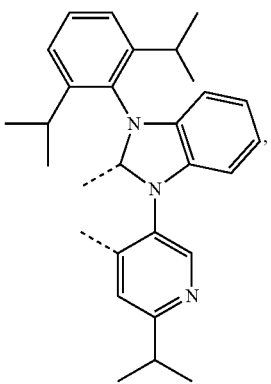
L199
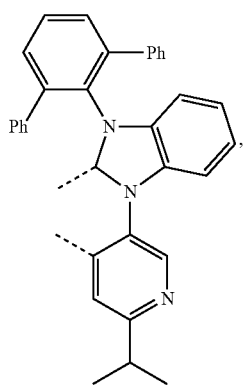
L200
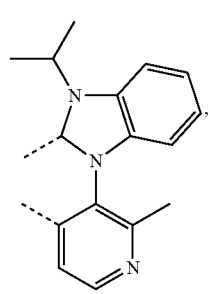
L201
456
-continued
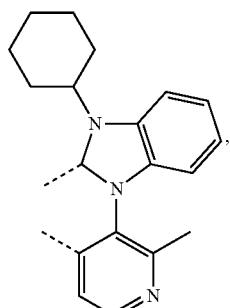
L202
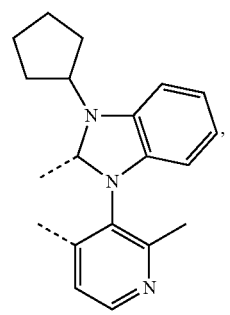
L203
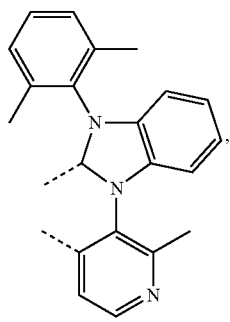
L204
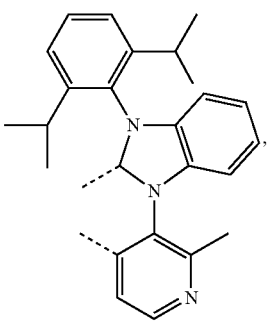
L205
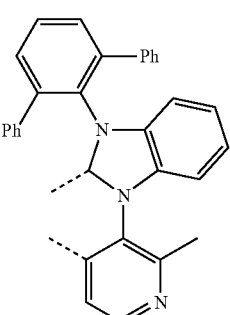
L206

457
-continued
458
-continued
L207
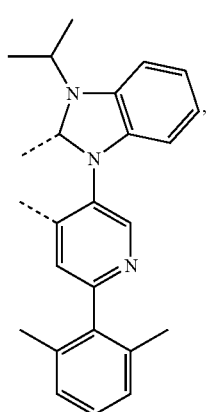
L210
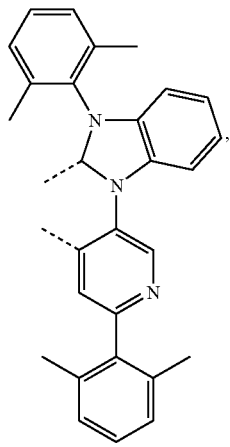
L208
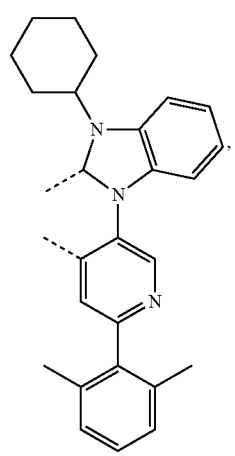
L211
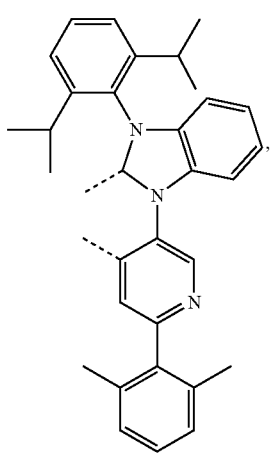
L209
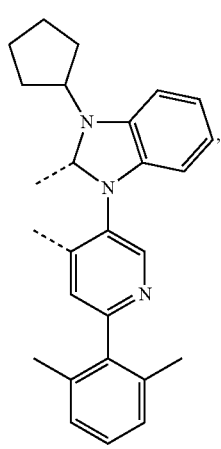
L212
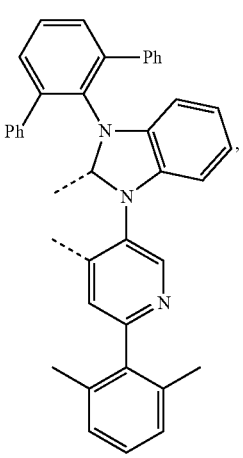

| | |
|---|---|
| L213 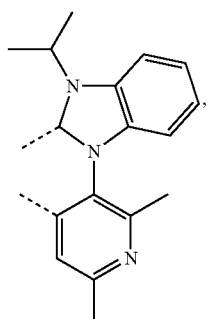 | L217 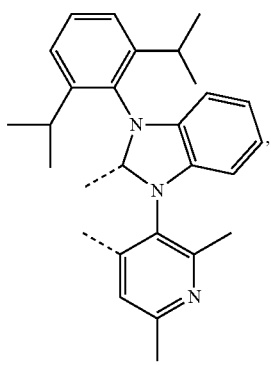 |
| L214 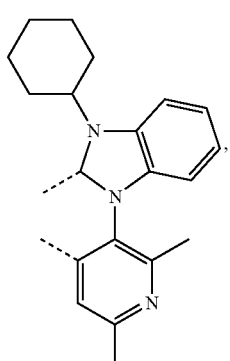 | L218 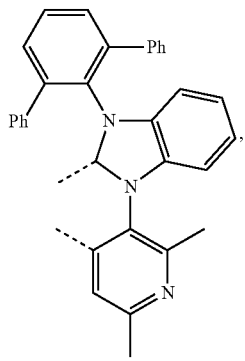 |
| L215 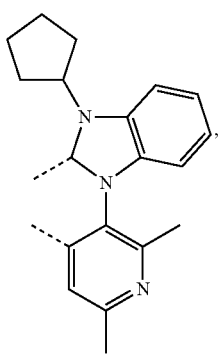 | L219 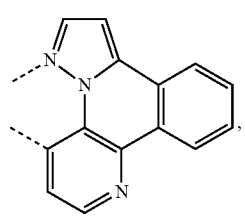 |
| | L220 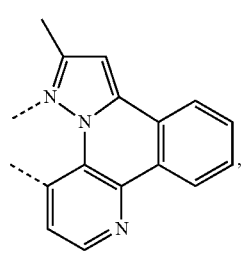 |
| L216 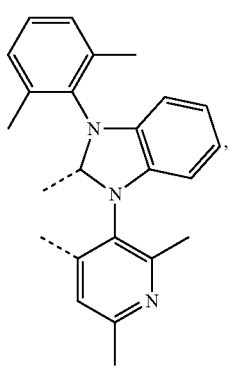 | L221 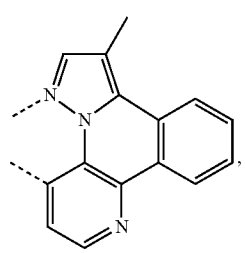 |

461
-continued
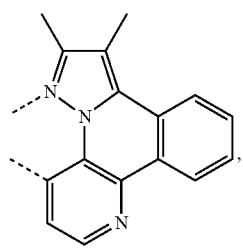
L222
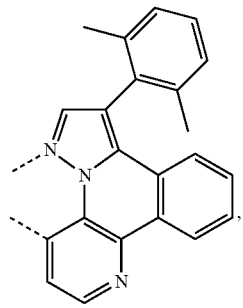
L223
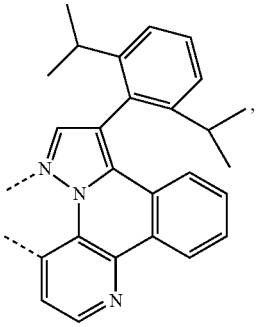
L224
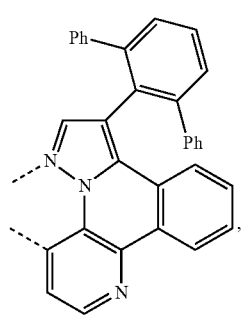
L225
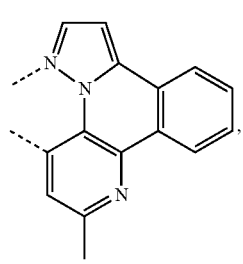
L226
462
-continued
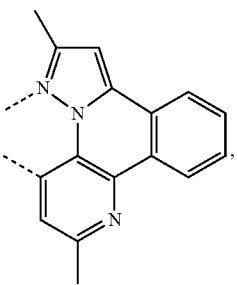
L227
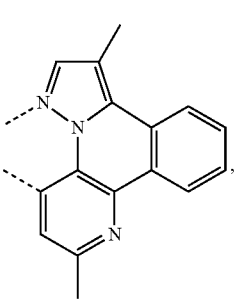
L228
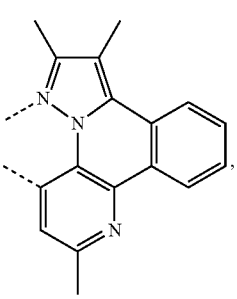
L229
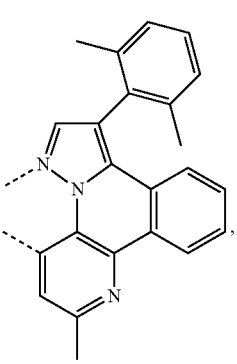
L230
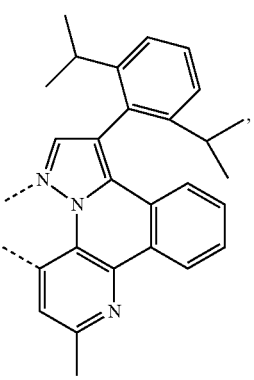
L231

463
-continued
L232
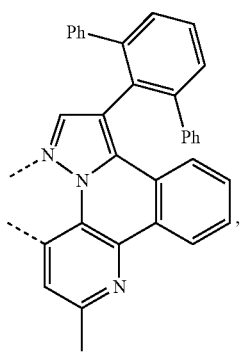
L233
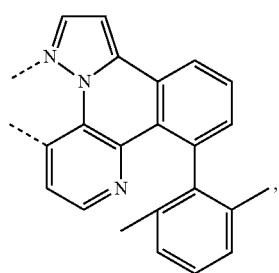
L234
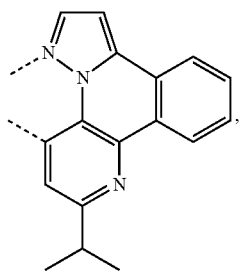
L235
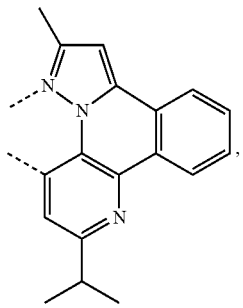
L236
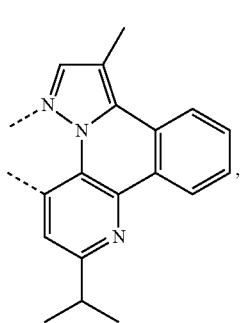
464
-continued
L237
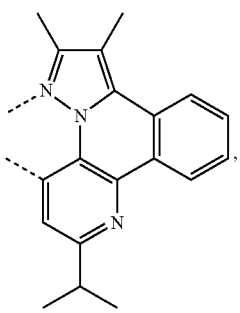
L238
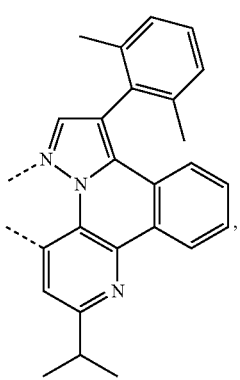
L239
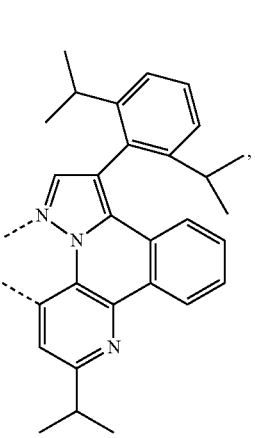
L240
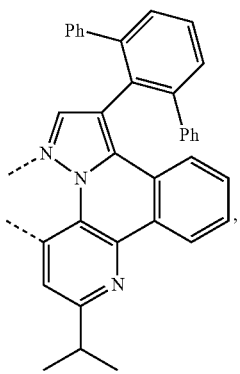

-continued
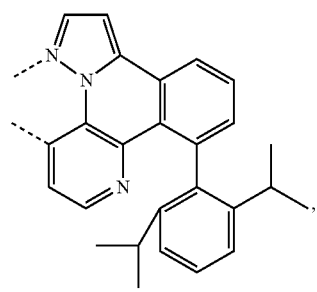
L241
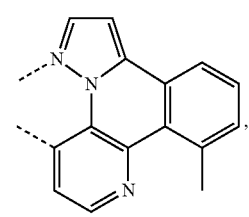
L242
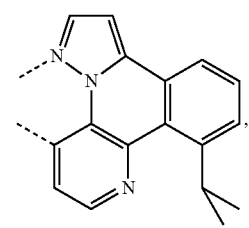
L243
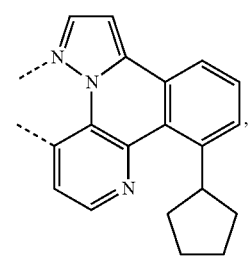
L244
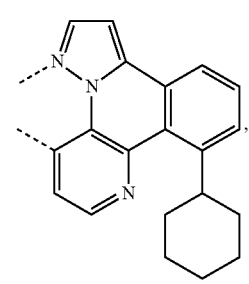
L245
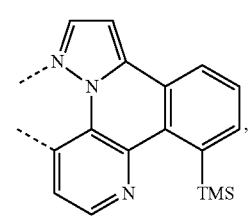
L246
-continued
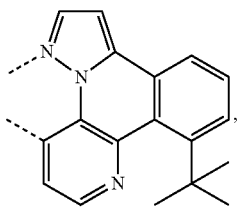
L247
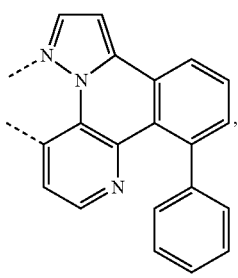
L248
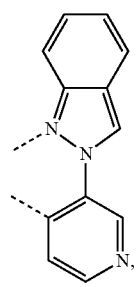
L249
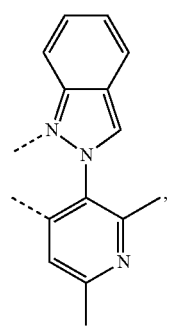
L250
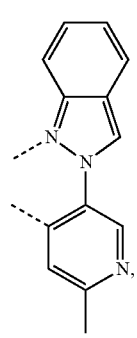
L251

-continued
L₂₅₂ 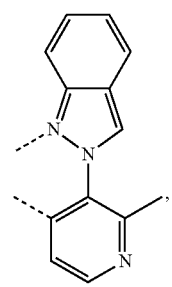
L₂₅₃ 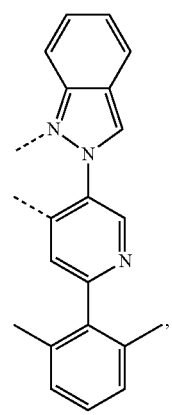
L₂₅₄ 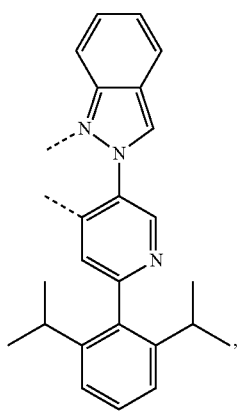
L₂₅₅ 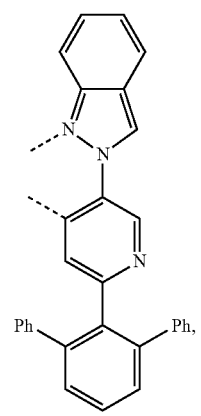
-continued
L₂₅₆ 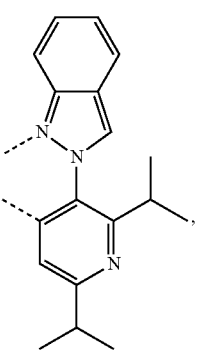
L₂₅₇ 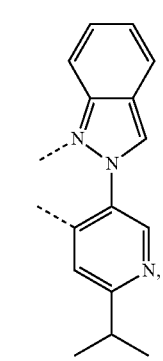
L₂₅₈ 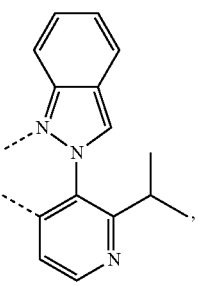
L₂₅₉ 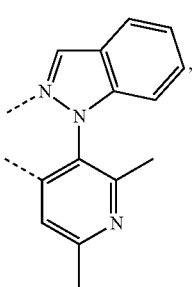
L₂₆₀ 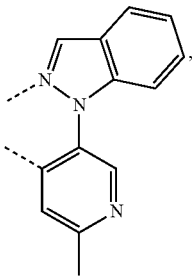

| | |
|---|---|
| 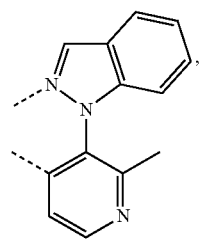 | L<sub>261</sub> |
| 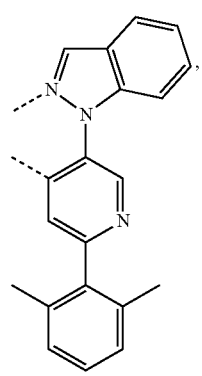 | L<sub>262</sub> |
| 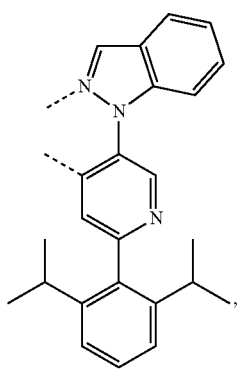 | L<sub>263</sub> |
| 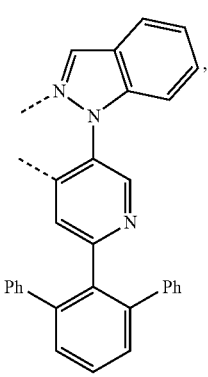 | L<sub>264</sub> |
| | |
|---|---|
| 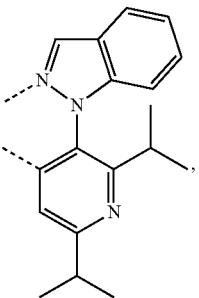 | L<sub>265</sub> |
| 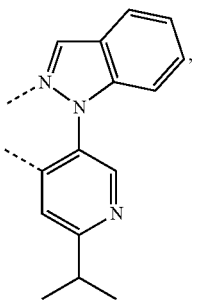 | L<sub>266</sub> |
| 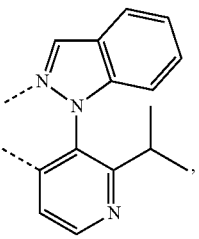 | L<sub>267</sub> |
| 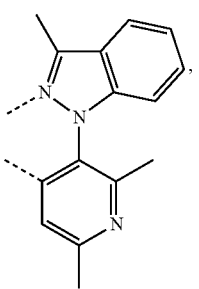 | L<sub>268</sub> |
| 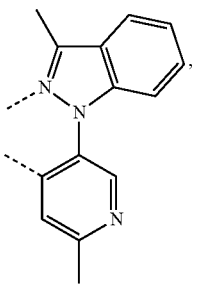 | L<sub>269</sub> |

L270 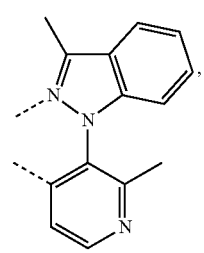
L271 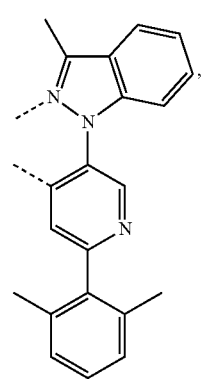
L272 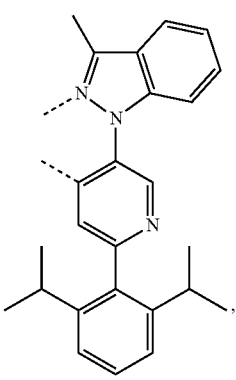
L273 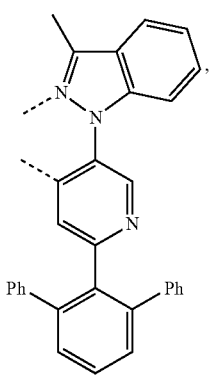
L274 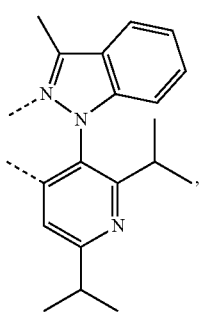
L275 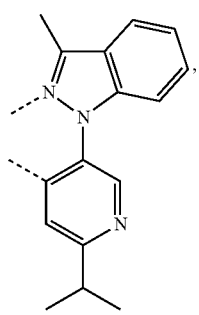
L276 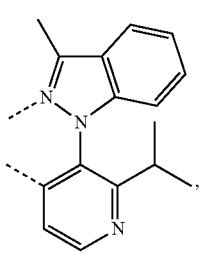
L277 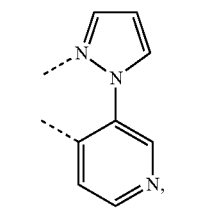
L278 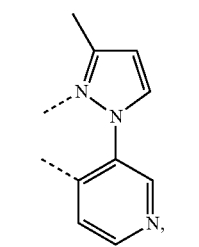
L279 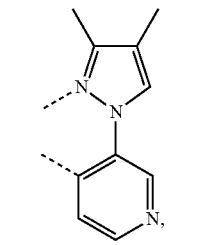

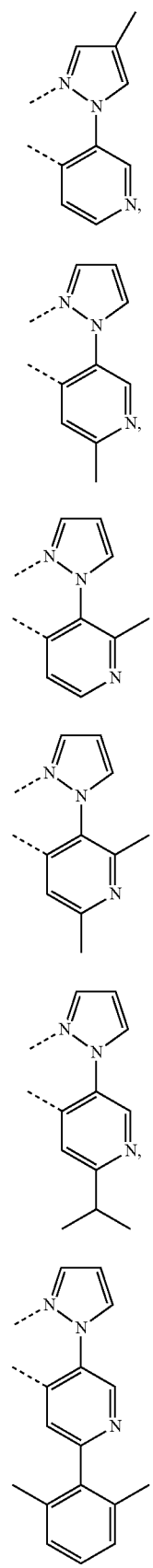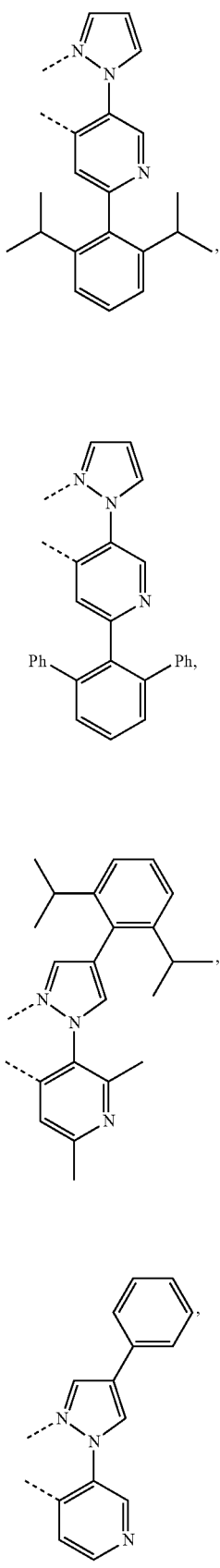

| | |
|---|---|
| L290 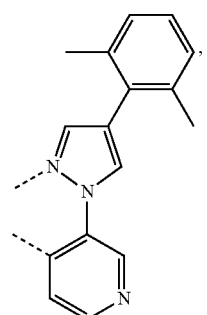 | L295 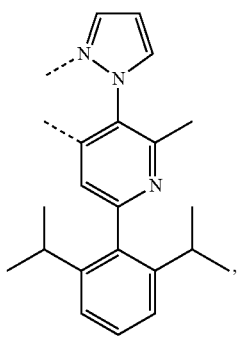 |
| L291 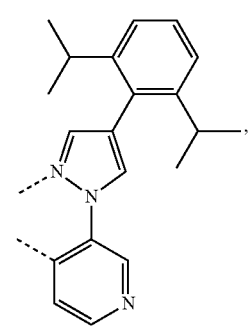 | L296 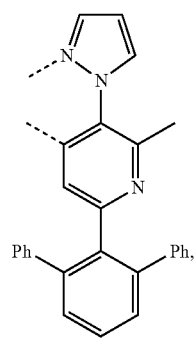 |
| L292 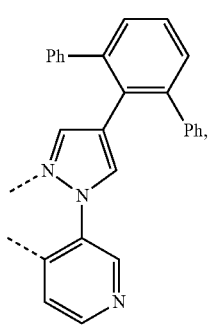 | L297 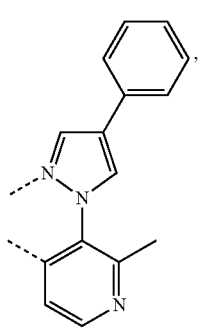 |
| L293 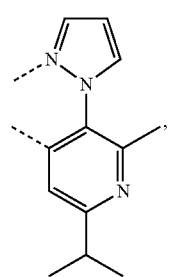 | L298 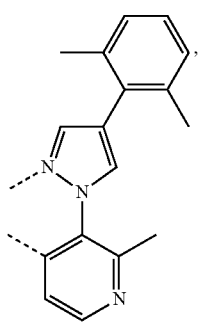 |
| L294 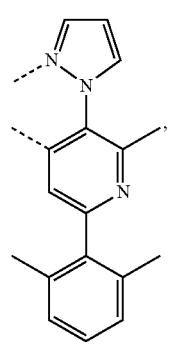 | L299 |

-continued

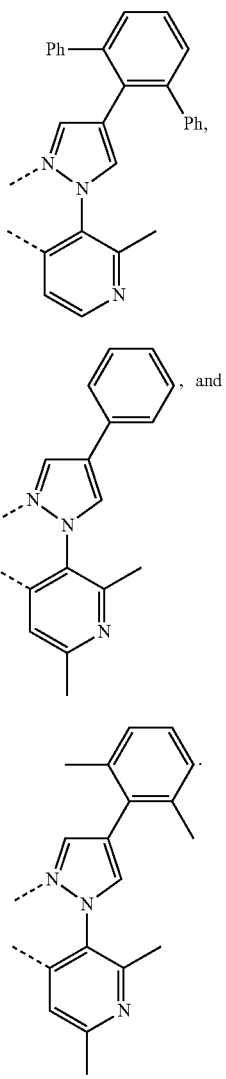

$L_{300}$

, and $L_{301}$ $L_{302}$

13. An organic light emitting device (OLED) comprising:
an anode;
a cathode; and
an organic layer, disposed between the anode and the cathode, comprising a compound comprising a ligand $L_A$ of Formula I:

Formula I

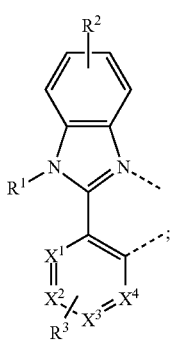

wherein $R^1$ is a substituted aryl or substituted heteroaryl with at least one substitution on at least one ortho position;
wherein $R^2$ represents mono, di, tri, or tetra substitution, or no substitution;
wherein $R^3$ represents from mono to the maximum number of substitutions it may represent, or no substitution;
wherein $X^1$, $X^2$, $X^3$, and $X^4$ are each independently selected from the group consisting of carbon and nitrogen, and at least one of $X^1$, $X^2$, $X^3$, and $X^4$ is nitrogen; and when any of $X^1$, $X^2$, $X^3$, and $X^4$ is nitrogen, there is no substitution on that nitrogen;
wherein $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acid, ester, nitrile, and isonitrile; combinations thereof;
or any adjacent $R^2$ and $R^3$ are optionally joined or fused into a ring;
wherein the ligand $L_A$ is coordinated to a metal M; and the ligand $L_A$ is optionally linked with other ligands to form a tridentate, tetradentate, ligand.

14. The OLED of claim 13, wherein the OLED is incorporated into a device selected from the group consisting of a consumer product, an electronic component module, and a lighting panel.

15. The OLED of claim 13, wherein the organic layer is an emissive layer and the compound is an emissive dopant or a non-emissive dopant.

16. The OLED of claim 13, wherein the organic layer further comprises a host;
wherein the host comprises a triphenylene containing benzo-fused thiophene or benzo-fused furan;
wherein any substituent in the host is an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, $CH=CH-C_nH_{2n+1}$, $C\equiv CC_nH_{2n+1}$, $Ar_1$, $Ar_1-Ar_2$, $C_nH_{2n}-Ar_1$, or no substitution;
wherein n is from 1 to 10; and
wherein $Ar_1$ and $Ar_2$ are independently selected from the group consisting of benzene, biphenyl, naphthalene, triphenylene, carbazole, and heteroaromatic analogs thereof.

17. The OLED of claim 13, wherein the organic layer further comprises a host;
wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

18. The OLED of claim 13, wherein the organic layer further comprises a host and the host is selected from the group consisting of:

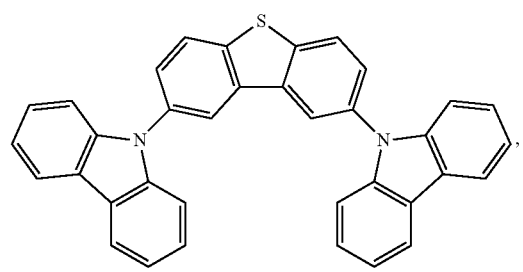

479
-continued
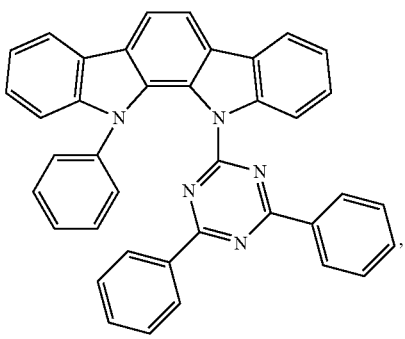
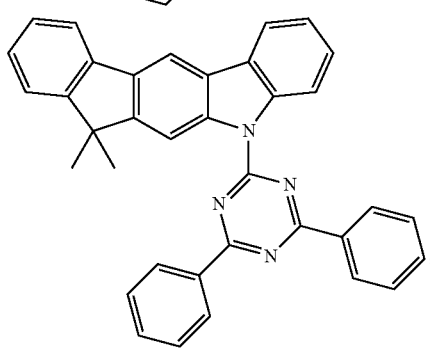
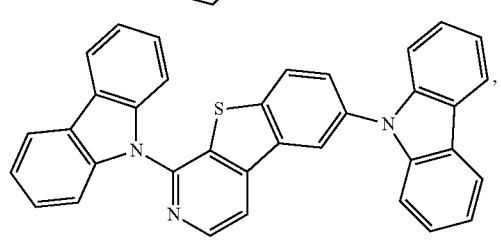
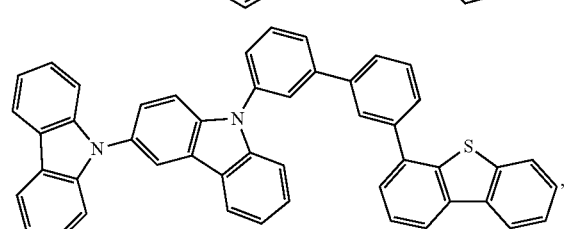
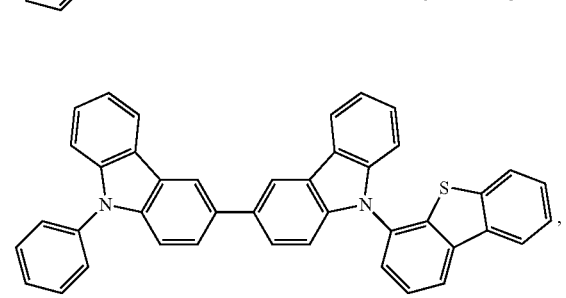
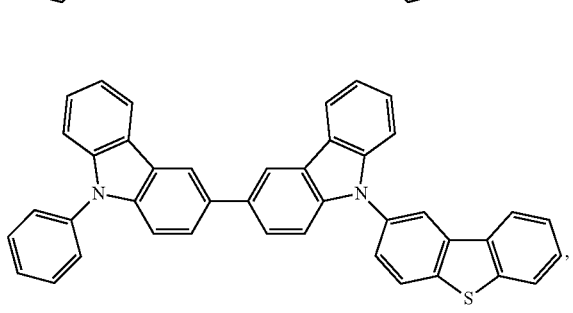
480
-continued
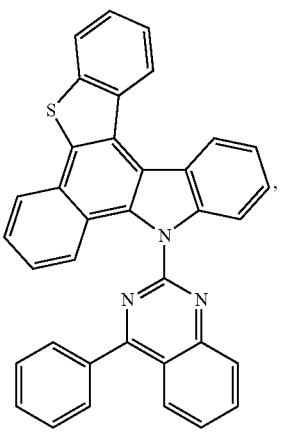
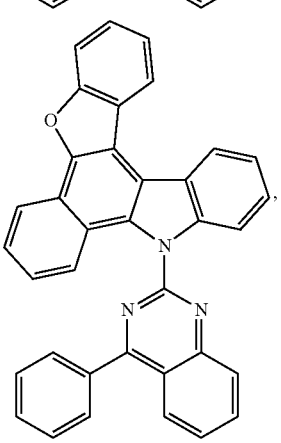
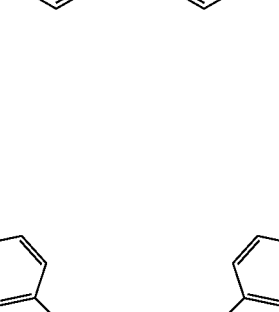
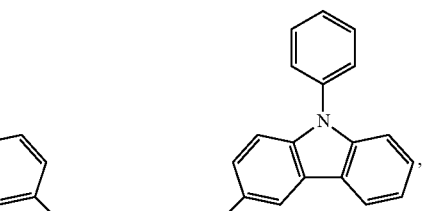

481
-continued
482
-continued
and combinations thereof.
19. The OLED of claim 13, wherein the organic layer further comprises a host and the host comprises a metal complex.
20. A formulation comprising a compound comprising a ligand $L_A$ of Formula I:
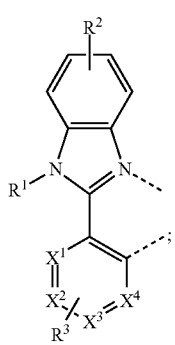
Formula I wherein $R^1$ is a substituted aryl or substituted heteroaryl with at least one substitution on at least one ortho position;

wherein $R^2$ represents mono, di, tri, or tetra substitution, or no substitution;

wherein $R^3$ represents from mono to the maximum number of substitutions it may represent, or no substitution;

wherein $X^1$, $X^2$, $X^3$, and $X^4$ are each independently selected from the group consisting of carbon and nitrogen, and at least one $X^1$, $X^2$, $X^3$, and $X^4$ is nitrogen; and when any of $X^1$, $X^2$, $X^3$, and $X^4$ is nitrogen, there is no substitution on that nitrogen;

wherein $R^2$ and $R^3$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, carboxylic acid, ester, nitrile, and isonitrile;

wherein any adjacent $R^2$ and $R^3$ are optionally joined or fused into a ring;

wherein the ligand $L_A$ is coordinated to a metal M; and wherein the ligand $L_A$ is optionally linked with other ligands to form a tridentate, tetradentate ligand.

\* \* \* \* \*